(12) United States Patent
Alsaker et al.

(10) Patent No.: US 8,906,666 B2
(45) Date of Patent: Dec. 9, 2014

(54) ENGINEERING RESISTANCE TO ALIPHATIC ALCOHOLS

(75) Inventors: Keith Alsaker, Wilmington, DE (US); Daniel Grenfell-Lee, Wilmington, DE (US); Michael Hudson, Wilmington, DE (US); Adam Lawrence, Wilmington, DE (US); Jessica McGrath, Wilmington, DE (US); David Young, Wilmington, DE (US)

(73) Assignee: Butamax Advanced Biofuels LLC DE (US)

( * ) Notice: Subject to any disclaimer, the term of this patent is extended or adjusted under 35 U.S.C. 154(b) by 434 days.

(21) Appl. No.: 12/994,100

(22) PCT Filed: May 22, 2009

(86) PCT No.: PCT/US2009/045031
§ 371 (c)(1),
(2), (4) Date: Apr. 7, 2011

(87) PCT Pub. No.: WO2009/143455
PCT Pub. Date: Nov. 26, 2009

(65) Prior Publication Data
US 2012/0040440 A1    Feb. 16, 2012

Related U.S. Application Data

(60) Provisional application No. 61/055,330, filed on May 22, 2008.

(51) Int. Cl.
| | | |
|---|---|---|
| C12N 1/21 | (2006.01) | |
| C12N 1/19 | (2006.01) | |
| C12P 7/16 | (2006.01) | |
| C12N 1/36 | (2006.01) | |
| C12N 15/52 | (2006.01) | |

(52) U.S. Cl.
CPC ... *C12P 7/16* (2013.01); *C12N 1/36* (2013.01); Y02E 50/10 (2013.01); *C12N 15/52* (2013.01)
USPC .............. 435/252.31; 435/252.3; 435/252.33; 435/254.21; 435/254.22; 435/254.23

(58) Field of Classification Search
CPC .............. C12N 1/36; C12N 15/52; C12P 7/16
USPC ............... 435/252.31, 252.3, 252.33, 252.34, 435/254.21, 254.22
See application file for complete search history.

(56) References Cited

U.S. PATENT DOCUMENTS

| | | | |
|---|---|---|---|
| 6,960,465 B1 | 11/2005 | Papoutsakis et al. | |
| 7,541,173 B2 | 6/2009 | Bramucci et al. | |
| 7,659,104 B2 | 2/2010 | Bramucci et al. | |
| 8,017,364 B2 | 9/2011 | Bramucci et al. | |
| 8,206,970 B2 | 6/2012 | Eliot et al. | |
| 8,372,612 B2 | 2/2013 | Larossa et al. | |
| 8,389,252 B2 | 3/2013 | Larossa et al. | |
| 2007/0092957 A1 | 4/2007 | Donaldson et al. | |
| 2007/0218533 A1* | 9/2007 | Gill et al. | 435/161 |
| 2007/0259411 A1 | 11/2007 | Bramucci et al. | |
| 2008/0090283 A1 | 4/2008 | Lefebvre et al. | |
| 2008/0124774 A1 | 5/2008 | Bramucci et al. | |
| 2008/0182308 A1 | 7/2008 | Donaldson et al. | |
| 2009/0162911 A1 | 6/2009 | Larossa et al. | |
| 2009/0203097 A1 | 8/2009 | Flint et al. | |
| 2009/0203139 A1 | 8/2009 | Larossa et al. | |
| 2012/0058541 A1 | 3/2012 | Alsaker et al. | |

OTHER PUBLICATIONS

Tomas et al J. Bactrol. 2004, pp. 2006-2018.*
Kisselev L., Structure, 2002, vol. 10: 8-9.*
Whisstock et al., Quarterly Reviews of Biophysics 2003, vol. 36 (3): 307-340.*
Devos et al., Proteins: Structure, Function and Genetics, 2000, vol. 41: 98-107.*
Witkowski et al., Biochemistry 38:11643-11650, 1999.*
International Search Report and Written Opinion for International Application PCT US2009/045031, mailed on Apr. 1, 2010.
Genbank Accession No. AL935260 (Apr. 16, 2005), (Printed on Apr. 17, 2013) (*Lactobacillus plantarum* WCFSI complete genome); last modified Apr. 16, 2005.
Kleerebezem et al., Complete genome sequence of *Lactobacillus plantarum* WCFS 1, PNAS, 2003, 100(4), 1990-1995.
Alper et al., Engineering yeast transcription machinery for improved ethoanol tolerance and production. Science, vol. 314, Dec. 8, 2006, pp. 1565-1568.
Yazawa et al., Disruption of URA7 and GLA6 improves the ethanol tolerance and fermentation capacity of *Saccharomyces cerevisiae*. Yeast 2007: 24: 551-560.
Tomas et al., Transcriptional analysis of butanol stress and tolerance in clostridium accetoburylicum. Journal of Bacteriology, 186(7):2006-2018 (2004).
Bowles et al., Effects of butanol on clostridium acetobutylicum, Applied and Environmental Microbiology, 1985, 50(5), 1165-1170.
LePage et al., Chanes in membrane lipid composition of clostridium acetobutylicum during acetone-butanol fermentation: effect of solvents, growth temp and pH, J. General Microbiology, 1987, 133, 103-110.
Baer et al., Effect of Butanol challenge and temperature on lipid composition and membrane fluidity of butanol tolerant clost-idium acetobutylicum, Applied and Environmental Microbiology, 1987, 53, 2854-2861.

(Continued)

*Primary Examiner* — Tekchand Saidha
*Assistant Examiner* — Younus Meah

(57) ABSTRACT

The present disclosure provides improved systems for the biological production of aliphatic alcohol compounds. In particular, the present disclosure provides biological systems that show improved resistance to aliphatic alcohol toxicity; in some embodiments, such improved resistance allows for increased levels of aliphatic alcohol production. In one aspect, the present disclosure provides engineered microorganisms that both produce an aliphatic alcohol compound and show resistance to that compound as measured by an ability to grow to predetermined levels in the presence of a given concentration of the compound.

14 Claims, 4 Drawing Sheets

(56) References Cited

OTHER PUBLICATIONS

Tomas et al., Overexpression of groESL in Clostribium acetobutylicum results in increased solvent production and tolerance, prolonged metabolism, and changes in the cell's transcriptional program, Applied and Environmental Microbiology, 2003, 69(8), 4951-4965.

Kleerebezem et al., Controlled gene expression systems for lactic acid bacteria: transferable nisin-inducible expression cassettes for *lactococcus*, leuconostoc, and *lactobacillus* spp, Applied and Environmental Microbiology, 1997, 63(11), 4581-4584.

Huang et al., Transmembrane pH gradient and membrane potential in *Clostridium acetobutylicum* during growth under acetogenic and solventogenic conditions, Appl. Environ. Microbiol. 50:1043-1047 (1985).

International Preliminary Report on Patentability for International Application PCT US2009/045031, mailed on Nov. 23, 2010.

\* cited by examiner

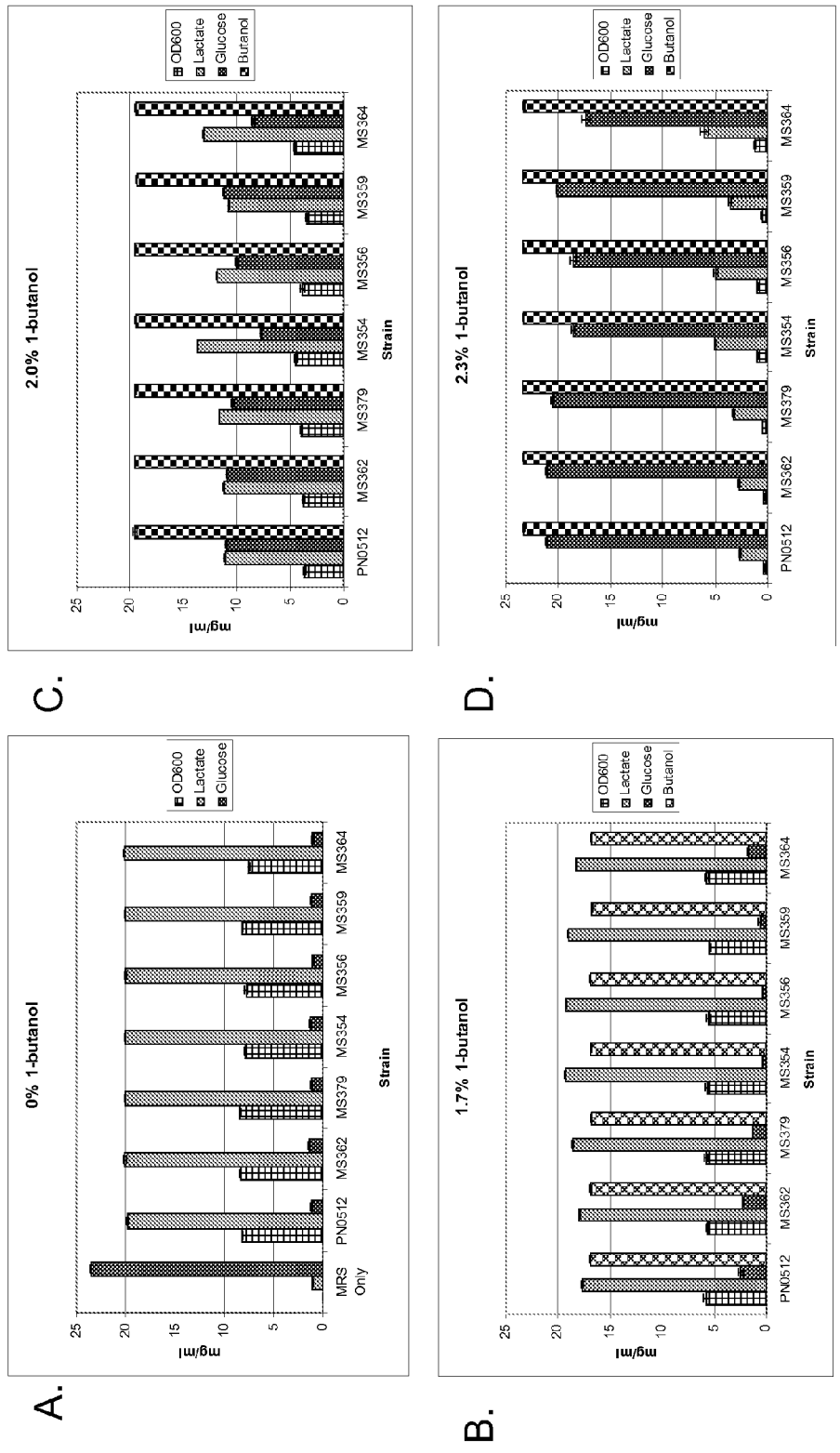
Figure 4. Metabolic tolerance assay results for *L. plantarum* strains engineered for higher butanol tolerance.

US 8,906,666 B2

ENGINEERING RESISTANCE TO ALIPHATIC ALCOHOLS

CROSS REFERENCE TO RELATED APPLICATIONS

This application is a 371 of PCT/US09/45031 May 22, 2009 and copending with, shares at least one common inventor with and claims priority to U.S. provisional patent application Ser. No. 61/055,330, filed May 22, 2008, the entire contents of which are incorporated herein by reference.

BACKGROUND

Aliphatic alcohols, such as butanol, are important industrial chemicals, useful among other things as fuel additives, as chemical feedstocks in the plastics industry, and as food-grade extractants in the food and flavor industry. For example, each year at least 10-12 billion pounds of butanol are produced by petrochemical means, and the need for this commodity chemical will likely increase.

There is a need for the development of new technologies for the production of aliphatic alcohols. Methods of chemical synthesis (typically starting from petrochemical by-products) are expensive and utilize or produce environmentally damaging agents. Efforts have been made to develop biotransformation and fermentation processes that employ microorganisms for some or all of the steps in aliphatic alcohol production. However, reported protocols are typically complicated. Moreover, such efforts often are hampered by toxicity of produced compounds toward the utilized microorganisms.

SUMMARY

The present disclosure provides improved systems for the biological production of certain aliphatic alcohol compounds. In particular, the present disclosure provides biological systems that show improved resistance to aliphatic alcohol toxicity; in some embodiments, such improved resistance allows for increased levels of aliphatic alcohol production.

Accordingly, the present disclosure provides, inter alia, engineered microorganisms that both produce an aliphatic alcohol compound and show resistance to that compound as measured by an ability to grow to predetermined levels in the presence of a given concentration of the compound.

In one aspect, the present disclosure provides a recombinant microbial cell, characterized in that the recombinant microbial cell comprises at least one alcohol tolerance modification as compared with a parent cell.

In some embodiments, an alcohol tolerance modification comprises introduction of a nucleic acid molecule comprising a 3' region of a gene encoding a CAAX protease polypeptide. In some embodiments, a 3' region of the gene is a 3' untranslated region (UTR). A 3' region of the gene can be a region sufficient to adjust susceptibility of the cell to one or more toxic effects of one or more aliphatic alcohol compounds. In some embodiments, a 3' region comprises at least 10 nucleotides, e.g., at least 20, 30, 40, 50, 60, 70, 80, 90, 100, 150, 200, 250, 300, 350, 400, 450, 500, 550, 600, or 650 nucleotides. A 3' region of the gene can include nucleotides within 500, 200, 100, 50, or fewer nucleotides, or immediately downstream of, sequence encoding the CAAX protease polypeptide. In some embodiments, a nucleic acid molecule comprises a 3' region of a gene encoding a CAAX protease polypeptide in *Lactobacillus*, e.g., a 3' region of a gene encoding a CAAX protease polypeptide in *Lactobacillus plantarum*. In some embodiments, a 3' region of the gene comprises 655 nucleotides immediately downstream of a sequence encoding a *Lactobacillus plantarum* CAAX protease polypeptide. Exemplary sequences from a 3' region of a gene encoding a CAAX protease polypeptide are shown, e.g., in Table 1B. In some embodiments, a 3' region of the gene comprises at least 10 consecutive nucleotides (e.g., at least 20, 30, 40, 50, 60, 70, 80, 90, 100, 150, 200, 250, 300, 350, 400, 450, 500, 550, 600, or 650 nucleotides) of the nucleotide sequence shown in Table 1B, row 42, or a homologous sequence thereof (e.g., a sequence having at least 60%, 70%, 80%, 85%, 90%, 95%, 97%, 99% identity).

A recombinant microbial cell can include a nucleic acid molecule comprising a 5' region of a gene encoding a CAAX protease polypeptide. In some embodiments, an alcohol tolerance modification comprises introduction of both a 3' region and a 5' region of a gene encoding a CAAX protease polypeptide. A 3' region and 5' regions may be from the same or from different organisms. A 5' region of the gene can include a 5' UTR. In some embodiments, a 5' region of the gene comprises at least 10, 20, 30, 40, 50, 60, 70, 80, 90, or 100 nucleotides. A 5' region of the gene can include nucleotides within 500, 200, 100, 50, or fewer nucleotides, or immediately upstream of, sequence encoding the CAAX protease polypeptide.

In some embodiments, a nucleic acid molecule includes a 5' region of a gene encoding a CAAX protease polypeptide in *Lactobacillus*, e.g., *Lactobacillus plantarum*. In one embodiment, a 5' region of the gene includes 111 nucleotides immediately upstream of sequence encoding a *Lactobacillus plantarum* CAAX protease polypeptide. Exemplary sequences from a 5' region of a gene encoding a CAAX protease polypeptide are shown, e.g., in Table 1B. In some embodiments, a 5' region of the gene comprises at least 10 consecutive nucleotides (e.g., at least 20, 30, 40, 50, 60, 70, 80, 90, or 100 nucleotides) of the nucleotide sequence shown in Table 1B, row 40, or a homologous sequence thereof (e.g., a sequence having at least 60%, 70%, 80%, 85%, 90%, 95%, 97%, 99% identity).

In some embodiments, a recombinant microbial cell provided herein exhibits increased tolerance to at least one aliphatic alcohol compound as compared with the parent cell. Increased tolerance to at least one aliphatic alcohol compound can include an increased aliphatic alcohol compound $IC_{50}$, wherein the $IC_{50}$ is increased at least 5%, 10%, 20%, 30%, 40%, 50%, 60%, 70%, 80%, 90%, 100%, or more. Increased tolerance to at least one aliphatic alcohol compound can include an increased aliphatic alcohol compound $IC_{50}$ of at least 10%, 50%, or 100%.

In some embodiments, the increased tolerance to at least one aliphatic alcohol compound comprises increased carbohydrate utilization (e.g., glucose and/or lignocellulosic-based carbohydrate utilization) as compared to the parent cell when grown in same amount of alcohol, e.g., wherein the carbohydrate utilization is increased at least 5%, 10%, 20%, 30%, 40%, 50%, 60%, 70%, 80%, 90%, 100%, or more.

In some embodiments, a recombinant microbial cell provided herein produces at least one aliphatic alcohol compound. In some embodiments, a cell provided herein exhibits increased alcohol production as compared with the parent cell. In some embodiments, alcohol production is increased by the at least one alcohol tolerance modification. Increased alcohol production can be determined by measuring a characteristic selected from the group consisting of: broth titer (grams aliphatic alcohol produced per liter broth (g l-1)), aliphatic alcohol yield (grams aliphatic alcohol produced per gram substrate consumed (g g-1), volumetric productivity (grams aliphatic alcohol produced per liter per hour (g l-1 h-1)), and specific productivity (grams aliphatic alcohol produced per gram host cell biomass per hour (g/g cells h-1)), and combinations thereof. In some embodiments, broth titer is increased at least 10%, 25%, 50%, 75%, 100%, or more. In some embodiments, aliphatic alcohol yield is increased at least 10%, 25%, 50%, 75%, 100%, or more. In some embodiments, volumetric productivity is increased at least 10%, 25%, 50%, 75%, 100%, or more. In some embodiments, specific productivity is increased at least 10%, 25%, 50%, 75%, 100%, or more.

In some embodiments, a parent cell of a cell provided herein naturally produces at least one aliphatic alcohol compound. In some embodiments, a parent cell of a cell provided herein does not naturally produce an aliphatic alcohol compound.

In some embodiments, a cell provided herein is a member of a genus selected from the group consisting of *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Acinetobacter, Pichia, Candida, Hansenula* and *Saccharomyces*. In some embodiments, a cell species is selected from the group consisting of *Clostridium acetobutylicum, Clostridium beijerinckii*, and *Clostridium saccaharoperbuylacetonicum*. In some embodiments, a cell species is *Escherichia coli*. In some embodiments, a cell species is *Alcaligenes eutrophus*. In some embodiments, a cell species is *Bacillus licheniformis*. In some embodiments, a cell species is *Paenibacillus macerans*. In some embodiments, a cell species is *Rhodococcus erythropolis*. In some embodiments, a cell species is *Pseudomonas putida*. In some embodiments, a cell species is *Bacillus subtilis*. In some embodiments, a cell species is *Lactobacillus plantarum*. In some embodiments, a cell species is *Enterococcus faecium*. In some embodiments, a cell species is *Enterococcus gallinarum*. In some embodiments, a cell species is *Enterococcus faecalis*. In some embodiments, a cell species is *Saccharomyces cerevisiae*.

In various embodiments, an alcohol tolerance modification increases expression or activity of at least one alcohol tolerance polypeptide in a recombinant microbial cell. For example, the alcohol tolerance modification decreases expression or activity of at least one alcohol tolerance polypeptide, or increases expression or activity of at least one alcohol tolerance polypeptide and decreases expression or activity of at least one other alcohol tolerance polypeptide.

In some embodiments, the at least one alcohol tolerance polypeptide is either encoded by or homologous to a polypeptide encoded by the genome of a parent cell. In some embodiments, the at least one alcohol tolerance polypeptide is at least one polypeptide selected from the group consisting of those encoded by determinant sequences in Table 1A, and combinations thereof. In some embodiments, the at least one alcohol tolerance polypeptide is at least one polypeptide selected from the group consisting of those encoded by determinant sequences in Table 1A, homologs thereof, and combinations thereof. In some embodiments, the at least one alcohol tolerance polypeptide is at least one polypeptide selected from the group consisting of those encoded by determinant sequences in Table 2, and combinations thereof. For example, in some embodiments, the at least one alcohol tolerance polypeptide is a polypeptide selected from the group consisting of a calcineurin-like phosphoesterase polypeptide, a cation transport protein (mntH3 related) polypeptide, a transcription regulator (lp_2159 related) polypeptide, a lp_2160 related polypeptide, a lp_2169 related polypeptide, a phosphoglycerate mutase polypeptide, a CAAX protease polypeptide, and a peptidylprolyl isomerase (prs2A related polypeptide).

The at least one alcohol tolerance modification can include introduction of an alcohol tolerance determinant found within the alcohol tolerance determinant sequences in Tables 1 and 2. In some embodiments, the at least one alcohol tolerance modification comprises introduction of an alcohol tolerance determinant selected from the group consisting of those found within a Table 1A row selected from the group consisting of row 20 (lp_1293), row 21 (lp_1295 [mntH3]), row 34 (lp_2159), row 35 (lp_2160), row 36 (lp_2169), row 37 (lp_2170), row 44 (lp_2911), row 50 (lp_3193), homologs thereof, and combinations of any of the foregoing. In some embodiments, homologs thereof are selected from among those found in one or more of Tables 2T, 2U, 2AH, 2AI, 2AJ, 2AK, 2AR, 2AX, and combinations thereof.

The at least one alcohol tolerance modification can further include introduction of an alcohol tolerance determinant selected from the group consisting of those found in Tables 3 and 4. In some embodiments, an alcohol tolerance determinant found in Tables 3 and 4 is selected from the group consisting of those found in sequences present in rows 2 (groES), 3 (groEL), 5 (cfa1) and/or 8 (cfa2) of Table 3, or in any of Tables 4B, 4C, 4E and 4H.

In some embodiments, the at least one alcohol tolerance modification further includes disruption or inhibition of an alcohol tolerance determinant selected from the group consisting of those found in Tables 3 and 4. In some embodiments, an alcohol tolerance determinant found in Tables 3 and 4 is selected from the group consisting of those found in sequences present in rows 1 (htrA), 4 (clpP), 6 (relA/spoT), 7 (hrcA), and/or 8 (cfa2) of Table 3, or in any of Tables 4A, 4D, 4F, 4G and 4H.

In some embodiments, the at least one alcohol tolerance polypeptide whose activity or expression is altered in a recombinant microbial cell provided herein comprises a CAAX protease. In some embodiments, the at least one alcohol tolerance polypeptide comprises a prs2A related polypeptide. In some embodiments, the at least one alcohol tolerance polypeptide comprises a calcineurin-like phosphoesterase. In some embodiments, the at least one alcohol tolerance polypeptide comprises a cation transport protein (mntH3 related).

In some embodiments, an alcohol tolerance modification comprises introduction of an alcohol determinant sequence found within a DNA insert sequence depicted in Table 1B. In some embodiments, an alcohol tolerance modification comprises introduction of an alcohol determinant sequence found within a DNA insert of p5AE4-1 depicted in Table 1B. In some embodiments, an alcohol tolerance modification comprises introduction of an alcohol determinant sequence found within a DNA insert of p5AE0-4, p5AE0-14, or p5AE0-24, depicted in Table 1B.

The at least one alcohol tolerance polypeptide whose activity or expression is altered in a recombinant microbial cell provided herein can be heterologous to the host cell. In some embodiments, the at least one alcohol tolerance polypeptide is at least one polypeptide selected from the group consisting of a polypeptide in Table 1, Table 2, or a homolog thereof. In some embodiments, a host cell is a *L. plantarum* cell, or a *C. acetobutylicum* cell. In some embodiments, the at least one alcohol tolerance polypeptide is selected from the group consisting of those presented in Table 2. In some embodiments, the at least one alcohol tolerance polypeptide is selected from the group consisting of those presented in Table 1 and Table 2. In some embodiments, the at least one alcohol tolerance polypeptide is at least one polypeptide selected from the group consisting of those encoded by determinant sequences in Table 1A, homologs thereof, and combinations thereof. In some embodiments, the at least one alcohol tolerance polypeptide is a polypeptide selected from the group consisting of a calcineurin-like phosphoesterase polypeptide, a cation transport protein (mntH3 related) polypeptide, a transcription regulator (lp_2159 related) polypeptide, a lp_2160 related polypeptide, a lp_2169 related polypeptide, a phosphoglycerate mutase polypeptide, a CAAX protease polypeptide, and a peptidylprolyl isomerase (prs2A related polypeptide).

In some embodiments, the at least one alcohol tolerance modification includes introduction of an alcohol tolerance determinant which is heterologous to the host cell, and which is found within the alcohol tolerance determinant sequences in Tables 1 and 2. The at least one alcohol tolerance modification can include introduction of an alcohol tolerance determinant selected from the group consisting of those found within a Table 1A row selected from the group consisting of row 20 (lp_1293), row 21 (lp_1295 [mntH3]), row 34 (lp_2159), row 35 (lp_2160), row 36 (lp_2169), row 37 (lp_2170), row 44 (lp_2911), row 50 (lp_3193), homologs thereof, and combinations of any of the foregoing. The homologs thereof can be selected from among those found in one or more of Tables 2T, 2U, 2AH, 2AI, 2AJ, 2AK, 2AR, 2AX, and combinations thereof. The at least one alcohol tolerance modification can further include introduction of an alcohol tolerance determinant selected from the group consisting of those found in Tables 3 and 4, e.g., wherein the alcohol tolerance determinant found in Tables 3 and 4 is selected from the group consisting of those found in sequences present in rows 2 (groES), 3 (groEL), 5 (cfa1) and/or 8 (cfa2) of Table 3, or in any of Tables 4B, 4C, 4E and 4H. The at least one alcohol tolerance modification can further include disruption or inhibition of an alcohol tolerance determinant selected from the group consisting of those found in Tables 3 and 4, e.g., wherein the alcohol tolerance determinant found in Tables 3 and 4 is selected from the group consisting of those found in sequences present in rows 1 (htrA), 4 (clpP), 6 (relA/spoT), 7 (hrcA), and/or 8 (cfa2) of Table 3, or in any of Tables 4A, 4D, 4F, 4G and 4H.

In some embodiments, an alcohol tolerance modification comprises expression of at least one heterologous alcohol tolerance polypeptide in a recombinant microbial cell. In some embodiments, an alcohol tolerance modification comprises expression of at least one heterologous gene encoding the at least one heterologous alcohol tolerance polypeptide. In some embodiments, the at least one heterologous alcohol tolerance polypeptide is a butanol tolerance polypeptide. In some embodiments, a butanol tolerance polypeptide is selected from the group consisting of a polypeptide in Table 1, or a homolog thereof. The at least one heterologous alcohol tolerance polypeptide can include at least two heterologous alcohol tolerance polypeptides.

In some embodiments, an alcohol tolerance modification comprises increased expression or activity of at least one endogenous alcohol tolerance polypeptide in a recombinant microbial cell, which endogenous alcohol tolerance polypeptide is endogenous to a parental cell. In some embodiments, the alcohol tolerance modification comprises increased expression or activity of at least one endogenous gene encoding the at least one endogenous alcohol tolerance polypeptide. In some embodiments, the at least one endogenous alcohol tolerance polypeptide is a butanol tolerance polypeptide, e.g., a butanol tolerance polypeptide selected from the group consisting of a polypeptide in Table 1, or a homolog thereof. In some embodiments, the at least one endogenous alcohol tolerance polypeptide comprises at least two endogenous alcohol tolerance polypeptides. In some embodiments, the at least two endogenous alcohol tolerance polypeptides are each butanol tolerance polypeptides. In some embodiments, butanol tolerance polypeptides are each selected from the group consisting of a polypeptide in Table 1, or a homolog thereof.

In some embodiments, an alcohol tolerance modification comprises decreased expression or activity of at least one endogenous alcohol tolerance polypeptide in a recombinant microbial cell, which endogenous alcohol tolerance polypeptide is endogenous to a parental cell. In some embodiments, an alcohol tolerance modification comprises decreased expression or activity of at least one endogenous gene encoding the at least one endogenous alcohol tolerance polypeptide. In some embodiments, the at least one endogenous alcohol tolerance polypeptide is a butanol tolerance polypeptide. In some embodiments, a butanol tolerance polypeptide is selected from the group consisting of a polypeptide in Table 1, or a homolog thereof. In some embodiments, the at least one endogenous alcohol tolerance polypeptide comprises at least two endogenous alcohol tolerance polypeptides. In some embodiments, the at least two endogenous alcohol tolerance polypeptides are each butanol tolerance polypeptides. In some embodiments, butanol tolerance polypeptides are each selected from the group consisting of a polypeptide in Table 1, or a homolog thereof.

A recombinant microbial cell provided herein can further include at least one alchologenic modification. In some embodiments, an alchologenic modification increases expression or activity of at least one alchologenic polypeptide. In some embodiments, an alchologenic modification decreases expression or activity of at least one alchologenic polypeptide. In some embodiments, an alchologenic modification increases expression or activity of at least one alchologenic polypeptide and decreases expression or activity of at least one other alchologenic polypeptide. In some embodiments, an alchologenic modification comprises expression of at least one heterologous alchologenic polypeptide in a recombinant microbial cell. In some embodiments, an alchologenic modification comprises expression of at least one heterologous gene encoding the at least one heterologous alchologenic polypeptide.

The at least one alchologenic polypeptide can be a polypeptide that increases production of an aliphatic alcohol selected from the group consisting of: methanol, ethanol, 1-propanol, 2-propanol, iso-propanol, 1-butanol, 2-butanol, iso-butanol, tert-butanol, 1-pentanol, 2-pentanol, 3-pentanol, iso-pentanol, 1-hexanol, 2-hexanol, 3-hexanol, 2-ethyl hexanol, iso-hexanol, 1-heptanol, 2-heptanol, 3-heptanol, 4-heptanol, iso-heptanol, 1-octanol, 2-octanol, 3-octanol, iso-octanol, and 4-octanol, and combinations thereof. In some embodiments, the at least one alchologenic polypeptide is a polypeptide that increases production of an aliphatic alcohol selected from the group consisting of: 1-butanol, 2-butanol, iso-butanol, tert-butanol, and combinations thereof. In some embodiments, the at least one alchologenic polypeptide is a polypeptide that increases production of 1-butanol, 2-butanol, or iso-butanol.

In some embodiments, the at least one alchologenic polypeptide catalyzes a substrate to product conversion selected from the group consisting of: a) acetyl-CoA to acetoacetyl-CoA; b) acetoacetyl-CoA to 3-hydroxybutyryl-CoA; c) 3-hydroxybutyryl-CoA to crotonyl-CoA; d) crotonyl-CoA to butyryl-CoA; e) butyryl-CoA to butyraldehyde; f) butyraldehyde to 1-butanol; and combinations thereof. In some embodiments, the polypeptide that catalyzes a substrate to product conversion of acetyl-CoA to acetoacetyl-CoA is acetyl-CoA acetyltransferase. In some embodiments, a polypeptide that catalyzes a substrate to product conversion of acetoacetyl-CoA to 3-hydroxybutyryl-CoA is 3-hydroxybutyryl-CoA dehydrogenase. In some embodiments, a polypeptide that catalyzes a substrate to product conversion of 3-hydroxybutyryl-CoA to crotonyl-CoA is crotonase. In some embodiments, a polypeptide that catalyzes a substrate to product conversion of crotonyl-CoA to butyryl-CoA is butyryl-CoA dehydrogenase. In some embodiments, a polypeptide that catalyzes a substrate to product conversion of butyryl-CoA to butyraldehyde is butyraldehyde dehydrogenase. In some embodiments, a polypeptide that catalyzes a substrate to product conversion of butyraldehyde to 1-butanol is butanol dehydrogenase.

In some embodiments, the at least one alcohologenic polypeptide catalyzes a substrate to product conversion selected from the group consisting of: a) pyruvate to acetolactate; b) acetolactate to 2,3-dihydroxyisovalerate; c) alpha-ketoisovalerate to isobutyraldehyde; d) isobutyraldehyde to isobutanol; e) 2,3-dihydroxyisovalerate to alpha-ketoisovalerate; f) alpha-ketoisovalerate to isobutyraldehyde; g) alpha-ketoisovalerate to isobutyryl-CoA; h) isobutyryl-CoA to isobutyraldehyde; i) alpha-ketoisovalerate to L-valine; j) L-valine to isobutylamine; k) isobutylamine to isobutyraldehyde; l) butyryl-CoA to isobutyryl-CoA; and combinations thereof.

In some embodiments, a polypeptide that catalyzes a substrate to product conversion of pyruvate to acetolactate is acetolactate synthase. In some embodiments, a polypeptide that catalyzes a substrate to product conversion of acetolactate to 2,3-dihydroxyisovalerate is acetohydroxy acid reductoisomerase. In some embodiments, a polypeptide that catalyzes a substrate to product conversion of acetolactate to 2,3-dihydroxyisovalerate is acetohydroxy acid isomeroreductase. In some embodiments, a polypeptide that catalyzes a substrate to product conversion of alpha-ketoisovalerate to isobutyraldehyde is branched-chain alpha-keto acid decarboxylase. In some embodiments, a polypeptide that catalyzes a substrate to product conversion of isobutyraldehyde to isobutanol is branched-chain alcohol dehydrogenase. In some embodiments, a polypeptide that catalyzes a substrate to product conversion of 2,3-dihydroxyisovalerate to alpha-ketoisovalerate is acetohydroxy acid dehydratase. In some embodiments, a polypeptide that catalyzes a substrate to product conversion of alpha-ketoisovalerate to isobutyraldehyde is branched-chain alpha-keto acid decarboxylase. In some embodiments, a polypeptide that catalyzes a substrate to product conversion of alpha-ketoisovalerate to isobutyryl-CoA is branched-chain keto acid dehydrogenase. In some embodiments, a polypeptide that catalyzes a substrate to product conversion of isobutyryl-CoA to isobutyraldehyde is acylating aldehyde dehydrogenase. In some embodiments, a polypeptide that catalyzes a substrate to product conversion of alpha-ketoisovalerate to L-valine is transaminase. In some embodiments, a polypeptide that catalyzes a substrate to product conversion of alpha-ketoisovalerate to L-valine is valine dehydrogenase. In some embodiments, a polypeptide that catalyzes a substrate to product conversion of L-valine to isobutylamine is valine decarboxylase. In some embodiments, a polypeptide that catalyzes a substrate to product conversion of isobutylamine to isobutyraldehyde is omega transaminase. In some embodiments, a polypeptide that catalyzes a substrate to product conversion of butyryl-CoA to isobutyryl-CoA is isobutyryl-CoA mutase.

In some embodiments, the at least one alcohologenic polypeptide catalyzes a substrate to product conversion selected from the group consisting of: a) pyruvic acid to alpha-acetolactate; b) alpha-acetolactate to acetoin; c) acetoin to 2,3-butanediol; d) 2,3-butanediol to 2-butanone; e) 2-butanone to 2-butanol; and combinations thereof.

In some embodiments, a polypeptide that catalyzes a substrate to product conversion of alpha-acetolactate to acetoin is acetolactate decarboxylase. In some embodiments, a polypeptide that catalyzes a substrate to product conversion of pyruvic acid to alpha-acetolactate is acetolactate synthase. In some embodiments, a polypeptide that catalyzes a substrate to product conversion of acetoin to 2,3-butanediol is butanediol dehydrogenase. In some embodiments, a polypeptide that catalyzes a substrate to product conversion of 2,3-butanediol to 2-butanone is butanediol dehydratase. In some embodiments, a polypeptide that catalyzes a substrate to product conversion of 2-butanone to 2-butanol is butanol dehydrogenase.

In some embodiments, a recombinant microbial cell provided herein exhibits increased alcohol production as compared with the parent cell. In some embodiments, alcohol production is increased by the at least one alcohologenic modification. In some embodiments, increased alcohol production is determined by measuring a characteristic selected from the group consisting of: broth titer (grams aliphatic alcohol produced per liter broth (g l-1)), aliphatic alcohol yield (grams aliphatic alcohol produced per gram substrate consumed (g g-1), volumetric productivity (grams aliphatic alcohol produced per liter per hour (g l-1 h-1)), and specific productivity (grams aliphatic alcohol produced per gram recombinant cell biomass per hour (g/g cells h-1)), and combinations thereof.

In some embodiments, broth titer is increased at least 10%, 25%, 50%, 75%, 100%, or more. In some embodiments, yield is increased at least 10%, 25%, 50%, 75%, 100%, or more. In some embodiments, volumetric productivity is increased at least 10%, 25%, 50%, 75%, 100%, or more. In some embodiments, specific productivity is increased at least 10%, 25%, 50%, 75%, 100%, or more.

In some embodiments, an aliphatic alcohol compound comprises a compound selected from the group consisting of: methanol, ethanol, 1-propanol, 2-propanol, iso-propanol, 1-butanol, 2-butanol, iso-butanol, tert-butanol, 1-pentanol, 2-pentanol, 3-pentanol, iso-pentanol, 1-hexanol, 2-hexanol, 3-hexanol, 2-ethyl hexanol, iso-hexanol, 1-heptanol, 2-heptanol, 3-heptanol, 4-heptanol, iso-heptanol, 1-octanol, 2-octanol, 3-octanol, iso-octanol, and 4-octanol, and combinations thereof.

In some embodiments, an aliphatic alcohol compound comprises a compound selected from the group consisting of: 1-butanol, 2-butanol, iso-butanol, tert-butanol, and combinations thereof. In particular embodiments, the aliphatic alcohol compound comprises 1-butanol.

In another aspect, the present disclosure provides a recombinant cell engineered to contain or express an alcohol tolerance determinant selected from the group consisting of: a) a determinant sequence set forth in Table 1A; b) a determinant sequence set forth in Table 1B; c) a determinant sequence set forth in Table 2; and combinations thereof. In some embodiments, a recombinant cell is engineered to contain or express an alcohol tolerance determinant which is a determinant sequence set forth in Table 1A. In some embodiments, a cell is engineered to contain or express a determinant sequence selected from the group consisting of those found within a Table 1A row selected from the group consisting of row 20 (lp__1293), row 21 (lp__1295 [mntH3]), row 34 (lp__2159), row 35 (lp__2160), row 36 (lp__2169), row 37 (lp__2170), row 44 (lp__2911), and row 50 (lp__3193).

In some embodiments, a cell is engineered to contain or express an alcohol tolerance determinant which is a determinant sequence set forth in Table 1B. In some embodiments, a cell is engineered to contain or express an alcohol tolerance determinant which is a determinant sequence set forth in Table 2. In some embodiments, a cell is engineered to contain or express a determinant sequence selected from the group consisting of those found within Tables 2T, 2U, 2AH, 2AI, 2AJ, 2AK, 2AR, and 2AX.

In another aspect, the present disclosure provides a recombinant cell that includes an alcohol tolerance modification (e.g., as compared with a parent cell), wherein the alcohol tolerance modification comprises introduction of alcohol tolerance determinant sequences selected from the group consisting of: a) a determinant sequence set forth in Table 1A; b) a determinant sequence set forth in Table 1B; c) determinant sequence set forth in Table 2; and combinations thereof. In some embodiments, a recombinant cell includes an alcohol tolerance determinant which is a determinant sequence set forth in Table 1A. In some embodiments, a cell includes a determinant sequence selected from the group consisting of those found within a Table 1A row selected from the group consisting of row 20 (lp__1293), row 21 (lp__1295 [mntH3]), row 34 (lp__2159), row 35 (lp__2160), row 36 (lp__2169), row 37 (lp__2170), row 44 (lp__2911), and row 50 (lp__3193). In some embodiments, a cell includes an alcohol tolerance determinant which is a determinant sequence set forth in Table 1B. In some embodiments, a cell includes an alcohol tolerance determinant which is a determinant sequence set forth in Table 2. In some embodiments, a cell includes a determinant sequence selected from the group consisting of those found within Tables 2T, 2U, 2AH, 2AI, 2AJ, 2AK, 2AR, and 2AX.

In another aspect, the present disclosure provides a recombinant cell that includes an alcohol tolerance modification (e.g., as compared with a parent cell), which alcohol tolerance modification comprises introduction of a first alcohol tolerance determinant sequence and introduction of a second alcohol tolerance determinant sequence, wherein the first alcohol tolerance determinant sequence is selected from the group consisting of those found in Tables 1 and 2, and the second alcohol tolerance determinant sequence is selected from the group consisting of those found in Tables 3 and 4.

In some embodiments, a first alcohol tolerance determinant sequence is an alcohol tolerance determinant sequence selected from the group consisting of: a) a determinant sequence set forth in Table 1A; b) a determinant sequence set forth in Table 1B; c) determinant sequence set forth in Table 2; and combinations thereof. In some embodiments, a recombinant cell includes an alcohol tolerance determinant which is a determinant sequence set forth in Table 1A. In some embodiments, a cell includes a determinant sequence selected from the group consisting of those found within a Table 1A row selected from the group consisting of row 20 (lp__1293), row 21 (lp__1295 [mntH3]), row 34 (lp__2159), row 35 (lp__2160), row 36 (lp__2169), row 37 (lp__2170), row 44 (lp__2911), and row 50 (lp__3193). In some embodiments, a cell includes an alcohol tolerance determinant which is a determinant sequence set forth in Table 1B.

In some embodiments, a cell includes an alcohol tolerance determinant which is a determinant sequence set forth in Table 2. In some embodiments, a cell includes a determinant sequence selected from the group consisting of those found within Tables 2T, 2U, 2AH, 2AI, 2AJ, 2AK, 2AR, and 2AX.

In some embodiments, a second alcohol tolerance determinant sequence is an alcohol tolerance determinant sequence found in Tables 3 and 4 which is selected from the group consisting of those found in sequences present in rows 2 (groES), 3 (groEL), 5 (cfa1) and/or 8 (cfa2) of Table 3, or in any of Tables 4B, 4C, 4E and 4H.

In some embodiments, the at least one alcohol tolerance modification further comprises disruption or inhibition of an alcohol tolerance determinant selected from the group consisting of those found in sequences present in rows 1 (htrA), 4 (clpP), 6 (relA/spoT), 7 (hrcA), and/or 8 (cfa2) of Table 3, or in any of Tables 4A, 4D, 4F, 4G and 4H.

In some embodiments, a recombinant microbial cell further comprises at least one alcohologenic modification. In some embodiments, an alcohologenic modification increases expression or activity of at least one alcohologenic polypeptide. In some embodiments, an alcohologenic modification decreases expression or activity of at least one alcohologenic polypeptide. In some embodiments, an alcohologenic modification increases expression or activity of at least one alcohologenic polypeptide and decreases expression or activity of at least one other alcohologenic polypeptide. In some embodiments, an alcohologenic modification comprises expression of at least one heterologous alcohologenic polypeptide in the recombinant microbial cell. In some embodiments, an alcohologenic modification comprises expression of at least one heterologous gene encoding the at least one heterologous alcohologenic polypeptide. In some embodiments, the at least one alcohologenic polypeptide is a polypeptide that increases production of an aliphatic alcohol selected from the group consisting of: methanol, ethanol, 1-propanol, 2-propanol, iso-propanol, 1-butanol, 2-butanol, iso-butanol, tert-butanol, 1-pentanol, 2-pentanol, 3-pentanol, iso-pentanol, 1-hexanol, 2-hexanol, 3-hexanol, 2-ethyl hexanol, iso-hexanol, 1-heptanol, 2-heptanol, 3-heptanol, 4-heptanol, iso-heptanol, 1-octanol, 2-octanol, 3-octanol, iso-octanol, and 4-octanol, and combinations thereof. In some embodiments, the at least one alcohologenic polypeptide is a polypeptide that increases production of an aliphatic alcohol selected from the group consisting of: 1-butanol, 2-butanol, iso-butanol, tert-butanol, and combinations thereof. In some embodiments, the at least one alcohologenic polypeptide is a polypeptide that increases production of 1-butanol, 2-butanol, or iso-butanol.

In some embodiments, the at least one alcohologenic polypeptide catalyzes a substrate to product conversion selected from the group consisting of: a) acetyl-CoA to acetoacetyl-CoA; b) acetoacetyl-CoA to 3-hydroxybutyryl-CoA; c) 3-hydroxybutyryl-CoA to crotonyl-CoA; d) crotonyl-CoA to butyryl-CoA; e) butyryl-CoA to butyraldehyde; f) butyraldehyde to 1-butanol; and combinations thereof.

In some embodiments, a polypeptide that catalyzes a substrate to product conversion of acetyl-CoA to acetoacetyl-CoA is acetyl-CoA acetyltransferase. In some embodiments, a polypeptide that catalyzes a substrate to product conversion of acetoacetyl-CoA to 3-hydroxybutyryl-CoA is 3-hydroxybutyryl-CoA dehydrogenase. In some embodiments, a polypeptide that catalyzes a substrate to product conversion of 3-hydroxybutyryl-CoA to crotonyl-CoA is crotonase. In some embodiments, a polypeptide that catalyzes a substrate to product conversion of crotonyl-CoA to butyryl-CoA is butyryl-CoA dehydrogenase. In some embodiments, a polypeptide that catalyzes a substrate to product conversion of butyryl-CoA to butyraldehyde is butyraldehyde dehydrogenase. In some embodiments, a polypeptide that catalyzes a substrate to product conversion of butyraldehyde to 1-butanol is butanol dehydrogenase.

In some embodiments, the at least one alcohologenic polypeptide catalyzes a substrate to product conversion selected from the group consisting of: a) pyruvate to acetolactate; b) acetolactate to 2,3-dihydroxyisovalerate; c) alpha-ketoisovalerate to isobutyraldehyde; d) isobutyraldehyde to isobutanol; e) 2,3-dihydroxyisovalerate to alpha-ketoisovalerate; f) alpha-ketoisovalerate to isobutyraldehyde; g) alpha-ketoisovalerate to isobutyryl-CoA; h) isobutyryl-CoA to isobutyraldehyde; i) alpha-ketoisovalerate to L-valine; j) L-valine to isobutylamine; k) isobutylamine to isobutyraldehyde; l) butyryl-CoA to isobutyryl-CoA; and combinations thereof.

In some embodiments, a polypeptide that catalyzes a substrate to product conversion of pyruvate to acetolactate is acetolactate synthase. In some embodiments, a polypeptide that catalyzes a substrate to product conversion of acetolactate to 2,3-dihydroxyisovalerate is acetohydroxy acid reductoisomerase. In some embodiments, a polypeptide that catalyzes a substrate to product conversion of acetolactate to 2,3-dihydroxyisovalerate is acetohydroxy acid isomeroreductase. In some embodiments, a polypeptide that catalyzes a substrate to product conversion of alpha-ketoisovalerate to isobutyraldehyde is branched-chain alpha-keto acid decarboxylase. In some embodiments, a polypeptide that catalyzes a substrate to product conversion of isobutyraldehyde to isobutanol is branched-chain alcohol dehydrogenase. In some embodiments, a polypeptide that catalyzes a substrate to product conversion of 2,3-dihydroxyisovalerate to alpha-ketoisovalerate is acetohydroxy acid dehydratase. In some embodiments, a polypeptide that catalyzes a substrate to product conversion of alpha-ketoisovalerate to isobutyraldehyde is branched-chain alpha-keto acid decarboxylase. In some embodiments, a polypeptide that catalyzes a substrate to product conversion of alpha-ketoisovalerate to isobutyryl-CoA is branched-chain keto acid dehydrogenase. In some embodiments, a polypeptide that catalyzes a substrate to product conversion of isobutyryl-CoA to isobutyraldehyde is acylating aldehyde dehydrogenase. In some embodiments, a polypeptide that catalyzes a substrate to product conversion of alpha-ketoisovalerate to L-valine is transaminase. In some embodiments, a polypeptide that catalyzes a substrate to product conversion of alpha-ketoisovalerate to L-valine is valine dehydrogenase. In some embodiments, a polypeptide that catalyzes a substrate to product conversion of L-valine to isobutylamine is valine decarboxylase. In some embodiments, a polypeptide that catalyzes a substrate to product conversion of isobutylamine to isobutyraldehyde is omega transaminase. In some embodiments, a polypeptide that catalyzes a substrate to product conversion of butyryl-CoA to isobutyryl-CoA is isobutyryl-CoA mutase.

In some embodiments, the at least one alchologenic polypeptide catalyzes a substrate to product conversion selected from the group consisting of: a) pyruvic acid to alpha-acetolactate; b) alpha-acetolactate to acetoin; c) acetoin to 2,3-butanediol; d) 2,3-butanediol to 2-butanone; e) 2-butanone to 2-butanol; and combinations thereof.

In some embodiments, a polypeptide that catalyzes a substrate to product conversion of alpha-acetolactate to acetoin is acetolactate decarboxylase. In some embodiments, a polypeptide that catalyzes a substrate to product conversion of pyruvic acid to alpha-acetolactate is acetolactate synthase. In some embodiments, a polypeptide that catalyzes a substrate to product conversion of acetoin to 2,3-butanediol is butanediol dehydrogenase. In some embodiments, a polypeptide that catalyzes a substrate to product conversion of 2,3-butanediol to 2-butanone is butanediol dehydratase. In some embodiments, a polypeptide that catalyzes a substrate to product conversion of 2-butanone to 2-butanol is butanol dehydrogenase.

In another aspect, the present disclosure features an engineered bacterial cell comprising one or more alcohol tolerance modifications, wherein the one or more alcohol tolerance modifications comprises introduction of an alcohol tolerance determinant sequence encoding a calcineurin-like phosphoesterase polypeptide.

In another aspect, the present disclosure features an engineered bacterial cell comprising one or more alcohol tolerance modifications, wherein the one or more alcohol tolerance modifications comprises introduction of an alcohol tolerance determinant sequence encoding a cation transport protein (mntH3 related) polypeptide.

In another aspect, the present disclosure features an engineered bacterial cell comprising one or more alcohol tolerance modifications, wherein the one or more alcohol tolerance modifications comprises introduction of an alcohol tolerance determinant sequence encoding a transcription regulator (lp_2159 related) polypeptide.

In another aspect, the present disclosure features an engineered bacterial cell comprising one or more alcohol tolerance modifications, wherein the one or more alcohol tolerance modifications comprises introduction of an alcohol tolerance determinant sequence encoding an lp_2160 related polypeptide.

In another aspect, the present disclosure features an engineered bacterial cell comprising one or more alcohol tolerance modifications, wherein the one or more alcohol tolerance modifications comprises introduction of an alcohol tolerance determinant sequence encoding a lp_2169 related polypeptide.

In another aspect, the present disclosure features an engineered bacterial cell comprising one or more alcohol tolerance modifications, wherein the one or more alcohol tolerance modifications comprises introduction of an alcohol tolerance determinant sequence encoding a phosphoglycerate mutase polypeptide.

In another aspect, the present disclosure features an engineered bacterial cell comprising one or more alcohol tolerance modifications, wherein the one or more alcohol tolerance modifications comprises introduction of an alcohol tolerance determinant sequence encoding a CAAX protease polypeptide.

In another aspect, the present disclosure features an engineered bacterial cell comprising one or more alcohol tolerance modifications, wherein the one or more alcohol tolerance modifications comprises introduction of an alcohol tolerance determinant sequence encoding a peptidylprolyl isomerase (prs2A related polypeptide).

In another aspect, the present disclosure features an engineered bacterial cell comprising one or more alcohol tolerance modifications, wherein the one or more alcohol tolerance modifications comprises introduction of an alcohol tolerance determinant sequence found within Table 1A row 20 (lp_1293).

In another aspect, the present disclosure features an engineered bacterial cell comprising one or more alcohol tolerance modifications, wherein the one or more alcohol tolerance modifications comprises introduction of an alcohol tolerance determinant sequence found within Table 1A, row 21 (lp_1295 [mntH3]).

In another aspect, the present disclosure features an engineered bacterial cell comprising one or more alcohol tolerance modifications, wherein the one or more alcohol tolerance modifications comprises introduction of an alcohol tolerance determinant sequence found within Table 1A, row 34 (lp_2159).

In another aspect, the present disclosure features an engineered bacterial cell comprising one or more alcohol tolerance modifications, wherein the one or more alcohol tolerance modifications comprises introduction of an alcohol tolerance determinant sequence found within Table 1A, row 35 (lp_2160).

In another aspect, the present disclosure features an engineered bacterial cell comprising one or more alcohol tolerance modifications, wherein the one or more alcohol tolerance modifications comprises introduction of an alcohol tolerance determinant sequence found within Table 1A, row 36 (lp_2169).

In another aspect, the present disclosure features an engineered bacterial cell comprising one or more alcohol tolerance modifications, wherein the one or more alcohol tolerance modifications comprises introduction of an alcohol tolerance determinant sequence found within Table 1A, row 37 (lp_2170).

In another aspect, the present disclosure features an engineered bacterial cell comprising one or more alcohol tolerance modifications, wherein the one or more alcohol tolerance modifications comprises introduction of an alcohol tolerance determinant sequence found within Table 1A, row 44 (lp_2911).

In another aspect, the present disclosure features an engineered bacterial cell comprising one or more alcohol tolerance modifications, wherein the one or more alcohol tolerance modifications comprises introduction of an alcohol tolerance determinant sequence found within Table 1A, row 50 (lp_3193).

In another aspect, the present disclosure provides a method of engineering a cell to include an alcohol tolerance modification, the method comprising: obtaining a parent cell, introducing into the parent cell at least one alcohol tolerance determinant sequence found within the alcohol tolerance determinant sequences in Tables 1 and 2, thereby engineering a cell to include an alcohol tolerance modification. In some embodiments, an alcohol tolerance determinant sequence comprises an alcohol tolerance determinant sequence in Table 1A. In some embodiments, an alcohol tolerance determinant sequence comprises an alcohol determinant sequence selected from the group consisting of those found within a Table 1A row selected from the group consisting of row 20 (lp_1293), row 21 (lp_1295 [mntH3]), row 34 (lp_2159), row 35 (lp_2160), row 36 (lp_2169), row 37 (lp_2170), row 44 (lp_2911), and row 50 (lp_3193). In some embodiments, an alcohol tolerance determinant sequence comprises an alcohol tolerance determinant sequence in Table 2. In some embodiments, an alcohol tolerance determinant sequence comprises an alcohol tolerance determinant sequence in one or more of Tables 2T, 2U, 2AH, 2AI, 2AJ, 2AK, 2AR, 2AX.

In some embodiments, a method further includes introducing a second alcohol tolerance determinant sequence selected from the group consisting of those found in Tables 3 and 4. In some embodiments, an alcohol tolerance determinant sequence found in Tables 3 and 4 is selected from the group consisting of those found in sequences present in rows 2 (groES), 3 (groEL), 5 (cfa1) and/or 8 (cfa2) of Table 3, or in any of Tables 4B, 4C, 4E and 4H. In some embodiments, the at least one alcohol tolerance modification further comprises disruption or inhibition of an alcohol tolerance determinant selected from the group consisting of those found in Tables 3 and 4. In some embodiments, an alcohol tolerance determinant found in Tables 3 and 4 is selected from the group consisting of those found in sequences present in rows 1 (htrA), 4 (clpP), 6 (relA/spoT), 7 (hrcA), and/or 8 (cfa2) of Table 3, or in any of Tables 4A, 4D, 4F, 4G and 4H.

In another aspect, the present disclosure features a method of producing an aliphatic alcohol compound, comprising steps of: a) cultivating the recombinant microbial cell provided herein under conditions and for a time sufficient that the aliphatic alcohol compound is produced; and b) isolating the produced aliphatic alcohol compound. In some embodiments, an aliphatic alcohol compound is selected from the group consisting of: methanol, 1-propanol, 2-propanol, iso-propanol, 1-butanol, 2-butanol, iso-butanol, tert-butanol, 1-pentanol, 2-pentanol, 3-pentanol, iso-pentanol, 1-hexanol, 2-hexanol, 3-hexanol, 2-ethyl hexanol, iso-hexanol, 1-heptanol, 2-heptanol, 3-heptanol, 4-heptanol, iso-heptanol, 1-octanol, 2-octanol, 3-octanol, iso-octanol, and 4-octanol, and combinations thereof.

In another aspect, the present disclosure features a method of producing a butanol compound, comprising steps of: a) cultivating a recombinant microbial cell provided herein under conditions that allow production of the aliphatic alcohol compound under conditions and for a time sufficient that the butanol compound accumulates to greater than 30 grams per liter; and b) isolating the produced butanol compound. In some embodiments, a butanol compound is selected from the group consisting of: 1-butanol, 2-butanol, iso-butanol, tert-butanol, and combinations thereof. In some embodiments, a butanol compound is 1-butanol.

In another aspect, the present disclosure provides a method of producing an aliphatic alcohol compound, comprising steps of: a) cultivating a recombinant microbial cell provided herein under conditions and for a time sufficient that the aliphatic alcohol compound is produced; and b) isolating the produced aliphatic alcohol compound. In some embodiments, an aliphatic alcohol compound is selected from the group consisting of: methanol, ethanol, 1-propanol, 2-propanol, iso-propanol, 1-butanol, 2-butanol, iso-butanol, tert-butanol, 1-pentanol, 2-pentanol, 3-pentanol, iso-pentanol, 1-hexanol, 2-hexanol, 3-hexanol, 2-ethyl hexanol, iso-hexanol, 1-heptanol, 2-heptanol, 3-heptanol, 4-heptanol, iso-heptanol, 1-octanol, 2-octanol, 3-octanol, iso-octanol, and 4-octanol, and combinations thereof.

In another aspect, the present disclosure provides a method of producing a butanol compound, comprising steps of: a) cultivating the recombinant microbial cell described herein under conditions and for a time sufficient that the butanol compound accumulates to greater than 30 grams per liter; and b) isolating the produced butanol compound. In some embodiments, a butanol compound is selected from the group consisting of: 1-butanol, 2-butanol, iso-butanol, tert-butanol, and combinations thereof. In some embodiments, a butanol compound is 1-butanol.

In another aspect, the present disclosure provides an aliphatic alcohol compound composition, prepared by a method comprising steps of: a) cultivating a recombinant microbial cell provided herein under conditions and for a time sufficient that the aliphatic alcohol compound is produced; and b) isolating the produced aliphatic alcohol compound. In some embodiments, an aliphatic alcohol compound is selected from the group consisting of: methanol, 1-propanol, 2-propanol, iso-propanol, 1-butanol, 2-butanol, iso-butanol, tert-butanol, 1-pentanol, 2-pentanol, 3-pentanol, iso-pentanol, 1-hexanol, 2-hexanol, 3-hexanol, 2-ethyl hexanol, iso-hexanol, 1-heptanol, 2-heptanol, 3-heptanol, 4-heptanol, iso-heptanol, 1-octanol, 2-octanol, 3-octanol, iso-octanol, and 4-octanol, and combinations thereof.

In another aspect, the present disclosure provides an aliphatic alcohol compound composition, prepared by a method comprising steps of: a) cultivating a recombinant microbial cell provided herein under conditions and for a time sufficient that the aliphatic alcohol compound is produced; and b) isolating the produced aliphatic alcohol compound. In some embodiments, an aliphatic alcohol compound is selected from the group consisting of: methanol, ethanol, 1-propanol, 2-propanol, iso-propanol, 1-butanol, 2-butanol, iso-butanol, tert-butanol, 1-pentanol, 2-pentanol, 3-pentanol, iso-pentanol, 1-hexanol, 2-hexanol, 3-hexanol, 2-ethyl hexanol, iso-hexanol, 1-heptanol, 2-heptanol, 3-heptanol, 4-heptanol, iso-heptanol, 1-octanol, 2-octanol, 3-octanol, iso-octanol, and 4-octanol, and combinations thereof.

In another aspect, the present disclosure provides a butanol compound composition, prepared by a method comprising steps of: a) cultivating a recombinant microbial cell provided herein under conditions and for a time sufficient that the butanol compound is produced; and b) isolating the produced butanol compound. In some embodiments, a butanol compound is selected from the group consisting of: 1-butanol, 2-butanol, iso-butanol, tert-butanol, and combinations thereof. In some embodiments, the butanol compound is 1-butanol.

In another aspect, the present disclosure provides a butanol compound composition, prepared by a method comprising steps of: a) cultivating a recombinant microbial cell provided herein under conditions and for a time sufficient that the butanol compound is produced; and b) isolating the produced butanol compound. In some embodiments, a butanol compound is selected from the group consisting of: 1-butanol, 2-butanol, iso-butanol, tert-butanol, and combinations thereof. In some embodiments, a butanol compound is 1-butanol.

In another aspect, the present disclosure provides a method of preparing an aliphatic alcohol compound-containing product, comprising steps of: a) cultivating a recombinant microbial cell provided herein under conditions and for a time sufficient that the aliphatic alcohol compound is produced; b) isolating the aliphatic alcohol compound; and c) combining the aliphatic alcohol compound with one or more other additive components. In some embodiments, an aliphatic alcohol compound is a butanol compound selected from the group consisting of 1-butanol, 2-butanol, iso-butanol, tert-butanol, and combinations thereof. In some embodiments, a butanol compound is 1-butanol. In some embodiments, a product comprises transport fuel. In some embodiments, a product comprises a solvent. In some embodiments, a product comprises a swelling agent. In some embodiments, a product comprises a brake fluid. In some embodiments, a product comprises an extractant. In some embodiments, a product comprises a cement additive. In some embodiments, a product comprises an ore flotation agent. In some embodiments, a product comprises a melamine formaldehyde resin.

The present disclosure also provides isolated nucleic acid molecules that include, or consist of, a nucleic acid molecule having a sequence disclosed herein. Thus, in one aspect, the disclosure provides an isolated nucleic acid molecule comprising a 3' region of a gene encoding a CAAX protease polypeptide. In some embodiments, a nucleic acid molecule comprises a nucleotide sequence at least 80% identical to the nucleotide sequence shown in Table 1B, row 42, a homolog thereof, or a portion thereof. In some embodiments, a nucleic acid molecule, when introduced into a host cell (e.g., a microbial host cell, e.g., a bacterial host cell), is sufficient to adjust susceptibility of the cell to a toxic effect of an alcohol compound. In some embodiments, a nucleic acid molecule lacks a nucleotide sequence encoding a CAAX protease polypeptide. In some embodiments, a nucleic acid molecule further includes a 5' region of a gene encoding a CAAX protease polypeptide, e.g., wherein the 5' region comprises a nucleotide sequence at least 80% identical to the nucleotide sequence shown in Table 1B, row 40, a homolog thereof, or a portion thereof.

In another aspect, the present disclosure provides an isolated nucleic acid molecule comprising a 5' region of a gene encoding a CAAX protease polypeptide. In some embodiments, a 5' region comprises a nucleotide sequence at least 80% identical to the nucleotide sequence shown in Table 1B, row 40, a homolog thereof, or a portion thereof. In some embodiments, a nucleic acid molecule lacks a nucleotide sequence encoding a CAAX protease polypeptide.

Vectors comprising the nucleic acid molecules are also provided herein.

BRIEF DESCRIPTION OF THE DRAWING

FIG. 3 shows four different isobutanol biosynthetic pathways. The steps labeled "a", "b", "c", "d", "e", "f", "g", "h", "i", "j" and "k" represent the substrate to product conversions FIG. 4, Panels A-D, show metabolic tolerance assay results for *Lactobacillus plantarum* strains comprising alcohol tolerant determinant sequences. Graphs depict $OD_{600}$ and HPLC measurements of lactate, glucose, and 1-butanol levels. The strains were grown in the presence of either 0% (panel A), 1.7% (panel B), 2.0% (panel C), or 2.3% (panel D) 1-butanol.

TABLES

Figure 1:
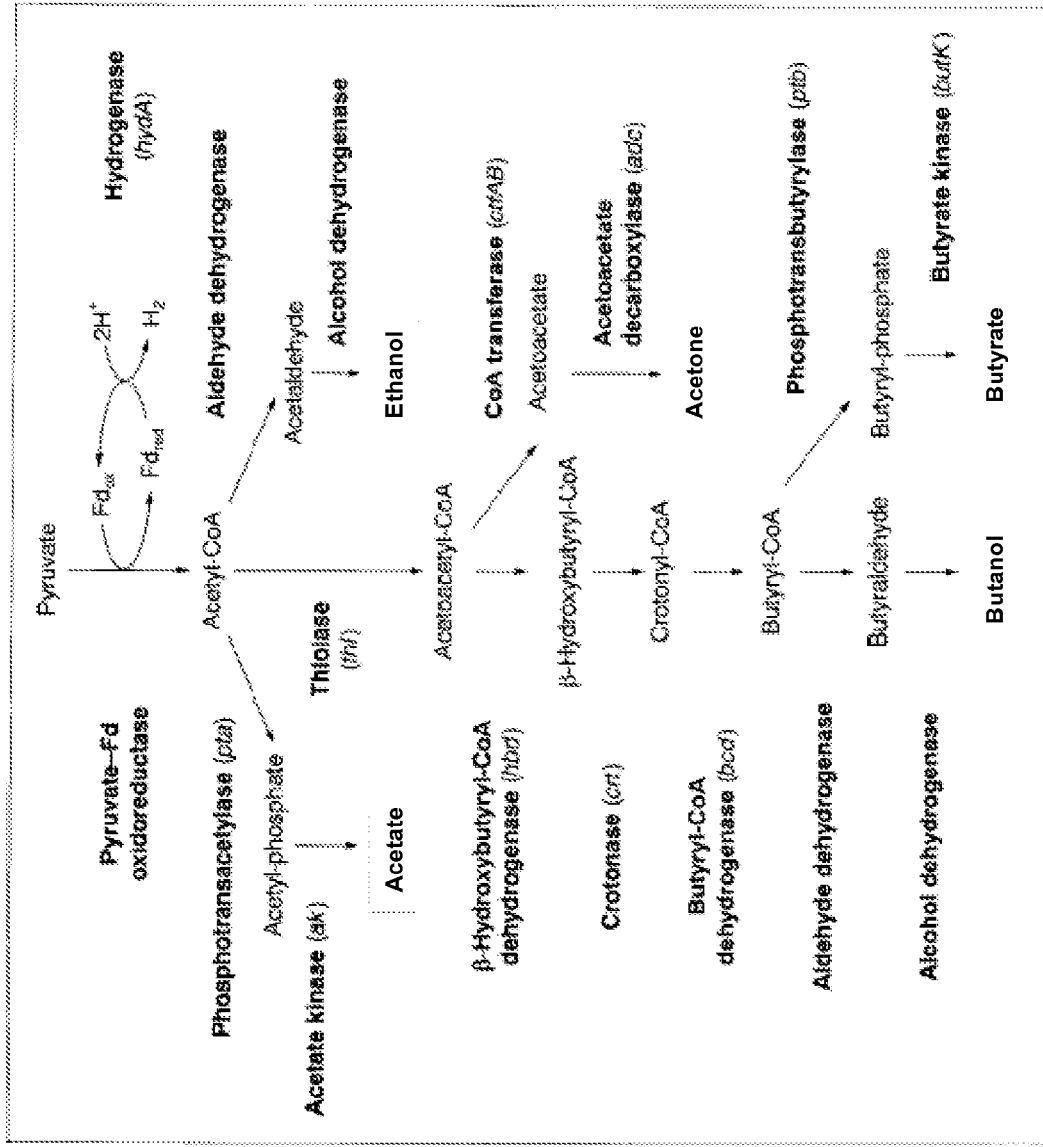
FIG. 1 presents a representative metabolic pathway that produces aliphatic alcohol compounds such as ethanol and 1-butanol. The depicted pathway is utilized, for example, in many *C. acetobutylicum* strains. Names of certain particular enzymes known to perform indicated steps in such strains are indicated, with their corresponding gene names indicated in parentheses.
Figure 2:
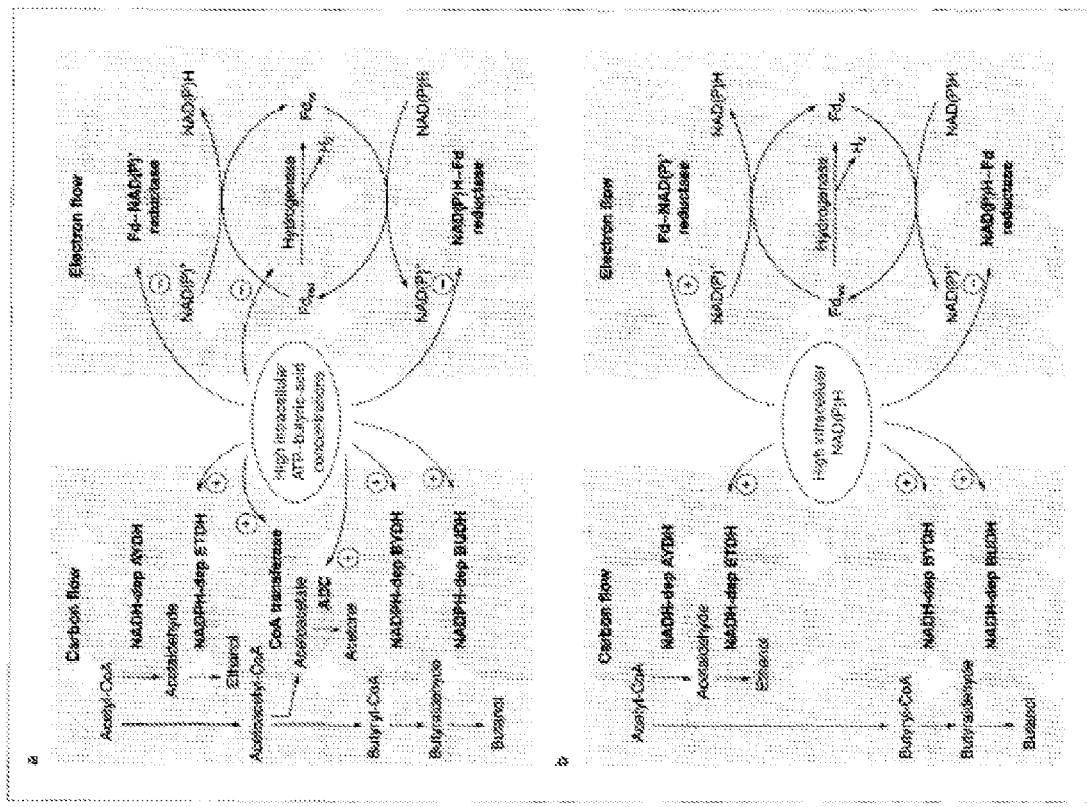
FIG. 2 illustrates different growth conditions that promote different metabolic states in certain microorganisms such as, for example, *C. acetobutylicum*. Panel A illustrates the solventogenesis state; Panel B illustrates the alcoholgenesis state. Abbreviations: Fd, ferredoxin; Fdred, reduced ferredoxin; Fdox, oxidized ferredoxin; dep, dependent; AYDH, acetaldehyde dehydrogenase; ETDH, ethanol dehydrogenase; ADC, acetoacetate decarboxylase; BYDH, butyraldehyde dehydrogenase; BUDH, butanol dehydrogenase; +, high level of in vitro enzyme activity; −, low level of in vitro enzyme activity.

The tables referenced in the description exceed more than 100 pages and are submitted electronically. The tables themselves and each reference and information designated by each of the Genbank Accession and GI numbers are hereby incorporated by reference in their entirety.

DEFINITIONS

Acetohydroxy acid dehydratase: The term "acetohydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9 (Enzyme Nomenclature 1992, Academic Press, San Diego). These enzymes are available from a vast array of microorganisms, including, but not limited to, *Escherichia coli* (GenBank Nos: YP_026248 (SEQ ID NO:6 in US patent application 2007/0092957), NC_000913 (SEQ ID NO:5 in US patent application 2007/0092957) NCBI (National Center for Biotechnology Information) amino acid sequence and NCBI nucleotide sequences), *Saccharomyces cerevisiae* (GenBank Nos: NP_012550 (SEQ ID NO:186 in US patent application 2007/0092957), NC_001142 (SEQ ID NO:83 in US patent application 2007/0092957)), *Methanococcus maripaludis* (GenBank Nos: CAF29874 (SEQ ID NO:188 in US patent application 2007/0092957), BX957219 (SEQ ID NO:187 in US patent application 2007/0092957)), and *Bacillus subtilis* (GenBank Nos: CAB14105 (SEQ ID NO:190 in US patent application 2007/0092957), Z99115 (SEQ ID NO:189 in US patent application 2007/0092957)).

Acetohydroxy acid isomeroreductase: The terms "acetohydroxy acid isomeroreductase" and "acetohydroxy acid reductoisomerase" are used interchangeably herein to refer to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *E. coli* (GenBank Nos: NP_418222 (SEQ ID NO:4 in US patent application 2007/0092957), NC_000913 (SEQ ID NO:3 in US patent application 2007/0092957)), *S. cerevisiae* (GenBank Nos: NP_013459 (SEQ ID NO:181 in US patent application 2007/0092957), NC_001144 (SEQ ID NO:80 in US patent application 2007/0092957)), *Methanococcus maripaludis* (GenBank Nos: CAF30210 (SEQ ID NO:183 in US patent application 2007/0092957), BX957220 (SEQ ID NO:182 in US patent application 2007/0092957)), and *B. subtilis* (GenBank Nos: CAB14789 (SEQ ID NO:185 in US patent application 2007/0092957), Z99118 (SEQ ID NO:184 in US patent application 2007/0092957)).

Acetolactate synthase: The terms "acetolactate synthase" and "acetolactate synthetase" are used interchangeably herein to refer to an enzyme that catalyzes the conversion of pyruvate to acetolactate and $CO_2$. Exemplary acetolactate synthases are known by the EC number 2.2.1.6. These enzymes are available from a number of sources, including, but not limited to, *B. subtilis* (GenBank Nos: CAB15618 (SEQ ID NO:178 of US patent application 2007/0092957), Z99122 (SEQ ID NO:78 of US patent application 2007/0092957)), *Klebsiella pneumoniae* (GenBank Nos: AAA25079 (SEQ ID NO:2 of US patent application 2007/0092957), M73842 (SEQ ID NO:1 of US patent application 2007/0092957)), and *Lactococcus lactis* (GenBank Nos: AAA25161 (SEQ ID NO:180), L16975 (SEQ ID NO:179)).

Acetyl-CoA acetyltransferase: The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyltransferases with substrate preferences (reaction in the forward direction) for a short chain acyl-CoA and acetyl-CoA and are classified as E.C.2.3.1.9.; although, enzymes with a broader substrate range (E.C.2.3.1.16) will be functional as well. Acetyl-CoA acetyltransferases are available from a number of sources, for example, *E. coli* (GenBank Nos: NP_416728 (SEQ ID NO:129 in WO 2007/041269), NC_000913 (SEQ ID NO:128 in WO 2007/041269)), *Clostridium acetobutylicum* (GenBank Nos: NP_349476.1 (SEQ ID NO:2 in WO 2007/041269), NC_003030 (SEQ ID NO:1 in WO 2007/041269), NP_149242 (SEQ ID NO:4 in WO 2007/041269), NC_001988 (SEQ ID NO:3 in WO 2007/041269)), *B. subtilis* (GenBank Nos: NP_390297 (SEQ ID NO:131 in WO 2007/041269), NC_000964 (SEQ ID NO:130 in WO 2007/041269)), and *S. cerevisiae* (GenBank Nos: NP_015297 (SEQ ID NO:133 in WO 2007/041269), NC_001148 (SEQ ID NO:132 in WO 2007/041269)).

Acylating aldehyde dehydrogenase: The term "acylating aldehyde dehydrogenase" refers to an enzyme that catalyzes the conversion of isobutyryl-CoA to isobutyraldehyde, using either NADH or NADPH as electron donor. Preferred acylating aldehyde dehydrogenases are known by the EC numbers 1.2.1.10 and 1.2.1.57. These enzymes are available from multiple sources, including, but not limited to, *Clostridium beijerinckii* (GenBank Nos: AAD31841 (SEQ ID NO:222 in US patent application 2007/0092957), AF157306 (SEQ ID NO:221 in US patent application 2007/0092957)), *C. acetobutylicum* (GenBank Nos: NP_149325 (SEQ ID NO:224 in US patent application 2007/0092957), NC_001988 (SEQ ID NO:223 in US patent application 2007/0092957), NP_149199 (SEQ ID NO:226 in US patent application 2007/0092957), NC_001988 (SEQ ID NO:225 in US patent application 2007/0092957)), *Pseudomonas putida* (GenBank Nos: AAA89106 (SEQ ID NO:228 in US patent application 2007/0092957), U13232 (SEQ ID NO:227 in US patent application 2007/0092957)), and *Thermus thermophilus* (GenBank Nos: YP_145486 (SEQ ID NO:230 in US patent application 2007/0092957), NC_006461 (SEQ ID NO:229 in US patent application 2007/0092957)).

Alcohol tolerance determinant: The term "alcohol tolerance determinant", as used herein, refers to a nucleic acid that, when introduced into an organism, alters its susceptibility to toxic effects of one or more aliphatic alcohol compounds, as described herein. Thus, introduction of an alcohol tolerance determinant into an organism constitutes applying an alcohol tolerance modification to that organism. In some embodiments, an alcohol tolerance determinant includes sequences that encode one or more polypeptides; in some embodiments such polypeptides may be alcohol tolerance polypeptides. In some embodiments, an alcohol tolerance determinant includes sequences that do not encode one or more polypeptides; in some embodiments, an alcohol tolerance determinant does not encode a polypeptide. In some embodiments, an alcohol tolerance determinant is found among determinant sequences presented in one or more of Tables 1-4 (i.e., in one or more of Tables 1A, 1B, 2A-2BE, 3, and 4A-4H). In some embodiments, introduction of an alcohol tolerance determinant into (or expression of an alcohol tolerance determinant in) a cell increases tolerance to one or more toxic effects of one or more aliphatic alcohols; in some embodiments, inactivation or inhibition of an alcohol tolerance determinant in a cell increases tolerance. To give but a few examples, alcohol tolerance determinants whose introduction into or expression in a cell increases alcohol tolerance may include, e.g., determinants in Table 1A in row 20 (lp_1293), row 21 (lp_1295 [mntH3]), row 34 (lp_2159), row 35 (lp_2160), row 36 (lp_2169), row 37 (lp_2170), row 44 (lp_2911), and row 50 (lp_3193); determinants in rows 2 (groES), 3 (groEL), 5 (cfa1) and/or 8 (cfa2) of Table 3, or determinants in any of Tables 2T, 2U, 2AH, 2AI, 2AJ, 2AK, 2AR, 2AX, 4B, 4C, 4E and/or 4H; alcohol tolerance determinants whose inactivation or inhibition in a cell increases tolerance may include, e.g., those in rows 1 (htrA), 4 (clpP), 6 (relA/spoT), 7 (hrcA), and/or 8 (cfa2) of Table 3, or in any of Tables 4A, 4D, 4F, 4G and/or 4H.

Alcohol tolerance modification: The term "alcohol tolerance modification" refers to a modification of a host organism that adjusts its susceptibility to one or more toxic effects of one or more aliphatic alcohol compounds, as described herein. For example, in some embodiments, an organism containing an alcohol tolerance modification exhibits an increased aliphatic alcohol compound $IC_{50}$ as compared with an otherwise identical organism lacking the modification; in some embodiments, the aliphatic alcohol compound $IC_{50}$ is increased 5%, 10%, 20%, 30%, 40%, 50%, 60%, 70%, 80%, 90%, 100% or more. In some embodiments, an organism containing an alcohol tolerance modification exhibits increased carbohydrate utilization as compared with an otherwise identical organism lacking the modification when grown in the presence of the same amount of aliphatic alcohol compound; in some cases the carbohydrate utilization is increased by 5%, 10%, 20%, 30%, 40%, 50%, 60%, 70%, 80%, 90%, 100% or more. In some embodiments, an organism containing an alcohol tolerance modification exhibits increased production of at least one aliphatic alcohol compound as compared with an otherwise identical organism lacking the modification; in some embodiments, such increased production results in a broth titer of the produced at least one aliphatic alcohol compound that is 10%, 25%, 50%, 75%, 100% or more higher than that observed with an otherwise identical organism lacking the modification under comparable conditions, and/or such increased production results in a yield that is 10%, 25%, 50%, 75%, 100% or more of that of an otherwise identical organism lacking the modification, under comparable conditions, and/or such increased production results in volumetric productivity that is 10%, 25%, 50%, 75%, 100% or more of that of an otherwise identical organism lacking the modification, under comparable conditions, and/or such increased production results in a specific productivity increase of 10%, 25%, 50%, 75%, 100% or more as compared with an otherwise identical organism lacking the modification under comparable conditions. In some embodiments, an alcohol tolerance modification comprises introduction and/or expression of an alcohol tolerance determinant (so that a modified cell has an increased amount and/or level of expression or activity of an alcohol tolerance determinant as compared with a parental cell); in some embodiments, an alcohol tolerance modification comprises inactivation and/or inhibition of an alcohol tolerance determinant (so that a modified cell has a decreased amount and/or level of expression or activity of the alcohol tolerance determinant) as compared with a parental cell. In some embodiments, an alcohol tolerance modification achieves (or enhances, or inhibits) expression of one or more alcohol tolerance polypeptides in a cell.

Alcohol tolerance polypeptide: An alcohol tolerance polypeptide, as that term is used herein is any polypeptide that, when expressed in a cell, contributes to the cell's tolerance (e.g., as measured by $IC_{50}$, carbohydrate utilization, etc.) to at least one aliphatic alcohol compound. For example, a butanol tolerance polypeptide is a polypeptide whose expression in a cell contributes to that cell's resistance to butanol, etc. In some embodiments, alcohol tolerance polypeptides are selected from the group consisting of calcineurin-like phosphoesterase polypeptides, cation transport (mntH3 related) polypeptides, transcription regulator (lp_2159 related) polypeptides, lp_2160 related polypeptides, lp_2169 related polypeptides, phosphoglycerate mutase polypeptides, CAAX protease polypeptides, peptidylprolyl isomerase (prs2A related) polypeptides, and combinations thereof. In some embodiments, certain stress-response polypeptides are alcohol tolerance polypeptides. For example, GroES chaperonin polypeptides, GroEL chaperonin polypeptides, and combinations thereof, are alcohol tolerance polypeptides in accordance with certain embodiments of the present disclosure. Alternatively or additionally, in some embodiments, alcohol tolerance polypeptides include serine protease HtrA polypeptides, GroES chaperonin polypeptides, GroEL chaperonin polypeptides, ATP-dependent Clp protease proteolytic subunit polypeptides, cyclopropane-fatty-acyl-phospholipid synthase #1 (cfa1) polypeptides, GTP pyrophosphokinase (relA/spoT) polypeptides, heat-inducible transcription repressor (hrca) polypeptides, cyclopropane-fatty-acyl-phospholipid synthase #2 (cfa2) polypeptides and combinations thereof. In some embodiments, alcohol tolerance polypeptides are encoded by an alcohol tolerance determinant, for example as set forth in any one or more of Tables 1-4. In some particular embodiments, alcohol tolerance polypeptides are encoded by an alcohol tolerance determinant, for example, included in determinant sequences set forth in any of rows 20 (lp_1293), 21 (lp_1295 [mntH3]), 34 (lp_2159), 35 (lp_2160), 36 (lp_2169), 37 (lp_2170), 44 (lp_2911), and/or 50 (lp_3193 [prs2A]) of Table 1A, and/or in any of Tables 2T, 2U, 2AH, 2AI, 2AJ, 2AK, 2AR, and/or 2AX. In some embodiments, alcohol tolerance polypeptides are encoded by an alcohol tolerance determinant, for example, set forth in Table 3 or Table 4. An alcohol tolerance modification may alter production and/or activity of any such alcohol tolerance polypeptide, or combination thereof. In some embodiments, increased expression or activity of an alcohol tolerance polypeptide increases tolerance; in some embodiments, decreased expression or activity of an alcohol tolerance polypeptide increases tolerance. To give but a few examples, alcohol tolerance polypeptides whose increased expression or activity in a cell increases alcohol tolerance may include, e.g., those encoded by alcohol tolerance determinants included in the determinant sequences found in Table 1A, row 20 (lp_1293), row 21 (lp_1295 [mntH3]), row 34 (lp_2159), row 35 (lp_2160), row 36 (lp_2169), row 37 (lp_2170), row 44 (lp_2911), row 50 (lp_3193); those encoded by alcohol tolerance determinants included in determinant sequences found in rows 2 (groES), 3 (groEL), 5 (cfa1) and/or 8 (cfa2) of Table 3, or in any of Tables 2T, 2U, 2AH, 2AI, 2AJ, 2AK, 2AR, 2AX, 4B, 4C, 4E and/or 4H; alcohol tolerance polypeptides whose decreased expression or activity in a cell increases tolerance may include, e.g., those encoded by alcohol tolerance determinants included in determinant sequences found in rows 1 (htrA), 4 (clpP), 6 (relA/spoT), 7 (hrcA), and/or 8 (cfa2) of Table 3, or in any of Tables 4A, 4D, 4F, 4G and/or 4H.

Alcohologenic modification: The term "alcohologenic modification" refers to a modification of a host organism that increases its production of at least one aliphatic alcohol compound. For example, in some embodiments, such increased production results in a broth titer of the produced at least one aliphatic alcohol compound that is 10%, 25%, 50%, 75%, 100% or more higher than that observed with an otherwise identical organism lacking the modification under comparable conditions, and/or such increased production results in a yield that is 10%, 25%, 50%, 75%, 100% or more higher than that observed with an otherwise identical organism lacking the modification under comparable conditions, and/or such increased production results in volumetric productivity that is 10%, 25%, 50%, 75%, 100% or more higher than that observed with an otherwise identical organism lacking the modification under comparable conditions, and/or such increased production results in a specific productivity increase of 10%, 25%, 50%, 75%, 100% or more higher than that observed with an otherwise identical organism lacking the modification under comparable conditions. In some embodiments, an alcohologenic modification is also an alcohol tolerance modification. In some embodiments, an alcohologenic modification comprises expression of an aliphatic alcohol biosynthesis polypeptide and/or inhibition of an aliphatic alcohol biosynthesis competitor polypeptide. In some embodiments, an alcohologenic modification increases expression of an alcohologenic polypeptide which is a homologous polypeptide (e.g., the alcohologenic modification increases expression of a polypeptide that naturally occurs in the organism in which it is being expressed). In some embodiments, an alcohologenic modification comprises expression of a heterologous alcohologenic polypeptide.

Aliphatic alcohol biosynthesis polypeptide: An "aliphatic alcohol biosynthesis polypeptide", as that term is used herein, refers to any polypeptide that is involved in the synthesis of an aliphatic alcohol compound. In some embodiments, an aliphatic alcohol compound catalyzes at least one synthetic step in production of at least one aliphatic alcohol compound. An aliphatic alcohol biosynthesis polypeptide involved in the synthesis of a particular aliphatic alcohol compound may be referred to by reference to that compound (e.g., ethanol biosynthesis polypeptide, 1-butanol biosynthesis polypeptide, butanol biosynthesis peptide, isobutanol biosynthesis polypeptide, etc.). Thus, in some embodiments, a butanol biosynthesis polypeptide catalyzes at least one step in the synthesis of butanol. In some embodiments, an aliphatic alcohol biosynthesis polypeptide catalyzes a substrate to product conversion selected from the group consisting of a) acetyl-CoA to acetoacetyl-CoA; b) acetoacetyl-CoA to 3-hydroxybutyryl-CoA; c) 3-hydroxybutyryl-CoA to crotonyl-CoA; d) crotonyl-CoA to butyryl-CoA; e) butyryl-CoA to butyraldehyde; f) butyraldehyde to 1-butanol; and combinations thereof. In some embodiments, an aliphatic alcohol biosynthesis polypeptide is an acetyl-CoA acetyltransferase polypeptide, a 3-hydroxybutyryl-CoA dehydrogenase polypeptide, a crotonase polypeptide, a butyryl-CoA dehydrogenase polypeptide, a butyraldehyde dehydrogenase polypeptide, a butanol dehydrogenase polypeptide, or a combination thereof. In some embodiments, an isobutanol biosynthesis polypeptide catalyzes at least one step in the synthesis of isobutanol. Thus, in some embodiments, an aliphatic alcohol biosynthesis polypeptide catalyzes a substrate to product conversion selected from the group consisting of a) pyruvate to acetolactate; b) acetolactate to 2,3-dihydroxyisovalerate; c) 2,3-dihydroxyisovalerate to α-ketoisovalerate; d) α-ketoisovalerate to isobutyraldehyde; e) isobutyraldehyde to isobutanol; f) α-ketoisovalerate to isobutyryl-CoA; g) isobutyryl-CoA to isobutyraldehyde; h) α-ketoisovalerate to valine; i) valine to isobutylamine; j) isobutylamine to isobutyraldehyde; k) butyryl-CoA to isobutyryl-CoA; and combinations thereof. In some embodiments, an aliphatic alcohol biosynthesis polypeptide is an acetolactate synthase polypeptide, an acetohydroxy acid isomeroreductase polypeptide, an acetohydroxy acid dehydratase polypeptide, a branched-chain keto acid decarboxylase polypeptide, a branched-chain alcohol dehydrogenase polypeptide, a branched-chain keto acid dehydrogenase polypeptide, an acylating aldehyde dehydrogenase polypeptide, a valine dehydrogenase polypeptide, a transaminase polypeptide, a valine decarboxylase polypeptide, an omega transaminase polypeptide, an isobutyryl-CoA mutase polypeptide, or a combination thereof. Representative examples of some such aliphatic alcohol biosynthesis polypeptides are presented in Tables 5 and 6.

Aliphatic alcohol biosynthesis competitor polypeptide: An "aliphatic alcohol biosynthesis competitor polypeptide", as that term is used here, is a polypeptide whose expression in a cell results in diversion of one or more metabolic intermediates away from a pathway that would otherwise produce one or more aliphatic alcohol compounds. In some embodiments of the present disclosure, aliphatic alcohol biosynthesis competitor polypeptides catalyze a metabolic reaction in a pathway that intersects an aliphatic alcohol biosynthesis pathway. In some embodiments of the present disclosure, expression of an aliphatic alcohol biosynthesis competitor polypeptide in a cell reduces levels of aliphatic alcohol compounds generally. In some embodiments of the present disclosure, expression of an aliphatic alcohol biosynthesis competitor polypeptide reduces levels of a particular aliphatic alcohol compound. In some embodiments of the present disclosure, expression of an aliphatic alcohol biosynthesis competitor polypeptide alters relative production levels of different aliphatic alcohol compounds. To give but one example, in some embodiments a butanol biosynthesis competitor polypeptide catalyzes the diversion of butanol metabolic intermediates to alternative pathways, such as those that promote the production of lactate, ethanol, butyrate, acetone, or acetoin. Thus, for example (see, for example as in FIG. 1), aliphatic alcohol biosynthesis competitor polypeptides may include but are not limited to phosphotransbutyrylase polypeptides, butyrate kinase polypeptides, CoA tranferase polypeptides, acetoacetate decarboxylase polypeptides, phosphotransacetylase polypeptides, acetate kinase polypeptides, aldehyde dehydrogenase polypeptides, alcohol dehydrogenase polypeptides, and combinations thereof.

Aliphatic alcohol compound: An "aliphatic alcohol compound" is a compound in which one or more hydroxyl groups is attached to an alkyl radical. Aliphatic alcohol compounds of particular interest in accordance with the present disclosure are those with fewer than 10 carbon atoms. For example, aliphatic alcohol compounds include 1-butanol, 2-butanol, iso-butanol, tert-butanol, ethanol, 1-heptanol, 2-heptanol, 3-heptanol, 4-heptanol, iso-heptanol, 1-hexanol, 2-hexanol, 3-hexanol, 2-ethyl hexanol, iso-hexanol, methanol, 1-octanol, 2-octanol, 3-octanol, iso-octanol, and 4-octanol, 1-pentanol, 2-pentanol, 3-pentanol, iso-pentanol, 1-propanol, 2-propanol, iso-propanol, and combinations thereof.

Biosynthesis polypeptide: The term "biosynthesis polypeptide" as used herein (typically in reference to a particular compound or class of compounds), refers to polypeptides involved in the production of the compound or class of compounds. In some embodiments of the disclosure, biosynthesis polypeptides are synthetic enzymes that catalyze particular steps in a synthesis pathway that ultimately produce a relevant compound. In some embodiments, the term "biosynthesis polypeptide" may also encompass polypeptides that do not themselves catalyze synthetic reactions, but that regulate expression and/or activity of other polypeptides that do so.

Branched chain α-keto acid decarboxylase: The term "branched-chain α-keto acid decarboxylase" (also referred to herein as branched-chain keto acid decarboxylase keto acid decarboxylase) refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *L. lactis* (GenBank Nos: AAS49166 (SEQ ID NO:193 in US patent application 2007/0092957), AY548760 (SEQ ID NO:192), CAG34226 (SEQ ID NO:8 in US patent application 2007/0092957), AJ746364 (SEQ ID NO:191 in US patent application 2007/0092957)), *Salmonella typhimurium* (GenBank Nos: NP_461346 (SEQ ID NO:195 in US patent application 2007/0092957), NC_003197 (SEQ ID NO:194 in US patent application 2007/0092957)), and *C. acetobutylicum* (GenBank Nos: NP_149189 (SEQ ID NO:197 in US patent application 2007/0092957), NC_001988 (SEQ ID NO:196 in US patent application 2007/0092957)).

Branched-chain alcohol dehydrogenase: The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as an electron donor and are available from a number of sources, including, but not limited to, *S. cerevisiae* (GenBank Nos: NP_010656 (SEQ ID NO:199 in US patent application 2007/0092957), NC_001136 (SEQ ID NO:198 in US patent application 2007/0092957), NP_014051 (SEQ ID NO:201 in US patent application 2007/0092957), NC_001145 (SEQ ID NO:200 in US patent application 2007/0092957)), *E. coli* (GenBank Nos: NP_417484 (SEQ ID NO:10 in US patent application 2007/0092957), NC_000913 (SEQ ID NO:9 in US patent application 2007/0092957)), and *C. acetobutylicum* (GenBank Nos: NP_349892 (SEQ ID NO:203 in US patent application 2007/0092957), NC_003030 (SEQ ID NO:202 in US patent application 2007/0092957), NP_349891 (SEQ ID NO:204 in US patent application 2007/0092957), NC_003030 (SEQ ID NO:158 in US patent application 2007/0092957)).

Branched-chain keto acid dehydrogenase: The term "branched-chain keto acid dehydrogenase" refers to an enzyme that catalyzes the conversion of α-ketoisovalerate to isobutyryl-CoA (isobutyryl-coenzyme A), using $NAD^+$ (nicotinamide adenine dinucleotide) as electron acceptor. Preferred branched-chain keto acid dehydrogenases are known by the EC number 1.2.4.4. These branched-chain keto acid dehydrogenases are comprised of four subunits and sequences from all subunits are available from a vast array of microorganisms, including, but not limited to, *B. subtilis* (GenBank Nos: CAB14336 (SEQ ID NO:206 in US patent application 2007/0092957), Z99116 (SEQ ID NO:205 in US patent application 2007/0092957), CAB14335 (SEQ ID NO:208 in US patent application 2007/0092957), Z99116 (SEQ ID NO:207 in US patent application 2007/0092957), CAB14334 (SEQ ID NO:210 in US patent application 2007/0092957), Z99116 (SEQ ID NO:209 in US patent application 2007/0092957), CAB14337 (SEQ ID NO:212 in US patent application 2007/0092957), Z99116 (SEQ ID NO:211 in US patent application 2007/0092957)) and *P. putida* (GenBank Nos: AAA65614 (SEQ ID NO:214 in US patent application 2007/0092957), M57613 (SEQ ID NO:213 in US patent application 2007/0092957), AAA65615 (SEQ ID NO:216 in US patent application 2007/0092957), M57613 (SEQ ID NO:215 in US patent application 2007/0092957), AAA65617 (SEQ ID NO:218 in US patent application 2007/0092957), M57613 (SEQ ID NO:217 in US patent application 2007/0092957), AAA65618 (SEQ ID NO:220 in US patent application 2007/0092957), M57613 (SEQ ID NO:219 in US patent application 2007/0092957)).

Butanol: The term "butanol", as used herein, refers to a material that consists of 1-butanol, 2-butanol, iso-butanol, and/or tert-butanol. In some embodiments, "butanol" is 1-butanol.

Butanol biosynthesis polypeptide: As used herein, the term "butanol biosynthesis polyepeptide" refers to an aliphatic alcohol biosynthesis polypeptide that participates in the synthesis of butanol. In some embodiments, a butanol biosynthesis polypeptide participates in the synthesis of 1-butanol. In some embodiments, a butanol biosynthesis polypeptide catalyzes at least one step in the synthesis of butanol (e.g., 1-butanol). In some embodiments, a butanol biosynthesis polypeptide catalyzes a substrate to product conversion selected from the group consisting of a) acetyl-CoA to acetoacetyl-CoA; b) acetoacetyl-CoA to 3-hydroxybutyryl-CoA; c) 3-hydroxybutyryl-CoA to crotonyl-CoA; d) crotonyl-CoA to butyryl-CoA; e) butyryl-CoA to butyraldehyde; f) butyraldehyde to 1-butanol; and combinations thereof. In some embodiments, a butanol biosynthesis polypeptide is an acetyl-CoA acetyltransferase polypeptide, a 3-hydroxybutyryl-CoA dehydrogenase polypeptide, a crotonase polypeptide, a butyryl-CoA dehydrogenase polypeptide, a butyraldehyde dehydrogenase polypeptide, a butanol dehydrogenase polypeptide, or a combination thereof. In some embodiments, a butanol biosynthesis polypeptide catalyzes at least one step in the synthesis of isobutanol (i.e., is an isobutanol biosynthesis polypeptide). In some such embodiments, a butanol biosynthesis polypeptide catalyzes a substrate to product conversion selected from the group consisting of i) pyruvate to acetolactate (isobutanol biosynthesis pathway step a); ii) acetolactate to 2,3-dihydroxyisovalerate (isobutanol biosynthesis pathway step b); iii) 2,3-dihydroxyisovalerate to α-ketoisovalerate (isobutanol biosynthesis pathway step c); iv) α-ketoisovalerate to isobutyraldehyde, (isobutanol biosynthesis pathway step d); v) isobutyraldehyde to isobutanol (isobutanol biosynthesis pathway step e); vi) α-ketoisovalerate to isobutyryl-CoA, (isobutanol biosynthesis pathway step f); vii) isobutyryl-CoA to isobutyraldehyde (isobutanol biosynthesis pathway step g); viii) α-ketoisovalerate to valine, (isobutanol biosynthesis pathway step h); ix) valine to isobutylamine (isobutanol biosynthesis pathway step i); x) isobutylamine to isobutyraldehyde (isobutanol biosynthesis pathway step j); xi) butyryl-CoA to isobutyryl-CoA (isobutanol biosynthesis pathway step k); and combinations thereof. For example, in some embodiments, a butanol biosynthesis polypeptide catalyzes a substrate to product conversion selected from the group consisting of i) pyruvate to acetolactate (isobutanol biosynthesis pathway step a) ii) acetolactate to 2,3-dihydroxyisovalerate (isobutanol biosynthesis pathway step b); iii) 2,3-dihydroxyisovalerate to α-ketoisovalerate (isobutanol biosynthesis pathway step c); iv) α-ketoisovalerate to isobutyraldehyde, (isobutanol biosynthesis pathway step d); and v) isobutyraldehyde to isobutanol (isobutanol biosynthesis pathway step e); and combinations thereof. In some embodiments, a butanol biosynthesis polypeptide catalyzes a substrate to product conversion selected from the group consisting of i) pyruvate to acetolactate, (isobutanol biosynthesis pathway step a); ii) acetolactate to 2,3-dihydroxyisovalerate, (isobutanol biosynthesis pathway step b); iii) 2,3-dihydroxyisovalerate to α-ketoisovalerate, (isobutanol biosynthesis pathway step c); iv) α-ketoisovalerate to isobutyryl-CoA, (isobutanol biosynthesis pathway step f); v) isobutyryl-CoA to isobutyraldehyde, (isobutanol biosynthesis pathway step g); and vi) isobutyraldehyde to isobutanol; (isobutanol biosynthesis pathway step e); and combinations thereof. In some embodiments, a butanol biosynthesis polypeptide catalyzes a substrate to product conversion selected from the group consisting of i) pyruvate to acetolactate (isobutanol biosynthesis pathway step a); ii) acetolactate to 2,3-dihydroxyisovalerate (isobutanol biosynthesis pathway step b); iii) 2,3-dihydroxyisovalerate to α-ketoisovalerate (isobutanol biosynthesis pathway step c); iv) α-ketoisovalerate to valine (isobutanol biosynthesis pathway step h); v) valine to isobutylamine (isobutanol biosynthesis pathway step i); vi) isobutylamine to isobutyraldehyde (isobutanol biosynthesis pathway step j); vii) isobutyraldehyde to isobutanol (isobutanol biosynthesis pathway step e) and combinations thereof. In some embodiments, a butanol biosynthesis polypeptide catalyzes a substrate to product conversion selected from the group consisting of i) butyryl-CoA to isobutyryl-CoA (isobutanol biosynthesis pathway step k); ii) isobutyryl-CoA to isobutyraldehyde, (isobutanol biosynthesis pathway step g); iii) isobutyraldehyde to isobutanol (isobutanol biosynthesis pathway step e); and combinations thereof.

Butanol dehydrogenase: The term "butanol dehydrogenase" refers to an enzyme that catalyzes the conversion of butyraldehyde to 1-butanol, using either NADH or NADPH as cofactor. Butanol dehydrogenases are available from, for example *C. acetobutylicum* (GenBank Nos: NP_149325 (SEQ ID NO:153 in WO 2007/041269), NC_001988 SEQ ID NO:152 in WO 2007/041269; note: this enzyme possesses both aldehyde and alcohol dehydrogenase activity), NP_349891 (SEQ ID NO:14 in WO 2007/041269), NC_003030 (SEQ ID NO:13 in WO 2007/041269), NP_349892 (SEQ ID NO: 16 in WO 2007/041269), NC_003030 (SEQ ID NO:15 in WO 2007/041269)) and *E. coli* (GenBank Nos: NP_417484 (SEQ ID NO: 155 in WO 2007/041269), NC_000913 (SEQ ID NO:154 in WO 2007/041269)).

Butyraldehyde dehydrogenase: The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.1.1.57 and are available from, for example, *C. beijerinckii* (Genbank Nos: AAD31841 (SEQ ID NO:12 in WO 2007/041269), AF157306 (SEQ ID NO:11 in WO 2007/041269)) and *C. acetobutylicum* (GenBank Nos: NP_149325 (SEQ ID NO:153 in WO 2007/041269), NC_001988 (SEQ ID NO:152 in WO 2007/041269)).

Butyryl-CoA dehydrogenase: The term "butyryl-CoA dehydrogenase" refers to an enzyme that catalyzes the conversion of crotonyl-CoA to butyryl-CoA. Butyryl-CoA dehydrogenases may be either NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank Nos: NP_347102 (SEQ ID NO:10 in WO 2007/041269), NC_003030 (SEQ ID NO:9 in WO 2007/041269)), *Euglena gracilis* (GenBank Nos: Q 5EU90 (SEQ ID NO:147 in WO 2007/041269), AY741582 SEQ ID NO:146 in WO 2007/041269)), *Streptomyces collinus* (GenBank Nos: AAA92890 (SEQ ID NO:149 in WO 2007/041269), U37135 (SEQ ID NO: 148 in WO 2007/041269)), and *Streptomyces coelicolor* (GenBank Nos: CAA22721 (SEQ ID NO:151 in WO 2007/041269), AL939127 (SEQ ID NO:150 in WO 2007/041269)).

Crotonase: The term "crotonase" refers to an enzyme that catalyzes the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank Nos: NP_415911 (SEQ ID NO:141 in WO 2007/041269), NC_000913 (SEQ ID NO:140 in WO 2007/041269)), *C. acetobutylicum* (GenBank Nos: NP_349318 (SEQ ID NO:8 in WO 2007/041269), NC_003030 (SEQ ID NO:6 in WO 2007/041269)), *B. subtilis* (GenBank Nos: CAB13705 (SEQ ID NO:143 in WO 2007/041269), Z99113 (SEQ ID NO: 142 in WO 2007/041269)), and *Aeromonas caviae* (GenBank Nos: BAA21816 (SEQ ID NO:145 in WO 2007/041269), D88825 (SEQ ID NO:144 in WO 2007/041269)).

Engineered microorganism: An "engineered microorganism", as that term is used herein, is one that contains a modification introduced by the hand of man, so that the engineered microorganism differs from a parent organism to which it is otherwise identical. Progeny of a microorganism that also contain the modification are encompassed by the term "engineered microorganism".

Gene: The term "gene", as used herein, generally refers to a nucleic acid encoding a polypeptide, optionally including certain regulatory elements that may affect expression of one or more gene products (i.e., RNA or protein).

Genetic compatibility: The phrase "genetic compatibility" is used herein to refer to pairs (or sets) of organisms for which genetic elements from cells of one organism operate (and/or are expressed) in the other organism. Those of ordinary skill in the art will appreciate, of course, that two organisms may be genetically compatible even though one or more particular genetic elements, and particularly genetic regulatory sequences, may not function in both organisms. The techniques of molecular biology may readily be applied, for example, to adjust and/or substitute expression control sequences, to account for codon bias preferences, etc. in order to increase expression of heterologous sequences from a source organism in cells of a host organism. Those of ordinary skill in the art will further appreciate that genetic compatibility can be determined by any of a variety of modes of assessment. In some embodiments, for example, genetic compatibility is determined by experimental success in achieving expression of source organism genetic elements in host recipient cells. In some embodiments, genetic compatibility is determined (or at least predicted) based on taxonomical relationship between source and host organisms. For example, there is a reasonable expectation of genetic compatibility between multiple members of the gram-positive, low G+C firmicutes group of bacteria (e.g. *Lactobacillus plantarum* and *Clostridium acetobutylicum*).

Heterologous: The term "heterologous", as used herein to refer to genes or polypeptides, refers to a gene or polypeptide that does not naturally occur in the organism in which it is being expressed. It will be understood that, in general, when a heterologous gene or polypeptide is selected for introduction into and/or expression by a host cell, the particular source organism from which the heterologous gene or polypeptide may be selected is not essential to the practice of the present disclosure. Relevant considerations may include, for example, how closely related the potential source and host organisms are in evolution, or how related the source organism is with other source organisms from which sequences of other relevant polypeptides have been selected. Where a plurality of different heterologous polypeptides are to be introduced into and/or expressed by a host cell, different polypeptides may be from different source organisms, or from the same source organism. To give but one example, in some cases, individual polypeptides may represent individual subunits of a complex protein activity and/or may be required to work in concert or in a sequential order with other polypeptides in order to achieve the goals of the present disclosure. In some embodiments, it will often be desirable for such polypeptides to be from the same source organism, and/or to be sufficiently related to function appropriately when expressed together in a host cell. In some embodiments, such polypeptides may be from different, even unrelated source organisms. It will further be understood that, where a heterologous polypeptide is to be expressed in a host cell, it will often be desirable to utilize nucleic acid sequences encoding the polypeptide that have been adjusted to accommodate codon preferences of the host cell and/or to link the encoding sequences with regulatory elements active in the host cell.

Homolog: A "homolog" is a polypeptide, gene, or portion thereof (e.g., a 3' region of a gene, e.g., a 3' untranslated region (UTR) of a gene, e.g., a 5' region of a gene, e.g., a 5' UTR) that shows a designated degree of sequence identity (and/or similarity) with another polypeptide, gene, or portion thereof. For example, any polypeptide that shows at least about 30-40% overall sequence identity with another polypeptide, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide is a homolog of that polypeptide. In many embodiments, a homolog of a polypeptide further shares sequence similarity with and/or at least one functional attribute or activity of the polypeptide. With regard to genes or nucleotide sequences, any gene or nucleotide sequence that (i) shows at least about 60% overall sequence identity with another gene or nucleotide sequence; and or (ii) has a same function as, and/or encodes a homolog of a polypeptide encoded by, the other gene or nucleotide sequence is a homolog of that gene or nucleotide sequence. With regard to a 3' region of a gene (e.g., 3' UTR) that adjusts susceptibility of an organism to one or more toxic effects of one or more aliphatic alcohol compounds, any nucleotide sequence that (i) either shows at least 60% overall sequence identity, and/or is a 3' region of a gene that is a homolog of the gene as defined above; and (ii) also adjusts susceptibility of an organism to toxic effects of alcohol compounds is a homolog of that 3' region. As is known by those of ordinary skill in the art, a variety of strategies are known, and tools are available, for performing comparisons of amino acid or nucleotide sequences in order to assess degrees of identity and/or similarity. These strategies include, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW, etc. When utilizing BLAST and Gapped BLAST programs, default parameters of the respective programs may be used. Alternatively, the practitioner may use non-default parameters depending on his or her experimental and/or other requirements (see for example, the Web site having URL www.ncbi.nlm.nih.gov).

Host cell: As used herein, the "host cell" is a microbial cell that is manipulated according to the present disclosure. For example, in some embodiments, a host cell is manipulated such that its tolerance for one or more aliphatic alcohol compounds is increased (e.g., via an alcohol tolerance modification); in some embodiments, a host cell is manipulated such that its production of one or more aliphatic alcohol compounds is increased (e.g., via an alcohologenic modification). A "modified host cell", as used herein, is any host cell which has been modified, engineered, or manipulated in accordance with the present disclosure as compared with an otherwise identical parental cell. In some embodiments, the modified host cell has at least one alcohol tolerance modification and/or at least one (and optionally more than one as compared with the parental cell) alcohologenic modification. In some embodiments, the parental cell is a naturally occurring parental cell. In some embodiments, the parental cell produces at least one aliphatic alcohol.

3-Hydroxybutyryl-CoA dehydrogenase: The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-hydroxybutyryl-CoA dehydrogenases are available from a number of sources, for example, *C. acetobutylicum* (GenBank Nos: NP_349314 (SEQ ID NO:6 in WO 2007/041269), NC_003030 (SEQ ID NO:5 in WO 2007/041269)), *B. subtilis* (GenBank Nos: AAB09614 (SEQ ID NO:135 in WO 2007/041269), U29084 (SEQ ID NO:134 in WO 2007/041269)), *Ralstonia eutropha* (GenBank Nos: YP_294481 (SEQ ID NO:137 in WO 2007/041269), NC_007347 (SEQ ID NO:136 in WO 2007/041269)), and *Alcaligenes eutrophus* (GenBank Nos: AAA21973 (SEQ ID NO:139 in WO 2007/041269), J04987 (SEQ ID NO:138 in WO 2007/041269)).

Introduce: The term "introduce", as used herein with reference to introduction of a nucleic acid into a cell or organism is intended to have its broadest meaning and to encompass introduction, for example by transformation methods (e.g., calcium-chloride-mediated transformation, electroporation, particle bombardment), and also introduction by other methods including transduction, conjugation, and mating. In some embodiments, a vector is utilized to introduce a nucleic acid into a cell or organism.

Isobutyryl-CoA mutase: The term "isobutyryl-CoA mutase" refers to an enzyme that catalyzes the conversion of butyryl-CoA to isobutyryl-CoA. This enzyme uses coenzyme $B_{12}$ as a cofactor. Preferred isobutyryl-CoA mutases are known by the EC number 5.4.99.13. These enzymes are found in a number of *Streptomycetes*, including, but not limited to, *Streptomyces cinnamonensis* (GenBank Nos: AAC08713 (SEQ ID NO:256 in US patent application 2007/0092957), U67612 (SEQ ID NO:255 in US patent application 2007/0092957), CAB59633 (SEQ ID NO:258 in US patent application 2007/0092957), AJ246005 (SEQ ID NO:257 in US patent application 2007/0092957)), *S. coelicolor* (GenBank Nos: CAB70645 (SEQ ID NO:260 in US patent application 2007/0092957), AL939123 (SEQ ID NO:259 in US patent application 2007/0092957), CAB92663 (SEQ ID NO:262 in US patent application 2007/0092957), AL939121 (SEQ ID NO:261 in US patent application 2007/0092957)), and *Streptomyces avermitilis* (GenBank Nos: NP_824008 (SEQ ID NO:264 in US patent application 2007/0092957), NC_003155 (SEQ ID NO:263 in US patent application 2007/0092957), NP_824637 (SEQ ID NO:266 in US patent application 2007/0092957), NC_003155 (SEQ ID NO:265 in US patent application 2007/0092957)).

Isolated: The term "isolated", as used herein, means that the isolated entity has been separated from at least one component with which it was previously associated. When most other components have been removed, the isolated entity is "purified" or "concentrated". Isolation and/or purification and/or concentration may be performed using any techniques known in the art including, for example, distillation, fractionation, gas stripping, extraction, precipitation, or other separation.

Modification: In principle, "modification", as that term is used herein, may be any chemical, physiological, genetic, or other modification of an organism that appropriately alters a designated feature of a host organism (e.g., an alcohologenic modification alters production of at least one aliphatic alcohol compound, an alcohol tolerance modification alters susceptibility to one or more aliphatic alcohol compounds, etc.) as compared with an otherwise identical organism not subject to the same modification. In most embodiments, however, the modification will comprise a genetic modification, typically resulting in decreased susceptibility to one or more selected aliphatic alcohol compounds (e.g., butanol). In some embodiments, the modification comprises at least one chemical, physiological, genetic, or other modification; in other embodiments, the modification comprises more than one chemical, physiological, genetic, or other modification. In certain embodiments where more than one modification is utilized, such modifications can comprise any combination of chemical, physiological, genetic, or other modification (e.g., one or more genetic, chemical and/or physiological modification(s)).

Omega transaminase: The term "omega transaminase" refers to an enzyme that catalyzes the conversion of isobutylamine to isobutyraldehyde using a suitable amino acid as an amine donor. Preferred omega transaminases are known by the EC number 2.6.1.18 and are available from a number of sources, including, but not limited to, *Alcaligenes denitrificans* (GenBank Nos: AAP92672 (SEQ ID NO:248 in US patent application 2007/0092957), AY330220 (SEQ ID NO:247 in US patent application 2007/0092957)), *Ralstonia eutropha* (GenBank Nos: YP_294474 (SEQ ID NO:250 in US patent application 2007/0092957), NC_007347 (SEQ ID NO:249 in US patent application 2007/0092957)), *Shewanella oneidensis* (GenBank Nos: NP_719046 (SEQ ID NO:252 in US patent application 2007/0092957), NC_004347 (SEQ ID NO:251 in US patent application 2007/0092957)), and *P. putida* (GenBank Nos: AAN66223 (SEQ ID NO:254 in US patent application 2007/0092957), AE016776 (SEQ ID NO:253 in US patent application 2007/0092957)).

Polypeptide: The term "polypeptide", as used herein, generally has its art-recognized meaning of a polymer of at least three amino acids. However, the term is also used to refer to specific functional classes of polypeptides, such as, for example, biosynthesis polypeptides, competitor polypeptides, alcohol tolerance polypeptides, etc. For each such class, the present specification provides several examples of known sequences of such polypeptides. Those of ordinary skill in the art will appreciate, however, that the term "polypeptide" is intended to be sufficiently general as to encompass not only polypeptides having the complete sequence recited herein (or referred to by specific reference to a description in publication or database, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Other regions of similarity and/or identity can be determined by those of ordinary skill in the art by analysis of the sequences of various polypeptides presented in the Tables herein.

Small Molecule: In general, a small molecule is understood in the art to be an organic molecule that is less than about 5 kilodaltons (Kd) in size. In some embodiments, the small molecule is less than about 3 Kd, 2 Kd, or 1 Kd. In some embodiments, the small molecule is less than about 800 daltons (D), 600 D, 500 D, 400 D, 300 D, 200 D, or 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Source organism: The term "source organism", as used herein, refers to the organism in which a particular polypeptide or nucleotide (e.g., gene) is found in nature. Thus, for example, if one or more heterologous polypeptides is/are being expressed in a host organism, the organism in which the polypeptides are expressed in nature (and/or from which their genes were originally cloned) is referred to as the "source organism". Where multiple heterologous polypeptides are being expressed in a host organism, one or more source organism(s) may be utilized for independent selection of each of the heterologous polypeptide(s). It will be appreciated that any and all organisms that naturally contain relevant polypeptide sequences may be used as source organisms in accordance with the present disclosure. Representative source organisms include, for example, animal, mammalian, insect, plant, fungal, yeast, algal, bacterial, archaebacterial, cyanobacterial, and protozoal source organisms.

Transaminase: The term "transaminase" refers to an enzyme that catalyzes the conversion of α-ketoisovalerate to valine, using either alanine or glutamate as amine donor. Preferred transaminases are known by the EC numbers 2.6.1.42 and 2.6.1.66. These enzymes are available from a number of sources. Examples of sources for alanine-dependent enzymes include, but are not limited to, *E. coli* (GenBank Nos: YP_026231 (SEQ ID NO:232 in US patent application 2007/0092957), NC_000913 (SEQ ID NO:231 in US patent application 2007/0092957)) and *Bacillus licheniformis* (GenBank Nos: YP_093743 (SEQ ID NO:234 in US patent application 2007/0092957), NC_006322 (SEQ ID NO:233 in US patent application 2007/0092957)). Examples of sources for glutamate-dependent enzymes include, but are not limited to, *E. coli* (GenBank Nos: YP_026247 (SEQ ID NO:236 in US patent application 2007/0092957), NC_000913 (SEQ ID NO:235 in US patent application 2007/0092957)), *S. cerevisiae* (GenBank Nos: NP_012682 (SEQ ID NO:238), NC_001142 (SEQ ID NO:237 in US patent application 2007/0092957)) and *Methanobacterium thermoautotrophicum* (GenBank Nos: NP_276546 (SEQ ID NO:240 in US patent application 2007/0092957), NC_000916 (SEQ ID NO:239 in US patent application 2007/0092957)).

Valine decarboxylase: The term "valine decarboxylase" refers to an enzyme that catalyzes the conversion of valine to isobutylamine and $CO_2$. Preferred valine decarboxylases are known by the EC number 4.1.1.14. These enzymes are found in *Streptomycetes*, such as for example, *Streptomyces viridifaciens* (GenBank Nos: AAN10242 (SEQ ID NO:246 in US patent application 2007/0092957), AY116644 (SEQ ID NO:245 in US patent application 2007/0092957)).

Valine dehydrogenase: The term "valine dehydrogenase" refers to an enzyme that catalyzes the conversion of α-ketoisovalerate to valine, using NAD(P)H as electron donor and ammonia as amine donor. Preferred valine dehydrogenases are known by the EC numbers 1.4.1.8 and 1.4.1.9 and are available from a number of sources, including, but not limited to, *Streptomyces coelicolor* (GenBank Nos: NP_628270 (SEQ ID NO:242 in US patent application 2007/0092957), NC_003888 (SEQ ID NO:241 in US patent application 2007/0092957)) and *B. subtilis* (GenBank Nos: CAB14339 (SEQ ID NO:244 in US patent application 2007/0092957), Z99116 (SEQ ID NO:243 in US patent application 2007/0092957)).

DETAILED DESCRIPTION OF CERTAIN EMBODIMENTS

The present disclosure embraces the reasoning that microbial strains can be engineered to have increased tolerance to aliphatic alcohols. According to the present disclosure, microbial strains are engineered to contain one or more modifications that increase their tolerance to one or more aliphatic alcohol compounds. Alternatively or additionally, microbial strains for use in accordance with the present disclosure may be engineered to contain one or more modifications that increase their ability to produce one or more aliphatic alcohol compounds. In some embodiments, a modification that increases a cell's tolerance to one or more aliphatic alcohol compounds will also allow higher production of one or more aliphatic alcohol compounds.

In certain embodiments, engineered microbial cells show an increased aliphatic alcohol $IC_{50}$ as compared with parental cells. In certain embodiments, the aliphatic alcohol $IC_{50}$ is increased at least 5%, 10%, 20%, 30%, 40%, 50%, 60%, 70%, 80%, 90%, 100%, or more. In certain embodiments, engineered microbial cells show increased carbohydrate utilization as compared to parental cells when grown in same amount of alcohol. For example, in some embodiments, carbohydrate utilization is increased at least 5%, 10%, 20%, 30%, 40%, 50%, 60%, 70%, 80%, 90%, 100%, or more. In some embodiments, the carbohydrate whose utilization is increased is glucose.

Engineered cells and processes of using them as described herein may provide one or more advantages as compared with parental cells. Such advantages may include, but are not limited to: increased yield (gram of aliphatic alcohol compound produced per gram of carbohydrate substrate consumed), increased titer (gram(s) of aliphatic alcohol compound produced per liter of broth), increased specific productivity (gram(s) of aliphatic alcohol compound produced per gram of host cell biomass per unit of time (e.g. hour)), and/or increased volumetric productivity (gram(s) of aliphatic alcohol compound produced per liter of broth per unit of time (e.g. hour) of the desired aliphatic alcohol compound (and/or intermediates thereof), and/or decreased formation of undesirable side products (for example, undesirable intermediates).

Thus, for example, the yield for one or more desired aliphatic alcohol compounds (or total aliphatic alcohol compound content) produced from a glucose-containing substrate, may be increased at least about 5%, 10%, 25%, 50%, 75%, 100% or more as compared with a parental cell. In some embodiments, the yield (g aliphatic alcohol/g glucose substrate) for one or more desired aliphatic alcohol compounds, or total aliphatic alcohol compound content, may be at or about 0.01, at or about 0.05, at or about 0.10, at or about 0.15, at or about 0.20, at or about 0.25, at or about 0.28, at or about 0.30, at or about 0.32, at or about 0.34, at or about 0.36, at or about 0.38, at or about 0.40 or more.

In some embodiments, aliphatic alcohol compound production is assessed by measuring broth titer (g aliphatic alcohol/liter broth). In some embodiments, broth titer for a particular aliphatic alcohol compound, or combination of compounds, is increased at least about 5%, 10%, 25%, 50%, 75%, 100% or more in cells engineered according to the present disclosure as compared with parental cells. In some embodiments, such broth titer achieves levels as high as at or about 1, at or about 5, at or about 10, at or about 15, at or about 20, at or about 25, at or about 30, at or about 35, at or about 40, at or about 50, at or about 55, at or about 60, at or about 65, at or about 70, at or about 75, at or about 80 or more.

Various aspects and features of certain embodiments of the disclosure are discussed in more detail below.

Host Cells

Inventive modifications may be applied to any of a variety of host cells in accordance with the present disclosure. For example, in some embodiments, parental cells already produce one or more aliphatic alcohol compounds before being engineered in accordance with the present disclosure. In other words, in some embodiments, modifications are applied to cells that already produce one or more aliphatic alcohol compounds. In some embodiments, however, parental cells do not produce one or more aliphatic alcohol compounds before being engineered in accordance with the present disclosure. In some embodiments of the present disclosure, cells are engineered to increase (whether from zero or from a base level) production of one or more aliphatic alcohol compounds, and/or to alter relative production levels of different aliphatic alcohol compounds. In some embodiments of the present disclosure, parental cells do not produce a particular aliphatic alcohol compound of interest (e.g., butanol, for example 1-butanol) prior to application of one or more modifications of the present disclosure. In some embodiments, cells are therefore engineered to produce the one or more particular aliphatic alcohol compounds. In some such embodiments, the cells are engineered to express (and/or activate) a plurality of biosynthesis polypeptides (e.g. aliphatic alcohol biosynthesis polypeptides), such that synthesis is achieved. In some embodiments, cells engineered to produce at least one aliphatic alcohol compound lack one or more aliphatic alcohol biosynthesis competitor polypeptides. Indeed, in some embodiments, it is desirable to engineer cells that lack one or more aliphatic alcohol biosynthesis competitor polypeptides such that diversion of carbon flow away from one or more desired aliphatic alcohol biosynthesis pathways is minimized.

In some embodiments of the present disclosure, parental cells already show some degree of tolerance to one or more aliphatic alcohol compounds before being engineered in accordance with the present disclosure. In other words, in some embodiments, modifications are applied to cells that already show tolerance to one or more aliphatic alcohol compounds. In some embodiments, however, parental cells do not show tolerance to one or more aliphatic alcohol compounds before being engineered in accordance with the present disclosure. In some embodiments of the present disclosure, cells are engineered to increase (whether from zero or from a base level) tolerance to one or more aliphatic alcohol compounds, and/or to alter relative tolerance levels to different aliphatic alcohol compounds.

In some embodiments, desirable cells or organisms to which modifications are applied in accordance with the present disclosure are characterized by one or more attributes such as (i) intrinsic tolerance to one or more aliphatic alcohol compounds; (ii) evidence of an ability to adapt to or be modified to (e.g. through chemical mutagenesis) enhanced tolerance to one or more aliphatic alcohol compounds; (iii) availability of genomic sequence information, or at least sequence information of relevant genetic elements (e.g., genes encoding polypeptides that contribute to tolerance); (iv) availability of tools to achieve molecular manipulation (e.g., of genetic sequences); (v) genetic stability; (vi) metabolic tendencies such as the ability to metabolize particular carbon sources (e.g., lignocellulosic biomass); (vii) potential for anaerobic growth; (viii) environmental niche (e.g., exposure to butane, butanol, etc); (ix) ability to biosynthesize one or more aliphatic alcohol compounds (e.g., butanol, and particularly 1-butanol); (x) minimal biosafety issues (e.g., infectious potential, etc.); and/or (xi) adaptability to growth under cost-effective, large scale commercial conditions (e.g., temperatures that do not require significant cooling of the fermentation vessel).

In some embodiments, host cells engineered in accordance with the present disclosure are members of a genus selected from the group consisting of *Clostridium*, *Zymomonas*, *Escherichia*, *Salmonella*, *Rhodococcus*, *Pseudomonas*, *Bacillus*, *Lactobacillus*, *Lactococcus*, *Enterococcus*, *Alcaligenes*, *Klebsiella*, *Paenibacillus*, *Arthrobacter*, *Corynebacterium*, *Brevibacterium*, *Acinetobacter*, *Pichia*, *Candida*, *Hansenula* and *Saccharomyces*.

In some embodiments, where host cells engineered in accordance with the present disclosure are members of the genus *Clostridium*, they are members of a species selected from the group consisting of *Clostridium acetobutylicum*, *Clostridium beijerinckii*, and *Clostridium saccaharoperbuylacetonicum*. Natural strains of each of these organisms have some ability to produce aliphatic alcohol compounds (e.g., butanol), maximally on the order of about 12 g/L. In some embodiments, host cells engineered in accordance with the present disclosure are members of the species *Clostridium acetobutylicum*.

In some embodiments, where host cells engineered in accordance with the present disclosure are members of the genus *Escherichia*, they are members of the species *Escherichia coli*.

In some embodiments, where host cells engineered in accordance with the present disclosure are members of the genus *Alcaligenes*, they are members of the species *Alcaligenes eutrophus*.

In some embodiments, where host cells engineered in accordance with the present disclosure are members of the genus *Bacillus*, they are members of the species *Bacillus licheniformis* or *Bacillus subtilis*.

In some embodiments, where host cells engineered in accordance with the present disclosure are members of the genus *Paenibacillus*, they are members of the species *Paenibacillus macerans*.

In some embodiments, where host cells engineered in accordance with the present disclosure are members of the genus *Rhodococcus*, they are members of the species *Rhodococcus erythropolis*.

In some embodiments, where host cells engineered in accordance with the present disclosure are members of the genus *Pseudomonas*, they are members of the species *Pseudomonas putida*.

In some embodiments, where host cells engineered in accordance with the present disclosure are members of the genus *Lactobacillus*, they are members of the species *Lactobacillus plantarum*.

In some embodiments, where host cells engineered in accordance with the present disclosure are members of the genus *Enterococcus*, they are members of the species *Enterococcus faecium*, *Enterococcus gallinarum*, or *Enterococcus faecalis*.

In some embodiments, where host cells engineered in accordance with the present disclosure are members of the genus *Saccharomyces*, they are members of the species *Saccharomyces cerevisiae*.

Those of ordinary skill in the art will appreciate that the selection of a particular host cell for use in accordance with the present disclosure will also affect, for example, the selection of expression sequences utilized with any heterologous polypeptide to be introduced into the cell, codon bias that can optionally be engineered into any nucleic acid to be expressed in the cell and will also influence various aspects of culture conditions, etc. Much is known about the different gene regulatory requirements and cultivation requirements of different host cells to be utilized in accordance with the present disclosure.

To give but a few examples, vectors or cassettes useful for the modification (e.g. transformation) of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically, the vector or cassette contains sequences directing transcription and translation of the relevant gene, a detectable or selectable marker and sequences allowing autonomous replication or chromosomal integration. Suitable vectors often comprise a region 5' of a gene coding sequence which harbors transcriptional initiation controls and a region 3' of the gene coding sequence which controls transcriptional termination. Both control regions may be derived from genes endogenous or homologous to the transformed host cell, although it is to be understood that such control regions may also be derived from genes that are not native to the specific species chosen as a production host.

Initiation control regions or promoters, which are useful to drive expression of genetic elements in a host cell are numerous and familiar to those skilled in the art. Virtually any promoter capable of driving these genetic elements is suitable for the present invention including, but not limited to, CYC1, HIS3, GAL1, GAL10, ADH1, PGK, PHO5, GAPDH, ADC1, TRP1, URA3, LEU2, ENO1, ENO2, TPI, CUP1, FBA, GPD, and GPM (useful for expression in *Saccharomyces*); AOX1 (useful for expression in *Pichia*); and lac, ara, tet, trp, $IP_L$, $IP_R$, T7, tac, and trc (useful for expression in *Escherichia coli*, *Alcaligenes*, and *Pseudomonas*); the amy, apr, npr promoters and various phage promoters useful for expression in *Bacillus subtilis*, *Bacillus licheniformis*, and *Paenibacillus macerans*; nisA (useful for expression in Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)).

Termination control regions may also be derived from various genes native or heterologous to the relevant host. Termination control regions are not required, but are often utilized in accordance with the present invention.

Certain vectors are capable of replicating in a broad range of host bacteria and can be transferred by conjugation. Many such vectors are well known. For example, the complete and annotated sequence of pRK404 and three related vectors—pRK437, pRK442, and pRK442(H) are available. These derivatives have proven to be valuable tools for genetic manipulation in Gram-negative bacteria (Scott et al., *Plasmid* 50(1):74, 2003). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to create gene replacement in a range of Gram-positive bacteria (Maguin et al., *J. Bacteriol.* 174(17):5633, 1992). Additionally, in vitro transposomes are available to create random mutations in a variety of genomes from commercial sources such as EPICENTRE®. Particular non-limiting examples of suitable vectors for use in transformation of *Lactobacillus* (e.g., *L. plantarum*) include pAMβ1 and derivatives thereof (Renault et al., *Gene* 183:175, 1996) and O'Sullivan et al., *Gene* 137:227, 1993); pMBB1 and pHW800, a derivative of pMBB1 (Wyckoff et al. *Appl. Environ. Microbiol.* 62:1481, 1996); pMG1, a conjugative plasmid (Tanimoto et al., *J. Bacteriol.* 184:5800, 2002); pNZ9520 (Kleerebezem et al., *Appl. Environ. Microbiol.* 63:4581, 1997); pAM401 (Fujimoto et al., *Appl. Environ. Microbiol.* 67:1262, 2001); and pAT392 (Arthur et al., *Antimicrob. Agents Chemother.* 38:1899, 1994). Several plasmids from *Lactobacillus plantarum* have also been reported (e.g., van Kranenburg et al., *Appl. Environ. Microbiol.* 71: 1223, 2005). For example, expression of the 1-butanol biosynthetic pathway in *Lactobacillus plantarum* is described in WO 2007/041269.

Engineering Alcohol Tolerance

As already noted herein, attempts to produce aliphatic alcohol compounds by fermentation of producing organisms have generally been limited by the toxicity of the produced compounds. Butanol is particularly toxic; it is generally reported that concentrations of butanol above about 12-13 g/L result in profound cellular degradation. Thus, butanol production levels above 12-13 g/L have rarely been achieved through fermentation. Moreover, butanol production levels at or about this level have never been reported for a modified organism that does not naturally produce butanol.

Without wishing to be bound by any particular theory, we note that it has been proposed that aliphatic alcohols exert their toxicity through effects on cell membranes, on metabolism, and/or on the stability and/or conformation of cellular proteins (see, for example, Bowles et al., *Appl Environ. Microbiol.* 50:1165, 1985; Huang et al., *Appl. Environ. Microbiol.* 50:1043, 1985; Baer et al., *Appl. Environ Microbiol.* 55:2854, 1987; Lepage et al., *J. Gen. Microbiol.* 133: 103, 1987; Tomas et al., *Appl. Environ. Microbiol.* 69:4951, 2003). For example, it has been proposed that aliphatic alcohols can permeabilize the cell membrane. Such permeabilization may, among others things, allow leakage and/or passive flux of solutes (e.g., ATP, protons, ions, even macromolecules) across the membrane. Permeabilization may also disrupt the proton and/or electrical potential gradients across cell membranes. Alternatively or additionally, aliphatic alcohols may alter membrane fluidity and/or affect the three-dimensional structure and/or activity of membrane proteins.

Among other strategies, cells may achieve increased tolerance to aliphatic alcohols through altered membrane composition, increased efflux of toxic compounds (particularly aliphatic alcohols and/or their metabolites), altered metabolism to toxic compounds into non-toxic compounds, and/or induction of systems that counteract effects of toxic compounds (e.g., of stress response systems).

According to the present disclosure, in some embodiments, cells are engineered to show increased alcohol tolerance through application of a modification that alters expression and/or activity of one or more membrane components that participates in aliphatic alcohol resistance. In some embodiments, cells are engineered to show increased alcohol tolerance through application of a modification that alters expression and/or activity of one or more membrane components that participates in achieving efflux (i.e., out-transport) of one or more toxic compounds. In some embodiments, cells are engineered to show increased alcohol tolerance through application of a modification that alters expression or activity of one or more components that participates in metabolism of toxic compounds into less toxic (or non-toxic) compounds. In some embodiments, cells are engineered to show increased alcohol tolerance through application of a modification that alters expression or activity of one or more components of a stress response system.

According to the present disclosure, tolerance to aliphatic alcohols may be assessed through any of a variety of means. For example, in some embodiments, aliphatic alcohol compound $IC_{50}$ is determined (expected to increase with increasing tolerance). In some embodiments, carbohydrate utilization is monitored (expected to increase with increasing tolerance). In some embodiments, broth titer of a produced aliphatic alcohol is measured (expected to increase with increasing tolerance). In some embodiments, aliphatic alcohol yield is measured (expected to increase with increasing tolerance). In some embodiments, specific or volumetric productivity of a one or more aliphatic alcohols is evaluated (both expected to increase with increasing tolerance). Alternatively or additionally, attributes such as, for example, membrane fluidity (expected to decrease with increasing tolerance), ratio of saturated to unsaturated lipids in a membrane (expected to decrease with increasing tolerance), activity of membrane-bound ATP-ases (expected to increase with increasing tolerance), internal cellular pH (expected to increase with increasing tolerance), presence of a pH gradient across a cellular membrane (expected to be present under conditions of tolerance), activity of certain membrane proteins (expected to increase with increasing tolerance), presence of membrane potential (expected to be present under conditions of tolerance), degree of active transport across cellular membrane (expected to increase with increasing tolerance), etc. may be assessed. Those of ordinary skill in the art will readily appreciate a wide range of assays that can be employed and/or parameters that can be assessed in order to evaluate the aliphatic alcohol tolerance of a given cell (e.g., an engineered cell and/or a parental cell or other comparator cell) in accordance with the present disclosure.

In some particular embodiments of the present disclosure, a cell or organism to which an alcohol tolerance modification has been applied exhibits an increased aliphatic alcohol compound $IC_{50}$ as compared with an otherwise identical organism lacking the modification; in some embodiments, the aliphatic alcohol compound $IC_{50}$ is increased 5%, 10%, 20%, 30%, 40%, 50%, 60%, 70%, 80%, 90%, 100% or more. In some embodiments, a cell or organism to which an alcohol tolerance modification has been applied exhibits increased carbohydrate utilization as compared with an otherwise identical organism lacking the modification when grown in the presence of the same amount of aliphatic alcohol compound; in some cases the carbohydrate utilization is increased by 5%, 10%, 20%, 30%, 40%, 50%, 60%, 70%, 80%, 90%, 100% or more. In some embodiments, a cell or organism to which an alcohol tolerance modification has been applied exhibits increased production of at least one aliphatic alcohol compound as compared with an otherwise identical organism lacking the modification; in some embodiments, such increased production results in a broth titer of the produced at least one aliphatic alcohol compound that is 10%, 25%, 50%, 75%, 100% or more higher than that observed with an otherwise identical organism lacking the modification under comparable conditions, and/or such increased production results in a yield that is 10%, 25%, 50%, 75%, 100% or more higher than that observed with an otherwise identical organism lacking the modification under comparable conditions, and/or such increased production results in volumetric productivity that is 10%, 25%, 50%, 75%, 100% or more higher than that observed with an otherwise identical organism lacking the modification under comparable conditions, and/or such increased production results in a specific productivity increase of 10%, 25%, 50%, 75%, 100% or more higher than that observed with an otherwise identical organism lacking the modification under comparable conditions.

In some embodiments of the present disclosure, application of an alcohol tolerance modification involves application of a genetic modification—i.e., a change in the genetic information content in a cell. In some embodiments, such a genetic modification comprises altering (i.e., increasing or decreasing) expression or activity of one or more genetic elements (e.g., alcohol tolerance determinants) already present in the cell; in some embodiments, such a genetic modification comprises introducing one or more genetic elements into a cell, and/or removing one or more genetic elements from a cell. In some embodiments, such genetic elements encode or regulate one or more alcohol tolerance polypeptides; in some embodiments, such genetic elements consist of or comprise noncoding sequences. Representative examples of particular alcohol tolerance determinants for use in accordance with certain embodiments of the present invention include sequences found within the determinant sequences presented Tables 1-4, and particularly in Tables 1 and/or 2.

In some embodiments of the present disclosure, at least two alcohol tolerance determinants are utilized. For example, in some embodiments, at least two alcohol tolerance determinants from the determinant sequences in Tables 1 and/or 2 are utilized; in some embodiments, at least two alcohol tolerance determinants from the determinant sequences in Tables 3 and/or 4 are utilized; in some embodiments, at least one alcohol tolerance determinant from the determinant sequences in Tables 1 and/or 2 and at least one alcohol tolerance determinant from the determinant sequences in Tables 3 and/or 4 are utilized.

In some embodiments of the present disclosure, at least one alcohol tolerance determinant from the determinant sequences in Table 1A or Table 1B is utilized in combination with at least one determinant from the determinant sequences in Table 3.

In some embodiments, the present invention utilizes one or more alcohol tolerance determinants found within determinant sequences selected from determinant sequences provided in rows 20 (lp_1293), 21 (lp_1295 [mntH3], 34 (lp_2159), 35 (lp_2160), 36 (lp_2169), 37 (lp_2170), 44 (lp_2911), and/or 50 (lp_3193 [prs2A]) of Table 1A, and/or in any of Tables 2T, 2U, 2AH, 2AI, 2AJ, 2AK, 2AR, and/or 2AX and combinations thereof. In one or more of these embodiments, an alcohol tolerance determinant is utilized in combination with one or more alcohol tolerance determinants found in the determinant sequences of Tables 3 and/or 4. In some embodiments, the determinants found in determinant sequences of Tables 3 and/or 4 are determinants whose introduction into or activity in a cell increases alcohol tolerance (e.g., those found in determinant sequences found in rows 2 (groES), 3 (groEL), 5 (cfa1) and/or 8 (cfa2) of Table 3, or in any of Tables 4B, 4C, 4E and/or 4H). In some embodiments, the determinant found in determinant sequences of Tables 3 and/or 4 are determinants whose disruption or inhibition in a cell increases alcohol tolerance (e.g., those found in determinant sequences found in rows 1 (htrA), 4 (clpP), 6 (relA/spoT), 7 (hrcA), and/or 8 (cfa2) of Table 3, or in any of Tables 4A, 4D, 4F, 4G and/or 4H).

In some embodiments of the present disclosure, a genetic modification that increases tolerance to one or more aliphatic alcohol compounds comprises introduction of heterologous genetic sequences (e.g., alcohol tolerance determinant sequences) into a cell. In some embodiments, such heterologous genetic sequences are ones that are found in source cells (e.g., in nature or in other engineered cells) that show tolerance to one or more aliphatic alcohol compounds.

In some embodiments, desirable source cells or organisms from which genetic sequences are obtained for introduction into host cells applied in accordance with the present disclosure are characterized by one or more attributes such as (i) intrinsic tolerance to one or more aliphatic alcohol compounds; (ii) environmental niche (e.g., exposure to butane, butanol, etc); (iii) potential to biosynthesize one or more aliphatic alcohol compounds (e.g., butanol); (iv) availability of genomic sequence information, or at least sequence information of relevant genetic elements (e.g., genes encoding polypeptides that contribute to tolerance); (v) taxonomic proximity to host cells; and/or (vi) minimal biosafety issues (e.g., infectious potential, etc).

In some embodiments, a source cell or organism is characterized by genetic compatibility with the intended host organism (i.e., the intended recipient of the source organism genetic information).

In some embodiments of the present disclosure, application of an alcohol tolerance modification involves increasing expression or activity of one or more alcohol tolerance polypeptides. In some embodiments, the alcohol tolerance polypeptide is heterologous to the host cell; in some embodiments, it is endogenous to the host cell.

As described herein, suitable alcohol tolerance polypeptides for use in accordance with the present disclosure include, among others, polypeptides that alter membrane composition, that participate in transport of undesirable factors (e.g., toxic compounds) out of the cell or desirable factors into the cell, that participate in metabolism of toxic compounds within the cell, and/or that otherwise protect cells from toxicity of aliphatic alcohol compounds. In some embodiments, such alcohol tolerance polypeptides are encoded by one or more alcohol tolerance determinants sequences presented in Tables 1 and/or 3. Alternatively or additionally, such alcohol tolerance polypeptides are homologs of those encoded by one or more alcohol tolerance determinants presented in Tables 1 and/or 3 and/or are encoded by determinant sequence presented in Tables 2 and/or 4.

In some embodiments of the present disclosure, cells are engineered to alter expression and/or activity of at least two alcohol tolerance polypeptides. For example, in some embodiments, a cell is separately or simultaneously engineered (e.g., by introduction of genetic elements [e.g., genes] encoding relevant polypeptides) to express (and/or activate) at least one alcohol tolerance polypeptide encoded by an alcohol tolerance determinant in Table 1 or 2 and also at least one alcohol tolerance polypeptide encoded by an alcohol tolerance determinant in determinant sequences of Tables 3 or 4. References to a Table herein include all subparts of the Table, unless otherwise noted. For example, "Table 1" includes both Table 1A and Table 1B.

One particular class of alcohol tolerance polypeptides whose expression or activity may desirably be altered by application of an alcohol tolerance modification in accordance with the present disclosure includes polypeptides (e.g., heat shock proteins) that participate in stress responses. In certain embodiments of the disclosure, modifications that alter expression or activity of such heat shock proteins are combined with one or more other alcohol tolerance modifications. Stress response polypeptides typically bind normative states of other proteins and assist in proper folding by recognizing exposed hydrophobic surfaces on normative protein species, which ultimately end up buried when the protein is in its properly folded, functional state. Stress response polypeptides typically form noncovalent interactions with the hydrophobic regions of misfolded proteins, thereby stabilizing them from irreversible multimeric aggregation, misfolding of nascent polypeptides, unfolding during exposure to stress and eventual degradation. The stabilized and properly folded proteins are therefore available to perform their cellular function(s).

The major established classes of heat shock proteins are the 90-kDa heat shock protein (HSP90), the 60-kDa heat shock protein (HSP60; including GroEL), the 70-kDa heat shock protein (HSP70; DnaK in *E. coli*) and 40-kDa heat shock protein (HSP40 or the DnaJ family). Another important protein involved in the heat shock response is a co-chaperone of HSP60 called chaperonin 10 (cpn10; GroES in *E. coli*).

DnaK operates by binding to nascent polypeptide chains on ribosomes, preventing premature folding, misfolding, or aggregation. DnaK is composed of two major functional domains. The $NH_2$-terminal ATPase domain and the COOH-terminal domain. The $NH_2$-terminal ATPase domain binds ADP and ATP and hydrolyzes ATP, whereas the COOH-terminal domain is responsible for polypeptide binding. DnaJ is a co-chaperone for DnaK. GrpE, another chaperone involved in the DnaKJ folding pathway, facilitates exchange between ADP and ATP. In many organisms, the genes for DnaK, DnaJ and GrpE are organized as an operon (the dnaK operon).

The GroEL/ES family of proteins binds to partially folded intermediates, preventing their aggregation, and facilitating folding and assembly. In addition, it has been suggested that GroEL, with the assistance of its co-chaperonin GroES, may allow misfolded structures to unfold and refold. The GroEL of *E. coli* consists of 14 identical subunits in two-stacked heptameric rings, each containing a central cavity. The size of the GroEL/ES complex cavity suggests that proteins of up to 50-60 kDa can be handled by this chaperone system. The genes for GroEL/ES are also typically organized as an operon (the groE operon). In *B. subtilis*, expression of the dnaK and groE operons is negatively regulated by a repressor protein through a CIRCE DNA element (a palindromic sequence between the promoter and the initiation codon). For example, in *B. subtilis*, inactivation of this repressor protein (HrcA), whose activity is modulated by GroEL/ES, results in constitutive expression of the two HSP operons, and this enhances the folding and secretory production of proteins which are difficult to fold.

In some embodiments, heat shock proteins, or other stress-related polypeptides are useful alcohol tolerance polypeptides. In certain embodiments, stress-related polypeptides that are heterologous to the host cell are employed; in some embodiments, stress-related polypeptides are utilized that are found in a source cell other than *E. coli*, *B. subtilis*, and/or *C. acetobutylicum*.

In some particular embodiments of the present disclosure, application of an alcohol tolerance modification involves increasing expression or activity of one or more alcohol tolerance polypeptides selected from the group consisting of a calcineurin-like phosphoesterase polypeptide, a cation transport protein (mntH3 related) polypeptide, a transcription regulator (lp_2159 related) polypeptide, an lp_2160 related polypeptide, an lp_2169 related polypeptide, a phosphoglycerate mutase polypeptide, a CAAX protease polypeptide, a peptidylprolyl isomerase (prs2A related) polypeptide, and combinations thereof, optionally in combination with increasing expression or activity of one or more of a GroES polypeptide, a GroEL polypeptide, a cyclopropane-fatty-acyl-phospholipid synthase #1 (cfa1) polypeptide, a cyclopropane-fatty-acyl-phospholipid synthase #2 (cfa2) polypeptide, and combinations thereof and/or with decreasing expression and/or activity of one or more of a serine protease HtrA polypeptide, an ATP-dependent Clp protease proteolytic subunit polypeptide, a GTP pyrophosphokinase (relA/spoT) polypeptide, a heat-inducible transcription repressor (hrca) polypeptide, and/or a cyclopropane-fatty-acyl-phospholipid synthase #2 (cfa2) polypeptide.

Biosynthesis of Aliphatic Alcohols

As discussed herein, a variety of organisms are known that produce one or more aliphatic alcohol compounds; metabolic pathways that operate in such organisms are well understood.

For example, FIG. 1 presents a schematic of a representative metabolic process that produces certain aliphatic alcohol compounds (e.g., ethanol, 1-butanol). This particular pathway is utilized, for example, in many strains of *C. acetobutylicum*.

In the pathway illustrated in FIG. 1, aliphatic alcohol compounds are produced from acetyl-CoA. In the production of ethanol, acetyl-CoA is reduced to acetaldehyde by the action of an aldehyde dehydrogenase, and then acetaldehyde is reduced to ethanol through the action of an alcohol dehydrogenase. In the production of butanol (in this case, 1-butanol), acetyl-CoA is first converted to acetoacetyl-CoA through action of acetyl-CoA acetyltransferase (a thiolase) that catalyzes the condensation of two acetyl-CoA molecules to produce acetoacetyl-CoA. Acetoacetyl-CoA is then converted to 3-hydroxybutyryl-CoA by 3-hydroxybutyryl-CoA dehydrogenase; 3-hydroxybutyryl-CoA is converted to crotonyl-CoA by crotonase; crotonyl-CoA is converted to butyryl-CoA by butyryl-CoA dehydrogenase; butyryl-CoA is converted to butyraldehyde by (butyrl)aldehyde dehydrogenase; and butyraldehyde is converted to 1-butanol by the alcohol dehydrogenase, butanol dehydrogenase. Each of the enzymes depicted in FIG. 1 as participating in production of ethanol and/or 1-butanol is an aliphatic alcohol biosynthesis polypeptide according to the present disclosure.

FIG. 1 also illustrates certain "competing reactions" that can occur and can divert carbon flow away from production of one or more aliphatic alcohol compounds. For example, butyryl-CoA can be diverted away from butanol production (and toward butyrate production) by action of phosphotransbutyrylase (optionally followed by butyrate kinase); acetoacetyl-CoA can be diverted away from production of butanol (and toward production of acetone) by action of CoA tranferase (optionally followed by acetoacetate decarboxylase); and acetyl-CoA can be diverted away from production of either butanol or ethanol (and toward production of acetate) by action of phosphotransacetylase (optionally followed by acetate kinase), and acetyl-CoA can be diverted away from production of butanol (and toward production of ethanol) by action of aldehyde dehydrogenase (optionally followed by alcohol dehydrogenase). Indeed, FIG. 1 is intended only as a representative illustration and not as an exhaustive depiction of all relevant metabolic pathways in a cell.

Those of ordinary skill will readily appreciate any of a variety of other competing reactions that may occur in any particular cell. Enzymes that participate in such competing reactions are considered aliphatic alcohol biosynthesis competitor polypeptides as described herein. In some embodiments of the present disclosure, a modification is applied that reduces level or activity of one or more aliphatic alcohol biosynthesis competitor polypeptides, such that higher levels of aliphatic alcohol compounds, or of a particular aliphatic alcohol compound (e.g., relative to other compounds, for example other aliphatic alcohol compounds) are produced.

Polypeptides that catalyze different steps of the pathway illustrated in FIG. 1 have been identified in a variety of source organisms; in many cases, their genes have been cloned. For example, international patent application number PCT/US2006/038001 (publication number WO 2007/041269) describes a variety of polypeptides and genes, from a number of source organisms that catalyze steps involved in butanol synthesis. Representative particular genes are presented in Table 2 of PCT/US2006/038001 (WO 2007/041269).

Figure 3:
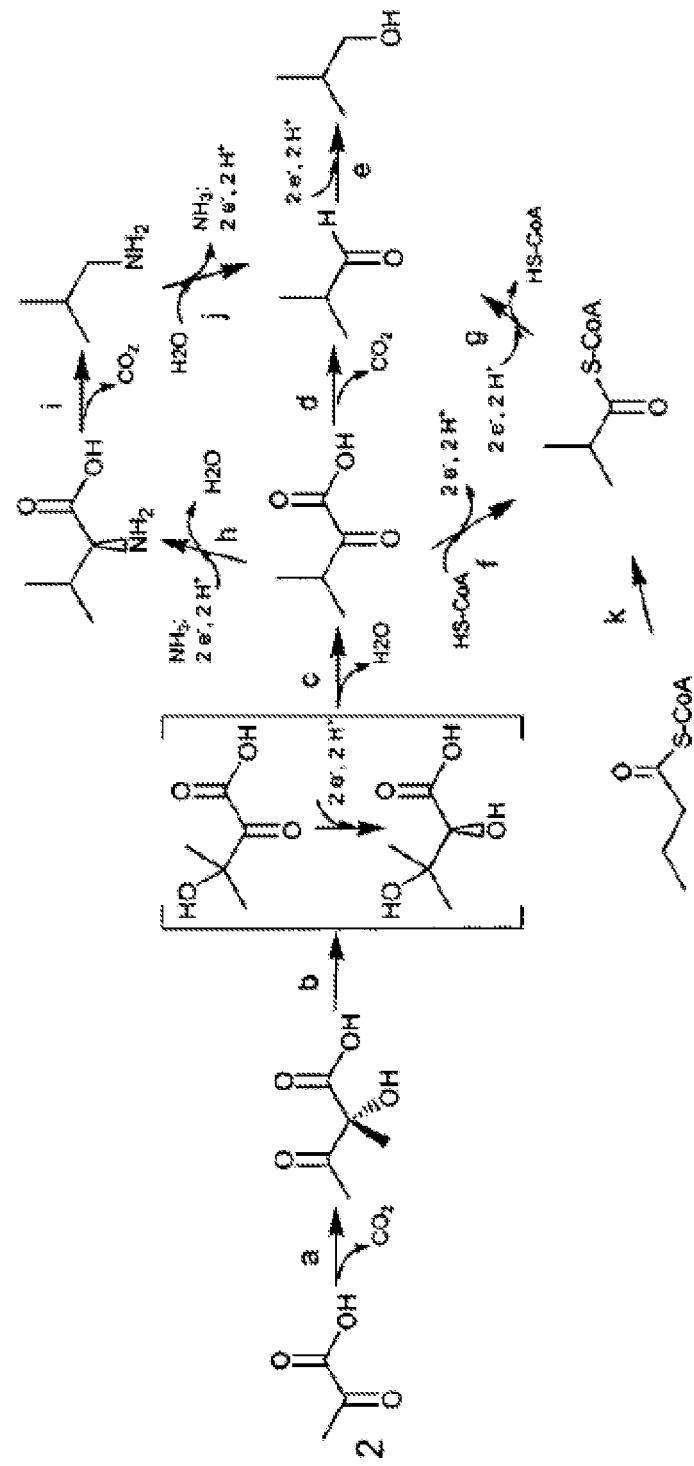
FIG. 3 illustrates certain metabolic pathways that operate to produce a particular aliphatic alcohol compound, isobutanol. In particular.

FIG. 3 illustrates certain metabolic pathways that operate to produce a particular aliphatic alcohol compound, isobutanol. In particular, FIG. 3 shows four different isobutanol biosynthetic pathways. The steps labeled "a", "b", "c", "d", "e", "f", "g", "h", "i", "j" and "k" represent the substrate to product conversions described below.

Three of the isobutanol biosynthetic pathways depicted in FIG. 3 comprise conversion of pyruvate to isobutanol via a series of enzymatic steps. The preferred isobutanol pathway (FIG. 3, steps a to e), comprises the following substrate to product conversions:

a) pyruvate to acetolactate, as catalyzed for example by acetolactate synthase, b) acetolactate to 2,3-dihydroxyisovalerate, as catalyzed for example by acetohydroxy acid isomeroreductase, c) 2,3-dihydroxyisovalerate to α-ketoisovalerate, as catalyzed for example by acetohydroxy acid dehydratase, d) α-ketoisovalerate to isobutyraldehyde, as catalyzed for example by a branched-chain keto acid decarboxylase, and e) isobutyraldehyde to isobutanol, as catalyzed for example by, a branched-chain alcohol dehydrogenase.

This pathway combines enzymes known to be involved in well-characterized pathways for valine biosynthesis (pyruvate to α-ketoisovalerate) and valine catabolism (α-ketoisovalerate to isobutanol). Since many valine biosynthetic enzymes also catalyze analogous reactions in the isoleucine biosynthetic pathway, substrate specificity can be an important consideration in selecting the gene sources. In some embodiments, genes of interest for the acetolactate synthase enzyme are those from *Bacillus* (alsS) and *Klebsiella* (budB). These particular acetolactate synthases are known to participate in butanediol fermentation in these organisms and show increased affinity for pyruvate over ketobutyrate (Gollop et al., *J. Bacteriol.* 172(6):3444, 1990; Holtzclaw et al., *J. Bacteriol.* 121(3):917, 1975).

The second and third steps are catalyzed by acetohydroxy acid reductoisomerase and dehydratase, respectively. These enzymes have been characterized from a number of sources, such as for example, *E. coli* (Chunduru et al., *Biochemistry* 28(2):486, 1989; Flint et al., *J. Biol. Chem.* 268(29):14732, 1993).

The final two steps of this isobutanol pathway are known to occur in yeast, which can use valine as a nitrogen source and, in the process, secrete isobutanol. α-ketoisovalerate can be converted to isobutyraldehyde by a number of keto acid decarboxylase enzymes, such as for example pyruvate decarboxylase. In some embodiments, a decarboxylase with decreased affinity for pyruvate is utilized in order to reduce or prevent routing of pyruvate away from isobutanol production. At least two such enzymes are known in the art (Smit et al., *Appl. Environ. Microbiol.* 71(1):303, 2005; de la Plaza et al., *FEMS Microbiol. Lett.* 238(2):367, 2004). Both enzymes are from strains of *Lactococcus lactis* and have a 50-200-fold preference for ketoisovalerate over pyruvate. Also, a number of aldehyde reductases have been identified in yeast, many with overlapping substrate specificity. Those known to prefer branched-chain substrates over acetaldehyde include, but are not limited to, alcohol dehydrogenase VI (ADH6) and Ypr1p (Larroy et al., *Biochem. J.* 361 (Pt 1):163, 2002; Ford et al., *Yeast* 19(12):1087, 2002), both of which use NADPH as an electron donor. An NADPH-dependent reductase, YqhD, active with branched-chain substrates has also been identified in *E. coli* (Sulzenbacher et al., *J. Mol. Biol.* 342(2):489, 2004).

Another pathway for converting pyruvate to isobutanol comprises the following substrate to product conversions (FIG. 3, steps a, b, c, f, g, e):

a) pyruvate to acetolactate, as catalyzed for example by acetolactate synthase, b) acetolactate to 2,3-dihydroxyisovalerate, as catalyzed for example by acetohydroxy acid isomeroreductase, c) 2,3-dihydroxyisovalerate to α-ketoisovalerate, as catalyzed for example by acetohydroxy acid dehydratase, f) α-ketoisovalerate to isobutyryl-CoA, as catalyzed for example by a branched-chain keto acid dehydrogenase, g) isobutyryl-CoA to isobutyraldehyde, as catalyzed for example by an acylating aldehyde dehydrogenase, and e) isobutyraldehyde to isobutanol, as catalyzed for example by, a branched-chain alcohol dehydrogenase.

The first three steps in this pathway (a,b,c) are the same as those described above. The α-ketoisovalerate is converted to isobutyryl-CoA by the action of a branched-chain keto acid dehydrogenase. While yeast typically can only use valine as a nitrogen source, many other organisms (both eukaryotes and prokaryotes) can use valine as the carbon source as well. These organisms have branched-chain keto acid dehydrogenase (Sokatch et al. *J. Bacteriol.* 148(2):647, 1981), which generates isobutyryl-CoA. Isobutyryl-CoA may be converted to isobutyraldehyde by an acylating aldehyde dehydrogenase. Dehydrogenases active with the branched-chain substrate have been described in at least *Leuconostoc* and *Propionibacterium* (Kazahaya et al., *J. Gen. Appl. Microbiol.* 18:43, 1972; Hosoi et al., *J. Ferment. Technol.* 57:418, 1979). However, it is also possible that acylating aldehyde dehydrogenases known to function with straight-chain acyl-CoAs (i.e. butyryl-CoA), may also work with isobutyryl-CoA. The isobutyraldehyde is then converted to isobutanol by a branched-chain alcohol dehydrogenase, as described above for the first pathway.

Another pathway for converting pyruvate to isobutanol comprises the following substrate to product conversions (FIG. 3, steps a, b, c, h, i, j, e):

a) pyruvate to acetolactate, as catalyzed for example by acetolactate synthase, b) acetolactate to 2,3-dihydroxyisovalerate, as catalyzed for example by acetohydroxy acid isomeroreductase, c) 2,3-dihydroxyisovalerate to α-ketoisovalerate, as catalyzed for example by acetohydroxy acid dehydratase, h) α-ketoisovalerate to valine, as catalyzed for example by valine dehydrogenase or transaminase, i) valine to isobutylamine, as catalyzed for example by valine decarboxylase, j) isobutylamine to isobutyraldehyde, as catalyzed for example by omega transaminase, and e) isobutyraldehyde to isobutanol, as catalyzed for example by, a branched-chain alcohol dehydrogenase.

The first three steps in this pathway (a, b, c) are the same as those described above.

This pathway involves the addition of a valine dehydrogenase or a suitable transaminase. Valine (and or leucine) dehydrogenase catalyzes reductive amination and uses ammonia; $K_m$ values for ammonia are in the millimolar range (Priestly et al., Biochem J. 261(3):853, 1989; Vancura et al., *J. Gen. Microbiol.* 134(12):3213, 1988; Zink et al., *Arch. Biochem. Biophys.* 99:72, 1962; Sekimoto et al. *J. Biochem* (Japan) 116(1):176, 1994). Transaminases typically use either glutamate or alanine as amino donors and have been characterized from a number of organisms (Lee-Peng et al., *J. Bacteriol.* 139(2):339, 1979; Berg et al., *J. Bacteriol.* 155(3): 1009, 1983). An alanine-specific enzyme may be desirable, since the generation of pyruvate from this step could be coupled to the consumption of pyruvate later in the pathway when the amine group is removed (see below).

The next step is decarboxylation of valine, a reaction that occurs in valanimycin biosynthesis in *Streptomyces* (Garg et al., *Mol. Microbiol.* 46(2):505, 2002). The resulting isobutylamine may be converted to isobutyraldehyde in a pyridoxal 5'-phosphate-dependent reaction by, for example, an enzyme of the omega-aminotransferase family. Such an enzyme from *Vibrio fluvialis* has demonstrated activity with isobutylamine (Shin et al., *Biotechnol. Bioeng.* 65(2):206, 1999). Another omega-aminotransferase from *Alcaligenes denitrificans* has been cloned and has some activity with butylamine (Yun et al., *Appl. Environ. Microbiol.* 70(4):2529, 2004). In this direction, these enzymes use pyruvate as the amino acceptor, yielding alanine. As mentioned above, adverse affects on the pyruvate pool may be offset by using a pyruvate-producing transaminase earlier in the pathway. The isobutyraldehyde is then converted to isobutanol by a branched-chain alcohol dehydrogenase, as described above for the first pathway.

The fourth isobutanol biosynthetic pathway depicted in FIG. 3 comprises the substrate to product conversions shown as steps k, g, e of that Figure. A number of organisms are known to produce butyrate and/or butanol via a butyryl-CoA intermediate (Dune et al., *FEMS Microbiol. Rev.* 17(3):251, 1995; Abbad-Andaloussi et al., *Microbiology* 142(5):1149, 1996). Isobutanol production may be engineered in these organisms by addition of a mutase able to convert butyryl-CoA to isobutyryl-CoA (FIG. 3, step k). Genes for both subunits of isobutyryl-CoA mutase, a coenzyme $B_{12}$-dependent enzyme, have been cloned from a *Streptomycete* (Ratnatilleke et al., *J. Biol. Chem.* 274(44):31679, 1999). The isobutyryl-CoA is converted to isobutyraldehyde (step g in FIG. 3), which is converted to isobutanol (step e in FIG. 3).

Those of ordinary skill are therefore aware of a variety of biosynthetic pathways that may be employed and/or engineered for the production of isobutanol according to the present disclosure. Furthermore, those of ordinary skill will be able to utilize publicly available sequences to construct and/or otherwise utilize such pathways. Representative such sequences (gene sequences) can be found, for example, in Table 2 of US patent application 2007/0092957.

Production of Aliphatic Alcohol Compounds

Aliphatic alcohol compounds can be produced by cultivating engineered microorganisms as described herein.

In general, cells engineered as described herein are grown in the presence of a suitable carbon source and other nutrients, under appropriate growth conditions. In some embodiments, modified cells are grown under aerobic conditions; in some embodiments, modified cells are grown under anaerobic conditions. As is known in the art, conditions under which cells having the ability to produce a particular compound are grown can often influence the amount of compound produced and/or the timing of its production. For example, it is known that factors such as temperature, pH, carbon source, availability of certain cofactors, growth rate, etc. can affect the metabolic state of cultured microorganisms, and therefore can alter production of particular compounds of interest.

For example, it is known that certain *C. acetobutylicum* strains have three different basic metabolic states that can be induced by changes in culture conditions. In particular, these strains have an "acidogenic" state characterized by production of acetic and butyric acids, a "solventogenic" state characterized by production of acetone, butanol, and ethanol, and an "alcohologenic" state characterized by production of butanol and ethanol. The acidogenic state is observed when these strains are grown under conditions of neutral pH with glucose as a carbon source and/or when these strains are grown under conditions of low ATP availability (e.g., under carbon limitation); the solventogenic state is observed when these strains are grown at low pH with glucose as a carbon source and/or when strains are grown under conditions of high ATP availability (e.g., under carbon-sufficient conditions and/or at low growth rates); and the alcohologenic state is observed when these strains are grown at neutral pH under conditions of high NAD(P)H availability (e.g., due to lowered electron flow toward molecular-hydrogen production, for example by decreasing hydrogenase activity as occurs under conditions of iron limitation, in the presence of carbon monoxide, and/or in the presence of artificial electron carriers such as viologen or neutral red; due to use of a more reduced substrate than glucose [e.g., use of glycerol]; etc). In some embodiments of the present disclosure, one or more aliphatic alcohol compounds is produced by growth of a *C. acetobutylicum* strain in its solventogenic or alcohologenic state.

In general, appropriate carbon sources for use in accordance with the present disclosure include, but are not limited to monosaccharides (e.g., fructose, glucose, etc), oligosaccharides (e.g., lactose, sucrose, etc), polysaccharides (e.g., cellulose, starch, etc), single carbon substrates (e.g., carbon dioxide, methanol, etc) and mixtures thereof. Particular sugar carbon sources of interest include, for example, fructose, glycerol, glucose, galactose, dextrose, and sucrose. Those of ordinary skill in the art will appreciate that the source of carbon may be provided by way of pure material or through complex or crude mixtures including, for example, cheese whey permeate, cornsteep liquor, sugar beet molasses, barley malt, etc.

Those of ordinary skill in the art are also aware of a variety of different nitrogen sources (e.g., ammonium sulfate, proline, sodium glutamate, soy acid hydrolysate, yeast extract-peptone, yeast nitrogen base, corn steep liquor, etc, and combinations thereof) that can be utilized in accordance with the present disclosure.

In some embodiments, cells are grown via batch or fed-batch fermentation; in some embodiments, cells are grown via continuous feed fermentation.

In general, classical batch fermentation typically utilizes a closed system where the composition of the medium is set at the beginning of the fermentation and is not subject to artificial alterations during the fermentation. Thus, at the beginning of the fermentation the medium is inoculated with the desired organism or organisms, and fermentation is permitted to occur. In some embodiments, no additions are made to the system once fermentation has begun. In some embodiments, additions are made, for example, of salts, etc., and/or of factors that modulate pH and/or oxygen concentration. In many embodiments, however, no carbon source additions are made.

In many batch fed fermentation embodiments, the metabolite and biomass compositions of the system change constantly up to the time that fermentation is stopped. Within batch cultures, cells often pass through a static lag phase to a high growth log phase and finally to a stationary phase where growth rate is diminished or halted. If untreated, cells in the stationary phase will eventually die. Cells in log phase are often responsible for the bulk of production of relevant compounds (e.g., aliphatic alcohol compounds and/or intermediates).

One variation on the standard batch system is the fed-batch system. In fed-batch fermentations, substrate is added in increments as the fermentation progresses. Fed-batch systems are particularly useful when catabolite repression is apt to inhibit metabolism of the cells and/or where it is desirable to have limited amounts of substrate in the medium. Measurement of actual amounts of a particular substrate can be performed, often by indirect assessment, for example through measurement of changes in factors such as pH, dissolved oxygen, and the partial pressure of gases such as $CO_2$. Batch and fed-batch fermentation protocols are well known in the art.

Continuous fermentation processes typically utilize an open system where a defined fermentation medium is added continuously to a bioreactor, and an equal amount of conditioned medium is removed for processing. Continuous fermentation can maintain cultures at a constant high density where cells are primarily in log phase growth.

Continuous fermentation allows for the modulation of one factor or any number of factors that affect cell growth and/or production of desired product (e.g., aliphatic alcohol compound). For example, in some embodiments, a particular nutrient is maintained at limiting levels and other factors are permitted to fluctuate. In some embodiments, a number of factors affecting growth can be simultaneously or sequentially altered continuously; cell concentration (e.g., measured by medium turbidity) may optionally be kept constant.

In some embodiments, a continuous system is operated at steady state growth, so that cell loss that is concomitant with medium removal is balanced against the cell growth rate. Methods of continuous fermentation, including methods of modulating nutrients and growth factors, and for maximizing rate and/or extent of production of a desired product (e.g., one or more aliphatic alcohol compounds) are known in the art.

In some embodiments, inventive modified cells are grown in a multi-phase feeding protocol, for example in which different phases are designed to induce different metabolic states. In some embodiments, inventive modified cells are grown in a multi-phase feeding protocol, for example in which some phases are continuous and some are batch fed (see, for example, U.S. Pat. No. 5,063,156).

In some embodiments, inventive modified cells are cultivated at constant temperature (e.g., between about 20-40, or 20-30 degrees, including for example at about 20, 20.5, 21, 21.5, 22, 22.5, 23, 23.5, 24, 24.5, 25, 25.5, 26, 26.5, 27, 27.5, 28, 28.5, 29, 29.5, 30° C. or above, typically within the range of about 35-40° C.) and/or pH (e.g., within a range of about 4-7.5, or 4-6.5, including at about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5 or above, typically within the range of about 5.0-9.0, and often with the range of about 6.0-8.0); in other embodiments, temperature and/or pH may be varied during the culture period, either gradually or in a stepwise fashion.

In some embodiments of the present disclosure, asporogenic strains are utilized, particularly of C. acetobutylicum, for example as described in U.S. Pat. No. 5,063,156.

Isolation of Aliphatic Alcohol Compounds

Aliphatic alcohol compounds produced as described herein may be isolated using any of a variety of known techniques. For example, solids may be removed from the fermentation medium, e.g., by centrifugation, filtration, decantation, etc. Techniques such as distillation, gas stripping, liquid-liquid extraction, membrane-based separation, etc. may be employed to isolate one or more aliphatic alcohol compounds.

Those of ordinary skill in the art will be well aware of the advantages and disadvantages of different techniques in different situations. To give one particular example, 1-butanol forms a low boiling point, azeotropic mixture with water, so that distillation generally can only be used to separate the mixture up to its azeotrophic composition. However, distillation may be used in combination with one or more other separation techniques to obtain separation around the azeotrope. Exemplary such techniques include, for example, decantation, liquid-liquid extraction, adsorption, pervaporation, membrane-based techniques, etc. Alternatively or additionally, 1-butanol may be isolated using azeotropic distillation with an entrainer (see, for example, Doherty & Malone, *Conceptual Design of Distillation Systems*, McGraw Hill, New York, 2001).

Uses of Aliphatic Alcohol Compounds

Aliphatic alcohol compounds produced and/or isolated as described herein may be utilized as and/or incorporated into any of a variety of commercial products. To give but a few examples, such aliphatic alcohol compounds may be employed as or in transport fuels, solvents, swelling agents, brake fluid, extractants, cement additives, ore flotation agents, melamine formaldehyde resins, etc.

In certain embodiments, the aliphatic alcohol compound is butanol (e.g., 1-butanol). Butanol may be employed as a transport fuel or fuel additive, bulk chemical precursor for production of acrylate and methacrylate esters, glycol ethers, butyl acetate, butylamines, and amino resins. It may also be useful for the production of adhesives/scalants, alkaloids, antibiotics, camphor, deicing fluid, dental products, detergents, elastomers, electronics, emulsifiers, eye makeup, fibers, flocculants, flotation aids (e.g., butyl xanthate), hard-surface cleaners, hormones and vitamins, hydraulic and brake fluids, industrial coatings, lipsticks, nail care products, paints, paint thinners, perfumes, pesticides, plastics, printing ink, resins, safety glass, shaving and personal hygiene products, surface coatings, super absorbents, synthetic fruit flavoring, textiles, as mobile phases in paper and thin-layer chromatography, as oil additive, as well as for leather and paper finishing.

EXEMPLIFICATION

All basic molecular biology and DNA manipulation procedures described herein are generally performed according to Sambrook et al., or Ausubel et al., (Sambrook J, Fritsch E F, Maniatis T (ed.) 1989, *Molecular Cloning: A Laboratory Manual*, Cold Spring Harbor Laboratory Press: New York; Ausubel F M, Brent R, Kingston R E, Moore D D, Seidman J G, Smith J A, Struhl K (ed.) 1998 *Current Protocols in Molecular Biology*, Wiley: New York).

Example 1

Oligonucleotide Primers Used in Plasmid Construction

Table 7 lists oligonucleotide sequences used in the plasmid construction described in the examples below.

TABLE 7

| Primer | SEQ ID NO: | Sequence |
|---|---|---|
| 5174 | 1 | 5'-TTTGGATCCGATTCTATTGTTAGCTAT TTTGGGTGG-3' |
| 5175 | 2 | 5'-AAAGTCGACATCGTGGTATTAGTGATG CAAAGAAAGG-3' |
| 5433 | 3 | 5'-AACGGCCGAAGGATTATTCGGCTGGTT GAGACGTTAAA-3' |
| 5434 | 4 | 5'-AACGGCCGAAATAACACCTTAAGTCTA GCACCACCCGC-3' |

TABLE 7-continued

| Primer | SEQ ID NO: | Sequence |
|---|---|---|
| 5435 | 5 | 5'-CTCCAGTAAGAATATTTGCATTGTGTATC-3' |
| 5436 | 6 | 5'-AAAAAGGCCCTTATAACTTACAAATAACCCC-3' |
| 5437 | 7 | 5'-AAAAAAGCGGCCGCTCTTTATTCTTCAACTAAAGCACC-3' |
| 5438 | 8 | 5'-AAAAAAGCGGCCGCAATGTATTTAGAAAAATAAACAAATAGG-3' |
| 5450 | 9 | 5'-AAAAAGCGGAAGAGCGAGGGCGGAGTTGTTGACAGCCGAGGTACCATGTGGTATAATCCCGAGTGTGGAATTGTGAGCGGATAACA-3' |
| 5451 | 10 | 5'-GTTTTCGAGGGGTTATTTGTAAGTTATAAGGCCCT-3' |
| 5452 | 11 | 5'-AAAAAGCGGAAGAGCGAGGGCGGAGTTG-3' |

Example 2

Description of *L. plantarum* Strains and Plasmids

Table 8 describes some of the *L. plantarum* strains (including the plasmids they contain) used in subsequent examples.

TABLE 8

| *L. plantarum* Strain | Plasmid | Plasmid Description |
|---|---|---|
| PNO512 | None | Wild Type Host CONTROL |
| MS362 | pMPE6 | Vector Only CONTROL |
| MS379 | pMPE41 | A plasmid construct for overexpression of open reading frame (1p_3193) from *L. plantarum* BAA-793. This ORF encodes the Prs2A protein foldase. |
| MS354 | p5AE4-1 | Randomly cloned, 1960-bp fragment of *L. plantarum* BAA-793 genomic DNA cloned in vector pMPE6. Fragment includes open reading frame (ORF) 1p_2911 which encodes a putative membrane bound protein that is predicted to be a member of the CAAX protease family. Also included on the fragment is 104 bp of DNA upstream of 1p_2911 and 655 by of downstream sequence. The p5AE4-1 plasmid insert sequence is shown in Table 1B. |
| MS356 | p5AE0-4 | A randomly cloned, 3240-bp fragment of *L. plantarum* BAA-793 genomic DNA cloned in vector pMPE6. Fragment includes 2 complete ORFs; 1p_1295 which encodes a putative cation transport protein and 1p_1293 which encodes a conserved hypothetical protein that shares similarity to a group of phosphoesterases. The p5AE0-4 plasmid insert sequence is shown in Table 1B. |
| MS359 | p5AE0-14 | A randomly cloned, 2341-bp fragment of *L. plantarum* BAA-793 genomic DNA cloned in vector pMPE6. Fragment includes 2 complete ORFs; 1p_2159 which encodes a predicted transcriptional regulator that shows homology to a group of sphingosine kinases, and 1p_2160 which encodes a small, 66 amino acids, hypothetical protein that shows no significant homology with proteins of known function. The p5AE0-14 plasmid insert sequence is shown in Table 1B. |
| MS364 | p5AE4-24 | A randomly cloned, 2477-bp fragment of *L. plantarum* BAA-793 genomic DNA cloned in vector pMPE6. Fragment includes 2 complete open reading frames (ORFs); 1p_2170 which encodes a predicted phosphoglycerate mutase and 1p_2169 which encodes a hypothetical protein of unknown function. Also included on the insert is a portion (1001 bp) of the 5'-end of recD. The p5AE4-24 plasmid insert sequence is shown in Table 1B. |

Example 3

Construction of *Lactobacillus plantarum* Plasmid Cloning Vector

The purpose of this example is to describe the construction a cloning vector that can be stably propagated in both *Escherichia coli* and *Lactobacillus plantarum*. Such a vector allows genes cloned as "inserts" within the vector multiple cloning site (MCS) to be expressed via an upstream promoter. Genes cloned as inserts will also be subject to increased expression as a result of their increased copy number which is due to the fact that multiple copies of a plasmid are replicated within each host cell.

A series of shuttle vectors that replicate in both *E. coli* and *L. plantarum* were constructed. pMPE1 was constructed by amplifying a 0.7 kb fragment of pLF1, a naturally occurring plasmid in *L. plantarum* strain ATCC 14917. The 0.7 kb fragment containing the predicted minimum sequence required for replication of pLF1 was amplified using primers 5436 and 5435. This sequence was identified by sequence comparisons with p256 a closely related plasmid for which the minimum required sequence for replication had been experimentally determined (Sorvig et al. 2005. Microbiology 151:421-431). The pLF1 PCR product was digested with EagI and ligated to a 2.6 kb DraI fragment obtained from pMK4 (Sullivan et al. 1984. Gene 29:21-26), a *Bacillus* shuttle vector obtained from the *Bacillus* Genetic Stock Center (Ohio State University). The DraI fragment contained the pMK4 *E. coli* origin of replication (pUC-ori), its multiple cloning site (MCS) and its chloramphenicol resistance gene. The resulting plasmid, designated pMPE1, was tested by transforming it into *L. plantarum* strain BAA-793 by electroporation where it was found to replicate and to allow selection by demanding resistance to chloramphenicol.

pMPE1 was modified to improve its stability in *L. plantarum* by the addition of a toxin/antitoxin stability cassette. The cassette was PCR amplified from pLF1 using the primers 5437 and 5438. The resulting 0.8 kb PCR product was digested with Eco0109I and then ligated with pMPE1 which had been digested with Eco0109I and DraI (a 2904 by fragment). The resulting plasmid was designated pMPE5. Stability tests subsequently showed that pMPE5 was significantly more stable than pMPE1 in *L. plantarum* (100% vs. ~75% after 80 generations of growth without selection respectively).

pMPE5 was modified to replace the lacZ promoter upstream of its MCS with a promoter that more closely resembled an *L. plantarum* native promoter. To do this, pMPE5 was cut with Eco0109I and SapI which removed the 5' end of the lacZα and the lacZ promoter from the vector. Using the PCR primers 5451, 5450, and 5452 in a 2 step PCR protocol, a PCR product containing the 5' portion of lacZα, a ribosomal binding site (RBS) and an *L. plantarum* rRNA promoter was generated using pMPE5 as a PCR template. The PCR product was digested with Eco0109I and SapI and ligated into the previously digested pMPE5 fragment producing pMPE6.

Example 4

Construction of a *Lactobacillus plantarum* Knock-Out Vector

The purpose of this example is to describe the construction of a plasmid vector that allows the inactivation of *L. plantarum* chromosomal genes via single crossover recombination. This technique has been described for many bacteria including *L. plantarum* (Leer et al. 1993. Mol. Gen. Genet. 239:269-272).

pMPE3 was constructed as a knockout vector for use in *L. plantarum*. pMPE3 was constructed by amplifying a 2.45 kb fragment of pMK4 using the primers 5433 and 5434. The amplified fragment contained the multiple cloning site, lacZα, pUC-ori and chloramphenicol resistance gene from pMK4. The amplified fragment was digested with NotI and then circularized by ligation, generating pMPE3. Because pMPE3 does not replicate in *L. plantarum*, portions of genes can be cloned into the MCS of the plasmid and the resulting recombinant plasmid can then be transformed into *L. plantarum* by electroporation. Selection for transformants that are resistant to chloramphenicol results in strains in which a single crossover recombination event has occurred between the cloned gene fragment and its analogous chromosomal gene. Such a recombination event results in the integration of the vector sequence into the chromosome and an insertional mutation in the target gene.

Example 5

Quantification of Glucose, Lactose, and 1-Butanol

The present example describes a particular protocol used to quantify glucose, lactate, and butanol levels in broth samples. Glucose, lactate, and butanol levels were quantified from broth samples using HPLC analysis. The instrumentation for detection was comprised of a Waters 717 Plus auto sampler fronting a Waters 515 pump, which was coupled to a Waters 2414 refractive index (RI) detector. An Aminex Fast Acid ion exclusion column (100-mm×7.8-mm, Bio-Rad), with Aminex HPX-87H guard column (20-mm×7.8-mm guard column, Bio-Rad), was used for separation.

Samples were prepared for HPLC analysis by first centrifuging (30,000×g) harvested shake flask cultures and transferring supernatant to a fresh Eppendorf tube. Samples were diluted 10-fold into mobile phase, and the resulting preparations were loaded onto the 96 vial autosampler carousel, which is maintained at 15° C. 20 µL of diluted sample is used for instrument injection.

An isocratic separation was performed at 30° C. using 0.05% trifluoracetic acid as the mobile phase at a flow rate of 0.6 mL/min (1400 PSI as high pressure limit).

Example 6

Metabolic Assay to Determine Relative Levels of 1-Butanol Tolerance

The purpose of this example is to describe a quantitative tolerance assay for *L. plantarum* strains growing in liquid cultures. The assay uses metabolic activity as a tolerance metric. Individual strains were grown in cultures containing varying 1-butanol concentrations and metabolic activity levels were determined by HPLC measurements of the levels of lactate produced and/or glucose removed by each strain. Strains with higher tolerance were identified by their ability to produce higher levels of lactate and/or to remove more glucose from the culture supernatant in the presence of 1-butanol.

10-ml De Man, Rogosa and Sharpe (MRS; J. Appl. Bact., 23; 130-135 (1960)) broth cultures containing 0%, 1.7%, 2.0% and 2.3% (w/v) 1-BuOH were grown (3 replicates for each strain at each BuOH concentration) in 15-ml tubes (1% stationary phase inoculum) at 30° C. Samples of individual cultures were removed after 48 hr for analysis by HPLC to determine concentrations of glucose, lactate and 1-butanol. Cell density was also determined at each time point by measuring $OD_{600}$.

FIG. 4 shows graphic depictions of $OD_{600}$ and HPLC lactate, glucose and butanol measurements for 7 strains grown for 48 hours in MRS broth in the presence of predetermined concentrations of 1-butanol (w/v) (0.1% (panel 4A), 1.7% (panel 4B), 2.0% (panel 4C) and 2.3% (panel 4D)). Five of the strains contained plasmids encoding different alcohol tolerance determinant sequences. Data are the averages of 3 replicates. Descriptions of the strains and plasmids are given in Table 8 in Example 2 above. All 5 of the strains that carried plasmids which contained alcohol tolerance determinant sequences exhibited increased metabolic activity (and thus, butanol tolerance) in the presence of butanol as demonstrated by higher glucose consumption and lactate production relative to the controls. All five strains showed significant increases in glucose uptake (107% for MS354, 106% for MS356, 40% for MS359, 156% for MS364, 27% for MS379) as well as lactate production (124% for MS354, 122% for MS356, 45% for MS359, 182% for MS364, 27% for MS379) relative to the vector only control strain in the presence of 2.3% butanol, the 1-butanol $IC_{90}$ of *L. plantarum* PN0512.

| MRS Medium | |
|---|---|
| Yeast extract | 5 g |
| Beef extract | 10 g |
| Peptone | 10 g |
| Glucose | 20 g |
| Tween 80 | 5 ml |
| $K_2HPO_4$ | 2 g |
| Sodium acetate | 5 g |
| Diamonium citrate | 2 g |
| $MgSO_4 \cdot 7H_2O$ | 0.2 g |
| $MnSO_4 \cdot 4H_2O$ | 0.05 g |
| Distilled water | 1000 ml |
| Dissolve the ingredients in water and adjust pH to 6.2-6.6. | |

Example 7

Assessment of Aliphatic Alcohol $IC_{50}$

The present example described methods used to determine $IC_{50}$ values for aliphatic alcohol compounds (with regard to particular microorganism strains or cultures).

$IC_{50}$ values were determined in shake flasks as follows. Duplicate glass test tubes containing 5 ml MRS medium plus 10 µg/ml chloramphenicol (MRS-Cm) were each inoculated with a single colony and grown for 24 h at 30° C. in a rollerdrum. 500 µl of each of these cultures were used to inoculate 25 ml MRS-Cm, which was grown for 16 h at 30° C. with shaking at 110 rpm. These precultures were then used to inoculate duplicate flasks containing 40 ml MRS plus aliphatic alcohol compound (e.g., butanol) at 0, 1.4%, 1.7%, 2.0% and 2.3% (w/v). Cultures were grown at 30° C. with shaking at 110 rpm, and growth was measured by monitoring $OD_{600}$. $OD_{600}$ values that were clearly off the growth curve were discarded (less than 1% of values were discarded).

For each flask, growth rates (µ) and doubling times ($T_d$) were determined by linear regression of the natural log of the OD using the set of points (minimum 3, usually 4 or 5) that gave the highest µ and lowest $T_d$. Inhibition in each shake flask was determined relative to 0% butanol flasks inoculated from the same preculture.

$IC_{50}$ was calculated using the formula $(C_2-C_1)/(I_2-I_1)*(50\%-I_1)+C_1$ where $C_1$ and $C_2$ are the compound (e.g., butanol) concentrations that exhibited just under and just over 50% inhibition, respectively, and $I_1$ and $I_2$ were the % inhibition at $C_1$ and $C_2$, respectively. This is mathematically equivalent to drawing a line between $(C_1,I_1)$ and $(C_2,I_2)$ and finding the concentration at which that line intersects I=50%. An $IC_{50}$ was calculated for each set of flasks inoculated from the same preculture. An average $IC_{50}$ was also calculated.

Finally, the change in $IC_{50}$ ($\Delta IC_{50}$) was determined by subtracting the simultaneously determined $IC_{50}$ of the vector only strain from the $IC_{50}$ of the strain being tested, and % $\Delta IC_{50}$ was determined by dividing $\Delta IC_{50}$ by the simultaneously determined $IC_{50}$ of the vector only strain.

Example 8

Identification of Butanol Responsive Genes by Whole-Genome Microarray Transcription Analysis The purpose of this example is to describe how potential tolerance genes can be identified using whole genome oligonucleotide microarrays.

Bacteria undergo changes in genomic expression patterns when faced with environmental challenges. The most significant changes are often observed for genes whose products are involved in protecting the cell from a given stress. Therefore, such stress-responsive genes can often be identified by comparing global transcription patterns in the presence and absence of the stress. Once the putative stress responsive genes are identified, they can be engineered to optimize their putative protective effect on the cell. In most cases this involves, but is not limited to, over-expressing the genes.

An oligonucleotide microarray was designed and constructed based on the published (Kleerebezem M. et al. 2003. PNAS 100(4) 1990-1995) genome sequence (NCIB Accession NC_004567) for *Lactobacillus plantarum* strain BAA-793 (ATCC). The microarray contains 3195 unique targets which consist of oligonucleotides that are 70 nucleotides in length. The targets were spotted on each microarray in triplicate and included:

Chromosome ORFs: 3002

Plasmid ORFs: 50

Pseudogenes: 42 rRNA Genes: 15

Negative Controls: 60

5'→3' Controls: 11

Opposite Strand Controls: 15

Microarrays were used to identify *L. plantarum* genes that demonstrated significantly different levels of expression when the cell was challenged with 1-butanol. Such butanol responsive genes were considered to be potential butanol-tolerance determinants and were targeted for genetic modification in an attempt to increase the overall butanol tolerance of *L. plantarum*.

In a typical experiment, a culture of *L. plantarum* BAA-793 was grown at 30° C. in MRS to early exponential phase ($Abs_{600}$~1.0). Equal aliquots of the culture were divided into separate 50 ml tubes. One half of the tubes were placed in a 30° C. water bath (controls) and the other half had prewarmed 1-butanol added, to a final concentration of 1.0% (w/v), and were then placed in the 30° C. water bath. The tubes were incubated for 30 minutes, and then each culture was removed and RNA was isolated using a hot phenol/chloroform method (Chuang et al. 1993 JBact. April; 175(7): 2026-36). For each butanol-treated culture, two cDNA probes are made by reverse transcription and indirect labeling (one Cy3-labeled and one Cy5-labeled for each treatment) and two microarray hybridizations were performed against Cy-labeled probe made from RNA isolated from the control culture. Microarray spot intensities were quantitated using GenePix software and the data was then analyzed using the TM4 Microarray Software Suite (www.tm4.org).

One example of the utility of this approach was seen in the identification of lp_3193, an *L. plantarum* butanol responsive gene encoding a predicted protein foldase. Microarray experiments indicated that lp_3193 was up-expressed in *L. plantarum* BAA-793 when the strain was exposed to 1% (w/v) 1-butanol in MRS broth. The gene was subsequently isolated by PCR amplification using primers 5174 and 5175. The PCR product was then digested with BamHI and SalI and ligated into vector pMPE6, which had previously been digested with BamHI and SalI. The resulting plasmid was designated, pMPE41 (Table 8; Example 2 above). Plasmid pMPE41 was transformed into *L. plantarum* PN0512. The resulting strain was shown to possess increased tolerance to 1-butanol on the basis of its improved ability (relative to controls strains) to remove glucose and produce higher levels of lactate in broth cultures containing 1-butanol (FIG. 4).

Example 9

Enrichment of *L. Plantarum* Populations Containing Random Genomic Libraries to Identify Plasmids Encoding Potential Tolerance Determinants The present example describes a method for identifying potential alcohol tolerance determinant sequences, in the form of plasmid inserts that contribute to increased tolerance within a recombinant *L. plantarum* strain.

A random genomic library was constructed using purified gDNA from *L. plantarum* strain BAA-793 and the shuttle vector pMPE6 using techniques that are well known to those practiced in the art. The gDNA from BAA-793 was partially digested with Sau3AI and size fractionated on an agarose gel. DNA fragments with an average size ranging from 1- to 6-kb were purified and used in ligation reactions with BamHI digested pMPE6. Multiple ligation reactions were performed and transformed into *E. coli* DH5α by electroporation. The *E. coli* transformation cultures were grown in 5-ml LB cultures containing chloramphenicol for 24 hours at which time the plasmids from each culture were isolated and pooled. The pooled plasmids were then transformed into *L. plantarum* via electroporation. Multiple transformations were performed. Following grow out in MRS for 4 hours the individual transformation cultures were used to inoculate 5 ml MRS plus chloramphenicol cultures which were grown for 24 hours and then pooled into a single library population. The library was aliquoted and frozen as 20% glycerol stocks at −80° C.

Serial enrichment cultures were used to isolate *L. plantarum* library strains that possessed increased levels of butanol tolerance relative to other members of a mixed population. Frozen stocks of *L. plantarum* containing the random gDNA plasmid library were thawed and used to inoculate MRS plus chloramphenicol broth overnight cultures. These cells were then used to inoculate MRS broth cultures containing 1.8% (w/v) 1-butanol. This culture was incubated at 30° C. (100 rpm) until it reached an $OD_{600}$ of ~4.0. This culture was then used to inoculate a new MRS culture containing 2.0% 1-butanol to starting $OD_{600}$ between 0.25 and 0.3. This culture was again grown to a final $OD_{600}$ of ~4.0 and subsequently passed to a third MRS 2.0% 1-butanol culture (starting $OD_{600}$ 0.25-0.3). This serial passaging was continued for a specified period of time (usually about 14 days or 6 transfers).

Two methods were used to identify genes that were enriched relative to others in the serially passaged population. The first was a phenotypic selection that involved spreading aliquots of the enriched cultures onto MRS plates containing 1-butanol and isolating single colonies. Strains that were more tolerant to butanol produced single colonies on the selective medium more quickly than others. The isolated strains were streak-purified, their plasmids isolated and the corresponding *L. plantarum* plasmid insert DNAs were sequenced. The plasmids were also re-transformed into a wild type *L. plantarum* host strain and the butanol tolerance of the resulting transformants was compared to control strains (either the host strain or the host strain containing the vector only). This step was performed to ensure that increases in tolerance seen in the enriched population were encoded by the plasmids and were not the result of background chromosomal mutations in the enriched host strains.

A second approach used to identify genes that were enriched within the selected population utilized *L. plantarum* microarrays and a procedure known as Parallel Gene Trait Mapping (Gill et al. 2002. PNAS 99(10) 7033-7038). In this procedure, the plasmids were isolated en masse from the cells remaining in the enrichment population. The isolated plasmid DNA was then labeled and hybridized to *L. plantarum* microarrays. The relative numbers of *L. plantarum* genes present in the plasmid sample were then analyzed by comparing their signal intensities on the hybridized arrays. Genes shown to be enriched were cloned and over expressed to test their influence on tolerance.

The utility of the library enrichment method was shown by the isolation of 4 separate plasmids. Plasmids p5AE4-1, p5AE0-4, p5AE0-14 and p5AE4-24 were all isolated by MRS enrichments followed by phenotypic selection for growth on MRS plates containing 3.2% (w/v) 1-butanol. Plasmids were isolated from enrichment strains. DNA sequence analysis identified the portion of *L. plantarum* BAA-793 chromosome contained within each of the plasmid inserts (Table 1B). The plasmids were transformed into *L. plantarum* PN0512 and their ability to increase tolerance was confirmed by demonstrating that strains containing the plasmids were able to produce higher levels of lactate than either the wild type parent strain or the parent strain containing vector pMPE6 only in the presence of 1-butanol with concomitant removal of glucose (FIG. 4).

Example 10

Batch Fed Fermentation of *C. beijerinckii* Under Conditions that Produce One or More Aliphatic Alcohol Compounds The present example provides a description of conditions that can be utilized to grow *C. beijerinckii* in batch fed cultures under conditions that produce one or more aliphatic alcohol compounds.

*C. beijerinckii* strains can be maintained under anaerobic conditions as spore suspensions in doubled distilled water ($ddH_2O$) at room temperature. Spores can be heat shocked at 80° C. for 10 minutes and inoculated into Tryptone, Glucose, Yeast (TGY) medium (Annous et al., *Appl. Environ. Microbiol.* 56:2559, 1990, herein incorporated by reference).

After overnight growth, cultures can be plated out on TGY agar plates and single colony isolates picked and inoculated into 10 ml TGY medium. The culture can be incubated anaerobically overnight at 37° C. until an optical density at 600 nm of 1.0 to 1.5 is achieved when using a Spectronic 20 spectrophotometer (Bausch and Lomb, Rochester, N.Y.). P-2 medium (Annous et al., *Appl. Environ. Microbiol.* 56:2559, 1990, herein incorporated by reference) containing 0.1% yeast extract can be prepared with either 6% glucose or 6% maltodextrin (STAR-DR15™; A. E. Staley Manufacturing Co., Decatur, Ill.) as a carbohydrate source. Semi-defined P2 medium (pH=6.5; 100 ml) can be inoculated with 5 ml of TGY medium culture and incubated anaerobically 18-20 hours at approximately 30° C. The culture can be decanted into 1 liter of semi-defined P2 medium and incubated anaerobically for 16-18 hours at approximately 30° C. until the optical density at 600 nm is 1.0 to 1.5. Batch fermentations can be performed using a 421 Braun fermentor (B. Braun Biotech International GMBH, Melsungen, Germany). Semi-defined P2 medium can be sterilized in the fermentor and agitated and sparged with nitrogen overnight prior to inoculation. Note that, in some embodiments, medium containing acetate is utilized in order to enhance solvent production by *C. beijerinckii*.

A 5% inoculum of *C. beijerinckii* can be used for the batch fermentation experiments. 20 liter batch fermentations can be performed at 33° C. in the absence of agitation and pH control. Sterilized nitrogen gas can be sparged (1950 ml/min)

through the fermentor to aid mixing and to exclude oxygen. During the course of the fermentation, temperature, pH, and percent oxygen can be measured continuously. Optical density can be monitored by spectrophotometric analysis of culture broth as described above.

Example 11

Continuous Feed Fermentation of C. beijerinckii Under Conditions that Produce One or More Aliphatic Alcohol Compounds The present example provides a description of conditions that can be utilized to grow C. beijerinckii in continuous feed cultures under conditions that produce one or more aliphatic alcohol compounds.

Continuous cultivation of C. beijerinckii strains can be carried out in P2 medium plus 6% glucose using a Braun Biostat 2 liter continuous culture apparatus (B. Braun Biotech International GMBH, Melsungen, Germany) set at 35° C. and 50 rpm stirring rate with no pH control. P2 medium containing 6% glucose can be flushed with nitrogen and inoculated with 100 ml of 18-20 hours old culture. The dilution rate can be set at 0.05 (h.sup.−1) or 0.20 (h.sup.−1). Samples (1 ml) can be routinely removed for solvent analysis. Volumetric solvent production rate can be calculated as g/L/h. Note that, in some embodiments, medium containing acetate is utilized in order to enhance solvent production by C. beijerinckii.

Production of relevant compounds (e.g., acetone and/or aliphatic alcohol compounds such as butanol, and ethanol) can be measured by using a gas chromatograph (5710A; Hewlett-Packard Co., Avondale, Pa.) equipped with a flame ionization detector and a glass column (1.83 m by 2 mm [inner diameter]) packed with 90/100 Carbopack C-0.1% SP-1000 (Supelco, Inc., Bellefonte, Pa.). Butyric and acetic acids can be determined using a Hewlett Packard 5890 series II gas chromatograph and a column packed with Supelco GP 10% SP-1200/1% $H_3PO_4$ on chromosorb WAW. Run conditions consisted of 175° C. injector temperature, 180° C. detector temperature and 125° C. oven temperature and a nitrogen carrier gas set at a flow rate of 72 mL/min. Total residual carbohydrate can be determined by using the phenol-sulfuric acid method (Dubois et al., *Anal. Chem.* 28:350, 1956). Product yield can be calculated by dividing the grams of solvent produced by the grams of carbohydrate consumed. Carbon recovery following fermentation by C. beijerinckii when grown in semi-defined P2 medium containing 6% carbohydrate can be examined by determining the moles of carbon substrate utilized and the moles of carbon product produced as described by Gottschalk (Gottschalk, Butyrate and butanol-acetone fermentation. pp. 231-232. In: Bacterial Metabolism, 2nd edition, 1986) for the ABE fermentation.

Example 12

Mapping the Butanol Tolerance Activity of the CAAX Gene

Plasmid p5AE4-1 insert sequence is as follows:

```
GATCTTTATTAGTTAGTCGTGGAATCCGATAAATCTAAACAAAATCAC
GTGTGAGCGTCCCCAATCTGGTATGATTAATGCATATCAGATTGGGGG
ATTTTTTT
(CAAX protease (lp_2911) upstream (5')
intergenic sequence; SEQ ID NO: 12)

ATGACGCCGGAAACCGAACAATTATTACGACGCTGGTACATGGGCAG
CTCATCGTGTTATTTGGCGCGGCCTTTATTCAACTATTTACGTTTGAT
GGTGGTGTGTTTTTCCCAGTTGGTGGTATGCAGTTGCTGATATGGGA
CTGTTAGCCTGGTGGCCAGCTGCCGAGGAGGACCAAGCACAGTGGCGG
CGTTTGCGACATGTTAATTATTATGTCCAAACAGTACTGCAGTTCACA
CTCTTGCCGATTTTACTGGCGAACCTCGTGGCTTGGTTAAGTCAGCTG
TCATGGTTAGACGAGCAGGGATTGATTGCTGTGGGGATGGCTTATTTA
ATGGTCGCATTCGTACCGGTGGCAGTGGTGGTCACTAAACCGATCGAA
TCTGTGATTGGCCGGATTGCGGTCCTAATTACGGCTATTTTTAGTGGT
GTCGTCAGTGCGCAGCAGACTTTTTTGATTTTACCGAATCTGCAAGCA
CCATCAGTATTCGAGATGGTCAGTGATACTGGTATTTTAGGCGCCCTG
GGCTTTGTGATTGCTGTTGGGGTCTTACTGCGGGGATGGGGATTGACG
GGCCCATCGTGGCGGTTTAATCGTCAGGCCCAAACTAGTTTAGTGGTT
GGGCTGATCGTGGTGGGAACGGCTTTTAGTCTATGGAATGCCTTTAGT
GCGGGTGGTTCATGGGCGACAACGTTCACACATTGGGACTTCCAGCTA
CGGTCAGCGACTTGGAAAATGTTTTTGAGTGGGTTAGAACCGGGAATC
GCAGAGGAATGGTTGTATCGTTTTGCCGTTTTAACCTTGTTATTACAA
GCTTTTCGGCATCGGCGTCACCAACTCGACTTGGCAGTGTGGCTAAGC
GGTGGCCTATTTGGAATGTGGCATATTACAAACGTTTTTGCGGGCCAA
CCCTTGTCAGCCACGGTTGAGCAAATCATTTTTGCAGCGACACTAGGC
TGGTTTTTAGCCTCGACGTACCTGTACTCAGGTAGTATCTTGCTGCCG
ATGGTGATCCATGCTGCTATTGATATTTTGAGCATGATGGCATCAGGT
AGCCAGACAATGGTTAAGCCGGATGCGTTCGAATGGCAAACAATCGGT
GCTACCGTCATTATTTTTGTTGGCATAACGATTTATTTCTTGACCGGT
TCTCGGCGACAAGTTATTCAAGCACATGTCAATCAACGGCTTTCAGTT
CAATAA
(CAAX protease (lp_2911) coding sequence;
SEQ ID NO: 13)

AGGCCGACTGTTAAGACCATAGTGGGCGACTTTGTTCGTTAAAGATAA
ACTGGGTGTCCGTAGCCAGAGACGATTAAGCAATACCAGGCTAACTTT
TAGTTGGTTTAGACCAGTTGTAACATTTTTGTAATCTTCGTGTTATCT
AAACGCAATGCTGGCTCGCTATACTAAAGACAAAGTTATGAAGCAATA
CATACGCTTTGTCAGCGGATTTAGGTTGGGAGCCGGATCGATTTACTT
TGTCAGGACATTGTTAATAAGCAATTATTGATAGTGATAAGTAGCTCA
GTTAGCTGAATCATAACGTTTGACAAGCATTTATACCTCTCGGGATGG
GCTGGGTCCATGACGAGGCACATACACAATGGCAAGCTTGGGGTTTGC
AAGTCGATCAGAGAAAGGGACGGTTGGTTACCGGCCCTTTTATTGTGG
TTAAAATTTGCAGAATTGGATTTAGAACTGCGCCCGATTTGAAGCGG
TAGGAACTGCGATGCTGGCACAGGTGACTTTGCCAAATCATTGAGAGT
GGAACGAAATAATTTACATTTGCCAGTAGATTATTATAATTAACGAAT
CAATAATAATTTGGAGATGGCAATTTGACTCAGTTTGAAACGGAACGG
TTGATATTACGACCAATGACAGCGGCGGATC-3'
(CAAX protease(lp_2911) downstream (3')
intergenic sequence; SEQ ID NO: 14).
```

To determine which region of p5AE4-1 is responsible for the butanol tolerance phenotype, 2 deletion constructs were created. Plasmid pMPE73 has a precise deletion that removes only the CAAX ORF DNA, leaving the upstream and downstream intergenic DNA intact. Plasmid pMPE74 has only the downstream intergenic DNA deleted, leaving the DNA upstream of the CAAX ORF and the CAAX ORF itself intact. Plasmids pMPE73, pMPE74, and the parent plasmid, p5AE4-1 were tested for their ability to confer butanol tolerance by spotting *L. plantarum* strains transformed with these individual plasmids onto MRS agar plates containing 1-butanol. The strains carrying either p5AE4-1 or pMPE73 (CAAX deletion) showed similar, increased levels of tolerance, whereas the strain carrying pMPE74 (deleted for the DNA downstream of CAAX) showed the same level of tolerance as a control carrying just the vector. Thus, it appears as though the tolerance increase conferred by p5AE4-1 is due to the DNA downstream of the CAAX ORF (lp_2911).

EQUIVALENTS

Those skilled in the art will recognize, or be able to understand that the foregoing description and examples are illustrative of practicing the provided disclosure. Those skilled in the art will be able to ascertain using no more than routine experimentation, many variations of the detail presented herein may be made to the specific embodiments of the disclosure described herein without departing from the spirit and scope of the present disclosure.

Lengthy table referenced here
US08906666-20141209-T00001
Please refer to the end of the specification for access instructions.

Lengthy table referenced here
US08906666-20141209-T00002
Please refer to the end of the specification for access instructions.

Lengthy table referenced here
US08906666-20141209-T00003
Please refer to the end of the specification for access instructions.

Lengthy table referenced here
US08906666-20141209-T00004
Please refer to the end of the specification for access instructions.

Lengthy table referenced here
US08906666-20141209-T00005
Please refer to the end of the specification for access instructions.

Lengthy table referenced here
US08906666-20141209-T00006
Please refer to the end of the specification for access instructions.

Lengthy table referenced here
US08906666-20141209-T00007
Please refer to the end of the specification for access instructions.

Lengthy table referenced here
US08906666-20141209-T00008
Please refer to the end of the specification for access instructions.

Lengthy table referenced here
US08906666-20141209-T00009
Please refer to the end of the specification for access instructions.

Lengthy table referenced here
US08906666-20141209-T00010
Please refer to the end of the specification for access instructions.

Lengthy table referenced here
US08906666-20141209-T00011
Please refer to the end of the specification for access instructions.

Lengthy table referenced here
US08906666-20141209-T00012
Please refer to the end of the specification for access instructions.

Lengthy table referenced here
US08906666-20141209-T00013
Please refer to the end of the specification for access instructions.

Lengthy table referenced here
US08906666-20141209-T00014
Please refer to the end of the specification for access instructions.

Lengthy table referenced here
US08906666-20141209-T00015
Please refer to the end of the specification for access instructions.

Lengthy table referenced here
US08906666-20141209-T00016
Please refer to the end of the specification for access instructions.

Lengthy table referenced here
US08906666-20141209-T00017

Please refer to the end of the specification for access instructions.

Lengthy table referenced here
US08906666-20141209-T00018

Please refer to the end of the specification for access instructions.

Lengthy table referenced here
US08906666-20141209-T00019

Please refer to the end of the specification for access instructions.

Lengthy table referenced here
US08906666-20141209-T00020

Please refer to the end of the specification for access instructions.

Lengthy table referenced here
US08906666-20141209-T00021

Please refer to the end of the specification for access instructions.

Lengthy table referenced here
US08906666-20141209-T00022

Please refer to the end of the specification for access instructions.

Lengthy table referenced here
US08906666-20141209-T00023

Please refer to the end of the specification for access instructions.

Lengthy table referenced here
US08906666-20141209-T00024

Please refer to the end of the specification for access instructions.

Lengthy table referenced here
US08906666-20141209-T00025

Please refer to the end of the specification for access instructions.

Lengthy table referenced here
US08906666-20141209-T00026

Please refer to the end of the specification for access instructions.

Lengthy table referenced here
US08906666-20141209-T00027

Please refer to the end of the specification for access instructions.

Lengthy table referenced here
US08906666-20141209-T00028

Please refer to the end of the specification for access instructions.

Lengthy table referenced here
US08906666-20141209-T00029

Please refer to the end of the specification for access instructions.

Lengthy table referenced here
US08906666-20141209-T00030

Please refer to the end of the specification for access instructions.

Lengthy table referenced here
US08906666-20141209-T00031

Please refer to the end of the specification for access instructions.

Lengthy table referenced here
US08906666-20141209-T00032

Please refer to the end of the specification for access instructions.

Lengthy table referenced here
US08906666-20141209-T00033

Please refer to the end of the specification for access instructions.

Lengthy table referenced here
US08906666-20141209-T00034

Please refer to the end of the specification for access instructions.

Lengthy table referenced here
US08906666-20141209-T00035

Please refer to the end of the specification for access instructions.

Lengthy table referenced here
US08906666-20141209-T00036

Please refer to the end of the specification for access instructions.

Lengthy table referenced here
US08906666-20141209-T00037

Please refer to the end of the specification for access instructions.

Lengthy table referenced here
US08906666-20141209-T00038

Please refer to the end of the specification for access instructions.

Lengthy table referenced here
US08906666-20141209-T00039

Please refer to the end of the specification for access instructions.

Lengthy table referenced here
US08906666-20141209-T00040

Please refer to the end of the specification for access instructions.

Lengthy table referenced here
US08906666-20141209-T00041

Please refer to the end of the specification for access instructions.

Lengthy table referenced here
US08906666-20141209-T00042

Please refer to the end of the specification for access instructions.

Lengthy table referenced here
US08906666-20141209-T00043

Please refer to the end of the specification for access instructions.

Lengthy table referenced here
US08906666-20141209-T00044

Please refer to the end of the specification for access instructions.

Lengthy table referenced here
US08906666-20141209-T00045

Please refer to the end of the specification for access instructions.

Lengthy table referenced here
US08906666-20141209-T00046

Please refer to the end of the specification for access instructions.

Lengthy table referenced here
US08906666-20141209-T00047

Please refer to the end of the specification for access instructions.

Lengthy table referenced here
US08906666-20141209-T00048

Please refer to the end of the specification for access instructions.

Lengthy table referenced here
US08906666-20141209-T00049

Please refer to the end of the specification for access instructions.

Lengthy table referenced here
US08906666-20141209-T00050

Please refer to the end of the specification for access instructions.

Lengthy table referenced here
US08906666-20141209-T00051

Please refer to the end of the specification for access instructions.

Lengthy table referenced here
US08906666-20141209-T00052

Please refer to the end of the specification for access instructions.

Lengthy table referenced here
US08906666-20141209-T00053

Please refer to the end of the specification for access instructions.

Lengthy table referenced here
US08906666-20141209-T00054

Please refer to the end of the specification for access instructions.

Lengthy table referenced here
US08906666-20141209-T00055

Please refer to the end of the specification for access instructions.

Lengthy table referenced here
US08906666-20141209-T00056

Please refer to the end of the specification for access instructions.

Lengthy table referenced here
US08906666-20141209-T00057

Please refer to the end of the specification for access instructions.

Lengthy table referenced here
US08906666-20141209-T00058

Please refer to the end of the specification for access instructions.

Lengthy table referenced here
US08906666-20141209-T00059

Please refer to the end of the specification for access instructions.

Lengthy table referenced here
US08906666-20141209-T00060

Please refer to the end of the specification for access instructions.

Lengthy table referenced here
US08906666-20141209-T00061

Please refer to the end of the specification for access instructions.

Lengthy table referenced here
US08906666-20141209-T00062

Please refer to the end of the specification for access instructions.

Lengthy table referenced here
US08906666-20141209-T00063

Please refer to the end of the specification for access instructions.

Lengthy table referenced here
US08906666-20141209-T00064

Please refer to the end of the specification for access instructions.

|  |  |
|---|---|
| Lengthy table referenced here | Lengthy table referenced here |
| US08906666-20141209-T00065 | US08906666-20141209-T00068 |
| Please refer to the end of the specification for access instructions. | Please refer to the end of the specification for access instructions. |

|  |  |
|---|---|
| Lengthy table referenced here | Lengthy table referenced here |
| US08906666-20141209-T00066 | US08906666-20141209-T00069 |
| Please refer to the end of the specification for access instructions. | Please refer to the end of the specification for access instructions. |

|  |  |
|---|---|
| Lengthy table referenced here | Lengthy table referenced here |
| US08906666-20141209-T00067 | US08906666-20141209-T00070 |
| Please refer to the end of the specification for access instructions. | Please refer to the end of the specification for access instructions. |

LENGTHY TABLES

The patent contains a lengthy table section. A copy of the table is available in electronic form from the USPTO web site (http://seqdata.uspto.gov/?pageRequest=docDetail&DocID=US08906666B2). An electronic copy of the table will also be available from the USPTO upon request and payment of the fee set forth in 37 CFR 1.19(b)(3).

What is claimed is:

1. A recombinant microbial cell, characterized in that the recombinant microbial cell comprises at least one alcohol tolerance modification as compared with a parent cell, wherein the alcohol tolerance modification comprises introduction of a nucleic acid molecule comprising a 3' untranslated region (UTR) of a gene encoding a CAAX protease polypeptide, and wherein the 3' UTR comprises a nucleotide sequence having at least 90% identity to the nucleotide sequence of SEQ ID NO: 187.

2. The recombinant microbial cell of claim 1, wherein the nucleic acid molecule comprises a 3' UTR of a gene encoding a *Lactobacillus* CAAX protease polypeptide.

3. The recombinant microbial cell of claim 2, wherein the 3' UTR comprises the nucleotide sequence of SEQ ID NO: 187.

4. The recombinant microbial cell of claim 1, wherein the nucleic acid molecule comprising the 3' UTR further comprises a 5' region of a gene encoding a CAAX protease polypeptide.

5. The recombinant microbial cell of claim 4, wherein the 5' region of the gene comprises a 5' UTR.

6. The recombinant microbial cell of claim 4, wherein the 5' region of the gene comprises nucleotides immediately upstream of sequence encoding the CAAX protease polypeptide.

7. The recombinant microbial cell of claim 4, wherein the nucleic acid molecule comprises a 5' region of a gene encoding a *Lactobacillus* CAAX protease polypeptide.

8. The recombinant microbial cell of claim 7, wherein the 5' region of the gene comprises the nucleotide sequence of SEQ ID NO: 185.

9. The recombinant microbial cell of claim 1, wherein the cell exhibits increased tolerance to butanol as compared with the parent cell.

10. The recombinant microbial cell of claim 9, wherein the increased tolerance to butanol comprises an increased butanol $IC_{50}$, wherein the $IC_{50}$ is increased at least 5%, 10%, 20%, 30%, 40%, 50%, 60%, 70%, 80%, 90%, 100%, or more.

11. The recombinant microbial cell of claim 9 or 10, wherein the increased tolerance to butanol comprises increased carbohydrate utilization as compared to the parent cell when grown in the same amount of butanol.

12. The recombinant microbial cell of claim 11, wherein the carbohydrate utilization is increased at least 5%, 10%, 20%, 30%, 40%, 50%, 60%, 70%, 80%, 90%, 100%, or more.

13. The recombinant cell of claim 1, wherein the cell exhibits increased butanol production as compared with the parent cell.

14. The recombinant microbial cell of claim 1, wherein the cell is a member of a genus selected from the group consisting of *Clostridium*, *Zymomonas*, *Escherichia*, *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, *Brevibacterium*, *Acinetobacter*, *Pichia*, *Candida*, *Hansenula*, and *Saccharomyces*.

* * * * *

```
                              SEQUENCE LISTING

<160> NUMBER OF SEQ ID NOS: 203

<210> SEQ ID NO 1
<211> LENGTH: 36
<212> TYPE: DNA
<213> ORGANISM: Artificial Sequence
<220> FEATURE:
<223> OTHER INFORMATION: Primer

<400> SEQUENCE: 1
tttggatccg attctattgt tagctatttt gggtgg                              36

<210> SEQ ID NO 2
<211> LENGTH: 37
<212> TYPE: DNA
<213> ORGANISM: Artificial Sequence
<220> FEATURE:
<223> OTHER INFORMATION: Primer

<400> SEQUENCE: 2
aaagtcgaca tcgtggtatt agtgatgcaa agaaagg                             37

<210> SEQ ID NO 3
<211> LENGTH: 38
<212> TYPE: DNA
<213> ORGANISM: Artificial Sequence
<220> FEATURE:
<223> OTHER INFORMATION: Primer

<400> SEQUENCE: 3
```
aacggccgaa ggattattcg gctggttgag acgttaaa          38

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
aacggccgaa ataacacctt aagtctagca ccacccgc          38

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
ctccagtaag aatatttgca ttgtgtatc                    29

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
aaaaaggccc ttataactta caaataaccc c                 31

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
aaaaaagcgg ccgctctttta ttcttcaact aaagcacc         38

<210> SEQ ID NO 8
<211> LENGTH: 42
<212> TYPE: DNA
<213> ORGANISM: Artificial Sequence
<220> FEATURE:
<223> OTHER INFORMATION: Primer

<400> SEQUENCE: 8
aaaaaagcgg ccgcaatgta tttagaaaaa taaacaaata gg     42

<210> SEQ ID NO 9
<211> LENGTH: 86
<212> TYPE: DNA
<213> ORGANISM: Artificial Sequence
<220> FEATURE:
<223> OTHER INFORMATION: Primer

<400> SEQUENCE: 9
aaaaagcgga agagcgaggg cggagttgtt gacagccgag gtaccatgtg gtataatccc    60
gagtgtggaa ttgtgagcgg ataaca                                         86

<210> SEQ ID NO 10

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
gttttcgagg ggttatttgt aagttataag gccct                         35

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
aaaaagcgga agagcgaggg cggagttg                                 28

<210> SEQ ID NO 12
<211> LENGTH: 104
<212> TYPE: DNA
<213> ORGANISM: Artificial Sequence
<220> FEATURE:
<223> OTHER INFORMATION: CAAX protease (lp_2911) upstream (5')
      intergenic sequence

<400> SEQUENCE: 12
gatctttatt agttagtcgt ggaatccgat aaatctaaac aaaatcacgt gtgagcgtcc   60
ccaatctggt atgattaatg catatcagat tgggggattt tttt                  104

<210> SEQ ID NO 13
<211> LENGTH: 1206
<212> TYPE: DNA
<213> ORGANISM: Artificial Sequence
<220> FEATURE:
<223> OTHER INFORMATION: CAAX protease (lp_2911) coding sequence

<400> SEQUENCE: 13
atgacgccgg aaaccgaaca attattacga cgctggtaca tggggcagct catcgtgtta   60
tttggcgcgg cctttattca actatttacg tttgatggtg gtgtgttttt cccagttggt  120
ggtatgcagt tgctgatatg gggactgtta gcctggtggc cagctgccga ggaggaccaa  180
gcacagtggc ggcgtttgcg acatgttaat tattatgtcc aaacagtact gcagttcaca  240
ctcttgccga ttttactggc gaacctcgtg gcttggttaa gtcagctgtc atggttagac  300
gagcagggat tgattgctgt ggggatggct tatttaatgg tcgcattcgt accggtggca  360
gtggtggtca ctaaaccgat cgaatctgtg attggccgga ttgcggtcct aattacggct  420
atttttagtg gtgtcgtcag tgcgcagcag acttttttga ttttaccgaa tctgcaagca  480
ccatcagtat tcgagatggt cagtgatact ggtatttag gcgccctggg ctttgtgatt  540
gctgttgggg tcttactgcg gggatgggga ttgacgggcc atcgtggcg gtttaatcgt  600 caggcccaaa ctagtttagt ggttgggctg atcgtggtgg aacggctttt tagtctatgg  660
aatgccttta gtgcgggtgg ttcatgggcg acaacgttca cacattggga cttccagcta  720
cggtcagcga cttggaaaat gttttgagt gggttagaac cggaatcgc agaggaatgg   780 ttgtatcgtt ttgccgtttt aaccttgtta ttacaagctt ttcggcatcg gcgtcaccaa   840
ctcgacttgg cagtgtggct aagcggtggc ctatttggaa tgtggcatat tacaaacgtt   900
tttgcgggcc aacccttgtc agccacggtt gagcaaatca tttttgcagc gacactaggc   960

```
tggtttttag cctcgacgta cctgtactca ggtagtatct tgctgccgat ggtgatccat    1020
gctgctattg atattttgag catgatggca tcaggtagcc agacaatggt taagccggat    1080
gcgttcgaat ggcaaacaat cggtgctacc gtcattattt ttgttggcat aacgatttat    1140
ttcttgaccg gttctcggcg acaagttatt caagcacatg tcaatcaacg ctttcagtt     1200 caataa                                                              1206

<210> SEQ ID NO 14
<211> LENGTH: 655
<212> TYPE: DNA
<213> ORGANISM: Artificial Sequence
<220> FEATURE:
<223> OTHER INFORMATION: CAAX protease(lp_2911) downstream (3')
      intergenic sequence

<400> SEQUENCE: 14
aggccgactg ttaagaccat agtgggcgac tttgttcgtt aaagataaac tgggtgtccg    60
tagccagaga cgattaagca ataccaggct aactttagt tggtttagac cagttgtaac     120 attttgtaa tcttcgtgtt atctaaacgc aatgctggct cgctatacta agacaaagt      180 tatgaagcaa tacatacgct ttgtcagcgg atttaggttg ggagccggat cgatttactt    240
tgtcaggaca ttgttaataa gcaattattg atagtgataa gtagctcagt tagctgaatc    300
ataacgtttg acaagcattt atacctctcg ggatgggctg ggtccatgac gaggcacata    360
cacaatggca agcttggggt ttgcaagtcg atcagagaaa gggacggttg gttaccggcc    420
cttttattgt ggttaaaatt tgcgagaatt ggatttagaa ctgcgcccga tttgaagcgg    480
taggaactgc gatgctggca caggtgactt tgccaaatca ttgagagtgg aacgaaataa    540
tttacatttg ccagtagatt attataatta acgaatcaat aataatttgg agatggcaat    600
ttgactcagt ttgaaacgga acggttgata ttacgaccaa tgacagcggc ggatc         655

<210> SEQ ID NO 15
<211> LENGTH: 423
<212> TYPE: DNA
<213> ORGANISM: Lactobacillus plantarum

<400> SEQUENCE: 15
atggctaata ctttaatgaa tcggaacgat ttcggcatgt tggatccgtt tgaacggatg    60
gcacgctcct tctgggcacc attagaaaac atggatcaag tattgaagac cgacattaac    120
gaaactgatg atcagtatca agtgaaggtt gatgtccctg gtattgataa gcaagatgtg    180
aagttggatt atcgtgacaa tgtgttgtct atcaaggttc aaaaagatag ctttgtggat    240
catgaagatc aagaccaaaa cattgtgatg aatgagcgtc atactggcac cttgcaacgg    300
cagtatatgt taccaaacgt tgcggcgaat aaaattacgg catcccaagc tgacggtgtc    360
ttaacgatta cgttacctaa gacccagccg agcgcgaatg acggtcaaat cgaaattcaa    420
taa                                                                 423

<210> SEQ ID NO 16
<211> LENGTH: 140
<212> TYPE: PRT
<213> ORGANISM: Lactobacillus plantarum

<400> SEQUENCE: 16

Met Ala Asn Thr Leu Met Asn Arg Asn Asp Phe Gly Met Leu Asp Pro
1               5                   10                  15

Phe Glu Arg Met Ala Arg Ser Phe Trp Ala Pro Leu Glu Asn Met Asp
```

```
            20                  25                  30
Gln Val Leu Lys Thr Asp Ile Asn Glu Thr Asp Gln Tyr Gln Val
         35                  40                  45

Lys Val Asp Val Pro Gly Ile Asp Lys Gln Asp Val Lys Leu Asp Tyr
     50                  55                  60

Arg Asp Asn Val Leu Ser Ile Lys Val Gln Lys Asp Ser Phe Val Asp
 65                  70                  75                  80

His Glu Asp Gln Asp Gln Asn Ile Val Met Asn Glu Arg His Thr Gly
                 85                  90                  95

Thr Leu Gln Arg Gln Tyr Met Leu Pro Asn Val Ala Ala Asn Lys Ile
            100                 105                 110

Thr Ala Ser Gln Ala Asp Gly Val Leu Thr Ile Thr Leu Pro Lys Thr
        115                 120                 125

Gln Pro Ser Ala Asn Asp Gly Gln Ile Glu Ile Gln
    130                 135                 140

<210> SEQ ID NO 17
<211> LENGTH: 273
<212> TYPE: DNA
<213> ORGANISM: Lactobacillus plantarum

<400> SEQUENCE: 17
gtggatccca agcgagttaa atatctgaaa ttgattagta agttagcgac atttacgtgt      60
attgcgatgt acgtgtcata tattccgcaa atcatttcga atttctcagg tgacccagta     120
tcgccgctac aaccactcgt ggcaatgatt aatgggatac tatggactgg ttacggctgg     180
ttcaagactt ataaggattg gccgttatt atttcaaatg ttcccggggt gattttgga      240 tttatcactg ttttaaccgt atatattcat taa                                  273

<210> SEQ ID NO 18
<211> LENGTH: 90
<212> TYPE: PRT
<213> ORGANISM: Lactobacillus plantarum

<400> SEQUENCE: 18

Met Asp Pro Lys Arg Val Lys Tyr Leu Lys Leu Ile Ser Lys Leu Ala
 1               5                  10                  15

Thr Phe Thr Cys Ile Ala Met Tyr Val Ser Tyr Ile Pro Gln Ile Ile
             20                  25                  30

Ser Asn Phe Ser Gly Asp Pro Val Ser Pro Leu Gln Pro Leu Val Ala
         35                  40                  45

Met Ile Asn Gly Ile Leu Trp Thr Gly Tyr Gly Trp Phe Lys Thr Tyr
     50                  55                  60

Lys Asp Trp Pro Val Ile Ile Ser Asn Val Pro Gly Val Ile Phe Gly
 65                  70                  75                  80

Phe Ile Thr Val Leu Thr Val Tyr Ile His
                 85                  90

<210> SEQ ID NO 19
<211> LENGTH: 1179
<212> TYPE: DNA
<213> ORGANISM: Lactobacillus plantarum

<400> SEQUENCE: 19
atgtatcaag ttaaaaccta taacgccatc gccccagccg ccctcaacac gtttactgct      60
gattacacgc tcaatcaatc tgagcatccg gatgcttact taattcgctc ggtcaaccta     120
```

```
cataccgaga cattaccgtc atcgttgaaa gtcattgtgc gcgctggtgc cggcgttaac    180
aacattccta tcgatcaggc aaccgccaac gggactgcag ttttcaacac cccgggaagt    240
aacgctaatg ccgttaagga actcatcatc ggcctgctca ttatggcatc ccgtaatcta    300
atagctgcaa cgacctattc ggcccagcat accgaagctg atatttctca acgcacagaa    360
cacgacaaga cgcaatttaa tggtattgaa ttaacgggta agaccttggc cgtcatcgga    420
ctcggccatg ttggcgctct cgttgccaat gcagcattga gtctaggcat gaatgtaatt    480
ggttacgacc cctatctatc tgcagatgcc gcttggaaca ttgctaaaca agtccagcga    540
gcggccacgc tgccagatgc agtcaaacaa gctgattttg tcaccgtcca cgttcctaaa    600
aatgccgaca cacttcatct gattaataaa gatgcgttag ccgccatgcc aacaggcgtt    660
caattattta attattcacg gctgggcatc gttgacaata ctgccgtcat gaatgcgtta    720
gccacgggac aagttgccca ctactacacc gattttggcg aaccccagct tgccaaccaa    780
tccgcggtta ccgtgacacc ccatatcggc ggctcgacta tcgaggctga atcaacggt     840
gccacacaag ctgcgcgcac tatcatgact tatttggaaa ccggtaacgt tcatgcggcc    900
atcaatctgc cagacttaaa cgtcccgttc aacgcggctt accgctttac agtcattcac    960
gaaaatgtgc ctaacatggt gagtcaaatc acggccaaac tagcagcggc caacctcaac   1020
atcactacca tggctaacgc cgctaagcac cagattgctt acaccatcat tgacgtcgac   1080
gacctacagc agccacaaca agccgaccta atagctgaac tgtctaaaat tccggcagtg   1140
agtcgcgttc gactattaaa acggggtagc gtcgaatga                          1179
```

<210> SEQ ID NO 20
<211> LENGTH: 392
<212> TYPE: PRT
<213> ORGANISM: Lactobacillus plantarum

<400> SEQUENCE: 20

```
Met Tyr Gln Val Lys Thr Tyr Asn Ala Ile Ala Pro Ala Gly Leu Asn
1               5                   10                  15

Thr Phe Thr Ala Asp Tyr Thr Leu Asn Gln Ser Glu His Pro Asp Ala
            20                  25                  30

Tyr Leu Ile Arg Ser Val Asn Leu His Thr Glu Thr Leu Pro Ser Ser
        35                  40                  45

Leu Lys Val Ile Val Arg Ala Gly Ala Gly Val Asn Asn Ile Pro Ile
    50                  55                  60

Asp Gln Ala Thr Ala Asn Gly Thr Ala Val Phe Asn Thr Pro Gly Ser
65                  70                  75                  80

Asn Ala Asn Ala Val Lys Glu Leu Ile Ile Gly Leu Leu Ile Met Ala
                85                  90                  95

Ser Arg Asn Leu Ile Ala Ala Thr Thr Tyr Ser Ala Gln His Thr Glu
            100                 105                 110

Ala Asp Ile Ser Gln Arg Thr Glu His Asp Lys Thr Gln Phe Asn Gly
        115                 120                 125

Ile Glu Leu Thr Gly Lys Thr Leu Ala Val Ile Gly Leu Gly His Val
    130                 135                 140

Gly Ala Leu Val Ala Asn Ala Ala Leu Ser Leu Gly Met Asn Val Ile
145                 150                 155                 160

Gly Tyr Asp Pro Tyr Leu Ser Ala Asp Ala Ala Trp Asn Ile Ala Lys
                165                 170                 175

Gln Val Gln Arg Ala Ala Thr Leu Pro Asp Ala Val Lys Gln Ala Asp
            180                 185                 190
```

Phe Val Thr Val His Val Pro Lys Asn Ala Asp Thr Leu His Leu Ile
            195                 200                 205

Asn Lys Asp Ala Leu Ala Ala Met Pro Thr Gly Val Gln Leu Phe Asn
        210                 215                 220

Tyr Ser Arg Leu Gly Ile Val Asp Asn Thr Ala Val Met Asn Ala Leu
225                 230                 235                 240

Ala Thr Gly Gln Val Ala His Tyr Tyr Thr Asp Phe Gly Glu Pro Gln
            245                 250                 255

Leu Ala Asn Gln Ser Ala Val Thr Val Thr Pro His Ile Gly Gly Ser
        260                 265                 270

Thr Ile Glu Ala Glu Ile Asn Gly Ala Thr Gln Ala Ala Arg Thr Ile
            275                 280                 285

Met Thr Tyr Leu Glu Thr Gly Asn Val His Ala Ala Ile Asn Leu Pro
        290                 295                 300

Asp Leu Asn Val Pro Phe Asn Ala Ala Tyr Arg Phe Thr Val Ile His
305                 310                 315                 320

Glu Asn Val Pro Asn Met Val Ser Gln Ile Thr Ala Lys Leu Ala Ala
            325                 330                 335

Ala Asn Leu Asn Ile Thr Thr Met Ala Asn Ala Ala Lys His Gln Ile
        340                 345                 350

Ala Tyr Thr Ile Ile Asp Val Asp Asp Leu Gln Gln Pro Gln Gln Ala
            355                 360                 365

Asp Leu Ile Ala Glu Leu Ser Lys Ile Pro Ala Val Ser Arg Val Arg
        370                 375                 380

Leu Leu Lys Arg Gly Ser Val Glu
385                 390

<210> SEQ ID NO 21
<211> LENGTH: 1074
<212> TYPE: DNA
<213> ORGANISM: Lactobacillus plantarum

<400> SEQUENCE: 21
atgccaattt taaattttc tgctgggcca gccgttctac cacaaccagt catcactcaa      60
attcaagcgg agctaccatc atttcgagac tccggcatga gcattttaga gatctcgcat     120
cgctccgatt tatttgcgca agtccttcaa gatgccgaac aagatcttcg cgatttaatg     180
gccattcctg caaactatca cgtgctcttc tttcaaggcg ggggcacgct acagttcaca     240
gctgcgccac taaatctggc gcctcatcat cgtatcgggt tgcttgacag cggtcactgg     300
gcacaacgcg ccgccgatga agctaaacgg gtcggtacta agtcacgat actggggagt      360
agcgctgcca accatttaa ccaactgcca acggtcgtcc agcccatcga tcaatccctc      420
gattatattc atcttacaac taataatact attgaaggaa ccatgatgac gcgcctgcca     480
gttacgggtc aagtaccact ggtagccgac atgtcatcaa acttttttagg tgaaccttac    540
caagtcagcg attttgggct catctttgct ggtgctcaga gaatctgggt cccgctggt     600
ttgacaatcg tcattgtccg tgatgattta attggtcaag tcgccaacct gccaagcatg     660
ctggattacc agctattcgc ggctaaagat tcgatgttca acacgccgcc tgttttgct     720
atttacgccg cgggtctcgt actcaagtgg ctaaaggccc aaggcgggct cagcacaatg     780
actgctcgca atcacgctaa agccgcctta ctctatgatt tcttagacca gtcacaacta     840
tttactaatc cagtcaagac cagcgaccgt tcgaccatga acgttccatt cgtcacaggt     900
caggccgacc tcgatgccgc agtcattcaa ggcgcccgtg agcacgggtt attaaaccta     960
aagggtcacc gcttagttgg cggtatgcgt gccagcctct ataacgccat gccgttagcc    1020
ggtgttcagg cattagttga ctatctagcc gcttttgaag cacaccatcg ttaa          1074

<210> SEQ ID NO 22
<211> LENGTH: 357
<212> TYPE: PRT
<213> ORGANISM: Lactobacillus plantarum

<400> SEQUENCE: 22

Met Pro Ile Tyr Asn Phe Ser Ala Gly Pro Ala Val Leu Pro Gln Pro
1               5                   10                  15

Val Ile Thr Gln Ile Gln Ala Glu Leu Pro Ser Phe Arg Asp Ser Gly
            20                  25                  30

Met Ser Ile Leu Glu Ile Ser His Arg Ser Asp Leu Phe Ala Gln Val
        35                  40                  45

Leu Gln Asp Ala Glu Gln Asp Leu Arg Asp Leu Met Ala Ile Pro Asp
    50                  55                  60

Asn Tyr His Val Leu Phe Phe Gln Gly Gly Gly Thr Leu Gln Phe Thr
65                  70                  75                  80

Ala Ala Pro Leu Asn Leu Ala Pro His His Arg Ile Gly Leu Leu Asp
                85                  90                  95

Ser Gly His Trp Ala Gln Arg Ala Ala Asp Glu Ala Lys Arg Val Gly
            100                 105                 110

Thr Lys Val Thr Ile Leu Gly Ser Ser Ala Ala Asn His Phe Asn Gln
        115                 120                 125

Leu Pro Thr Val Val Gln Pro Ile Asp Gln Ser Leu Asp Tyr Ile His
    130                 135                 140

Leu Thr Thr Asn Asn Thr Ile Glu Gly Thr Met Met Thr Arg Leu Pro
145                 150                 155                 160

Val Thr Gly Gln Val Pro Leu Val Ala Asp Met Ser Ser Asn Phe Leu
                165                 170                 175

Gly Glu Pro Tyr Gln Val Ser Asp Phe Gly Leu Ile Phe Ala Gly Ala
            180                 185                 190

Gln Lys Asn Leu Gly Pro Ala Gly Leu Thr Ile Val Ile Val Arg Asp
        195                 200                 205

Asp Leu Ile Gly Gln Val Ala Asn Leu Pro Ser Met Leu Asp Tyr Gln
    210                 215                 220

Leu Phe Ala Ala Lys Asp Ser Met Phe Asn Thr Pro Pro Val Phe Ala
225                 230                 235                 240

Ile Tyr Ala Ala Gly Leu Val Leu Lys Trp Leu Lys Ala Gln Gly Gly
                245                 250                 255

Leu Ser Thr Met Thr Ala Arg Asn His Ala Lys Ala Ala Leu Leu Tyr
            260                 265                 270

Asp Phe Leu Asp Gln Ser Gln Leu Phe Thr Asn Pro Val Lys Thr Ser
        275                 280                 285

Asp Arg Ser Thr Met Asn Val Pro Phe Val Thr Gly Gln Ala Asp Leu
    290                 295                 300

Asp Ala Ala Val Ile Gln Gly Ala Arg Glu His Gly Leu Leu Asn Leu
305                 310                 315                 320

Lys Gly His Arg Leu Val Gly Gly Met Arg Ala Ser Leu Tyr Asn Ala
                325                 330                 335

Met Pro Leu Ala Gly Val Gln Ala Leu Val Asp Tyr Leu Ala Ala Phe
            340                 345                 350

Glu Ala His His Arg
        355

<210> SEQ ID NO 23
<211> LENGTH: 1368
<212> TYPE: DNA
<213> ORGANISM: Lactobacillus plantarum

<400> SEQUENCE: 23

```
atgctgaaag aaatggaaga aacaaccgta tcacgttcaa tcgatcggtt agtcttaaat      60
gcttcgttag ctgccaaccg tcttgaagtc atggaccaaa gtcaagttga tcaggctgtc     120
gctgccatgg cccgcgctgc ccacgctgct cgtggcatgc tggccgctat ggccgtcgaa     180
gaaacgggtc gcggaaatta tcgtgataaa gttgcgaaga acgactttgc agccaaaaac     240
gtttataact acatcaagga tgacaagacg gtcggtatca ttaatgacga tccagtcagt     300
ggcgtgatga agttgctga  accagttgga attattgcgg gggtcacccc agttaccaac     360
ccaacatcaa ccgtcatttt caatgccatg ttagcattaa agactcgcaa tcccattatt     420
tttggtttcc atcccttgc  acaaaaatct tgtgttgaaa ctggccgaat catccgcgat     480
gctgctattg cctctggcgc tcctaaggat tggattcagt ggatcaagac gcctagcctt     540
gaagcaacca acaccttgat gaaccatccg ggcgtcgcta ccattattgc aactggcggt     600
gccggcatgg tcaagaccgc gtattcaact ggtaaaccgg cactcggtgt tggccctggt     660
aacgtgccat gcttcatcga gcaaaccgca gacattcaac aggcagtcag tgatgtcgtc     720
acttccaagt cattcgacaa cggcatgatc tgtgcttccg aatcaaactt aatcgttgct     780
gatcaaatct atgatcaagt taaacgtgaa ttaagtcaca acggtgtgta ctttgtcggt     840
accgagaact tcaaggcctt agaagcaact gtcatgaacc tggataaaca ggctgttgac     900
ccgaaagtag ctgggcaaac gccatggcaa atcgctcagt gggctggctt tgatgtccca     960
tccgatacca agtattagc  agttgagttg cctagcatcg gtggtgacca agtcttatca    1020
cgagaaaagt tatcaccagt cctcgccgtc gttcatgcca aggatactga ggccggcttc    1080
aacctgatga acgcagcct  agcacttggc ggactgggac atacggccgc cttgcatacg    1140
actgacgaag ctgttatgaa caagtttgcc ttagaaatga ctgcttgtcg agcattgatc    1200
aacgtgccgt cttcacaagg tgccattggt tataaatatg ataacgtcgc accatcctta    1260
acactcggtt gtggaacatg ggggcataac tcgatttcac acaacttgga agattgggat    1320
ctactaaata ttaagaccgt tgcaaaacgc ttaactaaga ttcgctaa               1368
```

<210> SEQ ID NO 24
<211> LENGTH: 455
<212> TYPE: PRT
<213> ORGANISM: Lactobacillus plantarum

<400> SEQUENCE: 24

Met Leu Lys Glu Met Glu Glu Thr Thr Val Ser Arg Ser Ile Asp Arg
1               5                   10                  15

Leu Val Leu Asn Ala Ser Leu Ala Ala Asn Arg Leu Glu Val Met Asp
                20                  25                  30

Gln Ser Gln Val Asp Gln Ala Val Ala Ala Met Ala Arg Ala Ala His
            35                  40                  45

Ala Ala Arg Gly Met Leu Ala Ala Met Ala Val Glu Glu Thr Gly Arg
        50                  55                  60

Gly Asn Tyr Arg Asp Lys Val Ala Lys Asn Asp Phe Ala Ala Lys Asn
65                  70                  75                  80

Val Tyr Asn Tyr Ile Lys Asp Asp Lys Thr Val Gly Ile Ile Asn Asp
            85                  90                  95

Asp Pro Val Ser Gly Val Met Lys Val Ala Glu Pro Val Gly Ile Ile
            100                 105                 110

Ala Gly Val Thr Pro Val Thr Asn Pro Thr Ser Thr Val Ile Phe Asn
            115                 120                 125

Ala Met Leu Ala Leu Lys Thr Arg Asn Pro Ile Ile Phe Gly Phe His
        130                 135                 140

Pro Phe Ala Gln Lys Ser Cys Val Glu Thr Gly Arg Ile Ile Arg Asp
145                 150                 155                 160

Ala Ala Ile Ala Ser Gly Ala Pro Lys Asp Trp Ile Gln Trp Ile Lys
            165                 170                 175

Thr Pro Ser Leu Glu Ala Thr Asn Thr Leu Met Asn His Pro Gly Val
            180                 185                 190

Ala Thr Ile Ile Ala Thr Gly Gly Ala Gly Met Val Lys Thr Ala Tyr
            195                 200                 205

Ser Thr Gly Lys Pro Ala Leu Gly Val Gly Pro Gly Asn Val Pro Cys
            210                 215                 220

Phe Ile Glu Gln Thr Ala Asp Ile Gln Gln Ala Val Ser Asp Val Val
225                 230                 235                 240

Thr Ser Lys Ser Phe Asp Asn Gly Met Ile Cys Ala Ser Glu Ser Asn
            245                 250                 255

Leu Ile Val Ala Asp Gln Ile Tyr Asp Gln Val Lys Arg Glu Leu Ser
            260                 265                 270

His Asn Gly Val Tyr Phe Val Gly Thr Glu Asn Phe Lys Ala Leu Glu
            275                 280                 285

Ala Thr Val Met Asn Leu Asp Lys Gln Ala Val Asp Pro Lys Val Ala
        290                 295                 300

Gly Gln Thr Pro Trp Gln Ile Ala Gln Trp Ala Gly Phe Asp Val Pro
305                 310                 315                 320

Ser Asp Thr Lys Val Leu Ala Val Glu Leu Pro Ser Ile Gly Gly Asp
            325                 330                 335

Gln Val Leu Ser Arg Glu Lys Leu Ser Pro Val Leu Ala Val Val His
            340                 345                 350

Ala Lys Asp Thr Glu Ala Gly Phe Asn Leu Met Lys Arg Ser Leu Ala
            355                 360                 365

Leu Gly Gly Leu Gly His Thr Ala Leu His Thr Thr Asp Glu Ala
        370                 375                 380

Val Met Asn Lys Phe Ala Leu Glu Met Thr Ala Cys Arg Ala Leu Ile
385                 390                 395                 400

Asn Val Pro Ser Ser Gln Gly Ala Ile Gly Tyr Lys Tyr Asp Asn Val
            405                 410                 415

Ala Pro Ser Leu Thr Leu Gly Cys Gly Thr Trp Gly His Asn Ser Ile
            420                 425                 430

Ser His Asn Leu Glu Asp Trp Asp Leu Leu Asn Ile Lys Thr Val Ala
        435                 440                 445

Lys Arg Leu Thr Lys Ile Arg
    450                 455

<210> SEQ ID NO 25
<211> LENGTH: 1527
<212> TYPE: DNA
<213> ORGANISM: Lactobacillus plantarum

<400> SEQUENCE: 25

```
atgcagacat taatacagac gtttatagat cgacgcgggg atttgctgac tgcgctatgg      60
caacacttgg ggatttcatt agcatcatta gtcatcgcaa tggtaattgc gattccgttg     120
gctatttggg tcgttcgacg accacggtgg gccgagggat tgttacagct cacgagtgtc     180
ctacagacga ttccgtcttt ggcactgtta gggttattga ttccgttagt tgggattgga     240
acggtgccag cagtaattgc gctggtgatc tatgctttac tgccgatttt tcaaaatact     300
tacttgggta tctcagaaat cgatgcctca attgaagagg ccgccgatgc ctttgggatg     360
tcacgaatgc gtaagttgtt taaagttgaa ctacccattg ccctaccaca gatcattgct     420
gggattcgga ccgcgctcgt tttaatcatt gggacggcta ctttggccgc tttgattggt     480
gctgggggtc tcgggacctt tatcatgctc ggtattgacc gtaatgatac ttcgttatta     540
ttgattgggg ccatctcatc agcattgtta gcaattctgc tgagtgcgct cgttcggtgg     600
tttcaaacgg ctaaaccacg ccacgcctta atcgtctttg tcggtatttt agctttactt     660
ggtggtggcg gggcttatag tgtctatgcc aatcgagttg aaacaattac gattgcaggt     720
aaacttggtt ccgaaccaga aatcttgatt aatatgtata agcagctgat tgaagctgaa     780
gatgaacacg ttcatgtgac gctcaagcct aactttggca agaccacgtt cttattcagc     840
gcgttaaaga ataatcaggt tgatatttat cctgaattta ctggctcggt gctggagacc     900
ttagttaagg gaaataaccc agctggtcaa acagctaacc agacctatca gctcgccaaa     960
cagcgcctcg ctaagcagga acaaatgact tacttgaagc cgatgcagta taacaatacg    1020
tacgcattgg cagtgactaa gaaatttcaa caagaacatc atttgaagac aatcagcgac    1080
ttaacgcaag ttgaatcgat tctgaaaccc ggaatgaccc tagagtttat tgatcgtaat    1140
gatggcttaa aaggaatcaa gaagactttat gggttagacg tgactgccaa gtcgatggag    1200
ccggcgctac gttatgaagc catcagtaag gggaaaatca acttggtaga tgcctatgcg    1260
acggatagtg aattacggca gtatcacttg gccttattga aggataacaa gcacttcttc    1320
ccaacgtatc aaggggcacc gttgatgaag acgagctttg ccaacaaaca tcctaaggtc    1380
gttaaagcgt tgaataagtt agcaggaaag atttcagaaa ctgatatgca agaaatgaac    1440
tatgaagtca atgttaagaa gcagtccgct tcgacggttg cacatcgcta tcttgtgaag    1500
cacggtttat tgaaggaggg acgttaa                                        1527
```

<210> SEQ ID NO 26
<211> LENGTH: 508
<212> TYPE: PRT
<213> ORGANISM: Lactobacillus plantarum

<400> SEQUENCE: 26

```
Met Gln Thr Leu Ile Gln Thr Phe Ile Asp Arg Arg Gly Asp Leu Leu
 1               5                  10                  15

Thr Ala Leu Trp Gln His Leu Gly Ile Ser Leu Ala Ser Leu Val Ile
             20                  25                  30

Ala Met Val Ile Ala Ile Pro Leu Ala Ile Trp Val Val Arg Arg Pro
         35                  40                  45

Arg Trp Ala Glu Gly Leu Leu Gln Leu Thr Ser Val Leu Gln Thr Ile
     50                  55                  60

Pro Ser Leu Ala Leu Leu Gly Leu Leu Ile Pro Leu Val Gly Ile Gly
 65                  70                  75                  80

Thr Val Pro Ala Val Ile Ala Leu Val Ile Tyr Ala Leu Leu Pro Ile
                 85                  90                  95
```

```
Phe Gln Asn Thr Tyr Leu Gly Ile Ser Glu Ile Asp Ala Ser Ile Glu
                100                 105                 110

Glu Ala Ala Asp Ala Phe Gly Met Ser Arg Met Arg Lys Leu Phe Lys
            115                 120                 125

Val Glu Leu Pro Ile Ala Leu Pro Gln Ile Ile Ala Gly Ile Arg Thr
130                 135                 140

Ala Leu Val Leu Ile Ile Gly Thr Ala Thr Leu Ala Ala Leu Ile Gly
145                 150                 155                 160

Ala Gly Gly Leu Gly Thr Phe Ile Met Leu Gly Ile Asp Arg Asn Asp
                165                 170                 175

Thr Ser Leu Leu Leu Ile Gly Ala Ile Ser Ser Ala Leu Leu Ala Ile
                180                 185                 190

Leu Leu Ser Ala Leu Val Arg Trp Phe Gln Thr Ala Lys Pro Arg His
            195                 200                 205

Ala Leu Ile Val Phe Val Gly Ile Leu Ala Leu Leu Gly Gly Gly Gly
            210                 215                 220

Ala Tyr Ser Val Tyr Ala Asn Arg Val Glu Thr Ile Thr Ile Ala Gly
225                 230                 235                 240

Lys Leu Gly Ser Glu Pro Glu Ile Leu Ile Asn Met Tyr Lys Gln Leu
                245                 250                 255

Ile Glu Ala Glu Asp Glu His Val His Val Thr Leu Lys Pro Asn Phe
                260                 265                 270

Gly Lys Thr Thr Phe Leu Phe Ser Ala Leu Lys Asn Asn Gln Val Asp
            275                 280                 285

Ile Tyr Pro Glu Phe Thr Gly Ser Val Leu Glu Thr Leu Val Lys Gly
            290                 295                 300

Asn Asn Pro Ala Gly Gln Thr Ala Asn Gln Thr Tyr Gln Leu Ala Lys
305                 310                 315                 320

Gln Arg Leu Ala Lys Gln Glu Gln Met Thr Tyr Leu Lys Pro Met Gln
                325                 330                 335

Tyr Asn Asn Thr Tyr Ala Leu Ala Val Thr Lys Lys Phe Gln Gln Glu
                340                 345                 350

His His Leu Lys Thr Ile Ser Asp Leu Thr Gln Val Glu Ser Ile Leu
            355                 360                 365

Lys Pro Gly Met Thr Leu Glu Phe Ile Asp Arg Asn Asp Gly Leu Lys
            370                 375                 380

Gly Ile Lys Lys Thr Tyr Gly Leu Asp Val Thr Ala Lys Ser Met Glu
385                 390                 395                 400

Pro Ala Leu Arg Tyr Glu Ala Ile Ser Lys Gly Lys Ile Asn Leu Val
                405                 410                 415

Asp Ala Tyr Ala Thr Asp Ser Glu Leu Arg Gln Tyr His Leu Ala Leu
            420                 425                 430

Leu Lys Asp Asn Lys His Phe Phe Pro Thr Tyr Gln Gly Ala Pro Leu
            435                 440                 445

Met Lys Thr Ser Phe Ala Asn Lys His Pro Lys Val Val Lys Ala Leu
            450                 455                 460

Asn Lys Leu Ala Gly Lys Ile Ser Glu Thr Asp Met Gln Glu Met Asn
465                 470                 475                 480

Tyr Glu Val Asn Val Lys Lys Gln Ser Ala Ser Thr Val Ala His Arg
                485                 490                 495

Tyr Leu Val Lys His Gly Leu Leu Lys Glu Gly Arg
                500                 505
```

<210> SEQ ID NO 27
<211> LENGTH: 972
<212> TYPE: DNA
<213> ORGANISM: Lactobacillus plantarum

<400> SEQUENCE: 27

```
atgacaacgg caattgaatt tcaacacgtc cagaaagact ttaatgggca gaccgtgatt        60
cccgacctta atttaacgat tgaccagggt gagctatttg ttttggtagg gacttctggg       120
agtggcaaaa cgacgtcact taaaatgatc aactgcttag agccactgac ggctggtaaa       180
attctagtta atggtactga tacaaccacg ataccagtcc gaagtctacg gtggcaaatg       240
gggtatgtct tacagcaaat tgccttgttc ccaacgatga cggtggcgca aaatatcgcc       300
gtgattccgg aaatgaaagg gacagctaag aaggaaatta atcaaacgat tgatgagcta       360
ttggcggaag ttggcctcga tccaaaggaa taccgtgacc ggatgccgtc agaattatcc       420
ggtggtgagc agcaacgcat cggtatctta cgggcgattg cggcgcaacc agatattgtt       480
tgatggatg aaccatttag tgcgttagac cccatctcgc ggcaacaatt gcaagacttg        540
gtcttacggc tacacgcccg ctatcacaac acgatcgtct cgtgacgca tgatatgaat        600
gaggcgttga agttgggtga ccggatcggt gtcatgcaac acggtcagtt aatacaagtc       660
gatacgccgg ctgctctggc tcagcatcca gtgaacgact ttgtgcggaa cttctttggt       720
gcgagccgag ctaaaaatgt ctatgatgtc tacgttgggc gtgtagggct tattcagggt       780
tatctcacag aagaacccag tgttgcgagt ggtcggattc aatcgttaga cgttcaagcc       840
acgttacgca ccgcctttac ggcattgaca gatcacgatt atgtggcggt cacggaagaa       900
atcggggttg ttggctattt ggatcgccaa cgaatcgtgg cttacttgag tcaacatgaa       960
gaagtatctt aa                                                           972
```

<210> SEQ ID NO 28
<211> LENGTH: 323
<212> TYPE: PRT
<213> ORGANISM: Lactobacillus plantarum

<400> SEQUENCE: 28

```
Met Thr Thr Ala Ile Glu Phe Gln His Val Gln Lys Asp Phe Asn Gly
1               5                   10                  15

Gln Thr Val Ile Pro Asp Leu Asn Leu Thr Ile Asp Gln Gly Glu Leu
            20                  25                  30

Phe Val Leu Val Gly Thr Ser Gly Ser Gly Lys Thr Thr Ser Leu Lys
        35                  40                  45

Met Ile Asn Cys Leu Glu Pro Leu Thr Ala Gly Lys Ile Leu Val Asn
    50                  55                  60

Gly Thr Asp Thr Thr Thr Ile Pro Val Arg Ser Leu Arg Trp Gln Met
65                  70                  75                  80

Gly Tyr Val Leu Gln Gln Ile Ala Leu Phe Pro Thr Met Thr Val Ala
                85                  90                  95

Gln Asn Ile Ala Val Ile Pro Glu Met Lys Gly Thr Ala Lys Lys Glu
            100                 105                 110

Ile Asn Gln Thr Ile Asp Glu Leu Leu Ala Glu Val Gly Leu Asp Pro
        115                 120                 125

Lys Glu Tyr Arg Asp Arg Met Pro Ser Glu Leu Ser Gly Gly Glu Gln
    130                 135                 140

Gln Arg Ile Gly Ile Leu Arg Ala Ile Ala Ala Gln Pro Asp Ile Val
145                 150                 155                 160
```

```
Leu Met Asp Glu Pro Phe Ser Ala Leu Asp Pro Ile Ser Arg Gln Gln
                165                 170                 175

Leu Gln Asp Leu Val Leu Arg Leu His Ala Arg Tyr His Asn Thr Ile
            180                 185                 190

Val Phe Val Thr His Asp Met Asn Glu Ala Leu Lys Leu Gly Asp Arg
        195                 200                 205

Ile Gly Val Met Gln His Gly Gln Leu Ile Gln Val Asp Thr Pro Ala
    210                 215                 220

Ala Leu Ala Gln His Pro Val Asn Asp Phe Val Arg Asn Phe Phe Gly
225                 230                 235                 240

Ala Ser Arg Ala Lys Asn Val Tyr Asp Val Tyr Val Gly Arg Val Gly
                245                 250                 255

Leu Ile Gln Gly Tyr Leu Thr Glu Glu Pro Ser Val Ala Ser Gly Arg
            260                 265                 270

Ile Gln Ser Leu Asp Val Gln Ala Thr Leu Arg Thr Ala Phe Thr Ala
        275                 280                 285

Leu Thr Asp His Asp Tyr Val Ala Val Thr Glu Glu Asn Arg Val Val
    290                 295                 300

Gly Tyr Leu Asp Arg Gln Arg Ile Val Ala Tyr Leu Ser Gln His Glu
305                 310                 315                 320

Glu Val Ser

<210> SEQ ID NO 29
<211> LENGTH: 1332
<212> TYPE: DNA
<213> ORGANISM: Lactobacillus plantarum

<400> SEQUENCE: 29
atggcggaac agtacgatgt tgttgtgatt ggtggcggac cagccggcaa tgccatggct      60
agcggattaa aggcccaggg caagacagtg ttgatcgttg aagcggatct gtgggcggc     120 acttgtccta accgcggttg tgaccctaag aaaatcctgt taagcgccgt cgaagcgcga     180
caagcggcgc aacatttaca agggcagggc ctgattggcg cgcccaaaat tgattggcca     240
gcactgatgg cgcataaacg aggctatacg gatggcatca cgatgggac gttgaacgga     300 ctaacggggc aagatattgc gacgttacat ggccaagcac actttcaatc cgacaatcag     360
ttagcggtcg gggatcgagt agtcagtgcc actgattacg tgattgctac tggtcagcgt     420
ccagcgattc taccgattac cgggcacgaa tactttaaga cgagcactga cttcttagat     480
ttggaccaga tgcctaaacg cgtgacattt gtaggtggtg gctacgtagg ctttgaattg     540
gcgacgattg cgaatgccgc tggcgctgat gtgcacgtga ttcatcataa tgaccgcccg     600
ttaaaagctt ttgatgcaga tttggttaag gatttgatgg ccgcaatgac ggctgatgga     660
atcacgtttg acttgaatac ggatgtccaa gcaattacta aaacggcgac cggtctacaa     720
ttgacagctg ataatttcga gctgacaacg gatctggtca tcagctcagc gggacggatt     780
ccgaacgcgg accagttagg tctagccaac gtgggcgtta cctttgatcg gcatgggatt     840
caagtcaacg atcatttgca gacggccaac ccgcacattt atgccattgg ggatgtcagc     900
gatacaccgg taccgaagtt aacgccagtt gcaggttttg aagcgcgtta tctggtcggt     960
gagttgacgc atcctggcgc agccataaag tatcccgttg tgccaacgca ggttttttgca   1020 gcgcccaagt tagcgcaagt cgggatcagc gcggccgtgg cgactgagca tccagatgag   1080
tatcgtgtca atacacttga tatgacgaag tggttcactt attaccgctt tggcgcacaa   1140
```

```
caagcccaag ctaaagtagt ggttgctaaa gcgagtgggc aggttgtggg tgctaccctt    1200
ctaagtgatg ttgccgacga gatgattaac tacttcacgt tgttaattga aaaacacgtg    1260
actttaccag atttacaacg gttggtattg gcttacccaa cgccggctag tgacttacaa    1320
tatttgtatt aa                                                        1332
```

<210> SEQ ID NO 30
<211> LENGTH: 443
<212> TYPE: PRT
<213> ORGANISM: Lactobacillus plantarum

<400> SEQUENCE: 30

```
Met Ala Glu Gln Tyr Asp Val Val Ile Gly Gly Pro Ala Gly
1               5                   10                  15

Asn Ala Met Ala Ser Gly Leu Lys Ala Gln Gly Lys Thr Val Leu Ile
            20                  25                  30

Val Glu Ala Asp Leu Trp Gly Gly Thr Cys Pro Asn Arg Gly Cys Asp
        35                  40                  45

Pro Lys Lys Ile Leu Leu Ser Ala Val Glu Ala Arg Gln Ala Ala Gln
    50                  55                  60

His Leu Gln Gly Gln Gly Leu Ile Gly Ala Pro Lys Ile Asp Trp Pro
65                  70                  75                  80

Ala Leu Met Ala His Lys Arg Gly Tyr Thr Asp Gly Ile Asn Asp Gly
                85                  90                  95

Thr Leu Asn Gly Leu Thr Gly Gln Asp Ile Ala Thr Leu His Gly Gln
            100                 105                 110

Ala His Phe Gln Ser Asp Asn Gln Leu Ala Val Gly Asp Arg Val Val
        115                 120                 125

Ser Ala Thr Asp Tyr Val Ile Ala Thr Gly Gln Arg Pro Ala Ile Leu
    130                 135                 140

Pro Ile Thr Gly His Glu Tyr Phe Lys Thr Ser Thr Asp Phe Leu Asp
145                 150                 155                 160

Leu Asp Gln Met Pro Lys Arg Val Thr Phe Val Gly Gly Gly Tyr Val
                165                 170                 175

Gly Phe Glu Leu Ala Thr Ile Ala Asn Ala Ala Gly Ala Asp Val His
            180                 185                 190

Val Ile His His Asn Asp Arg Pro Leu Lys Ala Phe Asp Ala Asp Leu
        195                 200                 205

Val Lys Asp Leu Met Ala Ala Met Thr Ala Asp Gly Ile Thr Phe Asp
    210                 215                 220

Leu Asn Thr Asp Val Gln Ala Ile Thr Lys Thr Ala Thr Gly Leu Gln
225                 230                 235                 240

Leu Thr Ala Asp Asn Phe Glu Leu Thr Thr Asp Leu Val Ile Ser Ser
                245                 250                 255

Ala Gly Arg Ile Pro Asn Ala Asp Gln Leu Gly Leu Ala Asn Val Gly
            260                 265                 270

Val Thr Phe Asp Arg His Gly Ile Gln Val Asn Asp His Leu Gln Thr
        275                 280                 285

Ala Asn Pro His Ile Tyr Ala Ile Gly Asp Val Ser Asp Thr Pro Val
    290                 295                 300

Pro Lys Leu Thr Pro Val Ala Gly Phe Glu Ala Arg Tyr Leu Val Gly
305                 310                 315                 320

Glu Leu Thr His Pro Gly Ala Ile Lys Tyr Pro Val Pro Thr
                325                 330                 335
```

Gln Val Phe Ala Ala Pro Lys Leu Ala Gln Val Gly Ile Ser Ala Ala
                340                 345                 350

Val Ala Thr Glu His Pro Asp Glu Tyr Arg Val Asn Thr Leu Asp Met
            355                 360                 365

Thr Lys Trp Phe Thr Tyr Tyr Arg Phe Gly Ala Gln Gln Ala Gln Ala
        370                 375                 380

Lys Val Val Ala Lys Ala Ser Gly Gln Val Val Gly Ala Thr Leu
385                 390                 395                 400

Leu Ser Asp Val Ala Asp Glu Met Ile Asn Tyr Phe Thr Leu Leu Ile
                405                 410                 415

Glu Lys His Val Thr Leu Pro Asp Leu Gln Arg Leu Val Leu Ala Tyr
            420                 425                 430

Pro Thr Pro Ala Ser Asp Leu Gln Tyr Leu Tyr
        435                 440

<210> SEQ ID NO 31
<211> LENGTH: 1614
<212> TYPE: DNA
<213> ORGANISM: Lactobacillus plantarum

<400> SEQUENCE: 31

| | | | | | |
|---|---|---|---|---|---|
| atgaccaaat | atattttgt | aactggtggc | gttgtgtcat | ccattggtaa | aggtatcgtc | 60 |
| gctgcttcgc | tagggcgttt | attgaagaac | cggggcttaa | aggtcacgat | tcaaaagttt | 120 |
| gatccctata | tcaacgttga | tcctggtacg | atgagtcctt | atcaacacgg | tgaagtcttc | 180 |
| gtgaccgatg | atgggaccga | aactgactta | gaccttggac | attatgaacg | gtttatcgac | 240 |
| attaacctta | ataaatattc | aaatgttacc | accggtaaga | tttattcaga | agttctgcaa | 300 |
| aaggaacggc | ggggcgatta | tttaggcgcc | acggtgcaag | tgattccgca | tatcacgaac | 360 |
| gctatcaagg | aaaaaatcat | gcgtgcgggt | acgacgacgg | attccgatat | cgtgattact | 420 |
| gaaatcggtg | gacggtcgg | tgatatcgaa | tccttgccat | ttattgaagc | gctacggcaa | 480 |
| atgaagagtg | atttaggttc | cgacaatgtt | ttctatatcc | ataccacatt | gatcccatat | 540 |
| ttacgggcag | ctggtgaaat | gaagacgaag | ccaacgcaac | attctgttaa | ggaattgcgg | 600 |
| agttatggga | ttcagccgaa | catgttagtt | gtccggactg | aacaaccaat | tacgcgggaa | 660 |
| atgcggaata | agattgcgtc | cttctgtgac | gtggaaccag | aagcagtcat | tgaatcctta | 720 |
| gacgttaaga | cgatttattc | aattccgttg | aatgttcaga | acaaaacat | ggaccaaatc | 780 |
| gtccttgacc | attttgatgt | acaggcacct | aaggccgaca | tgagtgaatg | gattgactta | 840 |
| gaacatcatg | ttcagaactt | atcacggacc | atcaagattg | cgctagtcgg | aaaatacgtc | 900 |
| gctttacagg | atgcttatat | ctcagtgacg | gaagcattga | agcatgctgg | ctatacggat | 960 |
| gatgccgaca | ttgatttgaa | gaagatttct | gctgaagatg | ttacgccaga | aaatgtcgaa | 1020 |
| gaactactcg | gcgatgctga | cggaatctta | gttcctggtg | gctttggtga | tcggggaatt | 1080 |
| gaaggtaaga | ttacgcaat | caagtatgcc | cgtgaaaacg | acgtgccatt | cttaggtatc | 1140 |
| tgcttgggaa | tgcaaatggc | cagtgtcgaa | tttgcacgta | acgtacttgg | attgaaggat | 1200 |
| gctaactctg | ctgaaatcga | tccgaagacg | ccggacaata | ttattgattt | gatggccgac | 1260 |
| caagaagacg | ttgaagacat | gggtggaacg | caacgtttag | gcgcttaccc | ttgcaagctg | 1320 |
| aagccgggaa | ctgtggcggc | taaagcctat | cacaatgaag | aagttgtgat | ggaacgtcat | 1380 |
| cgccaccgtt | atgaattcaa | taataagtat | cgtgaagcaa | tggctgctaa | gggcatggtc | 1440 |
| ttctccggaa | cttcgcctga | caaccggctc | gtcgaagtga | ttgaattacc | aagaagcgc | 1500 |

```
ttcttcgtgg cctcacaata ccatccagaa ttcttatcac ggcctaaccg tccagaaggg    1560
ttattcaagg cattcatcga tgccgctaac cagactggta aggtgaaggc ataa          1614
```

<210> SEQ ID NO 32
<211> LENGTH: 537
<212> TYPE: PRT
<213> ORGANISM: Lactobacillus plantarum

<400> SEQUENCE: 32

```
Met Thr Lys Tyr Ile Phe Val Thr Gly Gly Val Ser Ser Ile Gly
1               5                   10                  15

Lys Gly Ile Val Ala Ala Ser Leu Gly Arg Leu Leu Lys Asn Arg Gly
            20                  25                  30

Leu Lys Val Thr Ile Gln Lys Phe Asp Pro Tyr Ile Asn Val Asp Pro
        35                  40                  45

Gly Thr Met Ser Pro Tyr Gln His Gly Glu Val Phe Val Thr Asp Asp
    50                  55                  60

Gly Thr Glu Thr Asp Leu Asp Leu Gly His Tyr Glu Arg Phe Ile Asp
65                  70                  75                  80

Ile Asn Leu Asn Lys Tyr Ser Asn Val Thr Thr Gly Lys Ile Tyr Ser
                85                  90                  95

Glu Val Leu Gln Lys Glu Arg Arg Gly Asp Tyr Leu Gly Ala Thr Val
            100                 105                 110

Gln Val Ile Pro His Ile Thr Asn Ala Ile Lys Glu Lys Ile Met Arg
        115                 120                 125

Ala Gly Thr Thr Thr Asp Ser Asp Ile Val Ile Thr Glu Ile Gly Gly
    130                 135                 140

Thr Val Gly Asp Ile Glu Ser Leu Pro Phe Ile Glu Ala Leu Arg Gln
145                 150                 155                 160

Met Lys Ser Asp Leu Gly Ser Asp Asn Val Phe Tyr Ile His Thr Thr
                165                 170                 175

Leu Ile Pro Tyr Leu Arg Ala Ala Gly Glu Met Lys Thr Lys Pro Thr
            180                 185                 190

Gln His Ser Val Lys Glu Leu Arg Ser Tyr Gly Ile Gln Pro Asn Met
        195                 200                 205

Leu Val Val Arg Thr Glu Gln Pro Ile Thr Arg Glu Met Arg Asn Lys
    210                 215                 220

Ile Ala Ser Phe Cys Asp Val Glu Pro Glu Ala Val Ile Glu Ser Leu
225                 230                 235                 240

Asp Val Lys Thr Ile Tyr Ser Ile Pro Leu Asn Val Gln Lys Gln Asn
                245                 250                 255

Met Asp Gln Ile Val Leu Asp His Phe Asp Val Gln Ala Pro Lys Ala
            260                 265                 270

Asp Met Ser Glu Trp Ile Asp Leu Glu His His Val Gln Asn Leu Ser
        275                 280                 285

Arg Thr Ile Lys Ile Ala Leu Val Gly Lys Tyr Val Ala Leu Gln Asp
    290                 295                 300

Ala Tyr Ile Ser Val Thr Glu Ala Leu Lys His Ala Gly Tyr Thr Asp
305                 310                 315                 320

Asp Ala Asp Ile Asp Leu Lys Lys Ile Ser Ala Glu Val Thr Pro
                325                 330                 335

Glu Asn Val Glu Glu Leu Leu Gly Asp Ala Asp Gly Ile Leu Val Pro
            340                 345                 350

Gly Gly Phe Gly Asp Arg Gly Ile Glu Gly Lys Ile Thr Ala Ile Lys
```

```
                    355                 360                 365
Tyr Ala Arg Glu Asn Asp Val Pro Phe Leu Gly Ile Cys Leu Gly Met
                370                 375                 380

Gln Met Ala Ser Val Glu Phe Ala Arg Asn Val Leu Gly Leu Lys Asp
385                 390                 395                 400

Ala Asn Ser Ala Glu Ile Asp Pro Lys Thr Pro Asp Asn Ile Ile Asp
                405                 410                 415

Leu Met Ala Asp Gln Glu Asp Val Glu Asp Met Gly Gly Thr Gln Arg
                420                 425                 430

Leu Gly Ala Tyr Pro Cys Lys Leu Lys Pro Gly Thr Val Ala Ala Lys
                435                 440                 445

Ala Tyr His Asn Glu Glu Val Val Met Glu Arg His Arg His Arg Tyr
                450                 455                 460

Glu Phe Asn Asn Lys Tyr Arg Glu Ala Met Ala Ala Lys Gly Met Val
465                 470                 475                 480

Phe Ser Gly Thr Ser Pro Asp Asn Arg Leu Val Glu Val Ile Glu Leu
                485                 490                 495

Pro Lys Lys Arg Phe Phe Val Ala Ser Gln Tyr His Pro Glu Phe Leu
                500                 505                 510

Ser Arg Pro Asn Arg Pro Glu Gly Leu Phe Lys Ala Phe Ile Asp Ala
                515                 520                 525

Ala Asn Gln Thr Gly Lys Val Lys Ala
                530                 535

<210> SEQ ID NO 33
<211> LENGTH: 870
<212> TYPE: DNA
<213> ORGANISM: Lactobacillus plantarum

<400> SEQUENCE: 33
ttgacacatg gacaactaat cagaaaatta cgaaaagaac gtggcctaac tcaggcacaa      60
ttagcagaag gaatttctag tcgcactacc ctttccacat tagaaaatag taaaactgac    120
gttaatataa ataccctttt tagctatttg gatcgtttaa atgtatctat tcaggaatat    180
atgtttaatt tcaacgacag ttctaatacc gaaaaggaat tagcaaccaa atacttttac    240
gataacattg tgaaaaagcg tgatattgaa attgaacaac gaattttaga ttatcagtct    300
aaatataaag attctaagga tttctattac tgctgttttgt ctattgagct aaaactcttc    360
ttgaataaaa agaaagataa aactgtcttt gacgtaaggg aagatacaga gattataaaa    420
aagtatttgg aacgtgttac tcaatgggga catttttgaga tgtctatttt tgccaactgt    480
ctatacattt tcaccagtga ttatattcga gccacctttta caatcctatt gaaaagaact    540
aaaattctca gcaaaattga tacttatcaa atgatatttt ctatttttct aaataattgc    600
attgtactgg cacttgaaag aaagaattac caaaatgcac gcttctatat tcaacagctt    660
taccaaatat ctgagaaaac acctcgtaaa gcttatgaca gaatgatgtg tgcttattac    720
ctagcactac tcaaacaact taagggtgtt aacgcgaacg ttgatagtac gattagtcat    780
tttaaagaac taggtttttc tgagcacgct gaaatgcttg aaaatttacg ggatagatta    840
ctgtcttcga gtaaacaatc catagcttaa                                      870

<210> SEQ ID NO 34
<211> LENGTH: 289
<212> TYPE: PRT
<213> ORGANISM: Lactobacillus plantarum
```

<400> SEQUENCE: 34

Met Thr His Gly Gln Leu Ile Arg Lys Leu Arg Lys Glu Arg Gly Leu
1               5                   10                  15

Thr Gln Ala Gln Leu Ala Glu Gly Ile Ser Ser Arg Thr Thr Leu Ser
            20                  25                  30

Thr Leu Glu Asn Ser Lys Thr Asp Val Asn Ile Asn Thr Leu Phe Ser
        35                  40                  45

Tyr Leu Asp Arg Leu Asn Val Ser Ile Gln Tyr Met Phe Tyr Phe
    50                  55                  60

Asn Asp Ser Ser Asn Thr Glu Lys Glu Leu Ala Thr Lys Tyr Phe Tyr
65                  70                  75                  80

Asp Asn Ile Val Lys Lys Arg Asp Ile Glu Ile Gln Arg Ile Leu
                85                  90                  95

Asp Tyr Gln Ser Lys Tyr Lys Asp Ser Lys Asp Phe Tyr Cys Cys
            100                 105                 110

Leu Ser Ile Glu Leu Lys Leu Phe Leu Asn Lys Lys Asp Lys Thr
        115                 120                 125

Val Phe Asp Val Arg Glu Asp Thr Glu Ile Ile Lys Lys Tyr Leu Glu
    130                 135                 140

Arg Val Thr Gln Trp Gly His Phe Glu Met Ser Ile Phe Ala Asn Cys
145                 150                 155                 160

Leu Tyr Ile Phe Thr Ser Asp Tyr Ile Arg Ala Thr Phe Thr Ile Leu
                165                 170                 175

Leu Lys Arg Thr Lys Ile Leu Ser Lys Ile Asp Thr Tyr Gln Asn Asp
            180                 185                 190

Ile Ser Ile Phe Leu Asn Asn Cys Ile Val Leu Ala Leu Glu Arg Lys
        195                 200                 205

Asn Tyr Gln Asn Ala Arg Phe Tyr Ile Gln Gln Leu Tyr Gln Ile Ser
    210                 215                 220

Glu Lys Thr Pro Arg Lys Ala Tyr Asp Arg Met Met Cys Ala Tyr Tyr
225                 230                 235                 240

Leu Ala Leu Leu Lys Gln Leu Lys Gly Val Asn Ala Asn Val Asp Ser
                245                 250                 255

Thr Ile Ser His Phe Lys Glu Leu Gly Phe Ser Glu His Ala Glu Met
            260                 265                 270

Leu Glu Asn Leu Arg Asp Arg Leu Leu Ser Ser Lys Gln Ser Ile
        275                 280                 285

Ala

<210> SEQ ID NO 35
<211> LENGTH: 678
<212> TYPE: DNA
<213> ORGANISM: Lactobacillus plantarum

<400> SEQUENCE: 35
atggcagaaa caaaaattcc acgggcaacg gcaaaacggt taccgattta ttaccgctat     60
ttaaatatct tgctagatgc agataagaag cgggtctcat cgaccgagtt gtccgaggcg    120
gttaaagtag attcagcaac gattcggcga gatttctcgt attttgggc gctcggcaaa     180 cgagggtatg gatacgatgt tgaaacgtta cttgcatttt tcaaaaagat tttaaatcaa    240
gacaccttaa cgaatgttgc tttaattggg gtcggtaatt tgggccacgc cctactgaac    300
tttaattttc acaaaacag taatgtccgc atttcagcag catttgatgt caacgaggcg    360
attgccaata cagtccaaag tggggttcca gtgtacccaa tgacggagct caaaaagcaa    420

-continued

```
ttgatcgaac aacagattga gattgctatc ttaacggtgc caaccacggt tgttcagaaa      480
attaccgatg acttggttga tgcaaacgtc aaaggaatca tgaactttac gccgttacga      540
atctccgttc ctgagacagt acgggttcag aacgttgatt tgaccaacga attacaaaca      600
ttgatctact tcattgaaca ttacggtcag caattaggtg acaatggtaa tgacgatgaa      660
aatgagactg aagattaa                                                   678
```

<210> SEQ ID NO 36
<211> LENGTH: 225
<212> TYPE: PRT
<213> ORGANISM: Lactobacillus plantarum

<400> SEQUENCE: 36

```
Met Ala Glu Thr Lys Ile Pro Arg Ala Thr Ala Lys Arg Leu Pro Ile
1               5                   10                  15

Tyr Tyr Arg Tyr Leu Asn Ile Leu Leu Asp Ala Asp Lys Lys Arg Val
            20                  25                  30

Ser Ser Thr Glu Leu Ser Glu Ala Val Lys Val Asp Ser Ala Thr Ile
        35                  40                  45

Arg Arg Asp Phe Ser Tyr Phe Gly Ala Leu Gly Lys Arg Gly Tyr Gly
    50                  55                  60

Tyr Asp Val Glu Thr Leu Leu Ala Phe Phe Lys Lys Ile Leu Asn Gln
65                  70                  75                  80

Asp Thr Leu Thr Asn Val Ala Leu Ile Gly Val Gly Asn Leu Gly His
                85                  90                  95

Ala Leu Leu Asn Phe Asn Phe His Lys Asn Ser Asn Val Arg Ile Ser
            100                 105                 110

Ala Ala Phe Asp Val Asn Glu Ala Ile Ala Asn Thr Val Gln Ser Gly
        115                 120                 125

Val Pro Val Tyr Pro Met Thr Glu Leu Lys Lys Gln Leu Ile Glu Gln
    130                 135                 140

Gln Ile Glu Ile Ala Ile Leu Thr Val Pro Thr Thr Val Val Gln Lys
145                 150                 155                 160

Ile Thr Asp Asp Leu Val Asp Ala Asn Val Lys Gly Ile Met Asn Phe
                165                 170                 175

Thr Pro Leu Arg Ile Ser Val Pro Glu Thr Val Arg Val Gln Asn Val
            180                 185                 190

Asp Leu Thr Asn Glu Leu Gln Thr Leu Ile Tyr Phe Ile Glu His Tyr
        195                 200                 205

Gly Gln Gln Leu Gly Asp Asn Gly Asn Asp Asp Glu Asn Glu Thr Glu
    210                 215                 220

Asp
225
```

<210> SEQ ID NO 37
<211> LENGTH: 561
<212> TYPE: DNA
<213> ORGANISM: Lactobacillus plantarum

<400> SEQUENCE: 37

```
atgcgaaagg atgcacaaat taaccaacag aaaattttga ctgctgcgcg acaactcttt      60
gccgcgcgtt caatcgaaac cgttagtatg aaagatattg cgacggccgc tggtatcggt     120
cccgaaacgt tgtatcgtca ctatgcccat aaaagtacac tatgtttggc attggtaacg     180
gaccgagtcg caacttttat taaaaccaat caagtctact tgaccacgac ctcggtaggt     240
```

```
gcagcagcac gttttgatca tgttattggg gaatatttag cgattcgtga gcacaacatg    300
gcgttattaa tgaatgtcga ggccggtgaa cctggtcgcc gtcaatttta tcagagcgaa    360
ctttatcaac aattatgtga cctattaacg caactggttc gtgatttaaa gccaacgctt    420
tcgaaaccgg catgtgagtt tcaagctgat atgttaattg ccatgctgaa ggggactagt    480
tatgcttttc aacgtcaatg gcgaggacgg tcgcagtccg aactattggc gcaattgcac    540
gcgttaatgg tgactgaatg a                                               561
```

<210> SEQ ID NO 38
<211> LENGTH: 186
<212> TYPE: PRT
<213> ORGANISM: Lactobacillus plantarum

<400> SEQUENCE: 38

```
Met Arg Lys Asp Ala Gln Ile Asn Gln Gln Lys Ile Leu Thr Ala Ala
1               5                   10                  15

Arg Gln Leu Phe Ala Ala Arg Ser Ile Glu Thr Val Ser Met Lys Asp
            20                  25                  30

Ile Ala Thr Ala Ala Gly Ile Gly Pro Gly Thr Leu Tyr Arg His Tyr
        35                  40                  45

Ala His Lys Ser Thr Leu Cys Leu Ala Leu Val Thr Asp Arg Val Ala
    50                  55                  60

Thr Phe Ile Lys Thr Asn Gln Val Tyr Leu Thr Thr Thr Ser Val Gly
65                  70                  75                  80

Ala Ala Ala Arg Phe Asp His Val Ile Gly Glu Tyr Leu Ala Ile Arg
                85                  90                  95

Glu His Asn Met Ala Leu Leu Met Asn Val Glu Ala Gly Glu Pro Gly
            100                 105                 110

Arg Arg Gln Phe Tyr Gln Ser Glu Leu Tyr Gln Gln Leu Cys Asp Leu
        115                 120                 125

Leu Thr Gln Leu Val Arg Asp Leu Lys Pro Thr Leu Ser Lys Pro Ala
    130                 135                 140

Cys Glu Phe Gln Ala Asp Met Leu Ile Ala Met Leu Lys Gly Thr Ser
145                 150                 155                 160

Tyr Ala Phe Gln Arg Gln Trp Arg Gly Arg Ser Gln Ser Glu Leu Leu
                165                 170                 175

Ala Gln Leu His Ala Leu Met Val Thr Glu
            180                 185
```

<210> SEQ ID NO 39
<211> LENGTH: 882
<212> TYPE: DNA
<213> ORGANISM: Lactobacillus plantarum

<400> SEQUENCE: 39

```
atggaattta cttggcaaca ccaggggcaa ccaatggcaa tgaaacgatt cttgacgacg    60
catgccatca gtatgcgaac aatcaaggca atcaagcatg gcaccggcgc gtttcttgtc   120
aataatcaag ttcaaacggg cgttattacc attcatgatg cgatattgc gggaattcaa    180 ctaccagacg aggcaccgga tacagcggta gccgtcagcg aacaaccaat ccaaattgag   240
tatgaagacg ctaattggct cgttcttaat aaaacagccg ggttaaccag cgtgccgggg   300
cctagtaatc ggaccgatac gttggtcaat cgaatcaagg ttatttgat ggccagtcat    360 gccagtaatc aacgaccgca cctgatcacg cggttggacc gggatacgag tggccttgtg   420
```

-continued

```
ttagttgcta aacatcgggt ggcgcagggg atgttgacag agccccgaat tgcggcgcaa    480
ttagtgaaga cgtatcaagc ttggatcgaa gggaccatta cgccggctag tggcacaatt    540
gatcgcccga ttggccgggt ggctgacagt cctcggcgag tggtcaccac ggcgggccaa    600
cgcgccatta cgacgtatca agtggaggcg gaccaattgc agcataacgt gagtcggtta    660
cggttggaac ttgtgactgg acggacgcat caaattcggg tccatctaac gacgcttggg    720
caccccttat taggtgatgc gctgtatggc ggtaacttgg ggtggattca acggcaagcc    780
ttacacgccg ctagtttaca gttctttgac ccctttcgg aacagacttt acactttgag    840
gcggcattgc cagctgatct gcaagccttg aatcacgact aa                      882
```

```
<210> SEQ ID NO 40
<211> LENGTH: 293
<212> TYPE: PRT
<213> ORGANISM: Lactobacillus plantarum

<400> SEQUENCE: 40

Met Glu Phe Thr Trp Gln His Gln Gly Gln Pro Met Ala Met Lys Arg
1               5                   10                  15

Phe Leu Thr Thr His Ala Ile Ser Met Arg Thr Ile Lys Ala Ile Lys
            20                  25                  30

His Gly Thr Gly Ala Phe Leu Val Asn Asn Gln Val Gln Thr Gly Val
        35                  40                  45

Ile Thr Ile His Asp Gly Asp Ile Ala Gly Ile Gln Leu Pro Asp Glu
    50                  55                  60

Ala Pro Asp Thr Ala Val Ala Val Ser Glu Gln Pro Ile Gln Ile Glu
65                  70                  75                  80

Tyr Glu Asp Ala Asn Trp Leu Val Leu Asn Lys Thr Ala Gly Leu Thr
                85                  90                  95

Ser Val Pro Gly Pro Ser Asn Arg Thr Asp Thr Leu Val Asn Arg Ile
            100                 105                 110

Lys Gly Tyr Leu Met Ala Ser His Ala Ser Asn Gln Arg Pro His Leu
        115                 120                 125

Ile Thr Arg Leu Asp Arg Asp Thr Ser Gly Leu Val Leu Val Ala Lys
    130                 135                 140

His Arg Val Ala Gln Gly Met Leu Thr Glu Pro Arg Ile Ala Ala Gln
145                 150                 155                 160

Leu Val Lys Thr Tyr Gln Ala Trp Ile Glu Gly Thr Ile Thr Pro Ala
                165                 170                 175

Ser Gly Thr Ile Asp Arg Pro Ile Gly Arg Val Ala Asp Ser Pro Arg
            180                 185                 190

Arg Val Val Thr Thr Ala Gly Gln Arg Ala Ile Thr Thr Tyr Gln Val
        195                 200                 205

Glu Ala Asp Gln Leu Gln His Asn Val Ser Arg Leu Arg Leu Glu Leu
    210                 215                 220

Val Thr Gly Arg Thr His Gln Ile Arg Val His Leu Thr Thr Leu Gly
225                 230                 235                 240

His Pro Leu Leu Gly Asp Ala Leu Tyr Gly Gly Asn Leu Gly Trp Ile
                245                 250                 255

Gln Arg Gln Ala Leu His Ala Ala Ser Leu Gln Phe Phe Asp Pro Phe
            260                 265                 270

Ser Glu Gln Thr Leu His Phe Glu Ala Ala Leu Pro Ala Asp Leu Gln
        275                 280                 285

Ala Leu Asn His Asp
```

<210> SEQ ID NO 41
<211> LENGTH: 327
<212> TYPE: DNA
<213> ORGANISM: Lactobacillus plantarum

<400> SEQUENCE: 41

```
atggctaatt tcaacaatc cgaaacggca cttattgaaa gtgccacact aattaatatc      60
ttcgccgaaa aaattcggcg tcagattatc attgctctgg ggaacagtga taatggtctc    120
aacgttactg atattaccgc cttggtcaat atttcacgcc ccgccgtttc acatcatcta    180
cgcttaatgc gtgaagctgg ggtcattgat atgcgcagta acggagtcga gcatatttat    240
tttctcacgt taaccgcacc attacagcaa ttacaggcaa cttttgcgac gctaacggct    300
gataacgcgc cacttagtca gtcgtaa                                        327
```

<210> SEQ ID NO 42
<211> LENGTH: 108
<212> TYPE: PRT
<213> ORGANISM: Lactobacillus plantarum

<400> SEQUENCE: 42

```
Met Ala Asn Phe Gln Gln Ser Glu Thr Ala Leu Ile Glu Ser Ala Thr
1               5                   10                  15

Leu Ile Asn Ile Phe Ala Glu Lys Ile Arg Arg Gln Ile Ile Ile Ala
            20                  25                  30

Leu Gly Asn Ser Asp Asn Gly Leu Asn Val Thr Asp Ile Thr Ala Leu
        35                  40                  45

Val Asn Ile Ser Arg Pro Ala Val Ser His His Leu Arg Leu Met Arg
    50                  55                  60

Glu Ala Gly Val Ile Asp Met Arg Ser Asn Gly Val Glu His Ile Tyr
65                  70                  75                  80

Phe Leu Thr Leu Thr Ala Pro Leu Gln Gln Leu Gln Ala Thr Phe Ala
                85                  90                  95

Thr Leu Thr Ala Asp Asn Ala Pro Leu Ser Gln Ser
            100                 105
```

<210> SEQ ID NO 43
<211> LENGTH: 783
<212> TYPE: DNA
<213> ORGANISM: Lactobacillus plantarum

<400> SEQUENCE: 43

```
atgatgggag tggaaaatgt gaaagtctta ggaatattag gtgcgcatcg cgctgatggc      60
gtgactgccc agctactgca atccgtctta aaggggggccg cggccagcgc tgacacggaa    120
ctagtcaacc tcaacgatta tgagttgcga ccagatcacg atagtcaacc gaatgctgac    180
ttagacgcgc tggaagcaaa attaatgcgc gcggatgtct gggtattagc tgcaccaacc    240
tatttgggga gcttatcggg ggtaatgaaa aacttctgtg actgttttcg ggggcggatc    300
gcacggttta ttccgtgggt gaagcagta cctgatcgct taagaacaa gcattatgtg      360 acgatcacgg attgttacgc gggtggtatt gaaaattatt tgaccggcgt gactgacgca    420
acgtttaaaa cacttgataa attttttgacg atgggtggtc tcatcaaatt acgggagatt    480
gtcgtaacta aaacgtgggg tatgcaaacc atcacagctg ctaagcaagc agaatgtgaa    540
cgggtcggcg cgcggggctgc acataaaaag gaaagggatg acagtacggt gaaacggtat    600
```

```
attcaattat tcttcatgat tgcggtgatg gcactactaa caatgggaat cgaagcgggg      660
attcaacaat tgattccgct gaacaatttt tgggcctact acggcgtctt tgtcgtcgtc      720
ttttatgttc ttttagcaat gattttacat tcttcactg ttgttaaaca ccggcgtcgt       780
taa                                                                    783
```

<210> SEQ ID NO 44
<211> LENGTH: 260
<212> TYPE: PRT
<213> ORGANISM: Lactobacillus plantarum

<400> SEQUENCE: 44

```
Met Met Gly Val Glu Asn Val Lys Val Leu Gly Ile Leu Gly Ala His
1               5                   10                  15

Arg Ala Asp Gly Val Thr Ala Gln Leu Leu Gln Ser Val Leu Lys Gly
            20                  25                  30

Ala Ala Ala Ser Ala Asp Thr Glu Leu Val Asn Leu Asn Asp Tyr Glu
        35                  40                  45

Leu Arg Pro Asp His Asp Ser Gln Pro Asn Ala Asp Leu Asp Ala Leu
    50                  55                  60

Glu Ala Lys Leu Met Ala Ala Asp Val Trp Val Leu Ala Ala Pro Thr
65                  70                  75                  80

Tyr Leu Gly Ser Leu Ser Gly Val Met Lys Asn Phe Cys Asp Cys Phe
                85                  90                  95

Arg Gly Arg Ile Ala Arg Phe Asn Ser Val Gly Glu Ala Val Pro Asp
            100                 105                 110

Arg Phe Lys Asn Lys His Tyr Val Thr Ile Thr Asp Cys Tyr Ala Gly
        115                 120                 125

Gly Ile Glu Asn Tyr Leu Thr Gly Val Thr Asp Ala Thr Phe Lys Thr
    130                 135                 140

Leu Asp Lys Phe Leu Thr Met Gly Gly Leu Ile Lys Leu Arg Glu Ile
145                 150                 155                 160

Val Val Thr Lys Thr Trp Gly Met Gln Thr Ile Thr Ala Ala Lys Gln
                165                 170                 175

Ala Glu Cys Glu Arg Val Gly Ala Arg Ala Ala His Lys Lys Glu Arg
            180                 185                 190

Asp Asp Ser Thr Val Lys Arg Tyr Ile Gln Leu Phe Phe Met Ile Ala
        195                 200                 205

Val Met Ala Leu Leu Thr Met Gly Ile Glu Ala Gly Ile Gln Gln Leu
    210                 215                 220

Ile Pro Leu Asn Asn Phe Trp Ala Tyr Tyr Gly Val Phe Val Val Val
225                 230                 235                 240

Phe Tyr Val Leu Leu Ala Met Ile Leu His Phe Phe Thr Val Val Lys
                245                 250                 255

His Arg Arg Arg
            260
```

<210> SEQ ID NO 45
<211> LENGTH: 1002
<212> TYPE: DNA
<213> ORGANISM: Lactobacillus plantarum

<400> SEQUENCE: 45

```
atgcaagttt ttggacaatt tattgcaaca gtcggttggc taggattggc actagtcgcc      60
agcgaactag gtgcgacgtt aatccattgg ctcggtcagt gggtcggatt tcgattaatt     120
```

```
ggtgctcgaa ttgtccggat taccggtttt cgacttcaat taagtcgggt tcgtggtcat    180
tggaaattag aacgaccgct gacgcgtcat ccacatatcg tggcagcacc ctcggcggat    240
gccaaacggt tcaatcacgc catttattgt tttggcggtg gcctgttcaa cttactgacg    300
gtcatgctca gtttaataac tctgaatcaa tttaagttta gtttcgattt atggttgttt    360
gcgttcatta tttggatctg ggtcaatacg ttgaaagccg cccaattatt accaatgaac    420
ttgcacggtt atcccacggc gggacaggaa tttcggcagg cacgcgaatc aacgcggcg    480
atgaccgccg cgtatgtcac tgcgtgtgct gcggccgtta aggttcagac cggtagtgtc    540
cgtgaccttg atgcaagtat gattgttatg ccgcgcgatg gtggcaatcg gaattattta    600
gtcgtccggc aagcctggtt gattctggaa tggggacttc aacatgggct ggacaccccc    660
gaactgttag cggggttgag tcgcttggag ccaagtttca atacgttgcc gccagctgat    720
ttggcgaagt atttagatgc aacattgtac tggaacttgg tcaccaatca tcgtgacccc    780
cagatcatag cctggtatca agatgatggt gttcaacagt tattacgtcg ctaccaacct    840
ttggctcatt ataagttaac tgccgtttat gaatggcggg tccatcagca gcctgaacag    900
gccctagcat tgattgaaaa gggactaaaa attgctcagc gcctccacga tgaggaagaa    960
attgcttggc tgaaagcttt acgcgttcaa gtaacggcct ag                       1002

<210> SEQ ID NO 46
<211> LENGTH: 333
<212> TYPE: PRT
<213> ORGANISM: Lactobacillus plantarum

<400> SEQUENCE: 46

Met Gln Val Phe Gly Gln Phe Ile Ala Thr Val Gly Trp Leu Gly Leu
1               5                   10                  15

Ala Leu Val Ala Ser Glu Leu Gly Ala Thr Leu Ile His Trp Leu Gly
            20                  25                  30

Gln Trp Val Gly Phe Arg Leu Ile Gly Ala Arg Ile Val Arg Ile Thr
        35                  40                  45

Gly Phe Arg Leu Gln Leu Ser Arg Val Arg Gly His Trp Lys Leu Glu
    50                  55                  60

Arg Pro Leu Thr Arg His Pro His Ile Val Ala Ala Pro Ser Ala Asp
65                  70                  75                  80

Ala Lys Arg Phe Asn His Ala Ile Tyr Cys Phe Gly Gly Gly Leu Phe
                85                  90                  95

Asn Leu Leu Thr Val Met Leu Ser Leu Ile Thr Leu Asn Gln Phe Lys
            100                 105                 110

Phe Ser Phe Asp Leu Trp Leu Phe Ala Phe Ile Ile Trp Ile Trp Val
        115                 120                 125

Asn Thr Leu Lys Ala Ala Gln Leu Leu Pro Met Asn Leu His Gly Tyr
    130                 135                 140

Pro Thr Ala Gly Gln Glu Phe Arg Gln Ala Arg Glu Ser Thr Ala Ala
145                 150                 155                 160

Met Thr Ala Ala Tyr Val Thr Ala Cys Ala Ala Val Lys Val Gln
                165                 170                 175

Thr Gly Ser Val Arg Asp Leu Asp Ala Ser Met Ile Val Met Pro Arg
            180                 185                 190

Asp Gly Gly Asn Arg Asn Tyr Leu Val Val Arg Gln Ala Trp Leu Ile
        195                 200                 205

Leu Glu Trp Gly Leu Gln His Gly Leu Asp Thr Pro Glu Leu Leu Ala
    210                 215                 220
```

```
Gly Leu Ser Arg Leu Glu Pro Ser Phe Asn Thr Leu Pro Pro Ala Asp
225                 230                 235                 240

Leu Ala Lys Tyr Leu Asp Ala Thr Leu Tyr Trp Asn Leu Val Thr Asn
                245                 250                 255

His Arg Asp Pro Gln Ile Ile Ala Trp Tyr Gln Asp Asp Gly Val Gln
            260                 265                 270

Gln Leu Leu Arg Arg Tyr Gln Pro Leu Ala His Tyr Lys Leu Thr Ala
        275                 280                 285

Val Tyr Glu Trp Arg Val His Gln Gln Pro Glu Gln Ala Leu Ala Leu
    290                 295                 300

Ile Glu Lys Gly Leu Lys Ile Ala Gln Arg Leu His Asp Glu Glu Glu
305                 310                 315                 320

Ile Ala Trp Leu Lys Ala Leu Arg Val Gln Val Thr Ala
                325                 330
```

<210> SEQ ID NO 47
<211> LENGTH: 1134
<212> TYPE: DNA
<213> ORGANISM: Lactobacillus plantarum

<400> SEQUENCE: 47

```
ttgaagatga gaaaacggct agcaattgtg tgggggagcc tagcattgct cgcactatta      60
ttgggatatg cttgctacgc cctgagtatt cagcgcggtc aagacacggt cacgcggatt     120
tatcaaactg atcaaaatgg gacgccgatt atttcacccg gaccaattac cttagtaggt     180
aaggtcaatc accgcaattt atttcaatct ggcattaatg ctatgtctt  aacgaatcgc     240
gatccattgt cgactttgtt gccgcgccgt aatcaaacag tgcatctaaa gtatcgttct     300
gcacagacga cggcggagct acgcaagacg ctacgtcaag cacggtattt acaggccggt     360
actcagaata ccgccacgcc ggtctttcaa aatcgacagc agcgaggtga tgcgacaacg     420
tacggtcgta tcagtaccag ccaagacggc cggatatgga cgaaactacc cattagttat     480
ccgcatgtgc aattgtcacg gccgagtgtc tggtacgcga atggccgctt gacgttgata     540
gatgggaaag accgttactg gacgactaat tttaaagatt ggcaacatca acggttgaac     600
tttaacgggg ctgatttaa  gcaaggtcgg gttcaggccg tctttccagg tacgactcgt     660
tcagcggttg ttgtggttcg cggcattgat cgccaaagca gtcgcgccaa actctattat     720
ggacagctca cgaagactgg acgggtcaaa gcttggcacg cgttacaact aggaaagctc     780
ccagcgcgcc aagtcgctgg aatgagcttg attgatcaac acttataccct gtttcttcag     840
cgcggtacgc agttggccat ttatcgtgcc aatcggttga cgcgtccggt caggttggtt     900
ggtcgcgtta agctaaatca tgcgcagtca caacgagtga ccgcggtgaa tttgataccg     960
accaccaagc atcgctaccg gttaatattt gacttgacga cagctgaaaa agttcagaaa    1020
cagccacgtt atcggttact tgatcggcga tttaaagcag tggggcagca gcatctattg    1080
gtcactgatt atctctggag ccaatttcaa attagtctac gtgggagtga gtga          1134
```

<210> SEQ ID NO 48
<211> LENGTH: 377
<212> TYPE: PRT
<213> ORGANISM: Lactobacillus plantarum

<400> SEQUENCE: 48

```
Met Lys Met Arg Lys Arg Leu Ala Ile Val Trp Gly Ser Leu Ala Leu
1               5                   10                  15
```

Leu Ala Leu Leu Leu Gly Tyr Ala Cys Tyr Ala Leu Ser Ile Gln Arg
        20                  25                  30

Gly Gln Asp Thr Val Thr Arg Ile Tyr Gln Thr Asp Gln Asn Gly Thr
    35                  40                  45

Pro Ile Ile Ser Pro Gly Pro Ile Thr Leu Val Gly Lys Val Asn His
50                  55                  60

Arg Asn Leu Phe Gln Ser Gly Ile Asn Gly Tyr Val Leu Thr Asn Arg
65                  70                  75                  80

Asp Pro Leu Ser Thr Leu Leu Pro Arg Arg Asn Gln Thr Val His Leu
                85                  90                  95

Lys Tyr Arg Ser Ala Gln Thr Thr Ala Glu Leu Arg Lys Thr Leu Arg
            100                 105                 110

Gln Ala Arg Tyr Leu Gln Ala Gly Thr Gln Asn Thr Ala Thr Pro Val
        115                 120                 125

Phe Gln Asn Arg Gln Gln Arg Gly Asp Ala Thr Thr Tyr Gly Arg Ile
130                 135                 140

Ser Thr Ser Gln Asp Gly Arg Ile Trp Thr Lys Leu Pro Ile Ser Tyr
145                 150                 155                 160

Pro His Val Gln Leu Ser Arg Pro Ser Val Trp Tyr Ala Asn Gly Arg
                165                 170                 175

Leu Thr Leu Ile Asp Gly Lys Asp Arg Tyr Trp Thr Thr Asn Phe Lys
            180                 185                 190

Asp Trp Gln His Gln Arg Leu Asn Phe Asn Gly Ala Asp Phe Lys Gln
        195                 200                 205

Gly Arg Val Gln Ala Val Phe Pro Gly Thr Thr Arg Ser Ala Val Val
210                 215                 220

Val Val Arg Gly Ile Asp Arg Gln Ser Ser Arg Ala Lys Leu Tyr Tyr
225                 230                 235                 240

Gly Gln Leu Thr Lys Thr Gly Arg Val Lys Ala Trp His Ala Leu Gln
                245                 250                 255

Leu Gly Lys Leu Pro Ala Arg Gln Val Ala Gly Met Ser Leu Ile Asp
            260                 265                 270

Gln His Leu Tyr Leu Phe Leu Gln Arg Gly Thr Gln Leu Ala Ile Tyr
        275                 280                 285

Arg Ala Asn Arg Leu Thr Arg Pro Val Arg Leu Val Gly Arg Val Lys
290                 295                 300

Leu Asn His Ala Gln Ser Gln Arg Val Thr Ala Val Asn Leu Ile Pro
305                 310                 315                 320

Thr Thr Lys His Arg Tyr Arg Leu Ile Phe Asp Leu Thr Thr Ala Glu
                325                 330                 335

Lys Val Gln Lys Gln Pro Arg Tyr Arg Leu Leu Asp Arg Arg Phe Lys
            340                 345                 350

Ala Val Gly Gln Gln His Leu Leu Val Thr Asp Tyr Leu Trp Ser Gln
        355                 360                 365

Phe Gln Ile Ser Leu Arg Gly Ser Glu
370                 375

<210> SEQ ID NO 49
<211> LENGTH: 633
<212> TYPE: DNA
<213> ORGANISM: Lactobacillus plantarum

<400> SEQUENCE: 49
gtgaggcaca tgaaggtaca gccaaaggaa cgctttagtc tagcgtggcg gtggttgccg      60

```
ctcgaattgc tgatcattat gctaagcgtc ggccttggat gggcgggcaa tcgatggcta      120
cctaagccgg tgtatcaagc atctgttgat attcagattg cgcaaacgcc gcgttcaggg      180
ctgtcaacag cccgtctaaa acgtcagcga cgccaggata tcaaagctat cacgcagttc      240
aacgtgatgc cacaccagag tgcagtgctg actcaagcca gcacttatgc ctatgcgcat      300
tatggcattt ggcaaccgat tcaggaactg agtgagtcgg tccaagcggc accagttgcg      360
cggcgaccgg tcttacgggt gacagcaacg agtagttcac ggcaagtggc ccagcagaat      420
gctcaggcgt tcaatgtggc gattaaagct aatctgacgg gcttaaaaaa ttatcgagtg      480
aagacagtta aacgtaccgt aacgcgtgag acgaacgtga ttcgcggggc gctttggaag      540
ttaatattag ttgttggggg cggcttggcg ttgctgagtc cgtacctcgt gaaatatggt      600
cagggttggg ggcggcacga tgatgagacg tag                                  633
```

```
<210> SEQ ID NO 50
<211> LENGTH: 210
<212> TYPE: PRT
<213> ORGANISM: Lactobacillus plantarum

<400> SEQUENCE: 50

Met Arg His Met Lys Val Gln Pro Lys Glu Arg Phe Ser Leu Ala Trp
1               5                   10                  15

Arg Trp Leu Pro Leu Glu Leu Ile Ile Met Leu Ser Val Gly Leu
            20                  25                  30

Gly Trp Ala Gly Asn Arg Trp Leu Pro Lys Pro Val Tyr Gln Ala Ser
        35                  40                  45

Val Asp Ile Gln Ile Ala Gln Thr Pro Arg Ser Gly Leu Ser Thr Ala
    50                  55                  60

Arg Leu Lys Arg Gln Arg Arg Gln Asp Ile Lys Ala Ile Thr Gln Phe
65                  70                  75                  80

Asn Val Met Pro His Gln Ser Ala Val Leu Thr Gln Ala Ser Thr Tyr
                85                  90                  95

Ala Tyr Ala His Tyr Gly Ile Trp Gln Pro Ile Gln Glu Leu Ser Glu
            100                 105                 110

Ser Val Gln Ala Ala Pro Val Ala Arg Arg Pro Val Leu Arg Val Thr
        115                 120                 125

Ala Thr Ser Ser Arg Gln Val Ala Gln Gln Asn Ala Gln Ala Phe
    130                 135                 140

Asn Val Ala Ile Lys Ala Asn Leu Thr Gly Leu Lys Asn Tyr Arg Val
145                 150                 155                 160

Lys Thr Val Lys Arg Thr Val Thr Arg Glu Thr Asn Val Ile Arg Gly
                165                 170                 175

Ala Leu Trp Lys Leu Ile Leu Val Val Gly Gly Leu Ala Leu Leu
            180                 185                 190

Ser Pro Tyr Leu Val Lys Tyr Gly Gln Gly Trp Gly Arg His Asp Asp
        195                 200                 205

Glu Thr
    210

<210> SEQ ID NO 51
<211> LENGTH: 891
<212> TYPE: DNA
<213> ORGANISM: Lactobacillus plantarum

<400> SEQUENCE: 51
atgatgagac gtaggggagc aagtatgcag cagcaccgta atgtgctcta tctgattatc      60
```

```
ttcggaatct acttagcctc agtcacacta cagacgacga cctttaacga gatgataccg    120
catcgagtgg gcgttttgat tgaattagcg actttggccg cattactggg cctcgtggtt    180
tgcttagata ccttgacccc cggccaaatt attggagaag tcagtttact tgtactggtg    240
actgtcgtga cactcacatc gggtgcgcat tatttgatgc cgacaatcat gttggtgatt    300
gcagcccggg aagtttcgtt tcggcagatc attcaagttt atctgggcgt cgtggggacg    360
attctcttgt tagcgctagt tgctgcggaa gtcggactga ttaaaaatat tacgtttgca    420
actgccgatg ggttacgtca gtcgtttggt gtcgtgtata ccactgattt tgcggcccat    480
attttctatc tgtgtgcggc gtatttgtat ttattggccc gtcgttttcg attagtagcg    540
ctattacccg tgttgtttgg cctggcaatg atttaccagt ttacgaaaac gatgacggat    600
gtgattgctt tactcgtttt gatcagcttg tacttggtct atatctatcg ccgtcagctt    660
cggtggcttc ggccgatgat tcggtatagc ttttgatgt taccacttgc tagtgggcta    720
attattgggt tgtcgaatat ttttaattat caagaccggt tgctggtagc gctcaataat    780
accttgtcca cgcgactcgc gctagggaat aacgcgttat tagcatatgg cgttaaatta    840
ttcggccaag ccccgattcc aattaatggt tggggcggcg atccggtttg a              891
```

<210> SEQ ID NO 52
<211> LENGTH: 296
<212> TYPE: PRT
<213> ORGANISM: Lactobacillus plantarum
<400> SEQUENCE: 52

```
Met Met Arg Arg Arg Gly Ala Ser Met Gln Gln His Arg Asn Val Leu
1               5                   10                  15

Tyr Leu Ile Ile Phe Gly Ile Tyr Leu Ala Ser Val Thr Leu Gln Thr
            20                  25                  30

Thr Thr Phe Asn Glu Met Ile Pro His Arg Val Gly Val Leu Ile Glu
        35                  40                  45

Leu Ala Thr Leu Ala Ala Leu Leu Gly Leu Val Val Cys Leu Asp Thr
    50                  55                  60

Leu Thr Pro Gly Gln Ile Ile Gly Glu Val Ser Leu Leu Val Leu Val
65                  70                  75                  80

Thr Val Val Thr Leu Thr Ser Gly Ala His Tyr Leu Met Pro Thr Ile
                85                  90                  95

Met Leu Val Ile Ala Ala Arg Glu Val Ser Phe Arg Gln Ile Ile Gln
            100                 105                 110

Val Tyr Leu Gly Val Val Gly Thr Ile Leu Leu Leu Ala Leu Val Ala
        115                 120                 125

Ala Glu Val Gly Leu Ile Lys Asn Ile Thr Phe Ala Thr Ala Asp Gly
    130                 135                 140

Leu Arg Gln Ser Phe Gly Val Val Tyr Thr Thr Asp Phe Ala Ala His
145                 150                 155                 160

Ile Phe Tyr Leu Cys Ala Ala Tyr Leu Tyr Leu Ala Arg Arg Phe
                165                 170                 175

Arg Leu Val Ala Leu Leu Pro Val Leu Phe Gly Leu Ala Met Ile Tyr
            180                 185                 190

Gln Phe Thr Lys Thr Met Thr Asp Val Ile Ala Leu Leu Val Leu Ile
        195                 200                 205

Ser Leu Tyr Leu Val Tyr Ile Tyr Arg Arg Gln Leu Arg Trp Leu Arg
    210                 215                 220
```

Pro Met Ile Arg Tyr Ser Phe Leu Met Leu Pro Leu Ala Ser Gly Leu
225                 230                 235                 240

Ile Ile Gly Leu Ser Asn Ile Phe Asn Tyr Gln Asp Arg Leu Leu Val
            245                 250                 255

Ala Leu Asn Asn Thr Leu Ser Thr Arg Leu Ala Leu Gly Asn Asn Ala
        260                 265                 270

Leu Leu Ala Tyr Gly Val Lys Leu Phe Gly Gln Ala Pro Ile Pro Ile
    275                 280                 285

Asn Gly Trp Gly Gly Asp Pro Val
    290                 295

<210> SEQ ID NO 53
<211> LENGTH: 837
<212> TYPE: DNA
<213> ORGANISM: Lactobacillus plantarum

<400> SEQUENCE: 53
atggtaaaaa ttgcagtcct atctgacgtt cacggtaacg ctactgcact cgaagcagtc     60
ttagcagacg cccagaaaca acacgttgac gaatactgga cagtaggcga catgaccgtt    120
cgcgggccag aatcggagcg ctgtctcacc ttactagacc gcgttcaccc caccgcctac    180
gttctcggaa atcacgagga aaactaccaa aaagtaatgg cagccaatcc caacacgttt    240
actaaaccca acaaattat ggcaacggtt ctcaccgctt ttgatcggcg ccagctgagt    300
tcgacacact tgaacggtt actgaactta ccaatgacag tcatcaaaca cgtcggcccg    360
ttaaccatcc gtctccaaca cgttttaccg accgtcgcta gtggacacgc gctcgcacca    420
actgccagtc aggccaactt tgaccaagcc gctgaaggcg atgtcgatat cgtcatctac    480
gcgcacacac accagcccat catgcgctac gcaaccacgg acagttgat tctaaacgcc    540
gggacagttg gtcttccgac tgccattaat cccccacctac gccaaccacg agcaaactac    600
ttgcttctga caattgatga gactggcctc cagcatgttg attaccgcgc cgtagatttc    660
gattggcagc gtgctatcac gattgcgcaa atacccact tacccactact cgaattctat    720
gaacaaactt tgcagactaa tacttaccaa tatgcaccga gtgcggtcgc tgcttataat    780
acgcaacatg acatggcccg agaagcgcgc aagattttac ttgaaaatcg tcactga     837

<210> SEQ ID NO 54
<211> LENGTH: 278
<212> TYPE: PRT
<213> ORGANISM: Lactobacillus plantarum

<400> SEQUENCE: 54

Met Val Lys Ile Ala Val Leu Ser Asp Val His Gly Asn Ala Thr Ala
1               5                   10                  15

Leu Glu Ala Val Leu Ala Asp Ala Gln Lys Gln His Val Asp Glu Tyr
            20                  25                  30

Trp Thr Val Gly Asp Met Thr Val Arg Gly Pro Glu Ser Glu Arg Cys
        35                  40                  45

Leu Thr Leu Leu Asp Arg Val His Pro Thr Ala Tyr Val Leu Gly Asn
    50                  55                  60

His Glu Glu Asn Tyr Gln Lys Val Met Ala Ala Asn Pro Asn Thr Phe
65                  70                  75                  80

Thr Lys Pro Lys Gln Ile Met Ala Thr Val Leu Thr Ala Phe Asp Arg
                85                  90                  95

Arg Gln Leu Ser Ser Thr His Phe Glu Arg Leu Leu Asn Leu Pro Met
            100                 105                 110

```
Thr Val Ile Lys His Val Gly Pro Leu Thr Ile Arg Leu Gln His Val
        115                 120                 125
Leu Pro Thr Val Ala Ser Gly His Ala Leu Ala Pro Thr Ala Ser Gln
        130                 135                 140
Ala Asn Phe Asp Gln Ala Ala Glu Gly Asp Val Asp Ile Val Ile Tyr
145                 150                 155                 160
Ala His Thr His Gln Pro Ile Met Arg Tyr Ala Thr Thr Gly Gln Leu
                165                 170                 175
Ile Leu Asn Ala Gly Thr Val Gly Leu Pro Thr Ala Ile Asn Pro His
                180                 185                 190
Leu Arg Gln Pro Arg Ala Asn Tyr Leu Leu Leu Thr Ile Asp Glu Thr
        195                 200                 205
Gly Leu Gln His Val Asp Tyr Arg Ala Val Asp Phe Asp Trp Gln Arg
    210                 215                 220
Ala Ile Thr Ile Ala Gln Asn Thr His Leu Pro Tyr Phe Glu Phe Tyr
225                 230                 235                 240
Glu Gln Thr Leu Gln Thr Asn Thr Tyr Gln Tyr Ala Pro Ser Ala Val
                245                 250                 255
Ala Ala Tyr Asn Thr Gln His Asp Met Ala Arg Glu Ala Arg Lys Ile
            260                 265                 270
Leu Leu Glu Asn Arg His
        275

<210> SEQ ID NO 55
<211> LENGTH: 1326
<212> TYPE: DNA
<213> ORGANISM: Lactobacillus plantarum

<400> SEQUENCE: 55
atgcaatcac atcgtcatca aagtcttgaa gaaatcaatc agagcgtcgc ggttcccgac      60
gttcatcaga cggccttttg cgcaaatttt ttagcctata gtggtcccgg tgcactagtg     120
gcagtcggct atatggatcc cggcaactgg ttgacatccc tagccggtgg cggtcagttt     180
cagtaccggt ttttagccgt gctcgcatta gccatcattg tcgccatgtt catgcaaggc     240
ctggcaatca ggctaggcgt tgtagcccgg caagacttag cacaagccat cgctagcaag     300
ctgccccggc ccgtgcgtta cgccgcgtgg attttaaacg aagtcgcgat gatgcgact      360
gatatgacgg gcgtaattgg aaccgcaatc gccttaaaaa tgttattcgg cttaccacta     420
cttgcaggaa ttttactgac gattgcggac gtcttagttg tcttgttgtt tttgagattt     480
ggcattcggc gtgtcgaagt aatcgtcctc gtcgctattt tgaccgtcgg cattattttt     540
ggtatcgagg tgggacgggc ccacgttcaa tttggcaacg tgttgctcgg cttagttcca     600
acaccattga tcgtcaaaaa tcataccgca ctagtcctca gtctcggaat cttgggcgca     660
accatcatgc cacataactt atacttacac tcatcgcttg cacaaagccg gcgttatgat     720
tatcataatc cagcccaagt cacagaagca ctgcgcttcg ccaattggga ctcaacagtg     780
cacttgattg cggcttttct catcaacgca cttttgctcg tccttggtgg gacgcttttc     840
ttcggtcaca ccaacgcgtt agcgagtctg caggccgtct tcgatgggtt aaaaagtacc     900
accgtggttg gcgcccttgc tagcccggtc atgagctggt atttgcatt agccctacta     960
attaccggcc taatttcatc catcactagc accttagctg gtcagatcgt catggaaggt    1020
tatttacaca tccgcttacc gctatggcaa cgccggctgc ttactcgcgc tgtcacgcta    1080
attccgattc tgattatcgg tatgttagtc ggctttagtg acgctgcctt tgaaaacttg    1140
```

```
atcatttacg cgcaagtggc actcagcatc gccctcccct ttaccttgtt gccactagtt    1200
gcgctgacaa atgacgccag cctgatgaag gcccacgtta atcgcccggc ggtaacgtgg    1260
gtgggatatg gactggccgg aattattacg gtgttgaata tttatttggt gtatagcttg    1320
ttttga                                                               1326
```

<210> SEQ ID NO 56
<211> LENGTH: 441
<212> TYPE: PRT
<213> ORGANISM: Lactobacillus plantarum

<400> SEQUENCE: 56

```
Met Gln Ser His Arg His Gln Ser Leu Glu Glu Ile Asn Gln Ser Val
1               5                   10                  15

Ala Val Pro Asp Val His Gln Thr Ala Phe Trp Arg Lys Phe Leu Ala
            20                  25                  30

Tyr Ser Gly Pro Gly Ala Leu Val Ala Val Gly Tyr Met Asp Pro Gly
        35                  40                  45

Asn Trp Leu Thr Ser Leu Ala Gly Gly Gly Gln Phe Gln Tyr Arg Leu
    50                  55                  60

Leu Ala Val Leu Ala Leu Ala Ile Ile Val Ala Met Phe Met Gln Gly
65                  70                  75                  80

Leu Ala Ile Arg Leu Gly Val Val Ala Arg Gln Asp Leu Ala Gln Ala
                85                  90                  95

Ile Ala Ser Lys Leu Pro Arg Pro Val Arg Tyr Ala Ala Trp Ile Leu
            100                 105                 110

Asn Glu Val Ala Met Met Ala Thr Asp Met Thr Gly Val Ile Gly Thr
        115                 120                 125

Ala Ile Ala Leu Lys Met Leu Phe Gly Leu Pro Leu Leu Ala Gly Ile
    130                 135                 140

Leu Leu Thr Ile Ala Asp Val Leu Val Val Leu Leu Phe Leu Arg Phe
145                 150                 155                 160

Gly Ile Arg Arg Val Glu Val Ile Val Leu Val Ala Ile Leu Thr Val
                165                 170                 175

Gly Ile Ile Phe Gly Ile Glu Val Gly Arg Ala His Val Gln Phe Gly
            180                 185                 190

Asn Val Leu Leu Gly Leu Val Pro Thr Pro Leu Ile Val Lys Asn His
        195                 200                 205

Thr Ala Leu Val Leu Ser Leu Gly Ile Leu Gly Ala Thr Ile Met Pro
    210                 215                 220

His Asn Leu Tyr Leu His Ser Ser Leu Ala Gln Ser Arg Arg Tyr Asp
225                 230                 235                 240

Tyr His Asn Pro Ala Gln Val Thr Glu Ala Leu Arg Phe Ala Asn Trp
                245                 250                 255

Asp Ser Thr Val His Leu Ile Ala Ala Phe Leu Ile Asn Ala Leu Leu
            260                 265                 270

Leu Val Leu Gly Gly Thr Leu Phe Phe Gly His Thr Asn Ala Leu Ala
        275                 280                 285

Ser Leu Gln Ala Val Phe Asp Gly Leu Lys Ser Thr Thr Val Val Gly
    290                 295                 300

Ala Leu Ala Ser Pro Val Met Ser Trp Leu Phe Ala Leu Ala Leu Leu
305                 310                 315                 320

Ile Thr Gly Leu Ile Ser Ser Ile Thr Ser Thr Leu Ala Gly Gln Ile
                325                 330                 335
```

Val Met Glu Gly Tyr Leu His Ile Arg Leu Pro Leu Trp Gln Arg Arg
                340                 345                 350

Leu Leu Thr Arg Ala Val Thr Leu Ile Pro Ile Leu Ile Ile Gly Met
                355                 360                 365

Leu Val Gly Phe Ser Asp Ala Ala Phe Glu Asn Leu Ile Ile Tyr Ala
            370                 375                 380

Gln Val Ala Leu Ser Ile Ala Leu Pro Phe Thr Leu Pro Leu Val
385                 390                 395                 400

Ala Leu Thr Asn Asp Ala Ser Leu Met Lys Ala His Val Asn Arg Pro
                405                 410                 415

Ala Val Thr Trp Val Gly Tyr Gly Leu Ala Gly Ile Ile Thr Val Leu
                420                 425                 430

Asn Ile Tyr Leu Val Tyr Ser Leu Phe
            435                 440

<210> SEQ ID NO 57
<211> LENGTH: 897
<212> TYPE: DNA
<213> ORGANISM: Lactobacillus plantarum

<400> SEQUENCE: 57
atgaagaaat ggctcattgc ccttgctggt gtcttactaa ccttcacctt agctggttgt      60
ggtagcaaga ccgttgcatc aacttccggt ggtaagatta ccgaaagcca atattacagt     120
agtatgaagg gaacctcttc aggtaagcaa gtcttgcaac aaatgatcct gaataaggtg     180
ctcgaaaagg attatggctc aaaagtttcg actaagcaag tgacgaagca atataatact     240
tacaagtcac aatatggtag ttctttctca accgtcttat cgcaaaatgg tttgacgacc     300
aagaccttca aggaacaatt acgttctaac ttattattga aggaagccgt taagacaag      360 gtcaagatta ctgataaagc tttgaagaag caatggaagt cttacgaacc taaagtcacg     420
gttcaacata tcctagttgc caaatcagca actgctgaca agtcttaga cgctttgaag      480 aaggattcta gccaagccaa ctttacgaag ttagccaaga agtattcaac tgatacaacg     540
actaagaatg atggtggtaa gttatcagcc tttgataaca ctaacacgag ctactcatct     600
aaattcttaa cggctgcttt caagctgaag aacggtgaat acacgacttc cgctgttaag     660
accagcaacg ttatgaaat catccggatg atcaagaacc ctggtaaggg taagatgtct      720
gatcacaccg ctgatttgaa gaaacaaatt tgggacaatg atatgagcga ctccactgtc     780
ttacaaaacg ttgtttctaa agtgcttaag ggtgggaacg tttcaatcaa ggataacgat     840
ttgaaggata tcttatcgtc atacctttca acctcatctt catcaagctc taactaa       897

<210> SEQ ID NO 58
<211> LENGTH: 298
<212> TYPE: PRT
<213> ORGANISM: Lactobacillus plantarum

<400> SEQUENCE: 58

Met Lys Lys Trp Leu Ile Ala Leu Ala Gly Val Leu Leu Thr Phe Thr
1               5                   10                  15

Leu Ala Gly Cys Gly Ser Lys Thr Val Ala Ser Thr Ser Gly Gly Lys
                20                  25                  30

Ile Thr Glu Ser Gln Tyr Tyr Ser Ser Met Lys Gly Thr Ser Ser Gly
            35                  40                  45

Lys Gln Val Leu Gln Gln Met Ile Leu Asn Lys Val Leu Glu Lys Asp
50                  55                  60

```
Tyr Gly Ser Lys Val Ser Thr Lys Gln Val Thr Lys Gln Tyr Asn Thr
 65                  70                  75                  80

Tyr Lys Ser Gln Tyr Gly Ser Ser Phe Ser Thr Val Leu Ser Gln Asn
                 85                  90                  95

Gly Leu Thr Thr Lys Thr Phe Lys Glu Gln Leu Arg Ser Asn Leu Leu
            100                 105                 110

Leu Lys Glu Ala Val Lys Asp Lys Val Lys Ile Thr Asp Lys Ala Leu
        115                 120                 125

Lys Lys Gln Trp Lys Ser Tyr Glu Pro Lys Val Thr Val Gln His Ile
    130                 135                 140

Leu Val Ala Lys Ser Ala Thr Ala Asp Lys Val Leu Asp Ala Leu Lys
145                 150                 155                 160

Lys Asp Ser Ser Gln Ala Asn Phe Thr Lys Leu Ala Lys Lys Tyr Ser
                165                 170                 175

Thr Asp Thr Thr Thr Lys Asn Asp Gly Gly Lys Leu Ser Ala Phe Asp
            180                 185                 190

Asn Thr Asn Thr Ser Tyr Ser Ser Lys Phe Leu Thr Ala Ala Phe Lys
        195                 200                 205

Leu Lys Asn Gly Glu Tyr Thr Thr Ser Ala Val Lys Thr Ser Asn Gly
    210                 215                 220

Tyr Glu Ile Ile Arg Met Ile Lys Asn Pro Gly Lys Gly Lys Met Ser
225                 230                 235                 240

Asp His Thr Ala Asp Leu Lys Lys Gln Ile Trp Asp Asn Asp Met Ser
                245                 250                 255

Asp Ser Thr Val Leu Gln Asn Val Val Ser Lys Val Leu Lys Gly Gly
            260                 265                 270

Asn Val Ser Ile Lys Asp Asn Asp Leu Lys Asp Ile Leu Ser Ser Tyr
        275                 280                 285

Leu Ser Thr Ser Ser Ser Ser Ser Asn
    290                 295

<210> SEQ ID NO 59
<211> LENGTH: 891
<212> TYPE: DNA
<213> ORGANISM: Lactobacillus plantarum

<400> SEQUENCE: 59
atgaataagc aattattaac tgaatttgaa tccaagtggc gtcctcagat taatcagtat    60
ttagatgagc agcttcaagc gtgttctgac caatcaaccc tgactgacgc catgcgttat   120
tcggtactag caggtggcaa acggttacgg ccgttattga cgttagccat tttagatact   180
tttgatatca caacgacggc tgcaaacttg cgggcaagtg tggccgttga gttgatgcat   240
acttattcgc taattcacga tgatttaccg gcgatggata atgatcagct acgacgtggc   300
gaaccgacta accatgttaa gtttggggaa gacgttgcca ttcttgcagg ggatgcttta   360
caaccgttga ctttcgaatg gattgcggat agtgggttac cggcatcgat cgtcgctaat   420
caaaccttag cattagcgca ggccaccgga cctcgcggga tggtggctgg tcaagttgct   480
gatgtccttg gagcgggaca acatctggct ttgccagcct acaacagct gcatcgcgag   540 aagacggggg cgttaattca ctacgctgtc caggcagggt tgattcaagc tcaagtgcaa   600
ccaaccgtgc aggaattgct attacaatat gctgatgcct atggattggc gtttcaaatt   660
tacgatgata ttttagacgt gacgagtacg cctgctcagt taggaaaagc tacgcataag   720
gatgccgatg agcataagaa tacgtatcca ggtttgctgg ggcttgcagg cgcacgaaca   780
```
gcgttagaac aagcggtaac agctgctcaa acggcgttag taaaagctag tgctgctagt    840
caacgaggca tgggcttgct tgcagctttt ctaacgtatt ttacagatta a              891

<210> SEQ ID NO 60
<211> LENGTH: 296
<212> TYPE: PRT
<213> ORGANISM: Lactobacillus plantarum

<400> SEQUENCE: 60

Met Asn Lys Gln Leu Leu Thr Glu Phe Glu Ser Lys Trp Arg Pro Gln
1               5                   10                  15

Ile Asn Gln Tyr Leu Asp Glu Gln Leu Gln Ala Cys Ser Asp Gln Ser
            20                  25                  30

Thr Leu Thr Asp Ala Met Arg Tyr Ser Val Leu Ala Gly Gly Lys Arg
        35                  40                  45

Leu Arg Pro Leu Leu Thr Leu Ala Ile Leu Asp Thr Phe Asp Ile Thr
    50                  55                  60

Thr Thr Ala Ala Asn Leu Arg Ala Ser Val Ala Val Glu Leu Met His
65                  70                  75                  80

Thr Tyr Ser Leu Ile His Asp Asp Leu Pro Ala Met Asp Asn Asp Gln
                85                  90                  95

Leu Arg Arg Gly Glu Pro Thr Asn His Val Lys Phe Gly Glu Asp Val
            100                 105                 110

Ala Ile Leu Ala Gly Asp Ala Leu Gln Pro Leu Thr Phe Glu Trp Ile
        115                 120                 125

Ala Asp Ser Gly Leu Pro Ala Ser Ile Val Ala Asn Gln Thr Leu Ala
    130                 135                 140

Leu Ala Gln Ala Thr Gly Pro Arg Gly Met Val Ala Gly Gln Val Ala
145                 150                 155                 160

Asp Val Leu Gly Ala Gly Gln His Leu Ala Leu Pro Ala Leu Gln Gln
                165                 170                 175

Leu His Arg Glu Lys Thr Gly Ala Leu Ile His Tyr Ala Val Gln Ala
            180                 185                 190

Gly Leu Ile Gln Ala Gln Val Gln Pro Thr Val Gln Glu Leu Leu Leu
        195                 200                 205

Gln Tyr Ala Asp Ala Tyr Gly Leu Ala Phe Gln Ile Tyr Asp Asp Ile
    210                 215                 220

Leu Asp Val Thr Ser Thr Pro Ala Gln Leu Gly Lys Ala Thr His Lys
225                 230                 235                 240

Asp Ala Asp Glu His Lys Asn Thr Tyr Pro Gly Leu Leu Gly Leu Ala
                245                 250                 255

Gly Ala Arg Thr Ala Leu Glu Gln Ala Val Thr Ala Ala Gln Thr Ala
            260                 265                 270

Leu Val Lys Ala Ser Ala Ala Ser Gln Arg Gly Met Gly Leu Leu Ala
        275                 280                 285

Ala Phe Leu Thr Tyr Phe Thr Asp
    290                 295

<210> SEQ ID NO 61
<211> LENGTH: 759
<212> TYPE: DNA
<213> ORGANISM: Lactobacillus plantarum

<400> SEQUENCE: 61
atggatggaa ttttatcggg taagaccatt gtggtcatgg gtgtggccaa tcagcgcagt    60

```
attgcctggg ggtgtaccga ggcattaatt gcacagggg  cccaggttat cttgacttac    120
caaaatgacc gtttgaagca aagcttacaa cggtttgttg cgccagatgt gccgttaatt    180
gcctgtgatg ttgctgatga tgacaatgtt gagcgggcat ttgcaagcat aaacaacag     240 tatggtgcca tcgatgggat tatccatgcg attgcttatg cggataaagc aaccttagaa    300
ggtgattttg tgaataccac gaaagctgga tatgatttgg cacaaaatat tagtgcgtat    360
tcgctgattg cagttgcccg agcagctcgg ccaatgctga aaccaggagc cagtctcgta    420
acgttgacgt attttggatc agagcgagcc gtaccaaatt acaatatgat ggggttgct    480 aaggccgcgt tggaagcaaa tgtgcgttac ttggcgcgtg accttggacc acaacaagtc    540
cgcgtgaatg caatttcagc cggagcagtc aaaacgttgg cggtaacggg tattcatgag    600
catcagcaat tattaaaatt atctcgcagt atgacagttg atggagaacc ggtaaaaacg    660
cgtgagatcg gcaacgtggc tgccttttta ttaagcaatc tatcgactgg aatgaccggg    720
gacgtggtat acgtggataa agggggtccac ttaagttaa                          759
```

<210> SEQ ID NO 62
<211> LENGTH: 252
<212> TYPE: PRT
<213> ORGANISM: Lactobacillus plantarum
<400> SEQUENCE: 62

```
Met Asp Gly Ile Leu Ser Gly Lys Thr Ile Val Met Gly Val Ala
1               5                   10                  15

Asn Gln Arg Ser Ile Ala Trp Gly Cys Thr Glu Ala Leu Ile Ala Gln
            20                  25                  30

Gly Ala Gln Val Ile Leu Thr Tyr Gln Asn Asp Arg Leu Lys Gln Ser
        35                  40                  45

Leu Gln Arg Phe Val Ala Pro Asp Val Pro Leu Ile Ala Cys Asp Val
    50                  55                  60

Ala Asp Asp Asp Asn Val Glu Arg Ala Phe Ala Ser Ile Lys Gln Gln
65                  70                  75                  80

Tyr Gly Ala Ile Asp Gly Ile Ile His Ala Ile Ala Tyr Ala Asp Lys
                85                  90                  95

Ala Thr Leu Glu Gly Asp Phe Val Asn Thr Thr Lys Ala Gly Tyr Asp
            100                 105                 110

Leu Ala Gln Asn Ile Ser Ala Tyr Ser Leu Ile Ala Val Ala Arg Ala
        115                 120                 125

Ala Arg Pro Met Leu Lys Pro Gly Ala Ser Leu Val Thr Leu Thr Tyr
    130                 135                 140

Phe Gly Ser Glu Arg Ala Val Pro Asn Tyr Asn Met Met Gly Val Ala
145                 150                 155                 160

Lys Ala Ala Leu Glu Ala Asn Val Arg Tyr Leu Ala Arg Asp Leu Gly
                165                 170                 175

Pro Gln Gln Val Arg Val Asn Ala Ile Ser Ala Gly Ala Val Lys Thr
            180                 185                 190

Leu Ala Val Thr Gly Ile His Glu His Gln Gln Leu Leu Lys Leu Ser
        195                 200                 205

Arg Ser Met Thr Val Asp Gly Glu Pro Val Lys Thr Arg Glu Ile Gly
    210                 215                 220

Asn Val Ala Ala Phe Leu Leu Ser Asn Leu Ser Thr Gly Met Thr Gly
225                 230                 235                 240

Asp Val Val Tyr Val Asp Lys Gly Val His Leu Ser
                245                 250
```

<210> SEQ ID NO 63
<211> LENGTH: 552
<212> TYPE: DNA
<213> ORGANISM: Lactobacillus plantarum

<400> SEQUENCE: 63

```
atgccaatca ctcaagttgt ctttaaacgg cagtggcttc agatgccggt cgatgtttct    60
aaaaaaatgc ggcgggtcac tcagcgaacc gtgagtcgcc aattaattca gcaagtgtta   120
tcggtaccat tagcttatca tcgattgggc cagccctatt ttccaagtca tcctcgatta   180
ggtgttagtg ttagtcacac gcaccagtta gtgatggtag cggttggtcc gggacctctg   240
gggattgatg ttgaacaggt ccgtccatat gatgtgactg ccattcggcg agcctttaca   300
tcggtggaat ggcagctatt acaggtttta tcggtgcaag atcgttatcg gttagggtgg   360
caactttgga cggctaaaga agcggtatta aagttagtgg gctgtggctt gacccatgcg   420
ccccgccgtg ttgaggttct tgatttagaa cgtggactag cgtgctatca aacacagtta   480
taccagttga cgccgttaga attgcctgcg actcacgagg gattttttggc tcgtcccttg   540
tcggttggct ga                                                       552
```

<210> SEQ ID NO 64
<211> LENGTH: 183
<212> TYPE: PRT
<213> ORGANISM: Lactobacillus plantarum

<400> SEQUENCE: 64

```
Met Pro Ile Thr Gln Val Val Phe Lys Arg Gln Trp Leu Gln Met Pro
1               5                   10                  15

Val Asp Val Ser Lys Lys Met Arg Arg Val Thr Gln Arg Thr Val Ser
            20                  25                  30

Arg Gln Leu Ile Gln Gln Val Leu Ser Val Pro Leu Ala Tyr His Arg
        35                  40                  45

Leu Gly Gln Pro Tyr Phe Pro Ser His Pro Arg Leu Gly Val Ser Val
    50                  55                  60

Ser His Thr His Gln Leu Val Met Val Ala Val Gly Pro Gly Pro Leu
65                  70                  75                  80

Gly Ile Asp Val Glu Gln Val Arg Pro Tyr Asp Val Thr Ala Ile Arg
                85                  90                  95

Arg Ala Phe Thr Ser Val Glu Trp Gln Leu Leu Gln Val Leu Ser Val
            100                 105                 110

Gln Asp Arg Tyr Arg Leu Gly Trp Gln Leu Trp Thr Ala Lys Glu Ala
        115                 120                 125

Val Leu Lys Leu Val Gly Cys Gly Leu Thr His Ala Pro Arg Arg Val
    130                 135                 140

Glu Val Leu Asp Leu Glu Arg Gly Leu Ala Cys Tyr Gln Thr Gln Leu
145                 150                 155                 160

Tyr Gln Leu Thr Pro Leu Glu Leu Pro Ala Thr His Glu Gly Phe Leu
                165                 170                 175

Ala Arg Pro Leu Ser Val Gly
            180
```

<210> SEQ ID NO 65
<211> LENGTH: 1662
<212> TYPE: DNA
<213> ORGANISM: Lactobacillus plantarum

<400> SEQUENCE: 65

```
atgagtaatc atcaaatccg cttgtcctta tcaatcatca ccagttgctt gttggcaact      60
ctgattatcg gcccgttagt cgccctgatt ggtcaaacac tagtcgggca atcgccaagc     120
cagctatggt cacaactgac gcagccaacc aaccgtgtga gcattcaaca cagtctgttc     180
ctcagtgggg gcacggtcgt cgggacaacc ctgctagcca ccccttttggc atggatcatg    240
acgcacaccc gtttaacaaa gctcgcctgg ttgcattggc tcttgttagt gccattcatg    300
acaccaccat atattaacgc gatgggctgg ttatatttct ttcaaccaca cggattactg    360
gctcagctta atccgagttg gcaccaccaa tttcagtggc tattttcacc gttcgggatg    420
gtcattatca tgagtctgca tttgtatccc gtggcatact taggcttacg cgcagccctc    480
atgcaattca accagcgctg gcttcaagcg gccgaagttc atggggtcaa cacctggcaa    540
cgactagtgc gaatcacatt accaatcatg ttagtcccat acttagctgt atggatttta    600
gtctttacca aaaccttggc tgaatttgga acgccagcca cctttggtcg gagcatccac    660
ttcgaagttc tgacgactac gattcaaagg gacctcagtc agtggccctt agatttccaa    720
aacggggtac tcaccggcac cctcctactg accattgccc tgattgcctg ggtatccag    780
caatggttgt tacgccggcc agctgttaag ttcaccggac aacggtcagc gtcacaatat    840
cggcagcttg gagtgacaac attagcaggc actttcgtca ccctagtcat cagtattgct    900
attgtcctgc cattcagtgc catcgtgctc aatcgctac tcaaacaacg cagtcttggt    960
tggagtccgt ctaatttgac acttgtacac tatatagacc tcttacgctt tgatagtcct   1020
gcctggcagg ccattgttac gaccgtcgga ttggcattac tgattagcag tctcaatgtg   1080
atcgttggtt tattcttgag cgttgggagt ttaacaaaac gttttcccaa gtggctgcga   1140
cagttatgtc ataccttggg cgcattgcca ctcgcaattc caaacgtcgt cttagcattg   1200
agcttaatga tgctcttttc acaggtgctg gcgttcacca aattatacgg caccctaacc   1260
atcctcctga tcgcggatgt caccttattt ctaccaacaa cggtgcaata cttgacgacc   1320
gccctcaagg cctttgactc ggaattgctg gctagcgcgc gcatcttcga acctagtttc   1380
ggccgcatta tcctaaaaat tgcacttccg attctatggc ccgcgctact caacagcttt   1440
gtgatggctt tcattgccac gagtcgtgaa ttagtcgttg ccctattgtt actgccttcc   1500
ggtatgacga ccgtttcaac atttatctat caatcgttcg aacaaggtga gcggccgcc   1560
ggtatggccc tagcggtatt gacggtagca ttgacattca ttggactgat tgcagctaat   1620
cacctgcaat cagctaccaa gccagtacgc caaccaaact ag                      1662
```

<210> SEQ ID NO 66
<211> LENGTH: 553
<212> TYPE: PRT
<213> ORGANISM: Lactobacillus plantarum

<400> SEQUENCE: 66

```
Met Ser Asn His Gln Ile Arg Leu Ser Leu Ser Ile Ile Thr Ser Cys
1               5                   10                  15

Leu Leu Ala Thr Leu Ile Ile Gly Pro Leu Val Ala Leu Ile Gly Gln
            20                  25                  30

Thr Leu Val Gly Gln Ser Pro Ser Gln Leu Trp Ser Gln Leu Thr Gln
        35                  40                  45

Pro Thr Asn Arg Val Ser Ile Gln His Ser Leu Phe Leu Ser Gly Gly
    50                  55                  60
```

```
Thr Val Val Gly Thr Thr Leu Leu Ala Thr Pro Leu Ala Trp Ile Met
65                  70                  75                  80

Thr His Thr Arg Leu Thr Lys Leu Ala Trp Leu His Trp Leu Leu
                85                  90                  95

Val Pro Phe Met Thr Pro Pro Tyr Ile Asn Ala Met Gly Trp Leu Tyr
                100                 105                 110

Phe Phe Gln Pro His Gly Leu Leu Ala Gln Leu Asn Pro Ser Trp His
            115                 120                 125

His Gln Phe Gln Trp Leu Phe Ser Pro Phe Gly Met Val Ile Ile Met
    130                 135                 140

Ser Leu His Leu Tyr Pro Val Ala Tyr Leu Gly Leu Arg Ala Ala Leu
145                 150                 155                 160

Met Gln Phe Asn Gln Arg Trp Leu Gln Ala Ala Glu Val His Gly Val
                165                 170                 175

Asn Thr Trp Gln Arg Leu Val Arg Ile Thr Leu Pro Ile Met Leu Val
                180                 185                 190

Pro Tyr Leu Ala Val Trp Ile Leu Val Phe Thr Lys Thr Leu Ala Glu
            195                 200                 205

Phe Gly Thr Pro Ala Thr Phe Gly Arg Ser Ile His Phe Glu Val Leu
    210                 215                 220

Thr Thr Thr Ile Gln Arg Asp Leu Ser Gln Trp Pro Leu Asp Phe Gln
225                 230                 235                 240

Asn Gly Val Leu Thr Gly Thr Leu Leu Thr Ile Ala Leu Ile Ala
                245                 250                 255

Trp Gly Ile Gln Gln Trp Leu Leu Arg Arg Pro Ala Val Lys Phe Thr
            260                 265                 270

Gly Gln Arg Ser Ala Ser Gln Tyr Arg Gln Leu Gly Val Thr Thr Leu
    275                 280                 285

Ala Gly Thr Phe Val Thr Leu Val Ile Ser Ile Ala Ile Val Leu Pro
    290                 295                 300

Phe Ser Ala Ile Val Leu Gln Ser Leu Leu Lys Gln Arg Ser Leu Gly
305                 310                 315                 320

Trp Ser Pro Ser Asn Leu Thr Leu Val His Tyr Ile Asp Leu Leu Arg
                325                 330                 335

Phe Asp Ser Pro Ala Trp Gln Ala Ile Val Thr Thr Val Gly Leu Ala
            340                 345                 350

Leu Leu Ile Ser Ser Leu Asn Val Ile Val Gly Leu Phe Leu Ser Val
    355                 360                 365

Gly Ser Leu Thr Lys Arg Phe Pro Lys Trp Leu Arg Gln Leu Cys His
370                 375                 380

Thr Leu Gly Ala Leu Pro Leu Ala Ile Pro Asn Val Val Leu Ala Leu
385                 390                 395                 400

Ser Leu Met Met Leu Phe Ser Gln Val Leu Ala Phe Thr Lys Leu Tyr
                405                 410                 415

Gly Thr Leu Thr Ile Leu Leu Ile Ala Asp Val Thr Leu Phe Leu Pro
            420                 425                 430

Thr Thr Val Gln Tyr Leu Thr Thr Ala Leu Lys Ala Phe Asp Ser Glu
        435                 440                 445

Leu Leu Ala Ser Ala Arg Ile Phe Glu Pro Ser Phe Gly Arg Ile Ile
        450                 455                 460

Leu Lys Ile Ala Leu Pro Ile Leu Trp Pro Ala Leu Leu Asn Ser Phe
465                 470                 475                 480

Val Met Ala Phe Ile Ala Thr Ser Arg Glu Leu Val Val Ala Leu Leu
```

```
                485                 490                 495
Leu Leu Pro Ser Gly Met Thr Thr Val Ser Thr Phe Ile Tyr Gln Ser
            500                 505                 510

Phe Glu Gln Gly Glu Ala Ala Ala Gly Met Ala Leu Ala Val Leu Thr
            515                 520                 525

Val Ala Leu Thr Phe Ile Gly Leu Ile Ala Ala Asn His Leu Gln Ser
            530                 535                 540

Ala Thr Lys Pro Val Arg Gln Pro Asn
545                 550

<210> SEQ ID NO 67
<211> LENGTH: 1011
<212> TYPE: DNA
<213> ORGANISM: Lactobacillus plantarum

<400> SEQUENCE: 67
atgtctaaag cagcaattat cacattatcc acgctcggcg tgctcgcaat tggcacgtcg      60
ctttatgtta atcaacatca gaaaaaaacg ttaaccgcca acgcgcaaac cagtcaacaa     120
gtcttaacag tatacgctgc tggacctaaa ccccttctg atcaaatcat ccacggtttt      180
gaagccaaaa ctggcattaa agtcaaaagt tttgacggca cgaccgggaa aattttaagt     240
aaggtcaagg ccgagcaagg caatccccaa gctgatgtgc tgattttagc ttcaatggcc     300
gctggcgtcg atttacaaaa gaatggccag ctattaacct atcagccttc tcaagctaaa     360
cacctgaata acaatttaa agatactagc caccagttga tcaattacag tgcttcggca     420
gtcggcatca cctacaatac gcggcacatc aaatcggcac cgacagactg gtctgacttg     480
acaaccgctc cgtatcgcaa tcaagtgacc attccggacc cccaaacctc tggttctagc     540
ttggacttca ttaacgctta tcaaatgaaa acggtacgc aactacttaa agcccttcaa     600
gaaaacggtg ccgatatcgg gggtgctaac aaggaagtac tcgatgcagt catcactggc     660
caaaaaatcg ccgtctttgg tggggtcgat tacatgagtc taacagctat taaaaaaggc     720
gaaaaaattg gtttcgttta tcctaagagt gggactttgg tcaatccacg accggcgatg     780
attttgaagg ctagtcgtca tcaagccgcc gccaaacaat ttattgacta tctcttatca     840
gctaaagttc aaagacagat tcaaaaaagt aacttaattc caggtaccac gagcactttg     900
accgatccac gcaatggcga agccatcaaa gcctacacgg tcaattggac cagtgccaac     960
gcggccctga ccaaaaacgt tgtcgcattc aatcaggtct ttagccaatg a              1011

<210> SEQ ID NO 68
<211> LENGTH: 336
<212> TYPE: PRT
<213> ORGANISM: Lactobacillus plantarum

<400> SEQUENCE: 68

Met Ser Lys Ala Ala Ile Ile Thr Leu Ser Thr Leu Gly Val Leu Ala
1               5                   10                  15

Ile Gly Thr Ser Leu Tyr Val Asn Gln His Gln Lys Lys Thr Leu Thr
            20                  25                  30

Ala Asn Ala Gln Thr Ser Gln Gln Val Leu Thr Val Tyr Ala Ala Gly
        35                  40                  45

Pro Lys Pro Leu Ser Asp Gln Ile Ile His Gly Phe Glu Ala Lys Thr
    50                  55                  60

Gly Ile Lys Val Lys Ser Phe Asp Gly Thr Thr Gly Lys Ile Leu Ser
65                  70                  75                  80
```

Lys Val Lys Ala Glu Gln Gly Asn Pro Gln Ala Asp Val Leu Ile Leu
                85                  90                  95

Ala Ser Met Ala Ala Gly Val Asp Leu Gln Lys Asn Gly Gln Leu Leu
            100                 105                 110

Thr Tyr Gln Pro Ser Gln Ala Lys His Leu Asn Lys Gln Phe Lys Asp
        115                 120                 125

Thr Ser His Gln Leu Ile Asn Tyr Ser Ala Ser Ala Val Gly Ile Thr
    130                 135                 140

Tyr Asn Thr Arg His Ile Lys Ser Ala Pro Thr Asp Trp Ser Asp Leu
145                 150                 155                 160

Thr Thr Ala Pro Tyr Arg Asn Gln Val Thr Ile Pro Asp Pro Gln Thr
                165                 170                 175

Ser Gly Ser Ser Leu Asp Phe Ile Asn Ala Tyr Gln Met Lys His Gly
            180                 185                 190

Thr Gln Leu Leu Lys Ala Leu Gln Glu Asn Gly Ala Asp Ile Gly Gly
        195                 200                 205

Ala Asn Lys Glu Val Leu Asp Ala Val Ile Thr Gly Gln Lys Ile Ala
    210                 215                 220

Val Phe Gly Gly Val Asp Tyr Met Ser Leu Thr Ala Ile Lys Lys Gly
225                 230                 235                 240

Glu Lys Ile Gly Phe Val Tyr Pro Lys Ser Gly Thr Leu Val Asn Pro
                245                 250                 255

Arg Pro Ala Met Ile Leu Lys Ala Ser Arg His Gln Ala Ala Ala Lys
            260                 265                 270

Gln Phe Ile Asp Tyr Leu Leu Ser Ala Lys Val Gln Arg Gln Ile Gln
        275                 280                 285

Lys Ser Asn Leu Ile Pro Gly Thr Thr Ser Thr Leu Thr Asp Pro Arg
    290                 295                 300

Asn Gly Glu Ala Ile Lys Ala Tyr Thr Val Asn Trp Thr Ser Ala Asn
305                 310                 315                 320

Ala Ala Leu Thr Lys Asn Val Val Ala Phe Asn Gln Val Phe Ser Gln
                325                 330                 335

<210> SEQ ID NO 69
<211> LENGTH: 330
<212> TYPE: DNA
<213> ORGANISM: Lactobacillus plantarum

<400> SEQUENCE: 69
ttgagtaatg aggtgattag catgtttgat caagatgaag aacggtttgc aacgctaggg     60
ttagcggcca agctaccgag cgcggtgatt gatggcattt gggatattat tgatcaaaat    120
ctaaaggggg tcgttcgcct gccacgggtc ctgcaatttg ccctgatcgc acgtaatggg    180
caagtcaccg tggcttttga tgcgcagcac gatgccatca tggaattcga tttaccagtc    240
aattaccaac gggagtttcc cgagacggtg gcagtcttag acgatggtca gtatcagacc    300
atgatgttga tggacgaact ctccgtctga                                      330

<210> SEQ ID NO 70
<211> LENGTH: 109
<212> TYPE: PRT
<213> ORGANISM: Lactobacillus plantarum

<400> SEQUENCE: 70

Met Ser Asn Glu Val Ile Ser Met Phe Asp Gln Asp Glu Glu Arg Phe
1               5                   10                  15

Ala Thr Leu Gly Leu Ala Ala Lys Leu Pro Ser Ala Val Ile Asp Gly
            20                  25                  30

Ile Trp Asp Ile Ile Asp Gln Asn Leu Lys Gly Val Val Arg Leu Pro
        35                  40                  45

Arg Val Leu Gln Phe Ala Leu Ile Ala Arg Asn Gly Gln Val Thr Val
    50                  55                  60

Ala Phe Asp Ala Gln His Asp Ala Ile Met Glu Phe Asp Leu Pro Val
65                  70                  75                  80

Asn Tyr Gln Arg Glu Phe Pro Glu Thr Val Ala Val Leu Asp Asp Gly
                85                  90                  95

Gln Tyr Gln Thr Met Met Leu Met Asp Glu Leu Ser Val
            100                 105

<210> SEQ ID NO 71
<211> LENGTH: 747
<212> TYPE: DNA
<213> ORGANISM: Lactobacillus plantarum

<400> SEQUENCE: 71
gtgtgtctaa tggcgaaaac agcagtgtgc attgtcgatc aacaacgtta ccaagttgtg     60
gacggtatgc gattagaaga attggaaact agtttgcggc aaatgatttt aaaagatttt    120
ccgcaggccc ataatagcag tttcatttgt agtgagcatc tcgtacatta tcgcttagca    180
aagatggatg cgatgatcga gaacgattat caacaaaatg ataaggtcaa tgcgcaatta    240
tctaagattc tcgctaacca cacgtatcgg gtcgtcgatg ttaatagcga gctggaaagt    300
tcattgacat ttggtcaacg ggtcgcggat ggggtcgcac ggttcggggg gagctgggcg    360
tttatcattt cgtttgtcgt ggtgatgctc gtgtggatgt tgctcaacgt cttaccaatt    420
tttagccatc attttgaccc ttatcccttt attttattaa atttattttt aagcatggtc    480
gcagcaatcc aggcaccatt gatcatgatg agtcagaatc gggcagctga gtatgatcgg    540
ctacaagcgg ccaatgattt taaagtgaac tcgatgtctg aagaggagat ccgggtcctg    600
cactcgaaag tcgatcattt aattcaacaa gatgaaccaa acatgcttga atccagaaa    660
atgcaaacac aaatgttagg tgagattcaa gcacaagtca tgaattacg acgattgcag    720
ccgcggcgac gtcgcaatca aagttaa                                        747

<210> SEQ ID NO 72
<211> LENGTH: 248
<212> TYPE: PRT
<213> ORGANISM: Lactobacillus plantarum

<400> SEQUENCE: 72

Met Cys Leu Met Ala Lys Thr Ala Val Cys Ile Val Asp Gln Gln Arg
1               5                   10                  15

Tyr Gln Val Val Asp Gly Met Arg Leu Glu Glu Leu Glu Thr Ser Leu
            20                  25                  30

Arg Gln Met Ile Leu Lys Asp Phe Pro Gln Ala His Asn Ser Ser Phe
        35                  40                  45

Ile Cys Ser Glu His Leu Val His Tyr Arg Leu Ala Lys Met Asp Ala
    50                  55                  60

Met Ile Glu Asn Asp Tyr Gln Gln Asn Asp Lys Val Asn Ala Gln Leu
65                  70                  75                  80

Ser Lys Ile Leu Ala Asn His Thr Tyr Arg Val Val Asp Val Asn Ser
                85                  90                  95

Glu Leu Glu Ser Ser Leu Thr Phe Gly Gln Arg Val Ala Asp Gly Val

```
                100                 105                 110
Ala Arg Phe Gly Gly Ser Trp Ala Phe Ile Ile Ser Phe Val Val
            115                 120                 125

Met Leu Val Trp Met Leu Leu Asn Val Leu Pro Ile Phe Ser His His
            130                 135                 140

Phe Asp Pro Tyr Pro Phe Ile Leu Leu Asn Leu Phe Leu Ser Met Val
145                 150                 155                 160

Ala Ala Ile Gln Ala Pro Leu Ile Met Met Ser Gln Asn Arg Ala Ala
                165                 170                 175

Glu Tyr Asp Arg Leu Gln Ala Ala Asn Asp Phe Lys Val Asn Ser Met
            180                 185                 190

Ser Glu Glu Glu Ile Arg Val Leu His Ser Lys Val Asp His Leu Ile
            195                 200                 205

Gln Gln Asp Glu Pro Asn Met Leu Glu Ile Gln Lys Met Gln Thr Gln
            210                 215                 220

Met Leu Gly Glu Ile Gln Ala Gln Val Asn Glu Leu Arg Arg Leu Gln
225                 230                 235                 240

Pro Arg Arg Arg Arg Asn Gln Ser
                245

<210> SEQ ID NO 73
<211> LENGTH: 885
<212> TYPE: DNA
<213> ORGANISM: Lactobacillus plantarum

<400> SEQUENCE: 73
atgaattatc gcaacttgct cgtattacca cttgccgtct tgttggtcgg ctgttcatca      60
ccaacacacc aggattccaa gtcaactagt cagacgacca cgagtgccaa ggcaacggtt     120
agcagtaccc aaaagaaggc taaggctacc agtagtacta gtagtcggcc tcaaaccgca     180
gccacgcgct cgtctagaac agcgcgtgag cgggccgcca gcgccgctaa caagtcggtc     240
acccagccca cggctacgac ccggctggca gcattgaatc aacaattgac taagacgttg     300
ggaaagcagg cgctcgttcc acaagtcgat gggttaacta gtggcagttc gaagttgaac     360
atgcgctatt caggtgacgc agccaattac accatcaatt atagtgtggg acaacaggcc     420
cagccattca cgcggcggc cgtggtggat gaaacggctt atgcgactgt cactaagacg     480
acctatgcga caactaatgc cgcggcccag caggtgggt atcgtgataa taaatccaca     540
gctgggctgc caaccgtcga tctcggtcat caaatcaccg cgcatatcga cgcgggtgct     600
ggtcaacgat atatcatgtg aatgagggc cgctggtcgt tgaccgtgca tgcgaacatg     660
atgcacgaag atgcgggcgt cgcgttagct aaacaggccg tcgctacttt cgagcaggtc     720
tacttaccag caccacagtc ggtcggcgcc atcactttg acgcgatttc gtcaggctct     780 ggaccttag accaagttat ccaatggcaa gctggtaaag tggtttatca agtcaaggct     840
caagagatgg caacggctat caaaatggct gccagtatgc aataa                    885

<210> SEQ ID NO 74
<211> LENGTH: 294
<212> TYPE: PRT
<213> ORGANISM: Lactobacillus plantarum

<400> SEQUENCE: 74

Met Asn Tyr Arg Asn Leu Leu Val Leu Pro Leu Ala Val Leu Leu Val
1               5                   10                  15

Gly Cys Ser Ser Pro Thr His Gln Asp Ser Lys Ser Thr Ser Gln Thr
```

|            |            |            |            |            |            |
|------------|------------|------------|------------|------------|------------|
|            | 20         |            | 25         |            | 30         |

Thr Thr Ser Ala Lys Ala Thr Val Ser Ser Thr Gln Lys Lys Ala Lys
    35                  40                      45

Ala Thr Ser Ser Thr Ser Ser Arg Pro Gln Thr Ala Ala Thr Arg Ser
50                      55                      60

Ser Arg Thr Ala Arg Glu Arg Ala Ala Ser Ala Ala Asn Lys Ser Val
65                  70                  75                  80

Thr Gln Pro Thr Ala Thr Thr Arg Leu Ala Ala Leu Asn Gln Gln Leu
                85                  90                  95

Thr Lys Thr Leu Gly Lys Gln Ala Leu Val Pro Gln Val Asp Gly Leu
            100                 105                 110

Thr Ser Gly Ser Ser Lys Leu Asn Met Arg Tyr Ser Gly Asp Ala Ala
                115                 120                 125

Asn Tyr Thr Ile Asn Tyr Ser Val Gly Gln Gln Ala Gln Pro Phe Asn
            130                 135                 140

Ala Ala Val Val Asp Glu Thr Ala Tyr Ala Thr Val Thr Lys Thr
145                 150                 155                 160

Thr Tyr Ala Thr Thr Asn Ala Ala Ala Gln Gln Val Gly Tyr Arg Asp
                165                 170                 175

Asn Lys Ser Thr Ala Gly Leu Pro Thr Val Asp Leu Gly His Gln Ile
            180                 185                 190

Thr Ala His Ile Asp Ala Gly Ala Gly Gln Arg Tyr Ile Met Trp Asn
        195                 200                 205

Glu Gly Arg Trp Ser Leu Thr Val His Ala Asn Met Met His Glu Asp
    210                 215                 220

Ala Gly Val Ala Leu Ala Lys Gln Ala Val Ala Thr Phe Glu Gln Val
225                 230                 235                 240

Tyr Leu Pro Ala Pro Gln Ser Val Gly Ala Ile Thr Phe Asp Ala Ile
                245                 250                 255

Ser Ser Gly Ser Gly Pro Leu Asp Gln Val Ile Gln Trp Gln Ala Gly
            260                 265                 270

Lys Val Val Tyr Gln Val Lys Ala Gln Glu Met Ala Thr Ala Ile Lys
        275                 280                 285

Met Ala Ala Ser Met Gln
    290

<210> SEQ ID NO 75
<211> LENGTH: 351
<212> TYPE: DNA
<213> ORGANISM: Lactobacillus plantarum

<400> SEQUENCE: 75
atgcaagtgc gcttagtgcc aaacttacaa ctcggtgaac ggattatcgg gccgaccccc      60
gaccctgagg ccaatcgcgc gctttatcaa cgttatgcga acgattaca ggcgcggcta     120 ggtatcggct ttcaagtcta cctagatatg agtgacggtt atgatttact gcatgcgcgt     180
gattacgaca ccgatacttg ttgggtggtt gcagcggctg tttaccaagc attaactgat     240
tctgccgtga tcacccacca ccgtatcatc tcgctgagtg accaagcact tatcttaaaa     300
gcgacgcagc ccatcgaaca acaactgcgc caatctccga ctgatcaata g              351

<210> SEQ ID NO 76
<211> LENGTH: 116
<212> TYPE: PRT
<213> ORGANISM: Lactobacillus plantarum

<400> SEQUENCE: 76

Met Gln Val Arg Leu Val Pro Asn Leu Gln Leu Gly Glu Arg Ile Ile
1               5                   10                  15

Gly Pro Thr Pro Asp Pro Glu Ala Asn Arg Ala Leu Tyr Gln Arg Tyr
            20                  25                  30

Ala Lys Arg Leu Gln Ala Arg Leu Gly Ile Gly Phe Gln Val Tyr Leu
        35                  40                  45

Asp Met Ser Asp Gly Tyr Asp Leu Leu His Ala Arg Asp Tyr Asp Thr
    50                  55                  60

Asp Thr Cys Trp Val Val Ala Ala Ala Val Tyr Gln Ala Leu Thr Asp
65                  70                  75                  80

Ser Ala Val Ile Thr His His Arg Ile Ile Ser Leu Ser Asp Gln Ala
                85                  90                  95

Leu Ile Leu Lys Ala Thr Gln Pro Ile Glu Gln Leu Arg Gln Ser
            100                 105                 110

Pro Thr Asp Gln
        115

<210> SEQ ID NO 77
<211> LENGTH: 726
<212> TYPE: DNA
<213> ORGANISM: Lactobacillus plantarum

<400> SEQUENCE: 77

```
atgatagatt ggattaagct gctcaaaatg cactggcgga ttgttggtgg tgttactgcc      60
gtgatcatta ttttgataac gggatgggca ctgagtcaac ttaagcagcc tcaacccgcc     120
ggtacggata acttgttggc gcattcgttc aattccacat caatgggagg cgcgagtcga     180
acgtctgcca atgctgacca gcccgcaacg agtacccaac cgtcgaacgc tacaccgagc     240
ccagcccgac cgacaggtgc tagttcaccc gggtatgtcg atattaaggg tgcggttaat     300
aaaccagggt tgtatcaggt tactgctagt atgcgggtcg cggatgtcat ccaactggca     360
caaggcatgc agccacaggc agatgctcag cagatcaact tggctgccaa agtgactgat     420
cagcaagtga tctacgtgcc agctaagggc gaacaggccc cggctgttgc gccaccagtc     480
gtccagtcaa cggggcctac tggcggaaca ccaactagtg atcatgcggc aacggataag     540
gtcaatctca cacggctga tgtggccgcg ttgcaaacgt tgagcggaat cgggcagaag     600
aaggctgaaa aaatcattga ttatcgccag caacatggta attttaaaac aattgatgat     660
ttgaaaaatg tcagcggctt tggagaaaag actgtggtca aatacaaaga ccagctcacc     720
gtctag                                                                726
```

<210> SEQ ID NO 78
<211> LENGTH: 241
<212> TYPE: PRT
<213> ORGANISM: Lactobacillus plantarum

<400> SEQUENCE: 78

Met Ile Asp Trp Ile Lys Leu Leu Lys Met His Trp Arg Ile Val Gly
1               5                   10                  15

Gly Val Thr Ala Val Ile Ile Ile Leu Ile Thr Gly Trp Ala Leu Ser
            20                  25                  30

Gln Leu Lys Gln Pro Gln Pro Ala Gly Thr Asp Asn Leu Leu Ala His
        35                  40                  45

Ser Phe Asn Ser Thr Ser Met Gly Gly Ala Ser Arg Thr Ser Ala Asn
    50                  55                  60

```
Ala Asp Gln Pro Ala Thr Ser Thr Gln Pro Ser Asn Ala Thr Pro Ser
 65                  70                  75                  80

Pro Ala Arg Pro Thr Gly Ala Ser Ser Pro Gly Tyr Val Asp Ile Lys
                 85                  90                  95

Gly Ala Val Asn Lys Pro Gly Leu Tyr Gln Val Thr Ala Ser Met Arg
            100                 105                 110

Val Ala Asp Val Ile Gln Leu Ala Gln Gly Met Gln Pro Gln Ala Asp
            115                 120                 125

Ala Gln Gln Ile Asn Leu Ala Ala Lys Val Thr Asp Gln Gln Val Ile
130                 135                 140

Tyr Val Pro Ala Lys Gly Glu Gln Ala Pro Ala Val Ala Pro Pro Val
145                 150                 155                 160

Val Gln Ser Thr Gly Pro Thr Gly Gly Thr Pro Thr Ser Asp His Ala
                165                 170                 175

Ala Thr Asp Lys Val Asn Leu Asn Thr Ala Asp Val Ala Ala Leu Gln
            180                 185                 190

Thr Leu Ser Gly Ile Gly Gln Lys Lys Ala Glu Lys Ile Ile Asp Tyr
        195                 200                 205

Arg Gln Gln His Gly Asn Phe Lys Thr Ile Asp Leu Lys Asn Val
210                 215                 220

Ser Gly Phe Gly Glu Lys Thr Val Val Lys Tyr Lys Asp Gln Leu Thr
225                 230                 235                 240

Val
```

<210> SEQ ID NO 79
<211> LENGTH: 1047
<212> TYPE: DNA
<213> ORGANISM: Lactobacillus plantarum

<400> SEQUENCE: 79

```
atgactaagg gccgggagtt gttaaaacgt tactggggct tgctggtcgt gatactggtg      60
gtacttgcac tatttctaat tcctttaccg tactatattg aaggacccgg aagtgcaaac     120
aatttgaaga cttttgtgac cgtcaagcgg catccggatc atcaccgggg taagtttatg     180
ttgacctcgg tcgcagaagc tcgagcgacg ccgctgatgt ggctttacgc acaattgaat     240
ccgcactatg acgtggtcag tgctcaggat atgactggcg tcaggatga cgcgacttat      300
aatcgggttc agaagtttta tatgcgaagt gcaatcaacg aagctatcgc gacggcgtat     360
tcggctgcgc atcagcaata ccgcaaggtt tatcagggta tctacgtttt aacggttcag     420
tctaattcga aatttagaaa ccagttaaaa gttggcgata cgattacgaa agtcgatggc     480
caccatttta atacagccag tgcgtatcag cattatattg gtaagcaggg cgtcggacat     540
cgagtgacga tcacgtatcg gcgaaagggc catttgaagc aagcaagtgc gcccctaatc     600
aagctgagca cgcaccgcgc cgggattggt atcggcctaa ctgataatat taaagtgacg     660
acgactattc cggtcaaggt cgatcccgga caaatcgggg gtccctcggc gggcttgatg     720
tttagtttgc aaatttatca gcaattgacc aatcagaact tacgacacgg acgcaagatt     780
gccgggaccg gcaccatcga tcaaaatgga caagttggtg aaattggtgg tatcgacaag     840
aaagtgattg ctgctaagcg ggcaggggcg acaatttttct ttgcaccgta tgtgaaacca     900
accaaagcgc ttttggcggt tgaagaaaag ggtcaaacta actatcaact tgctaaagcg     960
accgcgaaaa agtacgcgcc taatatgaaa gttgttccag tgacctcatt taaacaggcc    1020
gttcattatt tgcagacaca ccaatag                                        1047
```

<210> SEQ ID NO 80
<211> LENGTH: 348
<212> TYPE: PRT
<213> ORGANISM: Lactobacillus plantarum

<400> SEQUENCE: 80

Met Thr Lys Gly Arg Glu Leu Leu Lys Arg Tyr Trp Gly Leu Leu Val
1               5                   10                  15

Val Ile Leu Val Val Leu Ala Leu Phe Leu Ile Pro Leu Pro Tyr Tyr
            20                  25                  30

Ile Glu Gly Pro Gly Ser Ala Asn Asn Leu Lys Thr Phe Val Thr Val
        35                  40                  45

Lys Arg His Pro Asp His His Arg Gly Lys Phe Met Leu Thr Ser Val
50                  55                  60

Ala Glu Ala Arg Ala Thr Pro Leu Met Trp Leu Tyr Ala Gln Leu Asn
65                  70                  75                  80

Pro His Tyr Asp Val Val Ser Ala Gln Asp Met Thr Gly Gly Gln Asp
                85                  90                  95

Asp Ala Thr Tyr Asn Arg Val Gln Lys Phe Tyr Met Arg Ser Ala Ile
            100                 105                 110

Asn Glu Ala Ile Ala Thr Ala Tyr Ser Ala Ala His Gln Gln Tyr Arg
        115                 120                 125

Lys Val Tyr Gln Gly Ile Tyr Val Leu Thr Val Gln Ser Asn Ser Lys
130                 135                 140

Phe Arg Asn Gln Leu Lys Val Gly Asp Thr Ile Thr Lys Val Asp Gly
145                 150                 155                 160

His His Phe Asn Thr Ala Ser Ala Tyr Gln His Tyr Ile Gly Lys Gln
                165                 170                 175

Gly Val Gly His Arg Val Thr Ile Thr Tyr Arg Arg Lys Gly His Leu
            180                 185                 190

Lys Gln Ala Ser Ala Pro Leu Ile Lys Leu Ser Thr His Arg Ala Gly
        195                 200                 205

Ile Gly Ile Gly Leu Thr Asp Asn Ile Lys Val Thr Thr Thr Ile Pro
210                 215                 220

Val Lys Val Asp Pro Gly Gln Ile Gly Gly Pro Ser Ala Gly Leu Met
225                 230                 235                 240

Phe Ser Leu Gln Ile Tyr Gln Gln Leu Thr Asn Gln Asn Leu Arg His
                245                 250                 255

Gly Arg Lys Ile Ala Gly Thr Gly Thr Ile Asp Gln Asn Gly Gln Val
            260                 265                 270

Gly Glu Ile Gly Gly Ile Asp Lys Lys Val Ile Ala Ala Lys Arg Ala
        275                 280                 285

Gly Ala Thr Ile Phe Phe Ala Pro Tyr Val Lys Pro Thr Lys Ala Leu
290                 295                 300

Leu Ala Val Glu Glu Lys Gly Gln Thr Asn Tyr Gln Leu Ala Lys Ala
305                 310                 315                 320

Thr Ala Lys Lys Tyr Ala Pro Asn Met Lys Val Val Pro Val Thr Ser
                325                 330                 335

Phe Lys Gln Ala Val His Tyr Leu Gln Thr His Gln
            340                 345

<210> SEQ ID NO 81
<211> LENGTH: 960
<212> TYPE: DNA

<213> ORGANISM: Lactobacillus plantarum

<400> SEQUENCE: 81

```
ttgattgctg aatactacat tattattaat gaactggcag gatctggtca cggtaaggtc      60
gtttgggaaa ccgtcaagcc gattctagaa caacgacaga ttcgatttga atatcgaatt     120
tctgaatatg ccggccacac aattcggctc gcaaatgagt acgttaaaac cattcaacga     180
cgaccaaacg tgaccccggt cattctggtc attggtggtg atggcacact gaacgaggcc     240
ttgaatggta ttatgcaggt cccacaagct gaaccgatcc cgctcgccta cattcctgga     300
ggttcgggca cgactttgc tcgcggtctg ggtatggcga ctgatccagc aattgcactt     360
gcacaagtac tcaacaatat gcggccccgt tcgttaaatg ttggttattt ccatgaaacc     420
ttgaaaaacg aacaccggta tttcgtcaac aacgttggtt taggatttga cgctcaaatc     480
gttgatgaca caaaccgtag caaaaagaag ggccgtctgg gtcgttgggc ttatctcagt     540
aacatgctgg ccgcatattc ccaacaggaa ggcttcccgc taaccgtaca cgttaaccgg     600
aagcgagact attataagcg ggctttcctt tgtacagtct cgaacattcc atactttggt     660
ggcggagtta aaattctgcc tcaggctaat ctgcacgata tcagctcga attgatcgtt      720
gtcgaagagc ctcactggtg gattatcctc tggttgttcg tcttactgct actgggtggc     780
cgtcatctta agtcgcgttt cgttcaccat tatcgcaacg ctaacttgca cttgttggtt     840
aactctgttg aaattggtca gatggatggt caaattattg ggaatcgtaa ttacgacctc     900
tacttgtcca cccatcccta cccattctgg atcgacacta gtatccatga ccaccactaa     960
```

<210> SEQ ID NO 82
<211> LENGTH: 319
<212> TYPE: PRT
<213> ORGANISM: Lactobacillus plantarum

<400> SEQUENCE: 82

```
Met Ile Ala Glu Tyr Tyr Ile Ile Asn Glu Leu Ala Gly Ser Gly
1               5                   10                  15

His Gly Lys Val Val Trp Glu Thr Val Lys Pro Ile Leu Glu Gln Arg
            20                  25                  30

Gln Ile Arg Phe Glu Tyr Arg Ile Ser Glu Tyr Ala Gly His Thr Ile
        35                  40                  45

Arg Leu Ala Asn Glu Tyr Val Lys Thr Ile Gln Arg Arg Pro Asn Val
    50                  55                  60

Thr Pro Val Ile Leu Val Ile Gly Gly Asp Gly Thr Leu Asn Glu Ala
65                  70                  75                  80

Leu Asn Gly Ile Met Gln Val Pro Gln Ala Glu Pro Ile Pro Leu Ala
                85                  90                  95

Tyr Ile Pro Gly Gly Ser Gly Asn Asp Phe Ala Arg Gly Leu Gly Met
            100                 105                 110

Ala Thr Asp Pro Ala Ile Ala Leu Ala Gln Val Leu Asn Asn Met Arg
        115                 120                 125

Pro Arg Ser Leu Asn Val Gly Tyr Phe His Glu Thr Leu Lys Asn Glu
    130                 135                 140

His Arg Tyr Phe Val Asn Asn Val Gly Leu Gly Phe Asp Ala Gln Ile
145                 150                 155                 160

Val Asp Asp Thr Asn Arg Ser Lys Lys Lys Gly Arg Leu Gly Arg Trp
                165                 170                 175

Ala Tyr Leu Ser Asn Met Leu Ala Ala Tyr Ser Gln Gln Glu Gly Phe
            180                 185                 190
```

```
Pro Leu Thr Val His Val Asn Arg Lys Arg Asp Tyr Tyr Lys Arg Ala
        195                 200                 205

Phe Leu Cys Thr Val Ser Asn Ile Pro Tyr Phe Gly Gly Val Lys
    210                 215                 220

Ile Leu Pro Gln Ala Asn Leu His Asp Asn Gln Leu Glu Leu Ile Val
225                 230                 235                 240

Val Glu Glu Pro His Trp Trp Ile Ile Leu Trp Leu Phe Val Leu Leu
                245                 250                 255

Leu Leu Gly Gly Arg His Leu Lys Ser Arg Phe Val His His Tyr Arg
            260                 265                 270

Asn Ala Asn Leu His Leu Leu Val Asn Ser Val Glu Ile Gly Gln Met
        275                 280                 285

Asp Gly Gln Ile Ile Gly Asn Arg Asn Tyr Asp Leu Tyr Leu Ser Thr
    290                 295                 300

His Pro Tyr Pro Phe Trp Ile Asp Thr Ser Ile His Asp His His
305                 310                 315
```

```
<210> SEQ ID NO 83
<211> LENGTH: 204
<212> TYPE: DNA
<213> ORGANISM: Lactobacillus plantarum

<400> SEQUENCE: 83
gtgagtaatc gttttgagat tctggaagaa tatcaagagg ctaataccga actcgatcat      60
ttaaggacgc tagccgttcg gcaacaggat cgctcacggg ttgtgaccat ttatccgcat     120
ttgaaagaac gggtgagtca cttatctcgt aaatgtgaac aacttgacat gcttctggaa     180
gcaatcaacg cttctgagga ctaa                                            204

<210> SEQ ID NO 84
<211> LENGTH: 67
<212> TYPE: PRT
<213> ORGANISM: Lactobacillus plantarum

<400> SEQUENCE: 84
```

```
Met Ser Asn Arg Phe Glu Ile Leu Glu Glu Tyr Gln Glu Ala Asn Thr
1               5                   10                  15

Glu Leu Asp His Leu Arg Thr Leu Ala Val Arg Gln Gln Asp Arg Ser
            20                  25                  30

Arg Val Val Thr Ile Tyr Pro His Leu Lys Glu Arg Val Ser His Leu
        35                  40                  45

Ser Arg Lys Cys Glu Gln Leu Asp Met Leu Leu Glu Ala Ile Asn Ala
    50                  55                  60

Ser Glu Asp
65
```

```
<210> SEQ ID NO 85
<211> LENGTH: 675
<212> TYPE: DNA
<213> ORGANISM: Lactobacillus plantarum

<400> SEQUENCE: 85
atggcaaaaa catcacgtcc tagcaaagct aaacagcaag cactagtcca tcaactcatt      60
ggtaagattg atgcacagcc cgaggactac catgcttatt atgaactagt ggtattatta     120
acggctggtc aagattttga acaggcagag gcgttagcaa tgaaggcgtt gggaaagttt     180
gaccaccaac aacccgcagc cgactacctg cgttatgcgt tgggaaatgt ctattatcaa     240
```

```
gctcaaactt atgacaaagc gttaccatat tatcaacaaa ttacggatga tcaactaaaa      300
caggatgctt atttaatgag tgcacaagct ttaatggccc aacacgatta ccaacatgcc      360
ctagtctggg ccattacggc tcaagaggca cgtccacaac aacttgacgc taatttgtta      420
gtagcagaca tattacttgc attaggcaat aatcagcaag catcggatta ctatcaacgc      480
gcatataaga ttgattcgca atctgggcga gctgcttttta accttggact gaccgcaatg      540
gtactgggaa aaccgtatgc cacctggttt gaacgcgcgc agaaattgga cagtcaatat      600
tttaaaagtc atcagcaaca gctaacggat attgaaaaaa tgttagccgc acaagcagat      660
aatcaaaatc actaa                                                       675

<210> SEQ ID NO 86
<211> LENGTH: 224
<212> TYPE: PRT
<213> ORGANISM: Lactobacillus plantarum

<400> SEQUENCE: 86

Met Ala Lys Thr Ser Arg Pro Ser Lys Ala Lys Gln Gln Ala Leu Val
1               5                   10                  15

His Gln Leu Ile Gly Lys Ile Asp Ala Gln Pro Glu Asp Tyr His Ala
            20                  25                  30

Tyr Tyr Glu Leu Val Val Leu Thr Ala Gly Gln Asp Phe Glu Gln
        35                  40                  45

Ala Glu Ala Leu Ala Met Lys Ala Leu Gly Lys Phe Asp His Gln Gln
    50                  55                  60

Pro Ala Ala Asp Tyr Leu Arg Tyr Ala Leu Gly Asn Val Tyr Tyr Gln
65                  70                  75                  80

Ala Gln Thr Tyr Asp Lys Ala Leu Pro Tyr Tyr Gln Gln Ile Thr Asp
                85                  90                  95

Asp Gln Leu Lys Gln Asp Ala Tyr Leu Met Ser Ala Gln Ala Leu Met
            100                 105                 110

Ala Gln His Asp Tyr Gln His Ala Leu Val Trp Ala Ile Thr Ala Gln
        115                 120                 125

Glu Ala Arg Pro Gln Gln Leu Asp Ala Asn Leu Leu Val Ala Asp Ile
    130                 135                 140

Leu Leu Ala Leu Gly Asn Asn Gln Gln Ala Ser Asp Tyr Tyr Gln Arg
145                 150                 155                 160

Ala Tyr Lys Ile Asp Ser Gln Ser Gly Arg Ala Ala Phe Asn Leu Gly
                165                 170                 175

Leu Thr Ala Met Val Leu Gly Lys Pro Tyr Ala Thr Trp Phe Glu Arg
            180                 185                 190

Ala Gln Lys Leu Asp Ser Gln Tyr Phe Lys Ser His Gln Gln Gln Leu
        195                 200                 205

Thr Asp Ile Glu Lys Met Leu Ala Ala Gln Ala Asp Asn Gln Asn His
    210                 215                 220

<210> SEQ ID NO 87
<211> LENGTH: 666
<212> TYPE: DNA
<213> ORGANISM: Lactobacillus plantarum

<400> SEQUENCE: 87
ttgacaaaac tattatttgt tcgccatggg aaaacagagt ggaatcttga ggggcgctat      60
caaggctctc agggagattc accattatta ccgactagtt atcaagaaat tcatgaattg      120
```

```
gcagcggcgc tccaggatat tcggtttagt catatctatg tcagtccgtt aaaacgggcg      180
cgtgatacag cgatgacact acgtaatgat ttgacacaat cagagttacc cataacggta      240
ctgagtcgtt tacgggagtt caatctcggt aagatggaag gaatggcctt cacggatgtt      300
gaagctacgt atccggccga attcgacgcg tttcgaaatc atccggatca gtatgacccg      360
acagcgattc aggggagag ctttcaacaa ctgctgaagc ggatgactcc cgctattaag       420
caaattgttc aagcaaatcc acgtcgcgat gacaatgttt tgatcgttag tcatggtgcg      480
gccttgaatg ccttggtcaa ctcattactg ggagcgacac tggcgacgtt acggcaacgg      540
ggtggcttgt cgaatacgtc aacaacaatt ttagagacgc gtgaccgtgg tcaacatttt      600
aagctattag attggaatga cacctcatac ctatcacggc ggcccgatgc aactgatacg      660
atttaa                                                                 666
```

```
<210> SEQ ID NO 88
<211> LENGTH: 221
<212> TYPE: PRT
<213> ORGANISM: Lactobacillus plantarum

<400> SEQUENCE: 88

Met Thr Lys Leu Leu Phe Val Arg His Gly Lys Thr Glu Trp Asn Leu
1               5                   10                  15

Glu Gly Arg Tyr Gln Gly Ser Gln Gly Asp Ser Pro Leu Leu Pro Thr
            20                  25                  30

Ser Tyr Gln Glu Ile His Glu Leu Ala Ala Ala Leu Gln Asp Ile Arg
        35                  40                  45

Phe Ser His Ile Tyr Val Ser Pro Leu Lys Arg Ala Arg Asp Thr Ala
    50                  55                  60

Met Thr Leu Arg Asn Asp Leu Thr Gln Ser Glu Leu Pro Ile Thr Val
65                  70                  75                  80

Leu Ser Arg Leu Arg Glu Phe Asn Leu Gly Lys Met Glu Gly Met Ala
                85                  90                  95

Phe Thr Asp Val Glu Ala Thr Tyr Pro Ala Glu Phe Asp Ala Phe Arg
            100                 105                 110

Asn His Pro Asp Gln Tyr Asp Pro Thr Ala Ile Gln Gly Glu Ser Phe
        115                 120                 125

Gln Gln Leu Leu Lys Arg Met Thr Pro Ala Ile Lys Gln Ile Val Gln
    130                 135                 140

Ala Asn Pro Arg Arg Asp Asp Asn Val Leu Ile Val Ser His Gly Ala
145                 150                 155                 160

Ala Leu Asn Ala Leu Val Asn Ser Leu Leu Gly Ala Thr Leu Ala Thr
                165                 170                 175

Leu Arg Gln Arg Gly Gly Leu Ser Asn Thr Ser Thr Thr Ile Leu Glu
            180                 185                 190

Thr Arg Asp Arg Gly Gln His Phe Lys Leu Leu Asp Trp Asn Asp Thr
        195                 200                 205

Ser Tyr Leu Ser Arg Arg Pro Asp Ala Thr Asp Thr Ile
    210                 215                 220
```

```
<210> SEQ ID NO 89
<211> LENGTH: 1086
<212> TYPE: DNA
<213> ORGANISM: Lactobacillus plantarum

<400> SEQUENCE: 89
atgttgatcg cgatggatgc ccagcatcaa ctcgttaatg cggcgacggc tgatcgccaa       60
```

-continued

```
atagaatatt actgtccagg atgtgtgcag ccggtgcgat tgaaacgggg ggcagtgatc    120
gtgccacatt ttgcccacgt ccatgccacg gattgtgatg ctttctctga aggggaaaca    180
acggaacatc ttcgtggtaa acaacaatta gcgacctggt tcgctgccag tggttatacg    240
gtgcgcttag aggctggttt gccagagata catcagcgcc cggatatctt ggttcgacga    300
ggtacagcgc aaccactcgc gttagaattt cagtgttcac ccttgtcagt ggagcgactc    360
gcagctcgga cgcagggcta tcgtcagcat ggctatcaag tgttatggtt gttgggacgc    420
ccctatcagc gacaattgca cctcaatagc aaggctttga agttttttgca gtaccagcaa   480
cggtggggcc tgtttctact ttttttggac actcaaagta ctagtgttcg tttattgcat    540
cacgtcttga cattggatac ggaaccgctg acctatcaaa cgattcgact ggatacgcgc    600
agccagtcgg tgttacattt tcgccaattg gctccaaaaa ttaaccacccc aactttgccg   660
gacacgcatt tacggcatta ttatcaacag ctaatgttgg cacggcttcg acatcaacgt    720
ggttttgatg cgttacaagt ggcttgctat caacgcgggg gaacgattgc ccagttaccg    780
acgtggacga tgcccactgt gccgcaacta ccgctgttat cggtaccata tctggtctgg    840
cacgcccacg tcttttttgc actgcggcaa cagtccggac ggcttgctgg gtcacaatta    900
gaggcattga tctgggccca attacggcca ttacttgccc ggcgtgcctg cctgcaagca    960
cgaggcacgt taatacaaca actgataacg accatgatta cgatgcttag cgagcagcaa   1020
gtgataaact ggcagaaaac tgagtggcag gtgaattccg accagcttcg atggcgcaaa   1080
cattga                                                              1086
```

<210> SEQ ID NO 90
<211> LENGTH: 361
<212> TYPE: PRT
<213> ORGANISM: Lactobacillus plantarum

<400> SEQUENCE: 90

```
Met Leu Ile Ala Met Asp Ala Gln His Gln Leu Val Asn Ala Ala Thr
1               5                   10                  15

Ala Asp Arg Gln Ile Glu Tyr Tyr Cys Pro Gly Cys Val Gln Pro Val
            20                  25                  30

Arg Leu Lys Arg Gly Ala Val Ile Val Pro His Phe Ala His Val His
        35                  40                  45

Ala Thr Asp Cys Asp Ala Phe Ser Glu Gly Glu Thr Thr Glu His Leu
    50                  55                  60

Arg Gly Lys Gln Gln Leu Ala Thr Trp Phe Ala Ser Gly Tyr Thr
65                  70                  75                  80

Val Arg Leu Glu Ala Gly Leu Pro Glu Ile His Gln Arg Pro Asp Ile
                85                  90                  95

Leu Val Arg Arg Gly Thr Ala Gln Pro Leu Ala Leu Glu Phe Gln Cys
            100                 105                 110

Ser Pro Leu Ser Val Glu Arg Leu Ala Ala Arg Thr Gln Gly Tyr Arg
        115                 120                 125

Gln His Gly Tyr Gln Val Leu Trp Leu Leu Gly Arg Pro Tyr Gln Arg
    130                 135                 140

Gln Leu His Leu Asn Ser Lys Ala Leu Lys Phe Leu Gln Tyr Gln Gln
145                 150                 155                 160

Arg Trp Gly Leu Phe Leu Leu Phe Leu Asp Thr Gln Ser Thr Ser Val
                165                 170                 175

Arg Leu Leu His His Val Leu Thr Leu Asp Thr Glu Pro Leu Thr Tyr
```

```
              180                 185                 190
Gln Thr Ile Arg Leu Asp Thr Arg Ser Gln Ser Val Leu His Phe Arg
            195                 200                 205

Gln Leu Ala Pro Lys Ile Asn Thr Pro Thr Leu Pro Asp Thr His Leu
        210                 215                 220

Arg His Tyr Tyr Gln Gln Leu Met Leu Ala Arg Leu Arg His Gln Arg
225                 230                 235                 240

Gly Phe Asp Ala Leu Gln Val Ala Cys Tyr Gln Arg Gly Gly Thr Ile
                245                 250                 255

Ala Gln Leu Pro Thr Trp Thr Met Pro Thr Val Pro Gln Leu Pro Leu
            260                 265                 270

Leu Ser Val Pro Tyr Leu Val Trp His Ala His Val Phe Phe Ala Leu
        275                 280                 285

Arg Gln Gln Ser Gly Arg Leu Ala Gly Ser Gln Leu Glu Ala Leu Ile
        290                 295                 300

Trp Ala Gln Leu Arg Pro Leu Leu Ala Arg Arg Ala Cys Leu Gln Ala
305                 310                 315                 320

Arg Gly Thr Leu Ile Gln Gln Leu Ile Thr Thr Met Ile Thr Met Leu
                325                 330                 335

Ser Glu Gln Gln Val Ile Asn Trp Gln Lys Thr Glu Trp Gln Val Asn
            340                 345                 350

Ser Asp Gln Leu Arg Trp Arg Lys His
        355                 360

<210> SEQ ID NO 91
<211> LENGTH: 2256
<212> TYPE: DNA
<213> ORGANISM: Lactobacillus plantarum

<400> SEQUENCE: 91
atggaattag atgccgttgg taaggcaatt gtacagtatc acttagtccc actcgttcat     60
caggctaatt taggactaga ggtcaccatg caccgggtgg acgcccatgg tcacttagcg    120
acgacagcac acccgcaagc gtttggatca gcgcaacaaa atcatcagtt acgtccgggc    180
ttttccgcaa gtgctttaaa gtttactacg ccggtgcgtc gtgacattcc tgcattgatg    240
gcgtatctga agggcttgaa taccgcagca cggcggtcac tcgatgcgga cgaacgactt    300
tggccactgt cgagtacgcc tgtgttgccg atgatctaa cgaacgtacc actggctgat    360
gttgatcaag tcagctatca gcgtcgtcgc gacttagctc gtaagtatga gttacagcga    420
ttaatgacga ctggtagtca cgtgaatatg agcttgaatg aagctttatt cacccgttta    480
tatactgaga ctttccatca gcagtatcac agttatgttg actttcgcaa tgcaatttat    540
ctgaaagtcg ctcagggatt ggtgcgcatg aactggctga ttcagtattt atttggcgct    600
tcaccacgcc tagccgttac ggatactacg agtcgtccac agcgcagtag tgttcaacat    660
cccgatggtc gctacagtca agtgacggga gactatacgt caattgatcg ctacgtggcc    720
aagttgacgg cggctgttcg tcaacagcag ttgttgtctg tcaatgattt tgacgggcca    780
gttcggcttc ggagtaatgg gcagctagct atgatggccc ggcaggggt ctattatctt    840 gaataccggg gcttggatct cgatccaact agtccagtcg gggtggacgc gaacgcggtg    900
gcatttgttc gtttgttggc gagttatttc gtaatgatgc cggcacttcc agctaagatg    960
gtatcccaag tcaacgctca agctgaccaa ttgacccgtc aagttttggg tgaaaatcca   1020
acgacggcta gtgctcaggc cgtgccggct gttcaagttt agatgcact tgctgatttt   1080
```

-continued

```
gttaaaacct atggcctacc aaatgaagat gccgtgttac tcaaacagtt gaagtcgtgg    1140
gtcactgatc caaagaagac gctgagtgcg cagattgcca tgcaagccga tccgttagca    1200
tgggcactcg aacgggctgc acgctatcag gaatcgagca atgaacgtcc gtttgaactt    1260
gcgggcttta ccgcgctaga tctatcgagc cagcaactag cccagcaggc cttgacgcgg    1320
ggagtgcagg tggacgttgt tgacccacac gctaacattt tacgattgac taagttagga    1380
cggtcgcaat tagttgtgaa tgggagcgga acggatttaa atccacaggc gctaacgacc    1440
gtactgacac ataaagcagc ggccaaacaa attctggctg agcacggggt tccggtgccg    1500
gcttcacaga catatcatac agctaatcag ttgattgctg attatgatcg gtacgttcaa    1560
gctggtggga tcgtattaaa agcggcggat gagtcgcaca aagtaattgt ctttcggatt    1620
atgcccgaac gcggactgtt tgaacaagtc gtccggcaac tattcgagca aacgtccgcg    1680
gtaatggccg aggaagtggt agtcgcatca agttatcgct ttttggttat cgatagtcgt    1740
gtgcaagcaa tcgtcgaacg aattccagcc aatattgttg gtgatggtcg ctcaacggtc    1800
aagacgttac ttgatcgcaa aaatggtcga gcgttgcgcg ggaccgcttt taagtggcct    1860
caatcagcgc tacagttagg aacgatcgaa cggtatcgcc tggactcata tcacttgacc    1920
ttagattctg tggtcagccg gggaactcag atcttattac gagaggatgc gacttttggt    1980
aacggggcgg acgtgctaga cgcgacggct gatatgcatc aatcctatgt gcaggcggtg    2040
gaaaagttgg tagcagactt acacttggcg gtcgctgggg tcgacgtgat gattcccaat    2100
ctctatgccg aattagtgcc agagcatcct gaaatggcgg tatacttggg tattcatgcg    2160
gcgccgtact tgtatccgca cttgttccca atgtttggta ctgcccaacc agtggcgggg    2220
cagttgttgg atgcattgtt taaaaatgaa gattaa                              2256
```

<210> SEQ ID NO 92
<211> LENGTH: 751
<212> TYPE: PRT
<213> ORGANISM: Lactobacillus plantarum

<400> SEQUENCE: 92

```
Met Glu Leu Asp Ala Val Gly Lys Ala Ile Val Gln Tyr His Leu Val
1               5                  10                  15

Pro Leu Val His Gln Ala Asn Leu Gly Leu Glu Val Thr Met His Arg
            20                  25                  30

Val Asp Ala His Gly His Leu Ala Thr Thr Ala His Pro Gln Ala Phe
        35                  40                  45

Gly Ser Ala Gln Gln Asn His Gln Leu Arg Pro Gly Phe Ser Ala Ser
    50                  55                  60

Ala Leu Lys Phe Thr Thr Pro Val Arg Arg Asp Ile Pro Ala Leu Met
65                  70                  75                  80

Ala Tyr Leu Lys Gly Leu Asn Thr Ala Ala Arg Arg Ser Leu Asp Ala
                85                  90                  95

Asp Glu Arg Leu Trp Pro Leu Ser Ser Thr Pro Val Leu Pro Asp Asp
            100                 105                 110

Leu Thr Asn Val Pro Leu Ala Asp Val Asp Gln Val Ser Tyr Gln Arg
        115                 120                 125

Arg Arg Asp Leu Ala Arg Lys Tyr Glu Leu Gln Arg Leu Met Thr Thr
    130                 135                 140

Gly Ser His Val Asn Met Ser Leu Asn Glu Ala Leu Phe Thr Arg Leu
145                 150                 155                 160

Tyr Thr Glu Thr Phe His Gln Gln Tyr His Ser Tyr Val Asp Phe Arg
```

```
                    165                 170                 175
Asn Ala Ile Tyr Leu Lys Val Ala Gln Gly Leu Val Arg Met Asn Trp
            180                 185                 190

Leu Ile Gln Tyr Leu Phe Gly Ala Ser Pro Arg Leu Ala Val Thr Asp
        195                 200                 205

Thr Thr Ser Arg Pro Gln Arg Ser Ser Val Gln His Pro Asp Gly Arg
    210                 215                 220

Tyr Ser Gln Val Thr Gly Asp Tyr Thr Ser Ile Asp Arg Tyr Val Ala
225                 230                 235                 240

Lys Leu Thr Ala Ala Val Arg Gln Gln Leu Leu Ser Val Asn Asp
                245                 250                 255

Phe Asp Gly Pro Val Arg Leu Arg Ser Asn Gly Gln Leu Ala Met Met
            260                 265                 270

Ala Arg Gln Gly Val Tyr Tyr Leu Glu Tyr Arg Gly Leu Asp Leu Asp
        275                 280                 285

Pro Thr Ser Pro Val Gly Val Asp Ala Asn Ala Val Ala Phe Val Arg
    290                 295                 300

Leu Leu Ala Ser Tyr Phe Val Met Met Pro Ala Leu Pro Ala Lys Met
305                 310                 315                 320

Val Ser Gln Val Asn Ala Gln Ala Asp Gln Leu Thr Arg Gln Val Leu
                325                 330                 335

Gly Glu Asn Pro Thr Thr Ala Ser Ala Gln Ala Val Pro Ala Val Gln
            340                 345                 350

Val Leu Asp Ala Leu Ala Asp Phe Val Lys Thr Tyr Gly Leu Pro Asn
        355                 360                 365

Glu Asp Ala Val Leu Leu Lys Gln Leu Lys Ser Trp Val Thr Asp Pro
    370                 375                 380

Lys Lys Thr Leu Ser Ala Gln Ile Ala Met Gln Ala Asp Pro Leu Ala
385                 390                 395                 400

Trp Ala Leu Glu Arg Ala Ala Arg Tyr Gln Glu Ser Ser Asn Glu Arg
                405                 410                 415

Pro Phe Glu Leu Ala Gly Phe Thr Ala Leu Asp Leu Ser Ser Gln Gln
            420                 425                 430

Leu Ala Gln Gln Ala Leu Thr Arg Gly Val Gln Val Asp Val Val Asp
        435                 440                 445

Pro His Ala Asn Ile Leu Arg Leu Thr Lys Leu Gly Arg Ser Gln Leu
    450                 455                 460

Val Val Asn Gly Ser Gly Thr Asp Leu Asn Pro Gln Ala Leu Thr Thr
465                 470                 475                 480

Val Leu Thr His Lys Ala Ala Lys Gln Ile Leu Ala Glu His Gly
                485                 490                 495

Val Pro Val Pro Ala Ser Gln Thr Tyr His Thr Ala Asn Gln Leu Ile
            500                 505                 510

Ala Asp Tyr Asp Arg Tyr Val Gln Ala Gly Gly Ile Val Leu Lys Ala
        515                 520                 525

Ala Asp Glu Ser His Lys Val Ile Val Phe Arg Ile Met Pro Glu Arg
    530                 535                 540

Gly Leu Phe Glu Gln Val Val Arg Gln Leu Phe Glu Gln Thr Ser Ala
545                 550                 555                 560

Val Met Ala Glu Glu Val Val Ala Ser Ser Tyr Arg Phe Leu Val
                565                 570                 575

Ile Asp Ser Arg Val Gln Ala Ile Val Glu Arg Ile Pro Ala Asn Ile
            580                 585                 590
```

```
Val Gly Asp Gly Arg Ser Thr Val Lys Thr Leu Leu Asp Arg Lys Asn
            595                 600                 605

Gly Arg Ala Leu Arg Gly Thr Ala Phe Lys Trp Pro Gln Ser Ala Leu
    610                 615                 620

Gln Leu Gly Thr Ile Glu Arg Tyr Arg Leu Asp Ser Tyr His Leu Thr
625                 630                 635                 640

Leu Asp Ser Val Val Ser Arg Gly Thr Gln Ile Leu Leu Arg Glu Asp
            645                 650                 655

Ala Thr Phe Gly Asn Gly Ala Asp Val Leu Asp Ala Thr Ala Asp Met
        660                 665                 670

His Gln Ser Tyr Val Gln Ala Val Glu Lys Leu Val Ala Asp Leu His
            675                 680                 685

Leu Ala Val Ala Gly Val Asp Val Met Ile Pro Asn Leu Tyr Ala Glu
690                 695                 700

Leu Val Pro Glu His Pro Glu Met Ala Val Tyr Leu Gly Ile His Ala
705                 710                 715                 720

Ala Pro Tyr Leu Tyr Pro His Leu Phe Pro Met Phe Gly Thr Ala Gln
            725                 730                 735

Pro Val Ala Gly Gln Leu Leu Asp Ala Leu Phe Lys Asn Glu Asp
        740                 745                 750

<210> SEQ ID NO 93
<211> LENGTH: 1029
<212> TYPE: DNA
<213> ORGANISM: Lactobacillus plantarum

<400> SEQUENCE: 93
atggcagacg tacaattaga ctggaacaac ttggggtttg aatatcggaa tcttccgtac      60
cgttatcgtg cgtattggaa agatggtgct tggtacaaaa agaattaac gggagatgca     120 actttacata ttagtgaagg ctcaacagca ttacactatg gtcaacaaga ctttgaaggc     180
ttaaaagctt accgcactaa agatggtagt gttcaattat tccggccaga tcgtaatgca     240
gcccgaatgc agaccagctg tgaacggtta ttaatgccac aagtgccgac agacatgttt     300
gtggacgctg ttaaacaggt tgttaaggct aatcaagatt acgtgccacc gtatggaact     360
ggtgcgactt tatacttacg gccattgatg atcggggttg ggtaacat tggtgttcat      420 ccagctcagg aatacatctt cacgtctttt gccatgccag ttggtagtta tttcaaaggc     480
gggatgacgc caaccaactt tacgacgtcc gaatatgatc gtgcggccca taaggaacc     540 ggggcttata agttggtgg gaattatgcg gctagcttat tcccaggtca agaagctcat     600
gccaacggtt ctccgactg tgtttatctt gacccggttg aacatcgtaa gattgaagaa      660
gtaggttcag cgaacttctt cgggattact aaggatggca cttttgtgac acccaagtca     720
ccatcaattc tacctgccgt tacgaaatat tcattactct acttggcaga acataaattt     780
gggatgaaga ctgaacaagg cgacgtctac attgatgatt tagaccggtt tgctgaagct     840
ggggcttgtg gacagctgc ggttatttca ccaatcggtg gcttggaaca tcaaggcaag     900
ttacacgtgt tctacagtga aacggaagtt ggtccggtaa cgaaaaaatt atatgatgaa     960
ttaactggaa ttcaatttgg cgatcgggaa gcgcctgaag gttgggtcca gaaagttgaa    1020
ttagactaa                                                           1029

<210> SEQ ID NO 94
<211> LENGTH: 342
<212> TYPE: PRT
```

<213> ORGANISM: Lactobacillus plantarum

<400> SEQUENCE: 94

Met Ala Asp Val Gln Leu Asp Trp Asn Asn Leu Gly Phe Glu Tyr Arg
1               5                   10                  15

Asn Leu Pro Tyr Arg Tyr Arg Ala Tyr Trp Lys Asp Gly Ala Trp Tyr
            20                  25                  30

Lys Lys Glu Leu Thr Gly Asp Ala Thr Leu His Ile Ser Glu Gly Ser
        35                  40                  45

Thr Ala Leu His Tyr Gly Gln Gln Asp Phe Glu Gly Leu Lys Ala Tyr
    50                  55                  60

Arg Thr Lys Asp Gly Ser Val Gln Leu Phe Arg Pro Asp Arg Asn Ala
65                  70                  75                  80

Ala Arg Met Gln Thr Ser Cys Glu Arg Leu Leu Met Pro Gln Val Pro
                85                  90                  95

Thr Asp Met Phe Val Asp Ala Val Lys Gln Val Val Lys Ala Asn Gln
            100                 105                 110

Asp Tyr Val Pro Pro Tyr Gly Thr Gly Ala Thr Leu Tyr Leu Arg Pro
        115                 120                 125

Leu Met Ile Gly Val Gly Gly Asn Ile Gly Val His Pro Ala Gln Glu
    130                 135                 140

Tyr Ile Phe Thr Val Phe Ala Met Pro Val Gly Ser Tyr Phe Lys Gly
145                 150                 155                 160

Gly Met Thr Pro Thr Asn Phe Thr Thr Ser Glu Tyr Asp Arg Ala Ala
                165                 170                 175

His Lys Gly Thr Gly Ala Tyr Lys Val Gly Gly Asn Tyr Ala Ala Ser
            180                 185                 190

Leu Phe Pro Gly Gln Glu Ala His Ala Asn Gly Phe Ser Asp Cys Val
        195                 200                 205

Tyr Leu Asp Pro Val Glu His Arg Lys Ile Glu Glu Val Gly Ser Ala
    210                 215                 220

Asn Phe Phe Gly Ile Thr Lys Asp Gly Thr Phe Val Thr Pro Lys Ser
225                 230                 235                 240

Pro Ser Ile Leu Pro Ala Val Thr Lys Tyr Ser Leu Tyr Leu Ala
                245                 250                 255

Glu His Lys Phe Gly Met Lys Thr Glu Gln Gly Asp Val Tyr Ile Asp
            260                 265                 270

Asp Leu Asp Arg Phe Ala Glu Ala Gly Ala Cys Gly Thr Ala Ala Val
        275                 280                 285

Ile Ser Pro Ile Gly Gly Leu Glu His Gln Gly Lys Leu His Val Phe
    290                 295                 300

Tyr Ser Glu Thr Glu Val Gly Pro Val Thr Lys Lys Leu Tyr Asp Glu
305                 310                 315                 320

Leu Thr Gly Ile Gln Phe Gly Asp Arg Glu Ala Pro Glu Gly Trp Val
                325                 330                 335

Gln Lys Val Glu Leu Asp
            340

<210> SEQ ID NO 95
<211> LENGTH: 321
<212> TYPE: DNA
<213> ORGANISM: Lactobacillus plantarum

<400> SEQUENCE: 95
atggcaactg caactttaag cgacgaagaa attcgcgaac gtatcaagac gggtaaacac    60

```
atgttattct ttacggcgga ctggtgcccg gattgcgctt ttattaaacc agtaatgccc      120
caaatcgaag cgaagtacga tcaatatgac tggatcacgg ttgatcgtga cgccaacatt      180
gaaattgccc aagacatggg tgtgatgggg attcctagtt tcgttgggat cgaagatggt      240
caagaaattg gtcgatatgt tgacaaattc cgtaagaccc aaaagcaagt tgaagatttc      300
ttagatacac ttgaaaagta g                                                321

<210> SEQ ID NO 96
<211> LENGTH: 106
<212> TYPE: PRT
<213> ORGANISM: Lactobacillus plantarum

<400> SEQUENCE: 96

Met Ala Thr Ala Thr Leu Ser Asp Glu Glu Ile Arg Glu Arg Ile Lys
1               5                  10                  15

Thr Gly Lys His Met Leu Phe Phe Thr Ala Asp Trp Cys Pro Asp Cys
            20                  25                  30

Ala Phe Ile Lys Pro Val Met Pro Gln Ile Glu Ala Lys Tyr Asp Gln
        35                  40                  45

Tyr Asp Trp Ile Thr Val Asp Arg Asp Ala Asn Ile Glu Ile Ala Gln
    50                  55                  60

Asp Met Gly Val Met Gly Ile Pro Ser Phe Val Gly Ile Glu Asp Gly
65                  70                  75                  80

Gln Glu Ile Gly Arg Tyr Val Asp Lys Phe Arg Lys Thr Gln Lys Gln
                85                  90                  95

Val Glu Asp Phe Leu Asp Thr Leu Glu Lys
            100                 105

<210> SEQ ID NO 97
<211> LENGTH: 1254
<212> TYPE: DNA
<213> ORGANISM: Lactobacillus plantarum

<400> SEQUENCE: 97
atggcagaaa cggcacagtt agaagctgct gtacaggcat taagcgatat tgtaaaaatg       60
aatacggtaa taaccatga gcaattggtg gcggattatt tggtcacact tttaaagcaa       120
catggtattg aagcacaatc aatcgagtac gctcccgggc gggtgaactt ggtgccgaa       180 attggtgatg gtcacggccc agtcgtcgcg ttggatggtc atgaagatac ggtggcgttg       240
ggtgatgcag ataaatggca cacggacccg ttggcagcaa ctatcaaaga taatcggttg       300
tatggtcgcg gtgtgacgga catgaaggct ggactaatgg ctgaagtctt cgcgatgatt       360
gcattgcacg atcaggacgc cccactccat ggcacggtga ggttactcgc aactgtggga       420
gaagaagtcg accatttagg cgctgaacaa ttgacggaac tcggttacgc cgatgatatt       480
caaacgttga tctgtgcgga accaagcggt gcggacaaac aacttttact gaccaagtcg       540
attcaagcca tgttaggtgt tgacggcgat acggcgcaac ggatggcgga tcgaatccg       600 acgaccgaac aacacttcat cgaattagcg cataagggtt cactgactta tacgattaaa       660
gcgcaagggg tggcggccca cagttcgatg ccagcgattg tcaaaacgc catcgatatg       720 ttgatgactt actatcagaa acaaactgcc tattttgaca gtttcaagac tattgttaat       780
cccgtattgg gccaaccgt gcctgtcgtg acgttaatta gtggtggcga acaggtcaac       840
accgtcccag ccagtgccga aatgtcagta aaaattcgga cgattccaga attacggaat       900
gaccgcttga ttaaggattt ggaagccatc attgctgaat gcaatgcaga tggtgccaat       960
```

```
ctaacgatgg acatcgcaag ttcgttctac ccagtgcata cgccggaaga tagccagttg   1020
gtccagttgg cgaagaaggt tggggaacaa gttttacagc aacggctccc gtactttggt   1080
gctcctggtg ggacggacgc atcgtcttat attgtaaaga gtcctgatat gcaagtgatt   1140
gtcttcggac ccggcaatat tacagcgcac caagttaatg aatatgttga tttggatatg   1200
tatgggcgct tcatcgagat ttatcaaaaa atgattacgg aattgctggc ttaa         1254
```

<210> SEQ ID NO 98
<211> LENGTH: 417
<212> TYPE: PRT
<213> ORGANISM: Lactobacillus plantarum

<400> SEQUENCE: 98

```
Met Ala Glu Thr Ala Gln Leu Glu Ala Ala Val Gln Ala Leu Ser Asp
1               5                   10                  15

Ile Val Lys Met Asn Thr Val Asn Asn His Glu Gln Leu Val Ala Asp
            20                  25                  30

Tyr Leu Val Thr Leu Leu Lys Gln His Gly Ile Glu Ala Gln Ser Ile
        35                  40                  45

Glu Tyr Ala Pro Gly Arg Val Asn Leu Val Ala Glu Ile Gly Asp Gly
    50                  55                  60

His Gly Pro Val Val Ala Leu Asp Gly His Glu Asp Thr Val Ala Leu
65                  70                  75                  80

Gly Asp Ala Asp Lys Trp His Thr Asp Pro Leu Ala Ala Thr Ile Lys
                85                  90                  95

Asp Asn Arg Leu Tyr Gly Arg Gly Val Thr Asp Met Lys Ala Gly Leu
            100                 105                 110

Met Ala Glu Val Phe Ala Met Ile Ala Leu His Asp Gln Asp Ala Pro
        115                 120                 125

Leu His Gly Thr Val Arg Leu Leu Ala Thr Val Gly Glu Glu Val Asp
    130                 135                 140

His Leu Gly Ala Glu Gln Leu Thr Glu Leu Gly Tyr Ala Asp Asp Ile
145                 150                 155                 160

Gln Thr Leu Ile Cys Ala Glu Pro Ser Gly Ala Asp Lys Gln Leu Leu
                165                 170                 175

Leu Thr Lys Ser Ile Gln Ala Met Leu Gly Val Asp Gly Asp Thr Ala
            180                 185                 190

Gln Arg Met Ala Asp Ala Asn Pro Thr Thr Glu Gln His Phe Ile Glu
        195                 200                 205

Leu Ala His Lys Gly Ser Leu Thr Tyr Thr Ile Lys Ala Gln Gly Val
    210                 215                 220

Ala Ala His Ser Ser Met Pro Ala Ile Gly Gln Asn Ala Ile Asp Met
225                 230                 235                 240

Leu Met Thr Tyr Tyr Gln Lys Gln Thr Ala Tyr Phe Asp Ser Phe Lys
                245                 250                 255

Thr Ile Val Asn Pro Val Leu Gly Pro Thr Val Pro Val Val Thr Leu
            260                 265                 270

Ile Ser Gly Gly Glu Gln Val Asn Thr Val Pro Ala Ser Ala Glu Met
        275                 280                 285

Ser Val Lys Ile Arg Thr Ile Pro Glu Leu Arg Asn Asp Arg Leu Ile
    290                 295                 300

Lys Asp Leu Glu Ala Ile Ile Ala Glu Cys Asn Ala Asp Gly Ala Asn
305                 310                 315                 320
```

```
Leu Thr Met Asp Ile Ala Ser Ser Phe Tyr Pro Val His Thr Pro Glu
            325                 330                 335

Asp Ser Gln Leu Val Gln Leu Ala Lys Lys Val Gly Glu Gln Val Leu
        340                 345                 350

Gln Gln Arg Leu Pro Tyr Phe Gly Ala Pro Gly Thr Asp Ala Ser
            355                 360             365

Ser Tyr Ile Val Lys Ser Pro Asp Met Gln Val Ile Val Phe Gly Pro
        370                 375                 380

Gly Asn Ile Thr Ala His Gln Val Asn Glu Tyr Val Asp Leu Asp Met
385                 390                 395                 400

Tyr Gly Arg Phe Ile Glu Ile Tyr Gln Lys Met Ile Thr Glu Leu Leu
            405                 410                 415

Ala

<210> SEQ ID NO 99
<211> LENGTH: 2592
<212> TYPE: DNA
<213> ORGANISM: Lactobacillus plantarum

<400> SEQUENCE: 99
```

| | | | | | |
|---|---|---|---|---|---|
| atggtaggtg | cagcgatgac | agcagcttat | tttaaaacaa | ttatgcgtga | gatttggtcg | 60 |
| tcgaaagccc | gttttgcttc | aatattactg | atcattttct | tagggggttgc | tttttatacg | 120 |
| ggaattcggg | cgactggtcc | ggatatgtca | caggcagcta | atgattatta | tgcgaagcaa | 180 |
| aagctggcga | ccaatagtgt | ccagtcgaca | atggggctga | ctaaggccga | tacacgagta | 240 |
| ctgaatcaac | accgctcaca | gctcacttac | caagcgacac | gctacgctga | tgttaatcag | 300 |
| ttgaacaata | gtcaagtcgt | gcgggtgatg | gtgttaccga | caacccaacg | actgaatcgg | 360 |
| ttacggatcg | ttaagggacg | attaccgcgg | catgccaatg | agatcgtgtt | agacgcgcaa | 420 |
| gcacagcgat | tgcagccgaa | gctaaaagtc | ggttcaacgt | atcgaattag | cagtacggct | 480 |
| aagcgcaatg | cacagttcac | gcggcgaaca | ttcaaggtcg | tggggtttgt | caattcacca | 540 |
| acatatgttg | aaaatacgaa | tcgtggcgtc | accaacgttg | gtaaagggac | tttggactac | 600 |
| ttggtctatg | tccgtccgca | ggtgattaag | tccagtgtga | taacgcgcat | tgacgtgcaa | 660 |
| ttcaaaaatt | tgcggggcgt | caccccctac | acggcgaagt | atcggcgctt | gaatcgcgag | 720 |
| aacaccgcgc | aactcaaacg | ctggttaaaa | ccacaagcgc | gtaagcggca | gcaggcatta | 780 |
| caagcccagg | cccaggctaa | gctgaaacca | ttgcgacagg | cgacccagca | acttgctagt | 840 |
| caagtgccag | cgggaacggc | acaactagtc | aagttacaaa | gccaattaaa | acgcgcgaag | 900 |
| gcccaggtcg | cggccatcac | aatgccgact | tatttgtaca | ctgaccgtac | ggataatccg | 960 |
| ggttacacag | aatatcacga | aaatacgcaa | cgagtcgtgg | cactgtcgac | tgtctttccg | 1020 |
| ctgttctta | ttgcgattgc | cgcgttaatt | tgtctaacga | cgatgacgcg | gatggttgaa | 1080 |
| gaattgcggc | tacagatggg | gacgttaaag | gccctcgggt | atacgaatac | cgcggtcggt | 1140 |
| agcgagttta | tgatttatgg | tggtttagcc | gcgctgattg | ggaccgcgct | aggtgtcctg | 1200 |
| ttcggcgtca | attttttccc | gcggtttatc | gcgcaggcct | atggtagtat | gtataatttg | 1260 |
| cccgcaatca | acgttcaata | catttggatg | acattggta | tcgccttagc | cattgcgttg | 1320 |
| ttgtgcacgt | tggggacggc | actggtcgtg | ctccgcgtgg | atttaaacag | tttacccgcg | 1380 |
| caactcttac | agccacgatc | acctaaggcc | ggtaagactt | tgctattaga | acgctggcaa | 1440 |
| tggctatggc | atcggctgag | tttaatcat | aaaatcacac | ttcgtaatct | atttcggtat | 1500 |
| aagcaacggt | tgctgatgac | cgtgctcggt | attgcgggct | gcatggcaat | gatgattacg | 1560 |

-continued

```
gggtttggct taaaggattc cattggtgat attagcgtca agcaatttaa cgaattgtgg    1620
cactacgatg ctgtggtgac gcgtagtggg aacgaaacgg accaacaacg gcaagcactc    1680
agtcgtggtc aactttacca ggctagtttg aaattacagg ccaagcaggt gacggtcaaa    1740
cagtccgggg tagcagaaca gacggctacg ctcggtatac cggcaccca ccaatcgcta     1800 agcaagttcg tggtattacg gcaccgacaa agtcatcagg ccattcatat tggtgatcgc    1860
ggtgcggtca tcgatgaaaa attagctaag ttatatggcg ttcaggcggg cgatgattta    1920
acgatcaagt tggccgggca aaccaccaag cggattcaca tcagtgcggt ggctgaaaat    1980
tacgtcaatc actttatcta tatgagtccg acttattatc gacgtgtctt caagcaggca    2040
ccagtatata acacgaacta tgtccggttt aagcaggcaa cgaaaaagca agaaaatgct    2100
tatgcggacc ggctattgaa acaggcgggg gttcagaacg tgacactgat gagtacagag    2160
aaagccacta attttaaaat gctggatagc atgaacttag tcgtattgat ctttgtcatc    2220
tcggcggggg cactagcgct agtagtgctc tataacttaa cgaatattaa tgtttctgaa    2280
cggatccggg aattgtcgac aatcaaagtg ttgggctttt acgatggtga agtgacgatg    2340
tatattttcc gtgaaaatct gatattgacg gttttaggca ttattgccgg ttgtttcttg    2400
ggcaactggt tgcacgcata tcttgcaa acggctgaaa cgaacgcgtt aatgttttca     2460
ccaacgattc atccgttgag ttacgtttac gcggcattat tgaccctggc ctttagttta    2520
ttagtcatgg gaatgatgca tcgtaagtta aagcgagtca atatgctgga tgcactgaaa    2580
tctgtcgatt aa                                                        2592
```

<210> SEQ ID NO 100
<211> LENGTH: 863
<212> TYPE: PRT
<213> ORGANISM: Lactobacillus plantarum

<400> SEQUENCE: 100

```
Met Val Gly Ala Ala Met Thr Ala Ala Tyr Phe Lys Thr Ile Met Arg
1               5                   10                  15

Glu Ile Trp Ser Ser Lys Ala Arg Phe Ala Ser Ile Leu Leu Ile Ile
            20                  25                  30

Phe Leu Gly Val Ala Phe Tyr Thr Gly Ile Arg Ala Thr Gly Pro Asp
        35                  40                  45

Met Ser Gln Ala Ala Asn Asp Tyr Tyr Ala Lys Gln Lys Leu Ala Thr
    50                  55                  60

Asn Ser Val Gln Ser Thr Met Gly Leu Thr Lys Ala Asp Thr Arg Val
65                  70                  75                  80

Leu Asn Gln His Arg Ser Gln Leu Thr Tyr Gln Ala Thr Arg Tyr Ala
                85                  90                  95

Asp Val Asn Gln Leu Asn Asn Ser Gln Val Val Arg Val Met Val Leu
            100                 105                 110

Pro Thr Thr Gln Arg Leu Asn Arg Leu Arg Ile Val Lys Gly Arg Leu
        115                 120                 125

Pro Arg His Ala Asn Glu Ile Val Leu Asp Ala Gln Ala Gln Arg Leu
    130                 135                 140

Gln Pro Lys Leu Lys Val Gly Ser Thr Tyr Arg Ile Ser Ser Thr Ala
145                 150                 155                 160

Lys Arg Asn Ala Gln Phe Thr Arg Arg Thr Phe Lys Val Val Gly Phe
                165                 170                 175

Val Asn Ser Pro Thr Tyr Val Glu Asn Thr Asn Arg Gly Val Thr Asn
```

```
                180             185             190
Val Gly Lys Gly Thr Leu Asp Tyr Leu Val Tyr Val Arg Pro Gln Val
            195                 200                 205

Ile Lys Ser Ser Val Ile Thr Arg Ile Asp Val Gln Phe Lys Asn Leu
210                 215                 220

Arg Gly Val Thr Pro Tyr Thr Ala Lys Tyr Arg Leu Asn Arg Glu
225                 230                 235                 240

Asn Thr Ala Gln Leu Lys Arg Trp Leu Lys Pro Gln Ala Arg Lys Arg
            245                 250                 255

Gln Gln Ala Leu Gln Ala Gln Ala Lys Leu Lys Pro Leu Arg
            260                 265                 270

Gln Ala Thr Gln Gln Leu Ala Ser Gln Val Pro Ala Gly Thr Ala Gln
            275                 280                 285

Leu Val Lys Leu Gln Ser Gln Leu Lys Arg Ala Lys Ala Gln Val Ala
            290                 295                 300

Ala Ile Thr Met Pro Thr Tyr Leu Tyr Thr Asp Arg Thr Asp Asn Pro
305                 310                 315                 320

Gly Tyr Thr Glu Tyr His Glu Asn Thr Gln Arg Val Val Ala Leu Ser
            325                 330                 335

Thr Val Phe Pro Leu Phe Phe Ile Ala Ile Ala Ala Leu Ile Cys Leu
            340                 345                 350

Thr Thr Met Thr Arg Met Val Glu Glu Leu Arg Leu Gln Met Gly Thr
            355                 360                 365

Leu Lys Ala Leu Gly Tyr Thr Asn Thr Ala Val Gly Ser Glu Phe Met
            370                 375                 380

Ile Tyr Gly Gly Leu Ala Ala Leu Ile Gly Thr Ala Leu Gly Val Leu
385                 390                 395                 400

Phe Gly Val Asn Phe Phe Pro Arg Phe Ile Ala Gln Ala Tyr Gly Ser
            405                 410                 415

Met Tyr Asn Leu Pro Ala Ile Asn Val Gln Tyr Ile Trp Met Asp Ile
            420                 425                 430

Gly Ile Ala Leu Ala Ile Ala Leu Leu Cys Thr Leu Gly Thr Ala Leu
            435                 440                 445

Val Val Leu Arg Val Asp Leu Asn Ser Leu Pro Ala Gln Leu Leu Gln
            450                 455                 460

Pro Arg Ser Pro Lys Ala Gly Lys Thr Leu Leu Leu Glu Arg Trp Gln
465                 470                 475                 480

Trp Leu Trp His Arg Leu Ser Phe Asn His Lys Ile Thr Leu Arg Asn
            485                 490                 495

Leu Phe Arg Tyr Lys Gln Arg Leu Leu Met Thr Val Leu Gly Ile Ala
            500                 505                 510

Gly Cys Met Ala Met Met Ile Thr Gly Phe Gly Leu Lys Asp Ser Ile
            515                 520                 525

Gly Asp Ile Ser Val Lys Gln Phe Asn Glu Leu Trp His Tyr Asp Ala
            530                 535                 540

Val Val Thr Arg Ser Gly Asn Glu Thr Asp Gln Gln Arg Gln Ala Leu
545                 550                 555                 560

Ser Arg Gly Gln Leu Tyr Gln Ala Ser Leu Lys Leu Gln Ala Lys Gln
            565                 570                 575

Val Thr Val Lys Gln Ser Gly Val Ala Glu Gln Thr Ala Thr Leu Gly
            580                 585                 590

Ile Pro Ala Pro His Gln Ser Leu Ser Lys Phe Val Val Leu Arg His
            595                 600                 605
```

```
Arg Gln Ser His Gln Ala Ile His Ile Gly Asp Arg Gly Ala Val Ile
    610                 615                 620
Asp Glu Lys Leu Ala Lys Leu Tyr Gly Val Gln Ala Gly Asp Asp Leu
625                 630                 635                 640
Thr Ile Lys Leu Ala Gly Gln Thr Thr Lys Arg Ile His Ile Ser Ala
                645                 650                 655
Val Ala Glu Asn Tyr Val Asn His Phe Ile Tyr Met Ser Pro Thr Tyr
            660                 665                 670
Tyr Arg Arg Val Phe Lys Gln Ala Pro Val Tyr Asn Thr Asn Tyr Val
        675                 680                 685
Arg Phe Lys Gln Ala Thr Lys Lys Gln Glu Asn Ala Tyr Ala Asp Arg
    690                 695                 700
Leu Leu Lys Gln Ala Gly Val Gln Asn Val Thr Leu Met Ser Thr Glu
705                 710                 715                 720
Lys Ala Thr Asn Phe Lys Met Leu Asp Ser Met Asn Leu Val Val Leu
                725                 730                 735
Ile Phe Val Ile Ser Ala Gly Ala Leu Ala Leu Val Val Leu Tyr Asn
            740                 745                 750
Leu Thr Asn Ile Asn Val Ser Glu Arg Ile Arg Glu Leu Ser Thr Ile
        755                 760                 765
Lys Val Leu Gly Phe Tyr Asp Gly Glu Val Thr Met Tyr Ile Phe Arg
    770                 775                 780
Glu Asn Leu Ile Leu Thr Val Leu Gly Ile Ile Ala Gly Cys Phe Leu
785                 790                 795                 800
Gly Asn Trp Leu His Ala Tyr Ile Leu Gln Thr Ala Glu Thr Asn Ala
                805                 810                 815
Leu Met Phe Ser Pro Thr Ile His Pro Leu Ser Tyr Val Tyr Ala Ala
            820                 825                 830
Leu Leu Thr Leu Ala Phe Ser Leu Leu Val Met Gly Met Met His Arg
        835                 840                 845
Lys Leu Lys Arg Val Asn Met Leu Asp Ala Leu Lys Ser Val Asp
    850                 855                 860

<210> SEQ ID NO 101
<211> LENGTH: 1206
<212> TYPE: DNA
<213> ORGANISM: Lactobacillus plantarum

<400> SEQUENCE: 101
atgacgccgg aaaccgaaca attattacga cgctggtaca tggggcagct catcgtgtta      60
tttggcgcgg cctttattca actatttacg tttgatggtg gtgtgttttt cccagttggt     120
ggtatgcagt tgctgatatg gggactgtta gcctggtggc cagctgccga ggaggaccaa     180
gcacagtggc ggcgtttgcg acatgttaat tattatgtcc aaacagtact gcagttcaca     240
ctcttgccga ttttactggc gaacctcgtg gcttggttaa gtcagctgtc atggttagac     300
gagcagggat tgattgctgt ggggatggct tatttaatgg tcgcattcgt accggtggca     360
gtggtggtca ctaaaccgat cgaatctgtg attggccgga ttgcggtcct aattacggct     420
atttttagtg gtgtcgtcag tgcgcagcag acttttttga ttttaccgaa tctgcaagca     480
ccatcagtat tcgagatggt cagtgatact ggtatttttag gcgccctggg ctttgtgatt     540
gctgttgggg tcttactgcg gggatgggga ttgacgggcc catcgtggcg gtttaatcgt     600
caggcccaaa ctagtttagt ggttgggctg atcgtggtgg gaacggcttt tagtctatgg     660
```

```
aatgccttta gtgcgggtgg ttcatgggcg acaacgttca cacattggga cttccagcta    720
cggtcagcga cttggaaaat gtttttgagt gggttagaac cgggaatcgc agaggaatgg    780
ttgtatcgtt ttgccgtttt aaccttgtta ttacaagctt ttcggcatcg gcgtcaccaa    840
ctcgacttgg cagtgtggct aagcggtggc ctatttggaa tgtggcatat tacaaacgtt    900
tttgcgggcc aaccttgtc agccacggtt gagcaaatca tttttgcagc gacactaggc     960 tggttttttag cctcgacgta cctgtactca ggtagtatct tgctgccgat ggtgatccat   1020
gctgctattg atattttgag catgatggca tcaggtagcc agacaatggt taagccggat   1080
gcgttcgaat ggcaaacaat cggtgctacc gtcattattt ttgttggcat aacgatttat   1140
ttcttgaccg gttctcggcg acaagttatt caagcacatg tcaatcaacg gctttcagtt   1200
caataa                                                              1206
```

<210> SEQ ID NO 102
<211> LENGTH: 401
<212> TYPE: PRT
<213> ORGANISM: Lactobacillus plantarum

<400> SEQUENCE: 102

```
Met Thr Pro Glu Thr Glu Gln Leu Leu Arg Arg Trp Tyr Met Gly Gln
1               5                   10                  15

Leu Ile Val Leu Phe Gly Ala Ala Phe Ile Gln Leu Phe Thr Phe Asp
            20                  25                  30

Gly Gly Val Phe Phe Pro Val Gly Gly Met Gln Leu Leu Ile Trp Gly
        35                  40                  45

Leu Leu Ala Trp Trp Pro Ala Ala Glu Glu Asp Gln Ala Gln Trp Arg
    50                  55                  60

Arg Leu Arg His Val Asn Tyr Tyr Val Gln Thr Val Leu Gln Phe Thr
65                  70                  75                  80

Leu Leu Pro Ile Leu Leu Ala Asn Leu Val Ala Trp Leu Ser Gln Leu
                85                  90                  95

Ser Trp Leu Asp Glu Gln Gly Leu Ile Ala Val Gly Met Ala Tyr Leu
            100                 105                 110

Met Val Ala Phe Val Pro Val Ala Val Val Thr Lys Pro Ile Glu
        115                 120                 125

Ser Val Ile Gly Arg Ile Ala Val Leu Ile Thr Ala Ile Phe Ser Gly
    130                 135                 140

Val Val Ser Ala Gln Gln Thr Phe Leu Ile Leu Pro Asn Leu Gln Ala
145                 150                 155                 160

Pro Ser Val Phe Glu Met Val Ser Asp Thr Gly Ile Leu Gly Ala Leu
                165                 170                 175

Gly Phe Val Ile Ala Val Gly Val Leu Leu Arg Gly Trp Gly Leu Thr
            180                 185                 190

Gly Pro Ser Trp Arg Phe Asn Arg Gln Ala Gln Thr Ser Leu Val Val
        195                 200                 205

Gly Leu Ile Val Val Gly Thr Ala Phe Ser Leu Trp Asn Ala Phe Ser
    210                 215                 220

Ala Gly Gly Ser Trp Ala Thr Thr Phe Thr His Trp Asp Phe Gln Leu
225                 230                 235                 240

Arg Ser Ala Thr Trp Lys Met Phe Leu Ser Gly Leu Glu Pro Gly Ile
                245                 250                 255

Ala Glu Glu Trp Leu Tyr Arg Phe Ala Val Leu Thr Leu Leu Gln
            260                 265                 270
```

```
Ala Phe Arg His Arg His Gln Leu Asp Leu Ala Val Trp Leu Ser
        275                 280                 285

Gly Gly Leu Phe Gly Met Trp His Ile Thr Asn Val Phe Ala Gly Gln
    290                 295                 300

Pro Leu Ser Ala Thr Val Glu Gln Ile Ile Phe Ala Ala Thr Leu Gly
305                 310                 315                 320

Trp Phe Leu Ala Ser Thr Tyr Leu Tyr Ser Gly Ser Ile Leu Leu Pro
                325                 330                 335

Met Val Ile His Ala Ala Ile Asp Ile Leu Ser Met Met Ala Ser Gly
                340                 345                 350

Ser Gln Thr Met Val Lys Pro Asp Ala Phe Glu Trp Gln Thr Ile Gly
            355                 360                 365

Ala Thr Val Ile Ile Phe Val Gly Ile Thr Ile Tyr Phe Leu Thr Gly
    370                 375                 380

Ser Arg Arg Gln Val Ile Gln Ala His Val Asn Gln Arg Leu Ser Val
385                 390                 395                 400

Gln

<210> SEQ ID NO 103
<211> LENGTH: 534
<212> TYPE: DNA
<213> ORGANISM: Lactobacillus plantarum

<400> SEQUENCE: 103
gtgccagtgg tcattagctc attaattccc gtagttgcgc cggttaaacg ccaagtgatc      60
aatgtgacga cccttgcaaa tacggttcac ttatatgggt tactaggatt taagcagcaa     120
attataccgg caacagatca aattgttgcg ccctttgctg gggttatcac agccgtggca     180
gccaatcaac ggttaattgg ctttcgagcg gccaatggtc tggtgggctg gctacgaatt     240
ggacaattaa ccagtgcttt ggaatcgcct acatttaagt tcaacgttaa accgggtgac     300
tgggtagttg ctgggcagat gttggttgaa gtgatttcac tactgacaca acggctccaa     360
ccagttaaaa cgacggtggt attgacgatt agacatgcgg ttgttcgtgt tcgagaacgg     420
ttgctggcag caagtaatca agtcgatccg atgggaactg ttatctcagg tattacgacc     480
agtatggctg gtaatcatcg ggtcgcaacg atcgggccac cccaaggtaa ttaa           534

<210> SEQ ID NO 104
<211> LENGTH: 177
<212> TYPE: PRT
<213> ORGANISM: Lactobacillus plantarum

<400> SEQUENCE: 104

Met Pro Val Val Ile Ser Ser Leu Ile Pro Val Val Ala Pro Val Lys
1               5                   10                  15

Arg Gln Val Ile Asn Val Thr Thr Leu Ala Asn Thr Val His Leu Tyr
            20                  25                  30

Gly Leu Leu Gly Phe Lys Gln Gln Ile Ile Pro Ala Thr Asp Gln Ile
        35                  40                  45

Val Ala Pro Phe Ala Gly Val Ile Thr Ala Val Ala Ala Asn Gln Arg
    50                  55                  60

Leu Ile Gly Phe Arg Ala Ala Asn Gly Leu Val Gly Trp Leu Arg Ile
65                  70                  75                  80

Gly Gln Leu Thr Ser Ala Leu Glu Ser Pro Thr Phe Lys Phe Asn Val
                85                  90                  95

Lys Pro Gly Asp Trp Val Val Ala Gly Gln Met Leu Val Glu Val Ile
```

```
            100                 105                 110
Ser Leu Leu Thr Gln Arg Leu Gln Pro Val Lys Thr Thr Val Val Leu
        115                 120                 125

Thr Ile Arg His Ala Val Val Arg Val Arg Glu Arg Leu Leu Ala Ala
        130                 135                 140

Ser Asn Gln Val Asp Pro Met Gly Thr Val Ile Ser Gly Ile Thr Thr
145                 150                 155                 160

Ser Met Ala Gly Asn His Arg Val Ala Thr Ile Gly Pro Pro Gln Gly
            165                 170                 175

Asn
```

<210> SEQ ID NO 105
<211> LENGTH: 1131
<212> TYPE: DNA
<213> ORGANISM: Lactobacillus plantarum

<400> SEQUENCE: 105

```
atgacatggt ctaattggcg aatttcgccg ttcgtaacga gtattttctt tatactaggt      60
gttctaacac tttactgggt cctctttaat tggattacga cgtggtttca tgcccgtcac    120
attaacattg acgatgatac cgtcaatgct ggcacggtg tgatttatat gttggtcttt     180
gtgtttgtca tgcaactgtc ggtcgtcggt aaagcagata gttgggagtt tgttaacttt    240
cacttgattg ccgtcgtgtt ctgctcgttt ttttgaata ttcgaatgcc gtattattca     300
ttgttacctg tggtcatagt gtacatggtt ttcgaccagt cgattttta ctgggaatcg     360
tggagttacg ccgtcgtgtt cgtgctattt ttctggagca tgaattatct acggctgtgg    420
gtacctaagc atcggtatcc ttggctatat tactatggcg cggtcgcttt ttacggcgga    480
atcttgtggg gcctgatcaa gcttaaatat tcgctggatt gggacaatac tttacaagaa    540
tatggctact aatgatttt tgcaggatta ttgtacgcct acgttaatat gctgacccaa     600
gatagtgaga ttaaattacg gttggcccag tttgcgagtc acgacgcttt gactgagact    660
gagaactttg ccgcttacac ggaacatatc aaatatttat tcgatgatag tgccaagaac    720
aatctcaact tatcgatgat gatgttcgat attgatcact ttaagcacgt taatgacacg    780
tacgggcacc ttgcagggga ccgcgttttg caagaagttg ccgccacggt cacaacggtc    840
ttggccgcca atgacgagaa ggtcaagctg tatcgcaccg tggtgaaga attcaatgtc     900
ctgtttcccg ttatgatct ggctagtacc aaagtgattg tccgtcaggt ctttgaagca     960
gtcaatcatc tcgttgttaa gtatgaagac gaggaaatca atgtgtcgat tcggttggt    1020
gtctcgacac tgcatcaagc cgatggtagt ccgattgatt tgtacaaccg tgttgatcag    1080
aacctctatt tttcaaagcg gcacgggcgg atgcgtgtta cggttgaata g            1131
```

<210> SEQ ID NO 106
<211> LENGTH: 376
<212> TYPE: PRT
<213> ORGANISM: Lactobacillus plantarum

<400> SEQUENCE: 106

```
Met Thr Trp Ser Asn Trp Arg Ile Ser Pro Phe Val Thr Ser Ile Phe
1               5                   10                  15

Phe Ile Leu Gly Val Leu Thr Leu Tyr Trp Val Leu Phe Asn Trp Ile
            20                  25                  30

Thr Thr Trp Phe His Ala Arg His Ile Asn Ile Asp Asp Asp Thr Val
        35                  40                  45
```

| | | | | | | | | | | | | |
|---|---|---|---|---|---|---|---|---|---|---|---|---|
|Asn|Ala|Trp|His|Gly|Val|Ile|Tyr|Met|Leu|Val|Phe|Val|Met|
| |50| | | | |55| | | |60| | | |

Asn Ala Trp His Gly Val Ile Tyr Met Leu Val Phe Val Met
    50                  55              60

Gln Leu Ser Val Val Gly Lys Ala Asp Ser Trp Glu Phe Val Asn Phe
65              70                  75                  80

His Leu Ile Ala Val Phe Cys Ser Phe Phe Leu Asn Ile Arg Met
                85                  90                  95

Pro Tyr Tyr Ser Leu Pro Val Val Ile Val Tyr Met Val Phe Asp
            100                 105                 110

Gln Ser Ile Phe Tyr Trp Glu Ser Trp Ser Tyr Ala Val Phe Val
            115                 120                 125

Leu Phe Phe Trp Ser Met Asn Tyr Leu Arg Leu Trp Val Pro Lys His
130                 135                 140

Arg Tyr Pro Trp Leu Tyr Tyr Gly Ala Val Ala Phe Tyr Gly Gly
145                 150                 155                 160

Ile Leu Trp Gly Leu Ile Lys Leu Lys Tyr Ser Leu Asp Trp Asp Asn
                165                 170                 175

Thr Leu Gln Glu Tyr Gly Tyr Leu Met Ile Phe Ala Gly Leu Leu Tyr
            180                 185                 190

Ala Tyr Val Asn Met Leu Thr Gln Asp Ser Glu Ile Lys Leu Arg Leu
            195                 200                 205

Ala Gln Phe Ala Ser His Asp Ala Leu Thr Glu Thr Glu Asn Phe Ala
210                 215                 220

Ala Tyr Thr Glu His Ile Lys Tyr Leu Phe Asp Asp Ser Ala Lys Asn
225                 230                 235                 240

Asn Leu Asn Leu Ser Met Met Met Phe Asp Ile Asp His Phe Lys His
                245                 250                 255

Val Asn Asp Thr Tyr Gly His Leu Ala Gly Asp Arg Val Leu Gln Glu
            260                 265                 270

Val Ala Ala Thr Val Thr Thr Val Leu Ala Ala Asn Asp Glu Lys Val
            275                 280                 285

Lys Leu Tyr Arg Thr Gly Gly Glu Glu Phe Asn Val Leu Phe Pro Gly
            290                 295                 300

Tyr Asp Leu Ala Ser Thr Lys Val Ile Val Arg Gln Val Phe Glu Ala
305                 310                 315                 320

Val Asn His Leu Val Val Lys Tyr Glu Asp Glu Ile Asn Val Ser
            325                 330                 335

Ile Ser Val Gly Val Ser Thr Leu His Gln Ala Asp Gly Ser Pro Ile
            340                 345                 350

Asp Leu Tyr Asn Arg Val Asp Gln Asn Leu Tyr Phe Ser Lys Arg His
            355                 360                 365

Gly Arg Met Arg Val Thr Val Glu
    370                 375

<210> SEQ ID NO 107
<211> LENGTH: 1485
<212> TYPE: DNA
<213> ORGANISM: Lactobacillus plantarum

<400> SEQUENCE: 107
atggcaacaa aagataatga aaagattaca ttgatggcgc tagtcatgat gatctttacg     60
accgttttcg gatttgccaa tagtacggtg gcctattatt taatgggtta cagctcgatt    120
ctattttacc tagtcgcagc cgtactgttc ttcatcccgt tcgcgctaat gatggcggag    180
ttcggggcag cggttaagtc tgatagtagc gggatgtaca gtggctgga agtgagtgtg    240

```
aatgcgaaat ttgcgttcgt gggcacgttc atgtggtttg cgtcgtacat tatttggtta    300
gtctcaacgt cagctaaagt ctggattccg tttacgacca tcttctttgg gagcgatcaa    360
acgcagcgct ttgcgatgtt tggtctgaat gcgacgcaga tgattgggat tttgtcctgt    420
ctatggatgg tgctagtgac gttcgtttcc atcaaaggga tgaaaggcat tgtgcgggtc    480
acgagtttag gcggcctggc ggtgaccagt ttgacggcaa tcctgttagt ggtttcgggg    540
gtcgttttag ccttgaatca cggacaattc gcacaaccgt tacaacatgt gatgacgtca    600
ccaaatccaa gttatcagca tccagtcggg ttactcgggt ttgccgtttt cgccattttt    660
gcttacggtg ggctagaagt tctcggtggg atggttgata agaccaagaa ccccgaaaag    720
accttcccac gcggaattat tatttctgcc atcgttatta ccttaggcta tggtctggga    780
atcttctgct gggggattag tacgaactgg caagccgttt tgtcgaatcc aacgactaac    840
ctcggtaata ttagttacgt catgatgcaa aacttgggct atgttttagg caagcgctt     900
ggtttgagta cagcggccgc taagacaatg ggactgtggt ttgcacggta caccggctta    960
gggatgttcc tcgcttacag tggggccttc ttcaccttaa cttattcacc attgaagacg   1020
cttatcttgg gaacacctaa ggaactgtgg ccgaagaaat ttacgaagct caacaaagct   1080
ggtatgccaa gttatgccat gatggttcaa tgtgccatcg tgattgtgat cattttggtg   1140
gcgtcctttg caacggcaga cgcgtcagcc ttttacaatg tgttgacctt gatggcgaac   1200
gtttcgatga cgttaccata cctcttcttg ctatacgcgt ttccgaagtt taaggaaaac   1260
cagaacattg ttaagccttt tgaagtgtac aagtcattga cttggacgaa aattattagt   1320
tgggtcgtgt tcattgtcgt cttaggtgcg aatgttttca cgttgatcca gccaatcttg   1380
gaaactgggc agattcaaaa tacgatttgg atgctagttg gaccaattgt cttcggtgtg   1440
gccgggatta tttggtatca agttcgagaa cggcatgtca attaa               1485
```

<210> SEQ ID NO 108
<211> LENGTH: 494
<212> TYPE: PRT
<213> ORGANISM: Lactobacillus plantarum

<400> SEQUENCE: 108

```
Met Ala Thr Lys Asp Asn Glu Lys Ile Thr Leu Met Ala Leu Val Met
1               5                   10                  15

Met Ile Phe Thr Thr Val Phe Gly Phe Ala Asn Ser Thr Val Ala Tyr
            20                  25                  30

Tyr Leu Met Gly Tyr Ser Ser Ile Leu Phe Tyr Leu Val Ala Ala Val
        35                  40                  45

Leu Phe Phe Ile Pro Phe Ala Leu Met Met Ala Glu Phe Gly Ala Ala
    50                  55                  60

Val Lys Ser Asp Ser Ser Gly Met Tyr Lys Trp Leu Glu Val Ser Val
65                  70                  75                  80

Asn Ala Lys Phe Ala Phe Val Gly Thr Phe Met Trp Phe Ala Ser Tyr
                85                  90                  95

Ile Ile Trp Leu Val Ser Thr Ser Ala Lys Val Trp Ile Pro Phe Thr
            100                 105                 110

Thr Ile Phe Phe Gly Ser Asp Gln Thr Gln Arg Phe Ala Met Phe Gly
        115                 120                 125

Leu Asn Ala Thr Gln Met Ile Gly Ile Leu Ser Cys Leu Trp Met Val
    130                 135                 140

Leu Val Thr Phe Val Ser Ile Lys Gly Met Lys Gly Ile Val Arg Val
145                 150                 155                 160
```

```
Thr Ser Leu Gly Gly Leu Ala Val Thr Ser Leu Thr Ala Ile Leu Leu
            165                 170                 175

Val Val Ser Gly Val Val Leu Ala Leu Asn His Gly Gln Phe Ala Gln
            180                 185                 190

Pro Leu Gln His Val Met Thr Ser Pro Asn Pro Ser Tyr Gln His Pro
            195                 200                 205

Val Gly Leu Leu Gly Phe Ala Val Phe Ala Ile Phe Ala Tyr Gly Gly
            210                 215                 220

Leu Glu Val Leu Gly Gly Met Val Asp Lys Thr Lys Asn Pro Glu Lys
225                 230                 235                 240

Thr Phe Pro Arg Gly Ile Ile Ser Ala Ile Val Ile Thr Leu Gly
            245                 250                 255

Tyr Gly Leu Gly Ile Phe Cys Trp Gly Ile Ser Thr Asn Trp Gln Ala
            260                 265                 270

Val Leu Ser Asn Pro Thr Thr Asn Leu Gly Asn Ile Ser Tyr Val Met
            275                 280                 285

Met Gln Asn Leu Gly Tyr Val Leu Gly Gln Ala Leu Gly Leu Ser Thr
            290                 295                 300

Ala Ala Ala Lys Thr Met Gly Leu Trp Phe Ala Arg Tyr Thr Gly Leu
305                 310                 315                 320

Gly Met Phe Leu Ala Tyr Ser Gly Ala Phe Phe Thr Leu Thr Tyr Ser
            325                 330                 335

Pro Leu Lys Thr Leu Ile Leu Gly Thr Pro Lys Glu Leu Trp Pro Lys
            340                 345                 350

Lys Phe Thr Lys Leu Asn Lys Ala Gly Met Pro Ser Tyr Ala Met Met
            355                 360                 365

Val Gln Cys Ala Ile Val Ile Val Ile Leu Val Ala Ser Phe Ala
            370                 375                 380

Thr Ala Asp Ala Ser Ala Phe Tyr Asn Val Leu Thr Leu Met Ala Asn
385                 390                 395                 400

Val Ser Met Thr Leu Pro Tyr Leu Phe Leu Leu Tyr Ala Phe Pro Lys
            405                 410                 415

Phe Lys Glu Asn Gln Asn Ile Val Lys Pro Phe Glu Val Tyr Lys Ser
            420                 425                 430

Leu Thr Trp Thr Lys Ile Ile Ser Trp Val Val Phe Ile Val Val Leu
            435                 440                 445

Gly Ala Asn Val Phe Thr Leu Ile Gln Pro Ile Leu Glu Thr Gly Gln
            450                 455                 460

Ile Gln Asn Thr Ile Trp Met Leu Val Gly Pro Ile Val Phe Gly Val
465                 470                 475                 480

Ala Gly Ile Ile Trp Tyr Gln Val Arg Glu Arg His Val Asn
            485                 490

<210> SEQ ID NO 109
<211> LENGTH: 6099
<212> TYPE: DNA
<213> ORGANISM: Lactobacillus plantarum

<400> SEQUENCE: 109
atgcaaagac gacgcttaca acgagcacaa ttaacagaaa aacgaactta taaaatgtat     60
aaaaaaggac gcctgtggtt aattgccggg ttgagtactt tcactttggg tgctagtctg    120
ctaccgatga cggggcgggc agacacgact agtacgcctg ctgagaaaca ggggacgagg    180
acagagacaa ctggcaacca aatcacattg gctagtaagt cggttggtag tagttcgatg    240
```

```
gccaatgatg gcgaagaaaa aactaataac agtcaggtag agacgagtag tgaagctagt    300
aatgttactg catcgactga agctaagtca acggaatcaa cgactcagac tgtggttgat    360
tccaccgtga ctagtacggc tactgaaaca acacgtgcaa acggtgctac taatcagacc    420
agcaaaatgt ccatagtcga tacgacgtct aacaacacag aacagaatca agcagtaggt    480
ggtacaacag acagtacggc aagtaccgca actattgagg atcaagctaa ggccgccaac    540
agagcaacca ctgatggcaa gataaatacg gctacagtag ctacgaaaac aactacaact    600
gccagttatg caaccgcgga tattagtacg aataccattc gcagtgcgca aaagctagca    660
cgagctactg tggccaccgt tgcgacagta aattcagcga ctaagacgta tgatggtaag    720
atagatacac caaatcgcta tacgattacg ctaactgacg aactaaggc gccctcagat     780 tgggctgtaa cgagtactgc gaatgtttat acggttactg acttaacgga cgttgatacg    840
tccaagtttg gatcgagtgt tggaacatac acattggcac tctcaacggc tggaattact    900
aagctagctg aagctaatag tagcgcggat ataacggctg ctaacgtggt gacaggaaca    960
ctaacaatca agcaagctcc ggtaccgact gcgataatta ccattggttc agctagtatt   1020
gactatgggg atgctaaacc aagtacgtat acaattacgg tgccgagtca gtatgcagtt   1080
cccagcacct ggacgttagc tagttcggct actgatggaa cgactaatac ttatatgatt   1140
gcaagttcta gtggcgatgt tatagttccc acagcaaccc aatctggaac gtatcagctt   1200
gtgttgtcag atcaaggctt gacagcttta caacaggcta atcctaatgc tgctattact   1260
gctgatacga ttattgctgg tagtttagtt attgcggcac atgacattat tacgatgggt   1320
gcgacgacaa ttgtcgttaa taaaacgact agtacggttc cggtgacggt caatagtcgt   1380
actattgtgg ttccaacagg ttggacaatt cgttacgatg atattcagac tgatgcgatt   1440
gtgtatgacg tccccgtttc cgatacgaca tattcggaag cggttaatac tgctgtggtt   1500
gataaataca ccattacatt gactgatgat acgatagaaa cattagctaa ccttaacagc   1560
agtacgactt ttaatagtac gacggttggt aagggcgtag tgcttgtcaa ggctagtgcc   1620
gcagttgcca tctcacctgc aaactatggc gcgcaggcta gtgccgaaac tccggtaaca   1680
gggctgacaa tttcacatgc ccgaacaaag ggaattgatt tagcatatgg tcaggcgctg   1740
tatttgatct tgccgcttat taatatgaat ccatcaggaa tgactgtggc taatcttact   1800
gattatgtta ttattccatc tggttttaag gttgctacta atagtgaagg agctattaac   1860
atagcgactg atccaagtag tgtgttaacg tctgctattg aagcaatgat gacgaaaaat   1920
gatgtgacct atcaggggtt aaaggtgacc caactgacag actacagggg tcgccaaaca   1980
tttaaaattc attttgataa aaccactgtt tatgacggtg gtgcatttgc aacgctaaaa   2040
tatgcattat taccggtcat tgctgttcaa aacactgggg tgactagtgg tttaattggt   2100
aatcaagttt caagcccgga ttcggcggtg gtttatgtta ctgatgattc taatgaaaat   2160
aatggtagtt attcgttgaa tttgcaaaat tatactaata ttgacagtgt cgctgatgca   2220
ttaggaattg cggatgctgt cacgattggt agtggtttca caagttacct atatcattac   2280
acgctatcgg ccaaaacgat taccgatact tatagtttag taggaaacga tggcacgtca   2340
ttaggcgaag taacttttac gggcgacagt ggtaagacgt atgtaccgat gactaaatta   2400
cccatgacaa ttcacaaaaa tggcgtgacg tattatttga acactagtgc agtttcgtta   2460
actcagacat attctggtga tagtaattca aattacacag ttacttacca gcgctacgtc   2520
acaacgacga ctgatactgc ggccaagata acgattgcac cagcttcaaa agtctatgat   2580
```

```
aacaacgcca cgactgatcc aagtcgctat acggtatact tgccaactga atatacggcc   2640
ccaagcgatt ggactgctga tagcgcggcg acggctgtgg atgggacgac ggcgtaccaa   2700
gtcagtaccg actaccttaa caccactgca atcgatcaaa acgtgggcac ttacgctgtc   2760
acgctgaata gcgccgggat ggcagcctta tccgctgcta atccagattt cttgattgca   2820
ggcgatgtga atgttggtgg gactctgacg attactcaac gtccagtgac gattactttg   2880
ccggatacga ttctgtgggc caatggtcag gaacaaaata ttacgccggt cattactggt   2940
gttgttgcgg tgcaaagttt ggattacacg ttaacgtcag ggttaactga tccggacacg   3000
acaaccatta cggccacgct gacgaatgcc gctgctaata gtaattataa attgacgaat   3060
tcacctagtg gtcagttgac ggtgggcgcc gtaacggttg tctatcagta tgggtaccgc   3120
gacaaagcgg ggacgctaca cgtggtaaca acggctaatg gaacggcgac gcacgggact   3180
gatgttaccg ctaaggacta tttgagctac accacgagtg atacgactgc tacgcatgcc   3240
aaaactggtt atacgttaca accagaaagt accggttacc aagccgatgg cactctagcg   3300
gacgttggtg ggcaggtcgt gtacacctat ttagcgaaca ccgaaaagat tgcggtcgtt   3360
tacgtcgacc aagataagaa caacgtgatt ttaaaacaga ttccccctcag tgggagcttt   3420 ggcacaccca cgaattatac gacagcgcag gacattgcgg cgtatgaaaa attaggctac   3480
gtgttagctt cggataaggt cccagcgccg cttgagtttg atcaggatac tgaacagacc   3540
tactacgtat acctgaaaca tggcaccatc acggcgacgg ttgatcagcc aggtaacgtg   3600
gccgttagtg atttgatgaa gaccagtcag cgaacgattc attacgttta tgctgataac   3660
acacccacgg acttagcgga tgtgcttcaa acggtcacgt atacgcgcac ggcaacgggg   3720
gatgcggtgg atagaacggt cctttcgtac ggtaattgga cgaccaatgt gaatagctat   3780
ccggccattg agtcgccgac cattactggt tacacggcgg atcaaacaac catcgcggcg   3840
gctgtacccg ctagcatggg cgagactacg gaaacaacgg tccgatacag cgttaattct   3900
gaaacgatcc gggttcaatt tgtcgatgga actacggata accaagtctt aagttatatt   3960
gatttgaatg ggaaatacgg tgatgctgcc gactatacgg tcactgctga tatcgcgaag   4020
tatgcaaaat taggctatga accagttaac tcggacttgc ctgatcagct gatttataag   4080
cagaataccc aagtttatac ggttacacta gcgcatcgtc acgtgacggt cagcgttgat   4140
catccgggcc aacctggtca ggccatcgat gctgattatc cagccggtcc taaatatccg   4200
gcaggcactg gtcgtgattc gttggaacaa acagtgactc ggacgattac gtatcaatat   4260
gcgtcaggtc aatcagcggc tgaaacggtt aaccagtcgg tcacgttcaa tcgcacggca   4320
actttcgaca tggcaacggg taagcagctg acttacggtg actggacagt ggcacctggt   4380
cagtcagcac tattggccgc ggtcacgtca ccaacgatta caggttatca agccagtgtt   4440
acagaagtcg aagcagcgtc ggtcactagt cacgataagc cgcacttgat tgcaatcacg   4500
tacacggcca aatcacagac cgcaaccgtt gcgtttgtgg atgtaacgag tggtaaaaca   4560
ctacctacga cggtagtaac tggtgcttat ggcactacga atagttattc gcccgtttcc   4620
caaattgctg cgtatgaaaa actgggctat cgattagttt cgaataatgt tccgacgact   4680
ggtatcacct ttgatcaaaa tgacgtcatt aagtcataca cggtcaagct agcgcatcaa   4740
atgacgacgg tcacgccaac taagcctggg caaccaggtc aaccagttga tcccgctcat   4800
ccagaagggc ccaagtaccc agctggtact gggcttaaag atttaacaac cagcgttcag   4860
cgagtcatta cctatgttta caatgatggt caaactgcgg cgccaaccgt cacgcaaacg   4920
gtcagttttg agcgcaaggc gacctttgat caagtgacaa aggtggtgac gtatacggat   4980
```

-continued

```
tggcgtacac ctgaatcagc gttgacgggg gcatacgcag tcgttgaatc gccaataatt    5040
gctggctaca ccccgaatgc aacccgtgtt gctagtgtaa ctgtcagtgc caaagatact    5100
gagtcgcgac aaacggttac ttaccaagca aatctggaaa cggcgacggt gacttatgtc    5160
gatgccacga cgggccaccg actgggtaca agcgtgacgt taaccggacg attcggtacg    5220
caagcggatt atcaaccaac gacaatgatt gcgcagtata cccaggcagg ctatgtcttg    5280
atggggagtg attatccggc aacgggtgtt acttttaatc aggcgggcgt cgttcagaag    5340
tatacggtgt acttggctca taacaaaatc gtgattacgg caccagatca gctcaccaaa    5400
acgatcacgc aaacggttca ctatcaggat caggctgggc acacgcttca agctgatacg    5460
atccgggcgc tgacgttcac gcgttctggg atgaaagatg cggtgactgg tgtggcaacg    5520
tatcgtgatt gggcaccgac cgggttgaac tttacagccg tgtctgcgcc aacgattgcg    5580
aaataccatg cgttgacggc gaccactcag gccgtggcaa tcacggctgc tagtgctgat    5640
gatgtccaaa cgctaacata tgcgctggac gtcccaacac cgacgaaacc ggtcaaactg    5700
actaagccag ccaaaccgac taagccgaca acatcggacg atttaatcaa gccaacgacg    5760
aaaccaatca cggctgctaa accaacgcaa ctcactaagc cagcaacggt tgtgaaggat    5820
tttcaagcca caactggcaa ccagacgcca gctaaatcga caaggacgtt ggtatcgagt    5880
cgcattaagg ctgtcaaaac agctccggca tcagcaatca tcaagccggg aagtaaagta    5940
acggagccgg ctcacaaggc tcaagcagat acaacgagtc gattgccaca gactggtgaa    6000
acgcggtggt ctgaaatggc tgctgaaaca ctagggctaa cactagcaac attattgctg    6060
ggctttggtg gcttgaagcg taagcggcat gaaaagtaa                           6099
```

<210> SEQ ID NO 110
<211> LENGTH: 2032
<212> TYPE: PRT
<213> ORGANISM: Lactobacillus plantarum

<400> SEQUENCE: 110

```
Met Gln Arg Arg Leu Gln Arg Ala Gln Leu Thr Glu Lys Arg Thr
1               5                   10                  15

Tyr Lys Met Tyr Lys Lys Gly Arg Leu Trp Leu Ile Ala Gly Leu Ser
                20                  25                  30

Thr Phe Thr Leu Gly Ala Ser Leu Leu Pro Met Thr Gly Arg Ala Asp
            35                  40                  45

Thr Thr Ser Thr Pro Ala Glu Lys Gln Gly Thr Arg Thr Glu Thr Thr
        50                  55                  60

Gly Asn Gln Ile Thr Leu Ala Ser Lys Ser Val Gly Ser Ser Ser Met
65                  70                  75                  80

Ala Asn Asp Gly Glu Glu Lys Thr Asn Asn Ser Gln Val Glu Thr Ser
                85                  90                  95

Ser Glu Ala Ser Asn Val Thr Ala Ser Thr Glu Ala Lys Ser Thr Glu
            100                 105                 110

Ser Thr Thr Gln Thr Val Val Asp Ser Thr Val Thr Ser Thr Ala Thr
        115                 120                 125

Glu Thr Thr Arg Ala Asn Gly Ala Thr Asn Gln Thr Ser Lys Met Ser
    130                 135                 140

Ile Val Asp Thr Thr Ser Asn Asn Thr Glu Gln Asn Gln Ala Val Gly
145                 150                 155                 160

Gly Thr Thr Asp Ser Thr Ala Ser Thr Ala Thr Ile Glu Asp Gln Ala
                165                 170                 175
```

```
Lys Ala Ala Asn Arg Ala Thr Thr Asp Gly Lys Ile Asn Thr Ala Thr
            180                 185                 190

Val Ala Thr Lys Thr Thr Thr Ala Ser Tyr Ala Thr Ala Asp Ile
        195                 200                 205

Ser Thr Asn Thr Ile Arg Ser Ala Gln Lys Leu Ala Arg Ala Thr Val
210                 215                 220

Ala Thr Val Ala Thr Val Asn Ser Ala Thr Lys Thr Tyr Asp Gly Lys
225                 230                 235                 240

Ile Asp Thr Pro Asn Arg Tyr Thr Ile Thr Leu Thr Asp Gly Thr Lys
                245                 250                 255

Ala Pro Ser Asp Trp Ala Val Thr Ser Thr Ala Asn Val Tyr Thr Val
                260                 265                 270

Thr Asp Leu Thr Asp Val Asp Thr Ser Lys Phe Gly Ser Ser Val Gly
            275                 280                 285

Thr Tyr Thr Leu Ala Leu Ser Thr Ala Gly Ile Thr Lys Leu Ala Glu
        290                 295                 300

Ala Asn Ser Ser Ala Asp Ile Thr Ala Ala Asn Val Val Thr Gly Thr
305                 310                 315                 320

Leu Thr Ile Lys Gln Ala Pro Val Pro Thr Ala Ile Ile Thr Ile Gly
                325                 330                 335

Ser Ala Ser Ile Asp Tyr Gly Asp Ala Lys Pro Ser Thr Tyr Thr Ile
                340                 345                 350

Thr Val Pro Ser Gln Tyr Ala Val Pro Ser Thr Trp Thr Leu Ala Ser
            355                 360                 365

Ser Ala Thr Asp Gly Thr Thr Asn Thr Tyr Met Ile Ala Ser Ser Ser
        370                 375                 380

Gly Asp Val Ile Val Pro Thr Ala Thr Gln Ser Gly Thr Tyr Gln Leu
385                 390                 395                 400

Val Leu Ser Asp Gln Gly Leu Thr Ala Leu Gln Gln Ala Asn Pro Asn
                405                 410                 415

Ala Ala Ile Thr Ala Asp Thr Ile Ile Ala Gly Ser Leu Val Ile Ala
                420                 425                 430

Ala His Asp Ile Ile Thr Met Gly Ala Thr Thr Ile Val Val Asn Lys
            435                 440                 445

Thr Thr Ser Thr Val Pro Val Thr Val Asn Ser Arg Thr Ile Val Val
        450                 455                 460

Pro Thr Gly Trp Thr Ile Arg Tyr Asp Asp Ile Gln Thr Asp Ala Ile
465                 470                 475                 480

Val Tyr Asp Val Pro Val Ser Asp Thr Thr Tyr Ser Glu Ala Val Asn
                485                 490                 495

Thr Ala Val Val Asp Lys Tyr Thr Ile Thr Leu Thr Asp Thr Ile
                500                 505                 510

Glu Thr Leu Ala Asn Leu Asn Ser Ser Thr Thr Phe Asn Ser Thr Thr
            515                 520                 525

Val Gly Lys Gly Val Val Leu Val Lys Ala Ser Ala Val Ala Ile
        530                 535                 540

Ser Pro Ala Asn Tyr Gly Ala Gln Ala Ser Ala Glu Thr Pro Val Thr
545                 550                 555                 560

Gly Leu Thr Ile Ser His Ala Arg Thr Lys Gly Ile Asp Leu Ala Tyr
                565                 570                 575

Gly Gln Ala Leu Tyr Leu Ile Leu Pro Leu Ile Asn Met Asn Pro Ser
                580                 585                 590
```

```
Gly Met Thr Val Ala Asn Leu Thr Asp Tyr Val Ile Ile Pro Ser Gly
            595                 600                 605

Phe Lys Val Ala Thr Asn Ser Glu Gly Ala Ile Asn Ile Ala Thr Asp
        610                 615                 620

Pro Ser Ser Val Leu Thr Ser Ala Ile Glu Ala Met Met Thr Lys Asn
625                 630                 635                 640

Asp Val Thr Tyr Gln Gly Leu Lys Val Thr Gln Leu Thr Asp Tyr Arg
                645                 650                 655

Gly Arg Gln Thr Phe Lys Ile His Phe Asp Lys Thr Thr Val Tyr Asp
                660                 665                 670

Gly Gly Ala Phe Ala Thr Leu Lys Tyr Ala Leu Leu Pro Val Ile Ala
            675                 680                 685

Val Gln Asn Thr Gly Val Thr Ser Gly Leu Ile Gly Asn Gln Val Ser
        690                 695                 700

Ser Pro Asp Ser Ala Val Val Tyr Val Thr Asp Asp Ser Asn Glu Asn
705                 710                 715                 720

Asn Gly Ser Tyr Ser Leu Asn Leu Gln Asn Tyr Thr Asn Ile Asp Ser
                725                 730                 735

Val Ala Asp Ala Leu Gly Ile Ala Asp Ala Val Thr Ile Gly Ser Gly
                740                 745                 750

Phe Thr Ser Tyr Leu Tyr His Tyr Thr Leu Ser Ala Lys Thr Ile Thr
            755                 760                 765

Asp Thr Tyr Ser Leu Val Gly Asn Asp Gly Thr Ser Leu Gly Glu Val
        770                 775                 780

Thr Phe Thr Gly Asp Ser Gly Lys Thr Tyr Val Pro Met Thr Lys Leu
785                 790                 795                 800

Pro Met Thr Ile Thr Gln Asn Gly Val Thr Tyr Tyr Leu Asn Thr Ser
                805                 810                 815

Ala Val Ser Leu Thr Gln Thr Tyr Ser Gly Asp Ser Asn Ser Asn Tyr
                820                 825                 830

Thr Val Thr Tyr Gln Arg Tyr Val Thr Thr Thr Asp Thr Ala Ala
            835                 840                 845

Lys Ile Thr Ile Ala Pro Ala Ser Lys Val Tyr Asp Asn Asn Ala Thr
        850                 855                 860

Thr Asp Pro Ser Arg Tyr Thr Val Tyr Leu Pro Thr Glu Tyr Thr Ala
865                 870                 875                 880

Pro Ser Asp Trp Thr Ala Asp Ser Ala Ala Thr Ala Val Asp Gly Thr
                885                 890                 895

Thr Ala Tyr Gln Val Ser Thr Asp Tyr Leu Asn Thr Thr Ala Ile Asp
                900                 905                 910

Gln Asn Val Gly Thr Tyr Ala Val Thr Leu Asn Ser Ala Gly Met Ala
            915                 920                 925

Ala Leu Ser Ala Ala Asn Pro Asp Phe Leu Ile Ala Gly Asp Val Asn
        930                 935                 940

Val Gly Gly Thr Leu Thr Ile Thr Gln Arg Pro Val Thr Ile Thr Leu
945                 950                 955                 960

Pro Asp Thr Ile Leu Trp Ala Asn Gly Gln Glu Gln Asn Ile Thr Pro
                965                 970                 975

Val Ile Thr Gly Val Val Ala Val Gln Ser Leu Asp Tyr Thr Leu Thr
                980                 985                 990

Ser Gly Leu Thr Asp Pro Asp Thr  Thr Thr Ile Thr Ala  Thr Leu Thr
            995                 1000                1005

Asn Ala  Ala Ala Asn Ser Asn  Tyr Lys Leu Thr Asn  Ser Pro Ser
```

```
                    1010                1015                1020

Gly Gln Leu Thr Val Gly Ala Val Thr Val Val Tyr Gln Tyr Gly
    1025                1030                1035

Tyr Arg Asp Lys Ala Gly Thr Leu His Val Val Thr Thr Ala Asn
    1040                1045                1050

Gly Thr Ala Thr His Gly Thr Asp Val Thr Ala Lys Asp Tyr Leu
    1055                1060                1065

Ser Tyr Thr Thr Ser Asp Thr Thr Ala Thr His Ala Lys Thr Gly
    1070                1075                1080

Tyr Thr Leu Gln Pro Glu Ser Thr Gly Tyr Gln Ala Asp Gly Thr
    1085                1090                1095

Leu Ala Asp Val Gly Gly Gln Val Val Tyr Thr Tyr Leu Ala Asn
    1100                1105                1110

Thr Glu Lys Ile Ala Val Val Tyr Val Asp Gln Asp Lys Asn Asn
    1115                1120                1125

Val Ile Leu Lys Gln Ile Pro Leu Ser Gly Ser Phe Gly Thr Pro
    1130                1135                1140

Thr Asn Tyr Thr Thr Ala Gln Asp Ile Ala Ala Tyr Glu Lys Leu
    1145                1150                1155

Gly Tyr Val Leu Ala Ser Asp Lys Val Pro Ala Pro Leu Glu Phe
    1160                1165                1170

Asp Gln Asp Thr Glu Gln Thr Tyr Tyr Val Tyr Leu Lys His Gly
    1175                1180                1185

Thr Ile Thr Ala Thr Val Asp Gln Pro Gly Asn Val Ala Val Ser
    1190                1195                1200

Asp Leu Met Lys Thr Ser Gln Arg Thr Ile His Tyr Val Tyr Ala
    1205                1210                1215

Asp Asn Thr Pro Thr Asp Leu Ala Asp Val Leu Gln Thr Val Thr
    1220                1225                1230

Tyr Thr Arg Thr Ala Thr Gly Asp Ala Val Asp Arg Thr Val Leu
    1235                1240                1245

Ser Tyr Gly Asn Trp Thr Thr Asn Val Asn Ser Tyr Pro Ala Ile
    1250                1255                1260

Glu Ser Pro Thr Ile Thr Gly Tyr Thr Ala Asp Gln Thr Thr Ile
    1265                1270                1275

Ala Ala Ala Val Pro Ala Ser Met Gly Glu Thr Thr Glu Thr Thr
    1280                1285                1290

Val Arg Tyr Ser Val Asn Ser Glu Thr Ile Arg Val Gln Phe Val
    1295                1300                1305

Asp Gly Thr Thr Asp Asn Gln Val Leu Ser Tyr Ile Asp Leu Asn
    1310                1315                1320

Gly Lys Tyr Gly Asp Ala Ala Asp Tyr Thr Val Thr Ala Asp Ile
    1325                1330                1335

Ala Lys Tyr Ala Lys Leu Gly Tyr Glu Pro Val Asn Ser Asp Leu
    1340                1345                1350

Pro Asp Gln Leu Ile Tyr Lys Gln Asn Thr Gln Val Tyr Thr Val
    1355                1360                1365

Thr Leu Ala His Arg His Val Thr Val Ser Val Asp His Pro Gly
    1370                1375                1380

Gln Pro Gly Gln Ala Ile Asp Ala Asp Tyr Pro Ala Gly Pro Lys
    1385                1390                1395

Tyr Pro Ala Gly Thr Gly Arg Asp Ser Leu Glu Gln Thr Val Thr
    1400                1405                1410
```

```
Arg Thr Ile Thr Tyr Gln Tyr Ala Ser Gly Glu Ser Ala Ala Glu
    1415            1420                1425

Thr Val Asn Gln Ser Val Thr Phe Asn Arg Thr Ala Thr Phe Asp
    1430            1435                1440

Met Ala Thr Gly Lys Gln Leu Thr Tyr Gly Asp Trp Thr Val Ala
    1445            1450                1455

Pro Gly Gln Ser Ala Leu Leu Ala Ala Val Thr Ser Pro Thr Ile
    1460            1465                1470

Thr Gly Tyr Gln Ala Ser Val Thr Glu Val Glu Ala Ala Ser Val
    1475            1480                1485

Thr Ser His Asp Lys Pro His Leu Ile Ala Ile Thr Tyr Thr Ala
    1490            1495                1500

Lys Ser Gln Thr Ala Thr Val Ala Phe Val Asp Val Thr Ser Gly
    1505            1510                1515

Lys Thr Leu Pro Thr Thr Val Val Thr Gly Ala Tyr Gly Thr Thr
    1520            1525                1530

Asn Ser Tyr Ser Pro Val Ser Gln Ile Ala Ala Tyr Glu Lys Leu
    1535            1540                1545

Gly Tyr Arg Leu Val Ser Asn Asn Val Pro Thr Thr Gly Ile Thr
    1550            1555                1560

Phe Asp Gln Asn Asp Val Ile Lys Ser Tyr Thr Val Lys Leu Ala
    1565            1570                1575

His Gln Met Thr Thr Val Thr Pro Thr Lys Pro Gly Gln Pro Gly
    1580            1585                1590

Gln Pro Val Asp Pro Ala His Pro Glu Gly Pro Lys Tyr Pro Ala
    1595            1600                1605

Gly Thr Gly Leu Lys Asp Leu Thr Thr Ser Val Gln Arg Val Ile
    1610            1615                1620

Thr Tyr Val Tyr Asn Asp Gly Gln Thr Ala Ala Pro Thr Val Thr
    1625            1630                1635

Gln Thr Val Ser Phe Glu Arg Lys Ala Thr Phe Asp Gln Val Thr
    1640            1645                1650

Lys Val Val Thr Tyr Thr Asp Trp Arg Thr Pro Glu Ser Ala Leu
    1655            1660                1665

Thr Gly Ala Tyr Ala Val Val Glu Ser Pro Ile Ile Ala Gly Tyr
    1670            1675                1680

Thr Pro Asn Ala Thr Arg Val Ala Ser Val Thr Val Ser Ala Lys
    1685            1690                1695

Asp Thr Glu Ser Arg Gln Thr Val Thr Tyr Gln Ala Asn Leu Glu
    1700            1705                1710

Thr Ala Thr Val Thr Tyr Val Asp Ala Thr Thr Gly His Arg Leu
    1715            1720                1725

Gly Thr Ser Val Thr Leu Thr Gly Arg Phe Gly Thr Gln Ala Asp
    1730            1735                1740

Tyr Gln Pro Thr Thr Met Ile Ala Gln Tyr Thr Gln Ala Gly Tyr
    1745            1750                1755

Val Leu Met Gly Ser Asp Tyr Pro Ala Thr Gly Val Thr Phe Asn
    1760            1765                1770

Gln Ala Gly Val Val Gln Lys Tyr Thr Val Tyr Leu Ala His Asn
    1775            1780                1785

Lys Ile Val Ile Thr Ala Pro Asp Gln Leu Thr Lys Thr Ile Thr
    1790            1795                1800
```

| | | | | | | | | | | | |
|---|---|---|---|---|---|---|---|---|---|---|---|
| Gln | Thr | Val | His | Tyr | Gln | Asp | Gln | Ala | Gly | His | Thr | Leu | Gln | Ala |
| | | | 1805 | | | | 1810 | | | | 1815 | | | |

Asp Thr Ile Arg Ala Leu Thr Phe Thr Arg Ser Gly Met Lys Asp
1820                1825                1830

Ala Val Thr Gly Val Ala Thr Tyr Arg Asp Trp Ala Pro Thr Gly
1835                1840                1845

Leu Asn Phe Thr Ala Val Ser Ala Pro Thr Ile Ala Lys Tyr His
1850                1855                1860

Ala Leu Thr Ala Thr Thr Gln Ala Val Ala Ile Thr Ala Ala Ser
1865                1870                1875

Ala Asp Asp Val Gln Thr Leu Thr Tyr Ala Leu Asp Val Pro Thr
1880                1885                1890

Pro Thr Lys Pro Val Lys Leu Thr Lys Pro Ala Lys Pro Thr Lys
1895                1900                1905

Pro Thr Thr Ser Asp Asp Leu Ile Lys Pro Thr Thr Lys Pro Ile
1910                1915                1920

Thr Ala Ala Lys Pro Thr Gln Leu Thr Lys Pro Ala Thr Val Val
1925                1930                1935

Lys Asp Phe Gln Ala Thr Thr Gly Asn Gln Thr Pro Ala Lys Ser
1940                1945                1950

Thr Arg Thr Leu Val Ser Ser Arg Ile Lys Ala Val Lys Thr Ala
1955                1960                1965

Pro Ala Ser Ala Ile Ile Lys Pro Gly Ser Lys Val Thr Glu Pro
1970                1975                1980

Ala His Lys Ala Gln Ala Asp Thr Thr Ser Arg Leu Pro Gln Thr
1985                1990                1995

Gly Glu Thr Arg Trp Ser Glu Met Ala Ala Glu Thr Leu Gly Leu
2000                2005                2010

Thr Leu Ala Thr Leu Leu Leu Gly Phe Gly Gly Leu Lys Arg Lys
2015                2020                2025

Arg His Glu Lys
2030

<210> SEQ ID NO 111
<211> LENGTH: 915
<212> TYPE: DNA
<213> ORGANISM: Lactobacillus plantarum

<400> SEQUENCE: 111

```
atggatttaa agcaaagcga tggttggcga tacttagctg ggtggagctt cattctatta     60
atggtggcga gtgccacatt gcaacatgat gcgaaaatca tttacccga atcggtgct     120
ctgacagccg ggacgtgggt ttatcgtaag acggcgtgga ctcggcaacc cttaaagtta    180
ttcttagtac catctggaac tgcaattatt ggcttcttag tcaatcaact accttggtcg    240
cacgccctca aagtgcttgt cggtctatta ctgatgctat tattattgaa ggggttaaaa    300
tcgaatttgg cgccagcctt tgctactggc ttactgccaa ttatcattaa tgcaacgcac    360
tggacctta tcgtagccat cttttttctgg actatttgcc tgatgattgg ggcttggatt    420
caacgaccgc gatcaatctc acgggtaacc gaagcttctg ctagtcgctg gcaaatgctc    480
ggctttatca gcctagtttt tgtctgggtg gtattgttt ggctagcggg acagccccag    540
atggccgcaa tcccacccgt gatcgtcgtt ttctttgaag cggctcaaca gtctgaatat    600
acggtaacga ccgcacttaa gcagtggctt gcattgtcgg ctgctgctag tattgggtc    660
ggcattcacc tattgattgc ttcgtggcta ttaacgacgg tcattgcctt accacttgtg    720
```

```
tatttgtggt tacgggcgct taacttacaa ttgccagcag cgtatgcctt tccactatta    780
gccttagtgt taccagccaa tatgtttaac aaactaccga catccgccgg cttagcggcc    840
gctttcttcc taggatcgtt actcatctac catcagatct tgggttgggt acgcatggcg    900
gtgactgaaa gctag                                                      915
```

```
<210> SEQ ID NO 112
<211> LENGTH: 304
<212> TYPE: PRT
<213> ORGANISM: Lactobacillus plantarum

<400> SEQUENCE: 112
```

Met Asp Leu Lys Gln Ser Asp Gly Trp Arg Tyr Leu Ala Gly Trp Ser
1               5                   10                  15

Phe Ile Leu Leu Met Val Ala Ser Ala Thr Leu Gln His Asp Ala Lys
            20                  25                  30

Ile Ile Leu Pro Glu Ile Gly Ala Leu Thr Ala Gly Thr Trp Val Tyr
        35                  40                  45

Arg Lys Thr Ala Trp Thr Arg Gln Pro Leu Lys Leu Phe Leu Val Pro
    50                  55                  60

Ser Gly Thr Ala Ile Ile Gly Phe Leu Val Asn Gln Leu Pro Trp Ser
65                  70                  75                  80

His Ala Leu Lys Val Leu Val Gly Leu Leu Met Leu Leu Leu Leu
                85                  90                  95

Lys Gly Leu Lys Ser Asn Leu Ala Pro Ala Phe Ala Thr Gly Leu Leu
            100                 105                 110

Pro Ile Ile Ile Asn Ala Thr His Trp Thr Phe Ile Val Ala Ile Phe
        115                 120                 125

Phe Trp Thr Ile Cys Leu Met Ile Gly Ala Trp Ile Gln Arg Pro Arg
    130                 135                 140

Ser Ile Ser Arg Val Thr Glu Ala Ser Ala Ser Arg Trp Gln Met Leu
145                 150                 155                 160

Gly Phe Ile Ser Leu Val Phe Val Trp Val Gly Ile Val Trp Leu Ala
                165                 170                 175

Gly Gln Pro Gln Met Ala Ala Ile Pro Pro Val Ile Val Phe Phe
            180                 185                 190

Glu Ala Ala Gln Gln Ser Glu Tyr Thr Val Thr Thr Ala Leu Lys Gln
        195                 200                 205

Trp Leu Ala Leu Ser Ala Ala Ser Ile Gly Val Gly Ile His Leu
    210                 215                 220

Leu Ile Ala Ser Trp Leu Leu Thr Thr Val Ile Ala Leu Pro Leu Val
225                 230                 235                 240

Tyr Leu Trp Leu Arg Ala Leu Asn Leu Gln Leu Pro Ala Ala Tyr Ala
                245                 250                 255

Phe Pro Leu Leu Ala Leu Val Leu Pro Ala Asn Met Phe Asn Lys Leu
            260                 265                 270

Pro Thr Ser Ala Gly Leu Ala Ala Ala Phe Phe Leu Gly Ser Leu Leu
        275                 280                 285

Ile Tyr His Gln Ile Leu Gly Trp Val Arg Met Ala Val Thr Glu Ser
    290                 295                 300

```
<210> SEQ ID NO 113
<211> LENGTH: 930
<212> TYPE: DNA
<213> ORGANISM: Lactobacillus plantarum
```

<400> SEQUENCE: 113

```
atgaagtatc ggttaatagg ggtaggtgcg agtctagtcg tcgcagtcat gttaacaggg    60
tgtcaagcga aggctacgac attggtcaag tcagatgctg gccaggtcac acaagcggaa   120
gtatttaaac aaattgaaaa ccaagcgacg acgcaacagg ctgttcaaga attgactcta   180
aacaaagtcc ttaatcaacg atatcatgtt tcacaagctg aagtaactgc taaattaaaa   240
gcattcaaac ggcaggcggg cgcaaattat cacatgattt tagaacgtaa tcatgtcact   300
gaaccgcgtt taaaatcgca aatcaaagcg aatttattga tggagaaagc cgttagtgct   360
aagtatccag tgactaaagc gcaactaaaa aaagcccgag cagcttatat gccaatgaca   420
acggttcaac acattgcgac gaccaatgag aagcaagcgc aaaaaattat tgctgaactg   480
aatgcgggtg ctagctttga ttcgcaagtg cgaaaatatc agaataatcg acaagcgcac   540
acaactgctg ggaaattagc gcagtttgac agttataatc aaactctagc accagcaatt   600
gtacaggcca cagctaaact acgagtggga cactatgtca cgaaaccggt caaacagtt    660
atggcaactg ccgacacgaa agacaaacca acttatgaaa ttatcaacgt tgtcagtcgt   720
cgatctaaga ctgcggctgt aactgatgat agcggtaagc agattgatgt gacaaattat   780
ttgcgtgaaa aaatccagca acagcggatg atggacaagc agacgcaagt tgcgacgatt   840
cggtcagttt tcaaagcggc ccacgttaag gtagttgatg cccatttcgc accagcgttt   900
aatgattatt taaccaccca aaatagctaa                                    930
```

<210> SEQ ID NO 114
<211> LENGTH: 309
<212> TYPE: PRT
<213> ORGANISM: Lactobacillus plantarum

<400> SEQUENCE: 114

```
Met Lys Tyr Arg Leu Ile Gly Val Gly Ala Ser Leu Val Ala Val
1               5                   10                  15

Met Leu Thr Gly Cys Gln Ala Lys Ala Thr Thr Leu Val Lys Ser Asp
                20                  25                  30

Ala Gly Gln Val Thr Gln Ala Glu Val Phe Lys Gln Ile Glu Asn Gln
            35                  40                  45

Ala Thr Thr Gln Gln Ala Val Gln Glu Leu Thr Leu Asn Lys Val Leu
        50                  55                  60

Asn Gln Arg Tyr His Val Ser Gln Ala Glu Val Thr Ala Lys Leu Lys
65                  70                  75                  80

Ala Phe Lys Arg Gln Ala Gly Ala Asn Tyr His Met Ile Leu Glu Arg
                85                  90                  95

Asn His Val Thr Glu Pro Arg Leu Lys Ser Gln Ile Lys Ala Asn Leu
            100                 105                 110

Leu Met Glu Lys Ala Val Ser Ala Lys Tyr Pro Val Thr Lys Ala Gln
        115                 120                 125

Leu Lys Lys Ala Arg Ala Ala Tyr Met Pro Met Thr Thr Val Gln His
    130                 135                 140

Ile Ala Thr Thr Asn Glu Lys Gln Ala Gln Lys Ile Ile Ala Glu Leu
145                 150                 155                 160

Asn Ala Gly Ala Ser Phe Asp Ser Gln Val Arg Lys Tyr Gln Asn Asn
                165                 170                 175

Arg Gln Ala His Thr Thr Ala Gly Lys Leu Ala Gln Phe Asp Ser Tyr
            180                 185                 190
```

```
Asn Gln Thr Leu Ala Pro Ala Ile Val Gln Ala Thr Ala Lys Leu Arg
        195                 200                 205

Val Gly His Tyr Val Thr Lys Pro Val Lys Thr Val Met Ala Thr Ala
    210                 215                 220

Asp Thr Lys Asp Lys Pro Thr Tyr Glu Ile Ile Asn Val Val Ser Arg
225                 230                 235                 240

Arg Ser Lys Thr Ala Ala Val Thr Asp Asp Ser Gly Lys Gln Ile Asp
                245                 250                 255

Val Thr Asn Tyr Leu Arg Glu Lys Ile Gln Gln Arg Met Met Asp
            260                 265                 270

Lys Gln Thr Gln Val Ala Thr Ile Arg Ser Val Phe Lys Ala Ala His
        275                 280                 285

Val Lys Val Val Asp Ala His Phe Ala Pro Ala Phe Asn Asp Tyr Leu
    290                 295                 300

Thr Thr Gln Asn Ser
305
```

<210> SEQ ID NO 115
<211> LENGTH: 1410
<212> TYPE: DNA
<213> ORGANISM: Lactobacillus plantarum

<400> SEQUENCE: 115

| | |
|---|---:|
| atggcaatgt tatacggtaa acacaatcat gaagctgaag aatacttgga accagtcttt | 60 |
| ggtgcgcctt ctgaacaaca tgatcttcct aagtatcggt taccaaagca ttcattatcc | 120 |
| cctcgagaag ccgatcgctt agttcgtgat gaattattag atgaaggcaa ttcacgactg | 180 |
| aacctggcaa cttttttgtca gacctatatg aacccgaag ccgttgaatt gatgaaggat | 240 |
| acgctggcta agaatgccat cgacaaatct gagtaccccc gcacggccga gattgaaaat | 300 |
| cggtgtgtga acattattgc caatctgtgg cacgcacctg atgacgaaca ctttacgggt | 360 |
| acctctacga ttggctcctc tgaagcttgt atgttaggcg gtttagcaat gaaattcgcc | 420 |
| tggcgtaaac gcgctcaagc ggcaggttta gatctgaatg cccatcgacc taacctcgtt | 480 |
| atttcggctg gctatcaagt ttgctgggaa aagttttgtg tctactggga cgttgacatg | 540 |
| cacgtggtcc caatggatga gcaacacatg gcccttgacg ttaaccacgt cttagactac | 600 |
| gtggacgaat acacaattgg tatcgtcggt atcatgggca tcacttatac cggtcaatat | 660 |
| gacgacctag ccgcactcga taaggtcgtt actcactaca atcatcagca tcccaaatta | 720 |
| ccagtctaca ttcacgtcga cgcagcgtca ggtggcttct atacccccatt tattgagccg | 780 |
| caactcatct gggacttccg gttggctaac gtcgtttcga tcaacgcctc cgggcacaag | 840 |
| tacggtttag tttatcccgg ggtcggctgg gtcgtttggc gtgatcgtca gtttttaccg | 900 |
| ccagaattag tcttcaaagt tagttattta ggtggggagt tgccgacaat ggcgatcaac | 960 |
| ttctcacata gtgcagccca gctcattgga caatactata atttcattcg ctttggtatg | 1020 |
| gacggttacc gcgagattca aacaaagact cacgatgttg cccgctacct ggcagccgct | 1080 |
| ctggataaag ttggtgagtt taagatgatc aataacggac accaactccc cctgatttgt | 1140 |
| taccaactag cctcgcgcga agatcgtgaa tggacccttt atgatttatc ggatcgccta | 1200 |
| ttaatgaacg gttggcaagt accaacgtat cctttacctg ctaatctgga acaacaagtc | 1260 |
| atccaacgaa tcgtcgttcg ggctgacttt ggcatgaata tggcccacga tttcatggat | 1320 |
| gacctgacca aggctgtcca tgacttaaac cacgcccaca ttgtctatca tcatgacgcg | 1380 |
| gcacctaaga aatacggatt cacacactga | 1410 |

<210> SEQ ID NO 116
<211> LENGTH: 469
<212> TYPE: PRT
<213> ORGANISM: Lactobacillus plantarum

<400> SEQUENCE: 116

```
Met Ala Met Leu Tyr Gly Lys His Asn His Glu Ala Glu Glu Tyr Leu
1               5                   10                  15

Glu Pro Val Phe Gly Ala Pro Ser Glu Gln His Asp Leu Pro Lys Tyr
            20                  25                  30

Arg Leu Pro Lys His Ser Leu Ser Pro Arg Glu Ala Asp Arg Leu Val
        35                  40                  45

Arg Asp Glu Leu Leu Asp Glu Gly Asn Ser Arg Leu Asn Leu Ala Thr
    50                  55                  60

Phe Cys Gln Thr Tyr Met Glu Pro Glu Ala Val Glu Leu Met Lys Asp
65                  70                  75                  80

Thr Leu Ala Lys Asn Ala Ile Asp Lys Ser Glu Tyr Pro Arg Thr Ala
                85                  90                  95

Glu Ile Glu Asn Arg Cys Val Asn Ile Ala Asn Leu Trp His Ala
            100                 105                 110

Pro Asp Asp Glu His Phe Thr Gly Thr Ser Thr Ile Gly Ser Ser Glu
        115                 120                 125

Ala Cys Met Leu Gly Gly Leu Ala Met Lys Phe Ala Trp Arg Lys Arg
    130                 135                 140

Ala Gln Ala Ala Gly Leu Asp Leu Asn Ala His Arg Pro Asn Leu Val
145                 150                 155                 160

Ile Ser Ala Gly Tyr Gln Val Cys Trp Glu Lys Phe Cys Val Tyr Trp
                165                 170                 175

Asp Val Asp Met His Val Val Pro Met Asp Glu Gln His Met Ala Leu
            180                 185                 190

Asp Val Asn His Val Leu Asp Tyr Val Asp Glu Tyr Thr Ile Gly Ile
        195                 200                 205

Val Gly Ile Met Gly Ile Thr Tyr Thr Gly Gln Tyr Asp Asp Leu Ala
    210                 215                 220

Ala Leu Asp Lys Val Val Thr His Tyr Asn His Gln His Pro Lys Leu
225                 230                 235                 240

Pro Val Tyr Ile His Val Asp Ala Ala Ser Gly Gly Phe Tyr Thr Pro
                245                 250                 255

Phe Ile Glu Pro Gln Leu Ile Trp Asp Phe Arg Leu Ala Asn Val Val
            260                 265                 270

Ser Ile Asn Ala Ser Gly His Lys Tyr Gly Leu Val Tyr Pro Gly Val
        275                 280                 285

Gly Trp Val Val Trp Arg Asp Arg Gln Phe Leu Pro Pro Glu Leu Val
    290                 295                 300

Phe Lys Val Ser Tyr Leu Gly Gly Glu Leu Pro Thr Met Ala Ile Asn
305                 310                 315                 320

Phe Ser His Ser Ala Ala Gln Leu Ile Gly Gln Tyr Tyr Asn Phe Ile
                325                 330                 335

Arg Phe Gly Met Asp Gly Tyr Arg Glu Ile Gln Thr Lys Thr His Asp
            340                 345                 350

Val Ala Arg Tyr Leu Ala Ala Leu Asp Lys Val Gly Glu Phe Lys
        355                 360                 365

Met Ile Asn Asn Gly His Gln Leu Pro Leu Ile Cys Tyr Gln Leu Ala
```

Ser Arg Glu Asp Arg Glu Trp Thr Leu Tyr Asp Leu Ser Asp Arg Leu
385                 390                 395                 400

Leu Met Asn Gly Trp Gln Val Pro Thr Tyr Pro Leu Pro Ala Asn Leu
                405                 410                 415

Glu Gln Gln Val Ile Gln Arg Ile Val Val Arg Ala Asp Phe Gly Met
            420                 425                 430

Asn Met Ala His Asp Phe Met Asp Asp Leu Thr Lys Ala Val His Asp
            435                 440                 445

Leu Asn His Ala His Ile Val Tyr His His Asp Ala Ala Pro Lys Lys
        450                 455                 460

Tyr Gly Phe Thr His
465

<210> SEQ ID NO 117
<211> LENGTH: 1113
<212> TYPE: DNA
<213> ORGANISM: Lactobacillus plantarum

<400> SEQUENCE: 117
ttacatgtgg atagcaaagc ttggtgtgta gtaagctgtg ctcttaattg aaacagtttc    60
accataagtt ggtgaagcga tgtattggcc accgcctaag taaatcccaa cgtggtaagg   120
tgctgaatca gaaccccaga aaatcaagtc gccagcttgg gcttgactga atgatacgtg   180
agtaccaatc gtagcttgag catatgtggt ccgaccgatt gaacgaccaa ccttagcaaa   240
ggcagcttgc gtgaatgcag agcagtccat ttgttcgtaa ggtgtgccaa tgaaggtctt   300
agcagcagca attactgaac tgtatgatgc agttgaacta gtcgttgatg tactagttga   360
tgctgaagca ctgtaggccg ttgcagtagc agtcgttgtt gatgaactag tcgtgttact   420
tgcagttgag ctagcttgtg agctcgttga agtagcagct gattgcgtac tagttgcagt   480
cgtgctagta gacgatgcta ctggagttga gcttttgtgat gcttgtgaag ctgaactttg   540
gctagctgag ctttgtgaag ttgctgaact agttacagca cttgagctag cttgtgaagc   600
tactgaactc gttgaagcac ttgaagtgac actgcttgca ctagcagttg aagtgctact   660
tgattgagca gctactgagc tacttgatac tgcttggctc gtactacttg cactagtagt   720
tgatgagctg gtagcagcag cgctagtagc ttgtgaacta gttgaagttg cggcactagt   780
tgacttagca ctgcttgcac tagcagtggt cgtcttagtc gtaaccttt caccagtttt   840
aacgccagga atattgatgg ttttaccagc aataattaag ttagggttgc ttaagccatt   900
agcttcagca atcttgtcaa cagaaacatg gtactttgt gcgtatgccc aaacagtatc   960
ccctgctttg attgtcattg aatcggcatt ggcaactgct tgactagtaa ctaacatacc  1020
agctaaagca gcagttccta acatcacttg tttaatattt actttcactt taataatgat  1080
cactccaaaa agaatgtcac gtatgtactt caa                                1113

<210> SEQ ID NO 118
<211> LENGTH: 370
<212> TYPE: PRT
<213> ORGANISM: Lactobacillus plantarum

<400> SEQUENCE: 118

Met Lys Tyr Ile Arg Asp Ile Leu Phe Gly Val Ile Ile Ile Lys Val
1               5                   10                  15

Lys Val Asn Ile Lys Gln Val Met Leu Gly Thr Ala Ala Leu Ala Gly
            20                  25                  30

```
Met Leu Val Thr Ser Gln Ala Val Ala Asn Ala Asp Ser Met Thr Ile
        35                  40                  45

Lys Ala Gly Asp Thr Val Trp Ala Tyr Ala Gln Lys Tyr His Val Ser
 50                  55                  60

Val Asp Lys Ile Ala Glu Ala Asn Gly Leu Ser Asn Pro Asn Leu Ile
 65                  70                  75                  80

Ile Ala Gly Lys Thr Ile Asn Ile Pro Gly Val Lys Thr Gly Glu Lys
                 85                  90                  95

Val Thr Thr Lys Thr Thr Thr Ala Ser Ala Ser Ser Ala Lys Ser Thr
                100                 105                 110

Ser Ala Ala Thr Ser Thr Ser Ser Gln Ala Thr Ser Ala Ala Ala Thr
            115                 120                 125

Ser Ser Ser Thr Thr Ser Ala Ser Ser Thr Ser Gln Ala Val Ser Ser
            130                 135                 140

Ser Ser Val Ala Ala Gln Ser Ser Ser Thr Ser Thr Ala Ser Ala Ser
145                 150                 155                 160

Ser Val Thr Ser Ser Ala Ser Thr Ser Ser Val Ala Ser Gln Ala Ser
                165                 170                 175

Ser Ser Ala Val Thr Ser Ser Ala Thr Ser Gln Ser Ser Ala Ser Gln
            180                 185                 190

Ser Ser Ala Ser Gln Ala Ser Gln Ser Ser Thr Pro Val Ala Ser Ser
            195                 200                 205

Thr Ser Thr Thr Ala Thr Ser Thr Gln Ser Ala Ala Thr Ser Thr Ser
            210                 215                 220

Ser Gln Ala Ser Ser Thr Ala Ser Asn Thr Thr Ser Ser Ser Thr Thr
225                 230                 235                 240

Thr Ala Thr Ala Thr Ala Tyr Ser Ala Ser Ala Ser Thr Ser Thr Ser
                245                 250                 255

Thr Thr Ser Ser Thr Ala Ser Tyr Ser Ser Val Ile Ala Ala Ala Lys
            260                 265                 270

Thr Phe Ile Gly Thr Pro Tyr Glu Gln Met Asp Cys Ser Ala Phe Thr
            275                 280                 285

Gln Ala Ala Phe Ala Lys Val Gly Arg Ser Ile Gly Arg Thr Thr Tyr
290                 295                 300

Ala Gln Ala Thr Ile Gly Thr His Val Ser Phe Ser Gln Ala Gln Ala
305                 310                 315                 320

Gly Asp Leu Ile Phe Trp Gly Ser Asp Ser Ala Pro Tyr His Val Gly
                325                 330                 335

Ile Tyr Leu Gly Gly Gln Tyr Ile Ala Ser Pro Thr Tyr Gly Glu
            340                 345                 350

Thr Val Ser Ile Lys Ser Thr Ala Tyr Tyr Thr Pro Ser Phe Ala Ile
            355                 360                 365

His Met
    370

<210> SEQ ID NO 119
<211> LENGTH: 345
<212> TYPE: DNA
<213> ORGANISM: Lactobacillus plantarum

<400> SEQUENCE: 119
ctatttagat attcgttggc gatgatgcgt tcgcggtaat cctaatagcc atcgaatatc      60
attacccgta aagttcaact tcaagaattc gccactttgt ccctgttgat acatggtcgg    120
```

```
taatacctgg tcttgcaact tgatcacttg ctgtgcgatc tcttcgtcaa ataaatattg    180
ccgtgtcgcg gcagcaattt caccgaccgt aaaaatctga gcagcgttag caaatatctg    240
ctctttgctc agcgccaact gggcttgttt aaactgggcg taggactgat ccaagacttg    300
gcctgcttga gtttccaatg cggttactgt ggtcatgatg cgcac                    345
```

```
<210> SEQ ID NO 120
<211> LENGTH: 114
<212> TYPE: PRT
<213> ORGANISM: Lactobacillus plantarum

<400> SEQUENCE: 120
```

```
Met Arg Ile Met Thr Thr Val Thr Ala Leu Glu Thr Gln Ala Gly Gln
1               5                   10                  15

Val Leu Asp Gln Ser Tyr Ala Gln Phe Lys Gln Ala Gln Leu Ala Leu
            20                  25                  30

Ser Lys Glu Gln Ile Phe Ala Asn Ala Ala Gln Ile Phe Thr Val Gly
        35                  40                  45

Glu Ile Ala Ala Ala Thr Arg Gln Tyr Leu Phe Asp Glu Glu Ile Ala
    50                  55                  60

Gln Gln Val Ile Lys Leu Gln Asp Gln Val Leu Pro Thr Met Tyr Gln
65                  70                  75                  80

Gln Gly Gln Ser Gly Glu Phe Leu Lys Leu Asn Phe Thr Gly Asn Asp
                85                  90                  95

Ile Arg Trp Leu Leu Gly Leu Pro Arg Thr His His Arg Gln Arg Ile
            100                 105                 110

Ser Lys
```

```
<210> SEQ ID NO 121
<211> LENGTH: 372
<212> TYPE: DNA
<213> ORGANISM: Lactobacillus plantarum

<400> SEQUENCE: 121
ttgacgaata cagacaatcg ttattatcaa ccaaccgaca tcaaagatgc gcttcaaaca    60
atccaaaaat tatttaatac ttataccgat gccccattaa cacccgaatt aatggcctac    120
catcaaaaat tagttaatca gttagctact aatttattac cactagcaca acaacaacat    180
gacaaattac ggatcaccca aattaattca atgatggccg ttatgcaaga ttggctaaaa    240
ttaaggctga atggtcaagt cttcggcggc aaaatgcaac acttcaagtt tgtcagcaac    300
caaaaagcac agtacaaacg acgagtgcat aaaattcgtg gcaatcaaaa tcatcgtgct    360
agtcgccatt ga                                                         372
```

```
<210> SEQ ID NO 122
<211> LENGTH: 123
<212> TYPE: PRT
<213> ORGANISM: Lactobacillus plantarum

<400> SEQUENCE: 122
```

```
Met Thr Asn Thr Asp Asn Arg Tyr Tyr Gln Pro Thr Asp Ile Lys Asp
1               5                   10                  15

Ala Leu Gln Thr Ile Gln Lys Leu Phe Asn Thr Tyr Thr Asp Ala Pro
            20                  25                  30

Leu Thr Pro Glu Leu Met Ala Tyr His Gln Lys Leu Val Asn Gln Leu
        35                  40                  45

Ala Thr Asn Leu Leu Pro Leu Ala Gln Gln Gln His Asp Lys Leu Arg
```

```
                    50                  55                  60
Ile Thr Gln Ile Asn Ser Met Met Ala Val Met Gln Asp Trp Leu Lys
 65                  70                  75                  80

Leu Arg Leu Asn Gly Gln Val Phe Gly Gly Lys Met Gln His Phe Lys
                 85                  90                  95

Phe Val Ser Asn Gln Lys Ala Gln Tyr Lys Arg Arg Val His Lys Ile
                100                 105                 110

Arg Gly Asn Gln Asn His Arg Ala Ser Arg His
                115                 120

<210> SEQ ID NO 123
<211> LENGTH: 960
<212> TYPE: DNA
<213> ORGANISM: Lactobacillus plantarum

<400> SEQUENCE: 123
atggcttaca caataatca actacacgtt atttacggcg acgggagttt aggactacag      60
ggggctaatt tccactacct ctttagctac gaacgtggcg acttgaatc actcgtcgtc     120 aacgataaag agtggctcta tcgtacaccc acgccatct tttggcgggc gacaaccgat     180
aatgatcacg tagcggctt ttcagtcaaa tccgcacagt ggtacgcggc cgataagttc     240
tcaacttgtc aagatatcga attgacggtt gacgaccaac cagtcacacc gttaccaatc     300
gcgccactca ataacaaata cacggatcac gaaatcgcca cgaaagtctc actggcttac     360
cacttcgtta ccacgaccgt tcctagtacc atcgtcacag tgacttatac ggtgacagca     420
gacggtcaga tcaatatcgc cacccattat agcggtcagt ctgatttgcc agagctaccc     480
gcatttggtc tgcggtttat cataccaact accgcgaccg gcttcgacta taccggtttg     540
tccggtgaga cttatcctga ccggctggcc ggcgcaacgc acgggcgatt ccacgttgac     600
agtctgccag tcacaccata cttggtccca caagaatgcg gcatgcacat gcaaactgaa     660
caagtgacag taacgcgatc aacaacacaa ataacgctg accacgacaa cacaccgttc     720
agtttgacat ttagccaagc cgatgcacca ttcgccttca gctgccttcc ctataccgcc     780
gctgaactag aaaacgcaac gcacatggaa gaattaccat tagcacggcg aacggtctta     840
tcaatctacg gtgccgttcg tggggtcggt ggcattgata gttggggaac agacgtagaa     900
tccccatatc atatccccgc tgatcaagac attgacttca gctttaatat tcatttctaa     960

<210> SEQ ID NO 124
<211> LENGTH: 319
<212> TYPE: PRT
<213> ORGANISM: Lactobacillus plantarum

<400> SEQUENCE: 124

Met Ala Tyr Thr Asn Asn Gln Leu His Val Ile Tyr Gly Asp Gly Ser
  1               5                  10                  15

Leu Gly Leu Gln Gly Ala Asn Phe His Tyr Leu Phe Ser Tyr Glu Arg
                 20                  25                  30

Gly Gly Leu Glu Ser Leu Val Val Asn Asp Lys Glu Trp Leu Tyr Arg
             35                  40                  45

Thr Pro Thr Pro Ile Phe Trp Arg Ala Thr Thr Asp Asn Asp His Gly
         50                  55                  60

Ser Gly Phe Ser Val Lys Ser Ala Gln Trp Tyr Ala Ala Asp Lys Phe
 65                  70                  75                  80

Ser Thr Cys Gln Asp Ile Glu Leu Thr Val Asp Asp Gln Pro Val Thr
                 85                  90                  95
```

-continued

```
Pro Leu Pro Ile Ala Pro Leu Asn Asn Lys Tyr Thr Asp His Glu Ile
            100                 105                 110

Ala Thr Lys Val Ser Leu Ala Tyr His Phe Val Thr Thr Val Pro
        115                 120                 125

Ser Thr Ile Val Thr Val Thr Tyr Thr Val Ala Asp Gly Gln Ile
    130                 135                 140

Asn Ile Ala Thr His Tyr Ser Gly Gln Ser Asp Leu Pro Glu Leu Pro
145                 150                 155                 160

Ala Phe Gly Leu Arg Phe Ile Ile Pro Thr Thr Ala Thr Gly Phe Asp
                165                 170                 175

Tyr Thr Gly Leu Ser Gly Glu Thr Tyr Pro Asp Arg Leu Ala Gly Ala
                180                 185                 190

Thr His Gly Arg Phe His Val Asp Ser Leu Pro Val Thr Pro Tyr Leu
                195                 200                 205

Val Pro Gln Glu Cys Gly Met His Met Gln Thr Glu Gln Val Thr Val
    210                 215                 220

Thr Arg Ser Thr Thr Gln Asn Asn Ala Asp His Asp Asn Thr Pro Phe
225                 230                 235                 240

Ser Leu Thr Phe Ser Gln Ala Asp Ala Pro Phe Ala Phe Ser Cys Leu
                245                 250                 255

Pro Tyr Thr Ala Ala Glu Leu Glu Asn Ala Thr His Met Glu Glu Leu
                260                 265                 270

Pro Leu Ala Arg Arg Thr Val Leu Ser Ile Tyr Gly Ala Val Arg Gly
                275                 280                 285

Val Gly Gly Ile Asp Ser Trp Gly Thr Asp Val Glu Ser Pro Tyr His
    290                 295                 300

Ile Pro Ala Asp Gln Asp Ile Asp Phe Ser Phe Asn Ile His Phe
305                 310                 315
```

<210> SEQ ID NO 125
<211> LENGTH: 924
<212> TYPE: DNA
<213> ORGANISM: Lactobacillus plantarum

<400> SEQUENCE: 125

```
atgaggaggt ctaaaatgac atatttaatt ggcgttgact gtggtggcac gcacatcgtt      60
ggtcaaactt ggacgacagc ccccgagcat ctagtccaaa gcgttacggg tggccctggt     120
aacgttgtcc tagactactc tgctgccgtt actaacttaa ccactgtctt agaccagctc     180
actgccgcaa ttccagctag tcagcttggg ttgattttaa tcggaattgc tggcattgaa     240
actgctggcc gggctgatca ggtccaacaa accatcaccc aacgttacca cgctaatacc     300
caggtcataa gcgatgcaaa actggcccta ctgaacggtc ttgcaggagc agacggcgcc     360
ttagtgattg ccggcacggg ctcggtcgtt tatggccgcc aagccggaaa atttctgcgc     420
gttggcggct ggggttacgt tttaggtgac gaaggcagtg cctatgacat tagcaagcgg     480
gcacttaaac aggttctgac ccagactgat aacggtcaaa ctagtcaact aacagctccc     540
ctattggcac aacttaaagt taccgatatt gctgccgccg tccagaaatt ttacgctcaa     600
gatcgacaaa ctaacgctca attagcacag ttaatcgcca aactggccga gcaacaaaat     660
tctgaagcca tcacggtatt agtcacgtca gcccaagcac tggcacaaca agtcgttacc     720
ttatatcagc ggtttgcaga gtcctggcca acagggtcg ccctctctgg ttccgtttta     780
caacacaatc gcctggtccg cgacacgtta acgacgacag tgcaccagtc aataccaaca     840
```

```
attgctttta acgatattac aactaacaac gcccacgccg tcatctattg gcaccggtgg      900
actcaggagg aaattaattc atga                                            924
```

<210> SEQ ID NO 126
<211> LENGTH: 307
<212> TYPE: PRT
<213> ORGANISM: Lactobacillus plantarum

<400> SEQUENCE: 126

```
Met Arg Arg Ser Lys Met Thr Tyr Leu Ile Gly Val Asp Cys Gly Gly
1               5                   10                  15

Thr His Ile Val Gly Gln Thr Trp Thr Thr Ala Pro Glu His Leu Val
            20                  25                  30

Gln Ser Val Thr Gly Gly Pro Gly Asn Val Val Leu Asp Tyr Ser Ala
        35                  40                  45

Ala Val Thr Asn Leu Thr Thr Val Leu Asp Gln Leu Thr Ala Ala Ile
    50                  55                  60

Pro Ala Ser Gln Leu Gly Leu Ile Leu Gly Ile Ala Gly Ile Glu
65                  70                  75                  80

Thr Ala Gly Arg Ala Asp Gln Val Gln Gln Thr Ile Thr Gln Arg Tyr
                85                  90                  95

His Ala Asn Thr Gln Val Ile Ser Asp Ala Lys Leu Ala Leu Leu Asn
            100                 105                 110

Gly Leu Ala Gly Ala Asp Gly Ala Leu Val Ile Ala Gly Thr Gly Ser
        115                 120                 125

Val Val Tyr Gly Arg Gln Ala Gly Lys Phe Leu Arg Val Gly Gly Trp
    130                 135                 140

Gly Tyr Val Leu Gly Asp Glu Gly Ser Ala Tyr Asp Ile Ser Lys Arg
145                 150                 155                 160

Ala Leu Lys Gln Val Leu Thr Gln Thr Asp Asn Gly Gln Thr Ser Gln
                165                 170                 175

Leu Thr Ala Pro Leu Leu Ala Gln Leu Lys Val Thr Asp Ile Ala Ala
            180                 185                 190

Ala Val Gln Lys Phe Tyr Ala Gln Asp Arg Gln Thr Asn Ala Gln Leu
        195                 200                 205

Ala Gln Leu Ile Ala Lys Leu Ala Glu Gln Gln Asn Ser Glu Ala Ile
    210                 215                 220

Thr Val Leu Val Thr Ser Ala Gln Ala Leu Ala Gln Gln Val Val Thr
225                 230                 235                 240

Leu Tyr Gln Arg Phe Ala Glu Ser Trp Pro Gln Arg Val Ala Leu Ser
                245                 250                 255

Gly Ser Val Leu Gln His Asn Arg Leu Val Arg Asp Thr Leu Thr Thr
            260                 265                 270

Thr Val His Gln Ser Ile Pro Thr Ile Ala Phe Asn Asp Ile Thr Thr
        275                 280                 285

Asn Asn Ala His Ala Val Ile Tyr Trp His Arg Trp Thr Gln Glu Glu
    290                 295                 300

Ile Asn Ser
305
```

<210> SEQ ID NO 127
<211> LENGTH: 438
<212> TYPE: DNA
<213> ORGANISM: Lactobacillus plantarum

<400> SEQUENCE: 127

```
atgattaggt tatatacaca atcaagctgt cattcttcta gagttgcacg gcaatggttg      60
gaagcacatg ggattgagtt caaggagaaa aattttagtg ttgattcgcc cacggtgcaa     120
gatctaaaac gtattttgag tttaaccgaa catggtgtag acgatattat ctcagctcga     180
tctaaagact atcctgaaat tgcgcctaag ttacccgaaa tgccattgaa tgaggcactt     240
aaattgttgt gtgatcatcc gaagttgtta cgtcggccta tcatcattag tgatagtaaa     300
attcaagttg gctttaatga agatgatatt cgccaattta ttccacgacc agttcggcga     360
ctaaagttca atgcattgtt gagtcgtcta gatggtaata caggggatca cattattaat     420
aaaaggatgg tcgagtag                                                    438
```

<210> SEQ ID NO 128
<211> LENGTH: 145
<212> TYPE: PRT
<213> ORGANISM: Lactobacillus plantarum

<400> SEQUENCE: 128

```
Met Ile Arg Leu Tyr Thr Gln Ser Ser Cys His Ser Ser Arg Val Ala
1               5                   10                  15

Arg Gln Trp Leu Glu Ala His Gly Ile Glu Phe Lys Glu Lys Asn Phe
            20                  25                  30

Ser Val Asp Ser Pro Thr Val Gln Asp Leu Lys Arg Ile Leu Ser Leu
        35                  40                  45

Thr Glu His Gly Val Asp Asp Ile Ile Ser Ala Arg Ser Lys Asp Tyr
    50                  55                  60

Pro Glu Ile Ala Pro Lys Leu Pro Glu Met Pro Leu Asn Glu Ala Leu
65                  70                  75                  80

Lys Leu Leu Cys Asp His Pro Lys Leu Leu Arg Arg Pro Ile Ile Ile
                85                  90                  95

Ser Asp Ser Lys Ile Gln Val Gly Phe Asn Glu Asp Asp Ile Arg Gln
            100                 105                 110

Phe Ile Pro Arg Pro Val Arg Arg Leu Lys Phe Asn Ala Leu Leu Ser
        115                 120                 125

Arg Leu Asp Gly Asn Thr Gly Asp His Ile Ile Asn Lys Arg Met Val
    130                 135                 140

Glu
145
```

<210> SEQ ID NO 129
<211> LENGTH: 912
<212> TYPE: DNA
<213> ORGANISM: Lactobacillus plantarum

<400> SEQUENCE: 129

```
gatcttcgcg atttaatggc cattcctgac aactatcacg tgctcttctt tcaaggcggg      60
ggcacgctac agttcacagc tgcgccacta aatctggcgc tcatcatcg tatcgggttg     120 cttgacagcg gtcactgggc acaacgcgcc gccgatgaag ctaaacgggt cggtactaaa     180
gtcacgatac tggggagtag cgctgccaac cattttaacc aactgccaac ggtcgtccag     240
cccatcgatc aatccctcga ttatattcat cttacaacta ataatactat tgaaggaacc     300
atgatgacgc gcctgccagt tacgggtcaa gtaccactgg tagccgacat gtcatcaaac     360 ttttaggtg aaccttacca agtcagcgat tttgggctca tctttgctgg tgctcagaag     420
aatctgggtc ccgctggttt gacaatcgtc attgtccgtg atgatttaat tggtcaagtc     480
```

```
gccaacctgc caagcatgct ggattaccag ctattcgcgg ctaaagattc gatgttcaac    540
acgccgcctg tttttgctat ttacgccgcg ggtctcgtac tcaagtggct aaaggcccaa    600
ggcgggctca gcacaatgac tgctcgcaat cacgctaaag ccgccttact ctatgatttc    660
ttagaccagt cacaactatt tactaatcca gtcaagacca cgaccgttc gaccatgaac     720 gttccattcg tcacaggtca ggccgacctc gatgccgcag tcattcaagg cgcccgtgag    780
cacgggttat aaacctaaa gggtcaccgc ttagttggcg gtatgcgtgc cagcctctat     840
aacgccatgc cgttagccgg tgttcaggca ttagttgact atctagccgc ttttgaagca    900
caccatcgtt aa                                                        912
```

<210> SEQ ID NO 130
<211> LENGTH: 304
<212> TYPE: PRT
<213> ORGANISM: Lactobacillus plantarum

<400> SEQUENCE: 130

```
Gln Asp Leu Arg Asp Leu Met Ala Ile Pro Asp Asn Tyr His Val Leu
1               5                   10                  15

Phe Phe Gln Gly Gly Gly Thr Leu Gln Phe Thr Ala Ala Pro Leu Asn
            20                  25                  30

Leu Ala Pro His His Arg Ile Gly Leu Leu Asp Ser Gly His Trp Ala
        35                  40                  45

Gln Arg Ala Ala Asp Glu Ala Lys Arg Val Gly Thr Lys Val Thr Ile
    50                  55                  60

Leu Gly Ser Ser Ala Ala Asn His Phe Asn Gln Leu Pro Thr Val Val
65                  70                  75                  80

Gln Pro Ile Asp Gln Ser Leu Asp Tyr Ile His Leu Thr Thr Asn Asn
                85                  90                  95

Thr Ile Glu Gly Thr Met Met Thr Arg Leu Pro Val Thr Gly Gln Val
            100                 105                 110

Pro Leu Val Ala Asp Met Ser Ser Asn Phe Leu Gly Glu Pro Tyr Gln
        115                 120                 125

Val Ser Asp Phe Gly Leu Ile Phe Ala Gly Ala Gln Lys Asn Leu Gly
    130                 135                 140

Pro Ala Gly Leu Thr Ile Val Ile Val Arg Asp Asp Leu Ile Gly Gln
145                 150                 155                 160

Val Ala Asn Leu Pro Ser Met Leu Asp Tyr Gln Leu Phe Ala Ala Lys
                165                 170                 175

Asp Ser Met Phe Asn Thr Pro Pro Val Phe Ala Ile Tyr Ala Ala Gly
            180                 185                 190

Leu Val Leu Lys Trp Leu Lys Ala Gln Gly Gly Leu Ser Thr Met Thr
        195                 200                 205

Ala Arg Asn His Ala Lys Ala Ala Leu Leu Tyr Asp Phe Leu Asp Gln
    210                 215                 220

Ser Gln Leu Phe Thr Asn Pro Val Lys Thr Ser Asp Arg Ser Thr Met
225                 230                 235                 240

Asn Val Pro Phe Val Thr Gly Gln Ala Asp Leu Asp Ala Ala Val Ile
                245                 250                 255

Gln Gly Ala Arg Glu His Gly Leu Leu Asn Leu Lys Gly His Arg Leu
            260                 265                 270

Val Gly Gly Met Arg Ala Ser Leu Tyr Asn Ala Met Pro Leu Ala Gly
        275                 280                 285

Val Gln Ala Leu Val Asp Tyr Leu Ala Ala Phe Glu Ala His His Arg
```

<210> SEQ ID NO 131
<211> LENGTH: 380
<212> TYPE: DNA
<213> ORGANISM: Lactobacillus plantarum

<400> SEQUENCE: 131

```
ggatcgaagg gaccattacg ccggctagtg gcacaattga tcgcccgatt ggccgggtgg      60
ctgacagtcc tcggcgagtg gtcaccacgg cgggccaacg cgccattacg acgtatcaag     120
tggaggcgga ccaattgcag cataacgtga gtcggttacg gttggaactt gtgactggac     180
ggacgcatca aattcgggtc catctaacga cgcttgggca ccccttatta ggtgatgcgc     240
tgtatggcgg taacttgggg tggattcaac ggcaagcctt acacgccgct agtttacagt     300
tctttgaccc cttttcggaa cagactttac actttgaggc ggcattgcca gctgatctgc     360
aagccttgaa tcacgactaa                                                 380
```

<210> SEQ ID NO 132
<211> LENGTH: 126
<212> TYPE: PRT
<213> ORGANISM: Lactobacillus plantarum

<400> SEQUENCE: 132

```
Trp Ile Glu Gly Thr Ile Thr Pro Ala Ser Gly Thr Ile Asp Arg Pro
1               5                  10                  15

Ile Gly Arg Val Ala Asp Ser Pro Arg Arg Val Val Thr Thr Ala Gly
            20                  25                  30

Gln Arg Ala Ile Thr Thr Tyr Gln Val Glu Ala Asp Gln Leu Gln His
        35                  40                  45

Asn Val Ser Arg Leu Arg Leu Glu Leu Val Thr Gly Arg Thr His Gln
    50                  55                  60

Ile Arg Val His Leu Thr Thr Leu Gly His Pro Leu Leu Gly Asp Ala
65                  70                  75                  80

Leu Tyr Gly Gly Asn Leu Gly Trp Ile Gln Arg Gln Ala Leu His Ala
                85                  90                  95

Ala Ser Leu Gln Phe Phe Asp Pro Phe Ser Glu Gln Thr Leu His Phe
            100                 105                 110

Glu Ala Ala Leu Pro Ala Asp Leu Gln Ala Leu Asn His Asp
        115                 120                 125
```

<210> SEQ ID NO 133
<211> LENGTH: 372
<212> TYPE: DNA
<213> ORGANISM: Lactobacillus plantarum

<400> SEQUENCE: 133

```
atgcaagttt ttggacaatt tattgcaaca gtcggttggc taggattggc actagtcgcc      60
agcgaactag gtgcgacgtt aatccattgg ctcggtcagt gggtcggatt cgattaatt     120
ggtgctcgaa ttgtccggat taccggtttt cgacttcaat taagtcgggt tcgtggtcat     180
tggaaattag aacgaccgct gacgcgtcat ccacatatcg tggcagcacc ctcggcggat     240
gccaaacggt tcaatcacgc catttattgt tttggcggtg gcctgttcaa cttactgacg     300
gtcatgctca gtttaataac tctgaatcaa tttaagttta gtttcgattt atggttgttt     360
gcgttcatta tt                                                         372
```

<210> SEQ ID NO 134
<211> LENGTH: 124
<212> TYPE: PRT
<213> ORGANISM: Lactobacillus plantarum

<400> SEQUENCE: 134

Met Gln Val Phe Gly Gln Phe Ile Ala Thr Val Gly Trp Leu Gly Leu
1               5                   10                  15

Ala Leu Val Ala Ser Glu Leu Gly Ala Thr Leu Ile His Trp Leu Gly
            20                  25                  30

Gln Trp Val Gly Phe Arg Leu Ile Gly Ala Arg Ile Val Arg Ile Thr
        35                  40                  45

Gly Phe Arg Leu Gln Leu Ser Arg Val Arg Gly His Trp Lys Leu Glu
    50                  55                  60

Arg Pro Leu Thr Arg His Pro His Ile Val Ala Ala Pro Ser Ala Asp
65                  70                  75                  80

Ala Lys Arg Phe Asn His Ala Ile Tyr Cys Phe Gly Gly Leu Phe
                85                  90                  95

Asn Leu Leu Thr Val Met Leu Ser Leu Ile Thr Leu Asn Gln Phe Lys
            100                 105                 110

Phe Ser Phe Asp Leu Trp Leu Phe Ala Phe Ile Ile
        115                 120

<210> SEQ ID NO 135
<211> LENGTH: 894
<212> TYPE: DNA
<213> ORGANISM: Lactobacillus plantarum

<400> SEQUENCE: 135
gatccattgt cgactttgtt gccgcgccgt aatcaaacag tgcatctaaa gtatcgttct      60
gcacagacga cggcggagct acgcaagacg ctacgtcaag cacggtattt acaggccggt     120
actcagaata ccgccacgcc ggtctttcaa aatcgacagc agcgaggtga tgcgacaacg     180
tacggtcgta tcagtaccag ccaagacggc cggatatgga cgaaactacc cattagttat     240
ccgcatgtgc aattgtcacg gccgagtgtc tggtacgcga atggccgctt gacgttgata     300
gatgggaaag accgttactg gacgactaat tttaaagatt ggcaacatca acggttgaac     360
tttaacgggg ctgattttaa gcaaggtcgg gttcaggccg tctttccagg tacgactcgt     420
tcagcggttg ttgtggttcg cggcattgat cgccaaagca gtcgcgccaa actctattat     480
ggacagctca cgaagactgg acgggtcaaa gcttggcacg cgttacaact aggaaagctc     540
ccagcgcgcc aagtcgctgg aatgagcttg attgatcaac actatatacct gtttcttcag     600
cgcggtacgc agttggccat ttatcgtgcc aatcggttga cgcgtccggt caggttggtt     660
ggtcgcgtta agctaaatca tgcgcagtca caacagagtga ccgcggtgaa tttgataccg     720
accaccaagc atcgctaccg gttaatattt gacttgacga cagctgaaaa agttcagaaa     780
cagccacgtt atcggttact tgatcggcga tttaaagcag tggggcagca gcatctattg     840
gtcactgatt atctctggag ccaatttcaa attagtctac gtgggagtga gtga          894

<210> SEQ ID NO 136
<211> LENGTH: 297
<212> TYPE: PRT
<213> ORGANISM: Lactobacillus plantarum

<400> SEQUENCE: 136

Asp Pro Leu Ser Thr Leu Leu Pro Arg Arg Asn Gln Thr Val His Leu
1               5                   10                  15

```
Lys Tyr Arg Ser Ala Gln Thr Thr Ala Glu Leu Arg Lys Thr Leu Arg
         20                  25                  30

Gln Ala Arg Tyr Leu Gln Ala Gly Thr Gln Asn Thr Ala Thr Pro Val
         35                  40                  45

Phe Gln Asn Arg Gln Arg Gly Asp Ala Thr Thr Tyr Gly Arg Ile
 50                  55                  60

Ser Thr Ser Gln Asp Gly Arg Ile Trp Thr Lys Leu Pro Ile Ser Tyr
 65                  70                  75                  80

Pro His Val Gln Leu Ser Arg Pro Ser Val Trp Tyr Ala Asn Gly Arg
                 85                  90                  95

Leu Thr Leu Ile Asp Gly Lys Asp Arg Tyr Trp Thr Thr Asn Phe Lys
                100                 105                 110

Asp Trp Gln His Gln Arg Leu Asn Phe Asn Gly Ala Asp Phe Lys Gln
                115                 120                 125

Gly Arg Val Gln Ala Val Phe Pro Gly Thr Thr Arg Ser Ala Val Val
130                 135                 140

Val Val Arg Gly Ile Asp Arg Gln Ser Ser Arg Ala Lys Leu Tyr Tyr
145                 150                 155                 160

Gly Gln Leu Thr Lys Thr Gly Arg Val Lys Ala Trp His Ala Leu Gln
                165                 170                 175

Leu Gly Lys Leu Pro Ala Arg Gln Val Ala Gly Met Ser Leu Ile Asp
                180                 185                 190

Gln His Leu Tyr Leu Phe Leu Gln Arg Gly Thr Gln Leu Ala Ile Tyr
                195                 200                 205

Arg Ala Asn Arg Leu Thr Arg Pro Val Arg Leu Gly Arg Val Lys
                210                 215                 220

Leu Asn His Ala Gln Ser Gln Arg Val Thr Ala Val Asn Leu Ile Pro
225                 230                 235                 240

Thr Thr Lys His Arg Tyr Arg Leu Ile Phe Asp Leu Thr Thr Ala Glu
                245                 250                 255

Lys Val Gln Lys Gln Pro Arg Tyr Arg Leu Leu Asp Arg Arg Phe Lys
                260                 265                 270

Ala Val Gly Gln Gln His Leu Leu Val Thr Asp Tyr Leu Trp Ser Gln
                275                 280                 285

Phe Gln Ile Ser Leu Arg Gly Ser Glu
                290                 295

<210> SEQ ID NO 137
<211> LENGTH: 330
<212> TYPE: DNA
<213> ORGANISM: Lactobacillus plantarum

<400> SEQUENCE: 137
atgatgagac gtaggggagc aagtatgcag cagcaccgta atgtgctcta tctgattatc      60
ttcggaatct acttagcctc agtcacacta cagacgacga cctttaacga gatgataccg     120
catcgagtgg gcgttttgat tgaattagcg actttggccg cattactggg cctcgtggtt     180
tgcttagata ccttgacccc cggccaaatt attggagaag tcagtttact tgtactggtg     240
actgtcgtga cactcacatc gggtgcgcat tatttgatgc cgacaatcat gttggtgatt     300
gcagcccggg aagtttcgtt tcggcagatc                                      330

<210> SEQ ID NO 138
<211> LENGTH: 110
<212> TYPE: PRT
```

<213> ORGANISM: Lactobacillus plantarum

<400> SEQUENCE: 138

```
Met Met Arg Arg Arg Gly Ala Ser Met Gln Gln His Arg Asn Val Leu
1               5                   10                  15
Tyr Leu Ile Ile Phe Gly Ile Tyr Leu Ala Ser Val Thr Leu Gln Thr
            20                  25                  30
Thr Thr Phe Asn Glu Met Ile Pro His Arg Val Gly Val Leu Ile Glu
        35                  40                  45
Leu Ala Thr Leu Ala Ala Leu Leu Gly Leu Val Val Cys Leu Asp Thr
    50                  55                  60
Leu Thr Pro Gly Gln Ile Ile Gly Glu Val Ser Leu Leu Val Leu Val
65                  70                  75                  80
Thr Val Val Thr Leu Thr Ser Gly Ala His Tyr Leu Met Pro Thr Ile
                85                  90                  95
Met Leu Val Ile Ala Ala Arg Glu Val Ser Phe Arg Gln Ile
            100                 105                 110
```

<210> SEQ ID NO 139
<211> LENGTH: 1033
<212> TYPE: DNA
<213> ORGANISM: Lactobacillus plantarum

<400> SEQUENCE: 139

```
atgagtaatc atcaaatccg cttgtcctta tcaatcatca ccagttgctt gttggcaact     60
ctgattatcg gccgttagt cgccctgatt ggtcaaacac tagtcgggca atcgccaagc    120
cagctatggt cacaactgac gcagccaacc aaccgtgtga gcattcaaca cagtctgttc    180
ctcagtgggg gcacggtcgt cgggacaacc ctgctagcca cccctttggc atggatcatg    240
acgcacaccc gtttaacaaa gctcgcctgg ttgcattggc tcttgttagt gccattcatg    300
acaccaccat atattaacgc gatgggctgg ttatatttct ttcaaccaca cggattactg    360
gctcagctta atccgagttg gcaccaccaa tttcagtggc tattttcacc gttcgggatg    420
gtcattatca tgagtctgca tttgtatccc gtggcatact taggcttacg cgcagccctc    480
atgcaattca accagcgctg gcttcaagcg gccgaagttc atggggtcaa cacctggcaa    540
cgactagtgc gaatcacatt accaatcatg ttagtcccat acttagctgt atggattta     600
gtctttacca aaaccttggc tgaatttgga acgccagcca cctttggtcg agcatccac     660
ttcgaagttc tgacgactac gattcaaagg gacctcagtc agtggccctt agatttccaa    720
aacgggtac tcaccggcac cctcctactg accattgccc tgattgcctg ggtatccag     780
caatggttgt tacgccggcc agctgttaag ttcaccggac aacggtcagc gtcacaatat    840
cggcagcttg gagtgacaac attagcaggc actttcgtca ccctagtcat cagtattgct    900
attgtcctgc cattcagtgc catcgtgctc caatcgctac tcaaacaacg cagtcttggt    960
tggagtccgt ctaatttgac acttgtacac tatatagacc tcttacgctt tgatagtcct   1020
gcctggcagg cca                                                      1033
```

<210> SEQ ID NO 140
<211> LENGTH: 344
<212> TYPE: PRT
<213> ORGANISM: Lactobacillus plantarum

<400> SEQUENCE: 140

```
Met Ser Asn His Gln Ile Arg Leu Ser Leu Ser Ile Ile Thr Ser Cys
1               5                   10                  15
```

Leu Leu Ala Thr Leu Ile Ile Gly Pro Leu Val Ala Leu Ile Gly Gln
            20                  25                  30

Thr Leu Val Gly Gln Ser Pro Ser Gln Leu Trp Ser Gln Leu Thr Gln
        35                  40                  45

Pro Thr Asn Arg Val Ser Ile Gln His Ser Leu Phe Leu Ser Gly Gly
    50                  55                  60

Thr Val Val Gly Thr Thr Leu Leu Ala Thr Pro Leu Ala Trp Ile Met
65                  70                  75                  80

Thr His Thr Arg Leu Thr Lys Leu Ala Trp Leu His Trp Leu Leu Leu
                85                  90                  95

Val Pro Phe Met Thr Pro Pro Tyr Ile Asn Ala Met Gly Trp Leu Tyr
            100                 105                 110

Phe Phe Gln Pro His Gly Leu Leu Ala Gln Leu Asn Pro Ser Trp His
        115                 120                 125

His Gln Phe Gln Trp Leu Phe Ser Pro Phe Gly Met Val Ile Ile Met
    130                 135                 140

Ser Leu His Leu Tyr Pro Val Ala Tyr Leu Gly Leu Arg Ala Ala Leu
145                 150                 155                 160

Met Gln Phe Asn Gln Arg Trp Leu Gln Ala Ala Glu Val His Gly Val
                165                 170                 175

Asn Thr Trp Gln Arg Leu Val Arg Ile Thr Leu Pro Ile Met Leu Val
            180                 185                 190

Pro Tyr Leu Ala Val Trp Ile Leu Val Phe Thr Lys Thr Leu Ala Glu
        195                 200                 205

Phe Gly Thr Pro Ala Thr Phe Gly Arg Ser Ile His Phe Glu Val Leu
    210                 215                 220

Thr Thr Thr Ile Gln Arg Asp Leu Ser Gln Trp Pro Leu Asp Phe Gln
225                 230                 235                 240

Asn Gly Val Leu Thr Gly Thr Leu Leu Leu Thr Ile Ala Leu Ile Ala
                245                 250                 255

Trp Gly Ile Gln Gln Trp Leu Leu Arg Arg Pro Ala Val Lys Phe Thr
            260                 265                 270

Gly Gln Arg Ser Ala Ser Gln Tyr Arg Gln Leu Gly Val Thr Thr Leu
        275                 280                 285

Ala Gly Thr Phe Val Thr Leu Val Ile Ser Ile Ala Ile Val Leu Pro
    290                 295                 300

Phe Ser Ala Ile Val Leu Gln Ser Leu Leu Lys Gln Arg Ser Leu Gly
305                 310                 315                 320

Trp Ser Pro Ser Asn Leu Thr Leu Val His Tyr Ile Asp Leu Leu Arg
                325                 330                 335

Phe Asp Ser Pro Ala Trp Gln Ala
            340

<210> SEQ ID NO 141
<211> LENGTH: 838
<212> TYPE: DNA
<213> ORGANISM: Lactobacillus plantarum

<400> SEQUENCE: 141
cggttttgaa gccaaaactg gcattaaagt caaaagtttt gacggcacga ccgggaaaat      60
tttaagtaag gtcaaggccg agcaaggcaa tccccaagct gatgtgctga ttttagcttc     120
aatggccgct ggcgtcgatt tacaaaagaa tggccagcta ttaacctatc agccttctca     180
agctaaacac ctgaataaac aatttaaaga tactagccac cagttgatca attacagtgc     240

```
ttcggcagtc ggcatcacct acaatacgcg gcacatcaaa tcggcaccga cagactggtc    300
tgacttgaca accgctccgt atcgcaatca agtgaccatt ccggaccccc aaacctctgg    360
ttctagcttg gacttcatta acgcttatca aatgaaacac ggtacgcaac tacttaaagc    420
ccttcaagaa aacggtgccg atatcggggg tgctaacaag gaagtactcg atgcagtcat    480
cactggccaa aaatcgccg tctttggtgg ggtcgattac atgagtctaa cagctattaa    540
aaaaggcgaa aaaattggtt tcgtttatcc taagagtggg actttggtca atccacgacc    600
ggcgatgatt ttgaaggcta gtcgtcatca agccgccgcc aaacaattta ttgactatct    660
cttatcagct aaagttcaaa gacagattca aaaagtaac  ttaattccag gtaccacgag    720
cactttgacc gatccacgca atggcgaagc catcaaagcc tacacggtca attggaccag    780
tgccaacgcg ccctgacca aaaacgttgt cgcattcaat caggtcttta gccaatga     838
```

<210> SEQ ID NO 142
<211> LENGTH: 278
<212> TYPE: PRT
<213> ORGANISM: Lactobacillus plantarum

<400> SEQUENCE: 142

```
Gly Phe Glu Ala Lys Thr Gly Ile Lys Val Lys Ser Phe Asp Gly Thr
1               5                   10                  15

Thr Gly Lys Ile Leu Ser Lys Val Lys Ala Glu Gln Gly Asn Pro Gln
            20                  25                  30

Ala Asp Val Leu Ile Leu Ala Ser Met Ala Ala Gly Val Asp Leu Gln
        35                  40                  45

Lys Asn Gly Gln Leu Leu Thr Tyr Gln Pro Ser Gln Ala Lys His Leu
    50                  55                  60

Asn Lys Gln Phe Lys Asp Thr Ser His Gln Leu Ile Asn Tyr Ser Ala
65                  70                  75                  80

Ser Ala Val Gly Ile Thr Tyr Asn Thr Arg His Ile Lys Ser Ala Pro
                85                  90                  95

Thr Asp Trp Ser Asp Leu Thr Thr Ala Pro Tyr Arg Asn Gln Val Thr
            100                 105                 110

Ile Pro Asp Pro Gln Thr Ser Gly Ser Ser Leu Asp Phe Ile Asn Ala
        115                 120                 125

Tyr Gln Met Lys His Gly Thr Gln Leu Leu Lys Ala Leu Gln Glu Asn
    130                 135                 140

Gly Ala Asp Ile Gly Gly Ala Asn Lys Glu Val Leu Asp Ala Val Ile
145                 150                 155                 160

Thr Gly Gln Lys Ile Ala Val Phe Gly Gly Val Asp Tyr Met Ser Leu
                165                 170                 175

Thr Ala Ile Lys Lys Gly Glu Lys Ile Gly Phe Val Tyr Pro Lys Ser
            180                 185                 190

Gly Thr Leu Val Asn Pro Arg Pro Ala Met Ile Leu Lys Ala Ser Arg
        195                 200                 205

His Gln Ala Ala Ala Lys Gln Phe Ile Asp Tyr Leu Leu Ser Ala Lys
    210                 215                 220

Val Gln Arg Gln Ile Gln Lys Ser Asn Leu Ile Pro Gly Thr Thr Ser
225                 230                 235                 240

Thr Leu Thr Asp Pro Arg Asn Gly Glu Ala Ile Lys Ala Tyr Thr Val
                245                 250                 255

Asn Trp Thr Ser Ala Asn Ala Ala Leu Thr Lys Asn Val Val Ala Phe
            260                 265                 270
```

Asn Gln Val Phe Ser Gln
        275

<210> SEQ ID NO 143
<211> LENGTH: 166
<212> TYPE: DNA
<213> ORGANISM: Lactobacillus plantarum

<400> SEQUENCE: 143
gatcgcacgt aatgggcaag tcaccgtggc ttttgatgcg cagcacgatg ccatcatgga    60
attcgattta ccagtcaatt accaacggga gtttcccgag acggtggcag tcttagacga   120
tggtcagtat cagaccatga tgttgatgga cgaactctcc gtctga                  166

<210> SEQ ID NO 144
<211> LENGTH: 54
<212> TYPE: PRT
<213> ORGANISM: Lactobacillus plantarum

<400> SEQUENCE: 144

Ile Ala Arg Asn Gly Gln Val Thr Val Ala Phe Asp Ala Gln His Asp
1               5                   10                  15

Ala Ile Met Glu Phe Asp Leu Pro Val Asn Tyr Gln Arg Glu Phe Pro
            20                  25                  30

Glu Thr Val Ala Val Leu Asp Asp Gly Gln Tyr Gln Thr Met Met Leu
        35                  40                  45

Met Asp Glu Leu Ser Val
    50

<210> SEQ ID NO 145
<211> LENGTH: 504
<212> TYPE: DNA
<213> ORGANISM: Lactobacillus plantarum

<400> SEQUENCE: 145
gtgtgtctaa tggcgaaaac agcagtgtgc attgtcgatc aacaacgtta ccaagttgtg    60
gacggtatgc gattagaaga attggaaact agtttgcggc aaatgatttt aaaagatttt   120
ccgcaggccc ataatagcag tttcatttgt agtgagcatc tcgtacatta tcgcttagca   180
aagatggatg cgatgatcga gaacgattat caacaaaatg ataaggtcaa tgcgcaatta   240
tctaagattc tcgctaacca cacgtatcgg gtcgtcgatg ttaatagcga gctggaaagt   300
tcattgacat ttggtcaacg ggtcgcggat ggggtcgcac ggttcggggg gagctgggcg   360
tttatcattt cgtttgtcgt ggtgatgctc gtgtggatgt tgctcaacgt cttaccaatt   420
tttagccatc attttgaccc ttatcccttt attttattaa atttattttt aagcatggtc   480
gcagcaatcc aggcaccatt gatc                                          504

<210> SEQ ID NO 146
<211> LENGTH: 168
<212> TYPE: PRT
<213> ORGANISM: Lactobacillus plantarum

<400> SEQUENCE: 146

Val Cys Leu Met Ala Lys Thr Ala Val Cys Ile Val Asp Gln Gln Arg
1               5                   10                  15

Tyr Gln Val Val Asp Gly Met Arg Leu Glu Glu Leu Glu Thr Ser Leu
            20                  25                  30

Arg Gln Met Ile Leu Lys Asp Phe Pro Gln Ala His Asn Ser Ser Phe

```
              35                  40                  45
Ile Cys Ser Glu His Leu Val His Tyr Arg Leu Ala Lys Met Asp Ala
         50                  55                  60

Met Ile Glu Asn Asp Tyr Gln Gln Asn Asp Lys Val Asn Ala Gln Leu
 65                  70                  75                  80

Ser Lys Ile Leu Ala Asn His Thr Tyr Arg Val Val Asp Val Asn Ser
                 85                  90                  95

Glu Leu Glu Ser Ser Leu Thr Phe Gly Gln Arg Val Ala Asp Gly Val
                100                 105                 110

Ala Arg Phe Gly Gly Ser Trp Ala Phe Ile Ile Ser Phe Val Val Val
            115                 120                 125

Met Leu Val Trp Met Leu Leu Asn Val Leu Pro Ile Phe Ser His His
        130                 135                 140

Phe Asp Pro Tyr Pro Phe Ile Leu Leu Asn Leu Phe Leu Ser Met Val
145                 150                 155                 160

Ala Ala Ile Gln Ala Pro Leu Ile
                165

<210> SEQ ID NO 147
<211> LENGTH: 1965
<212> TYPE: DNA
<213> ORGANISM: Lactobacillus plantarum

<400> SEQUENCE: 147
gatcaagtca gctatcagcg tcgtcgcgac ttagctcgta agtatgagtt acagcgatta      60
atgacgactg gtagtcacgt gaatatgagc ttgaatgaag ctttattcac ccgtttatat     120
actgagactt ccatcagca gtatcacagt tatgttgact ttcgcaatgc aatttatctg     180
aaagtcgctc agggattggt gcgcatgaac tggctgattc agtatttatt tggcgcttca     240
ccacgcctag ccgttacgga tactacgagt cgtccacagc gcagtagtgt tcaacatccc     300
gatggtcgct acagtcaagt gacgggagac tatacgtcaa ttgatcgcta cgtggccaag     360
ttgacggcgg ctgttcgtca acagcagttg ttgtctgtca atgattttga cgggccagtt     420
cggcttcgga gtaatgggca gctagctatg atggcccggc aggggtcta ttatcttgaa     480 taccggggct tggatctcga tccaactagt ccagtcgggg tggacgcgaa cgcggtggca     540
tttgttcgtt tgttggcgag ttatttcgta atgatgccgg cacttccagc taagatggta     600
tcccaagtca acgctcaagc tgaccaattg acccgtcaag ttttgggtga aaatccaacg     660
acggctagtg ctcaggccgt gccggctgtt caagttttag atgcacttgc tgattttgtt     720
aaaacctatg gcctaccaaa tgaagatgcc gtgttactca aacagttgaa gtcgtgggtc     780
actgatccaa agaagacgct gagtgcgcag attgccatgc aagccgatcc gttagcatgg     840
gcactcgaac gggctgcacg ctatcaggaa tcgagcaatg aacgtccgtt tgaacttgcg     900
ggctttaccg cgctagatct atcgagccag caactagccc agcaggcctt gacgcgggga     960
gtgcaggtgg acgttgttga cccacacgct aacattttac gattgactaa gttaggacgg    1020
tcgcaattag ttgtgaatgg gagcggaacg gatttaaatc cacaggcgct aacgaccgta    1080
ctgacacata aagcagcggc caaacaaatt ctggctgagc acggggttcc ggtgccggct    1140
tcacagacat atcatacagc taatcagttg attgctgatt atgatcggta cgttcaagct    1200
ggtgggatcg tattaaaagc ggcggatgag tcgcacaaag taattgtctt tcggattatg    1260
cccgaacgcg gactgtttga acaagtcgtc cggcaactat tcgagcaaac gtccgcggta    1320
atggccgagg aagtggtagt cgcatcaagt tatcgctttt tggttatcga tagtcgtgtg    1380
```

-continued

```
caagcaatcg tcgaacgaat tccagccaat attgttggtg atggtcgctc aacggtcaag   1440
acgttacttg atcgcaaaaa tggtcgagcg ttgcgcggga ccgcttttaa gtggcctcaa   1500
tcagcgctac agttaggaac gatcgaacgg tatcgcctgg actcatatca cttgacctta   1560
gattctgtgg tcagccgggg aactcagatc ttattacgag aggatgcgac ttttggtaac   1620
ggggcggacg tgctagacgc gacggctgat atgcatcaat cctatgtgca ggcggtggaa   1680
aagttggtag cagacttaca cttggcggtc gctggggtcg acgtgatgat tcccaatctc   1740
tatgccgaat tagtgccaga gcatcctgaa atggcggtat acttgggtat tcatgcggcg   1800
ccgtacttgt atccgcactt gttcccaatg tttggtactg cccaaccagt ggcggggcag   1860
ttgttggatg cattgtttaa aaatgaagat taaaaacaag aaagctggcc ttgtccagct   1920
tttttgatag ctcataatta agtgtcatga ttgaaaacac ccatt              1965
```

<210> SEQ ID NO 148
<211> LENGTH: 630
<212> TYPE: PRT
<213> ORGANISM: Lactobacillus plantarum

<400> SEQUENCE: 148

```
Asp Gln Val Ser Tyr Gln Arg Arg Arg Asp Leu Ala Arg Lys Tyr Glu
1               5                   10                  15

Leu Gln Arg Leu Met Thr Thr Gly Ser His Val Asn Met Ser Leu Asn
            20                  25                  30

Glu Ala Leu Phe Thr Arg Leu Tyr Thr Glu Thr Phe His Gln Gln Tyr
        35                  40                  45

His Ser Tyr Val Asp Phe Arg Asn Ala Ile Tyr Leu Lys Val Ala Gln
    50                  55                  60

Gly Leu Val Arg Met Asn Trp Leu Ile Gln Tyr Leu Phe Gly Ala Ser
65                  70                  75                  80

Pro Arg Leu Ala Val Thr Asp Thr Thr Ser Arg Pro Gln Arg Ser Ser
                85                  90                  95

Val Gln His Pro Asp Gly Arg Tyr Ser Gln Val Thr Gly Asp Tyr Thr
            100                 105                 110

Ser Ile Asp Arg Tyr Val Ala Lys Leu Thr Ala Val Arg Gln Gln
        115                 120                 125

Gln Leu Leu Ser Val Asn Asp Phe Asp Gly Pro Val Arg Leu Arg Ser
    130                 135                 140

Asn Gly Gln Leu Ala Met Met Ala Arg Gln Gly Val Tyr Tyr Leu Glu
145                 150                 155                 160

Tyr Arg Gly Leu Asp Leu Asp Pro Thr Ser Pro Val Gly Val Asp Ala
                165                 170                 175

Asn Ala Val Ala Phe Val Arg Leu Leu Ala Ser Tyr Phe Val Met Met
            180                 185                 190

Pro Ala Leu Pro Ala Lys Met Val Ser Gln Val Asn Ala Gln Ala Asp
        195                 200                 205

Gln Leu Thr Arg Gln Val Leu Gly Glu Asn Pro Thr Thr Ala Ser Ala
    210                 215                 220

Gln Ala Val Pro Ala Val Gln Val Leu Asp Ala Leu Ala Asp Phe Val
225                 230                 235                 240

Lys Thr Tyr Gly Leu Pro Asn Glu Asp Ala Val Leu Leu Lys Gln Leu
                245                 250                 255

Lys Ser Trp Val Thr Asp Pro Lys Lys Thr Leu Ser Ala Gln Ile Ala
            260                 265                 270
```

Met Gln Ala Asp Pro Leu Ala Trp Ala Leu Glu Arg Ala Ala Arg Tyr
            275                 280                 285

Gln Glu Ser Ser Asn Glu Arg Pro Phe Glu Leu Ala Gly Phe Thr Ala
        290                 295                 300

Leu Asp Leu Ser Ser Gln Gln Leu Ala Gln Ala Leu Thr Arg Gly
305                 310                 315                 320

Val Gln Val Asp Val Asp Pro His Ala Asn Ile Leu Arg Leu Thr
                325                 330                 335

Lys Leu Gly Arg Ser Gln Leu Val Val Asn Gly Ser Gly Thr Asp Leu
                340                 345                 350

Asn Pro Gln Ala Leu Thr Thr Val Leu Thr His Lys Ala Ala Lys
            355                 360                 365

Gln Ile Leu Ala Glu His Gly Val Pro Val Pro Ala Ser Gln Thr Tyr
            370                 375                 380

His Thr Ala Asn Gln Leu Ile Ala Asp Tyr Asp Arg Tyr Val Gln Ala
385                 390                 395                 400

Gly Gly Ile Val Leu Lys Ala Ala Asp Glu Ser His Lys Val Ile Val
                405                 410                 415

Phe Arg Ile Met Pro Glu Arg Gly Leu Phe Glu Gln Val Val Arg Gln
            420                 425                 430

Leu Phe Glu Gln Thr Ser Ala Val Met Ala Glu Val Val Ala
            435                 440                 445

Ser Ser Tyr Arg Phe Leu Val Ile Asp Ser Arg Val Gln Ala Ile Val
            450                 455                 460

Glu Arg Ile Pro Ala Asn Ile Val Gly Asp Gly Arg Ser Thr Val Lys
465                 470                 475                 480

Thr Leu Leu Asp Arg Lys Asn Gly Arg Ala Leu Arg Gly Thr Ala Phe
                485                 490                 495

Lys Trp Pro Gln Ser Ala Leu Gln Leu Gly Thr Ile Glu Arg Tyr Arg
            500                 505                 510

Leu Asp Ser Tyr His Leu Thr Leu Asp Ser Val Val Ser Arg Gly Thr
            515                 520                 525

Gln Ile Leu Leu Arg Glu Asp Ala Thr Phe Gly Asn Gly Ala Asp Val
            530                 535                 540

Leu Asp Ala Thr Ala Asp Met His Gln Ser Tyr Val Gln Ala Val Glu
545                 550                 555                 560

Lys Leu Val Ala Asp Leu His Leu Ala Val Ala Gly Val Asp Val Met
                565                 570                 575

Ile Pro Asn Leu Tyr Ala Glu Leu Val Pro Glu His Pro Glu Met Ala
            580                 585                 590

Val Tyr Leu Gly Ile His Ala Ala Pro Tyr Leu Tyr Pro His Leu Phe
            595                 600                 605

Pro Met Phe Gly Thr Ala Gln Pro Val Ala Gly Gln Leu Leu Asp Ala
610                 615                 620

Leu Phe Lys Asn Glu Asp
625                 630

<210> SEQ ID NO 149
<211> LENGTH: 2017
<212> TYPE: DNA
<213> ORGANISM: Lactobacillus plantarum

<400> SEQUENCE: 149
cgttggtaaa gggactttgg actacttggt ctatgtccgt ccgcaggtga ttaagtccag    60

```
tgtgataacg cgcattgacg tgcaattcaa aaatttgcgg ggcgtcaccc cctacacggc      120
gaagtatcgg cgcttgaatc gcgagaacac cgcgcaactc aaacgctggt taaaaccaca      180
agcgcgtaag cggcagcagg cattacaagc ccaggcccag gctaagctga aaccattgcg      240
acaggcgacc cagcaacttg ctagtcaagt gccagcggga acggcacaac tagtcaagtt      300
acaaagccaa ttaaaacgcg cgaaggccca ggtcgcggcc atcacaatgc gacttatttt      360
gtacactgac cgtacggata tccggggtta cacagaatat cacgaaaata cgcaacgagt      420
cgtggcactg tcgactgtct ttccgctgtt ctttattgcg attgccgcgt taatttgtct      480
aacgacgatg acgcggatgg ttgaagaatt gcggctacag atggggacgt aaaggcccct      540
cgggtatacg aataccgcgg tcggtagcga gtttatgatt tatggtggtt tagccgcgct      600
gattgggacc gcgctaggtg tcctgttcgg cgtcaatttt ttcccgcggt ttatcgcgca      660
ggcctatggt agtatgtata atttgcccgc aatcaacgtt caatacattt ggatggacat      720
tggtatcgcc ttagccattg cgttgttgtg cacgttgggg acggcactgg tcgtgctccg      780
cgtggattta aacagtttac ccgcgcaact cttacagcca cgatcaccta aggccggtaa      840
gactttgcta ttagaacgct ggcaatggct atggcatcgg ctgagttta atcataaaat      900 cacacttcgt aatctatttc ggtataagca acggttgctg atgaccgtgc tcggtattgc      960
gggctgcatg gcaatgatga ttacgggggtt tggcttaaag gattccattg gtgatattag     1020
cgtcaagcaa tttaacgaat tgtggcacta cgatgctgtg gtgacgcgta gtgggaacga     1080
aacggaccaa caacgcaag cactcagtcg tggtcaactt taccaggcta gtttgaaatt     1140
acaggccaag caggtgacgg tcaaacagtc cggggtagca aacagacgg ctacgctcgg     1200 tataccggca ccccaccaat cgctaagcaa gttcgtggta ttacggcacc gacaaagtca     1260
tcaggccatt catattggtg atcgcggtgc ggtcatcgat gaaaaattag ctaagttata     1320
tggcgttcag gcgggcgatg atttaacgat caagttggcc gggcaaacca ccaagcggat     1380
tcacatcagt gcggtggctg aaaattacgt caatcacttt atctatatga gtccgactta     1440
ttatcgacgt gtcttcaagc aggcaccagt atataacacg aactatgtcc ggtttaagca     1500
ggcaacgaaa aagcaagaaa atgcttatgc ggaccggcta ttgaaacagg cggggggttca     1560 gaacgtgaca ctgatgagta cagagaaagc cactaatttt aaaatgctgg atagcatgaa     1620
cttagtcgta ttgatctttg tcatctcggc gggggcacta gcgctagtag tgctctataa     1680
cttaacgaat attaatgttt ctgaacggat ccgggaattg tcgacaatca agtgttggg      1740 cttttacgat ggtgaagtga cgatgtatat tttccgtgaa aatctgatat tgacggtttt     1800
aggcattatt gccggttgtt tcttgggcaa ctggttgcac gcatatatct tgcaaacggc     1860
tgaaacgaac gcgttaatgt tttccaccaa gattcatccg ttgagttacg tttacgcggc     1920
attattgacc ctggccttta gtttattagt catgggaatg atgcatcgta agttaaagcg     1980
agtcaatatg ctggatgcac tgaaatctgt cgattaa                              2017
```

<210> SEQ ID NO 150
<211> LENGTH: 671
<212> TYPE: PRT
<213> ORGANISM: Lactobacillus plantarum

<400> SEQUENCE: 150

Val Gly Lys Gly Thr Leu Asp Tyr Leu Val Tyr Val Arg Pro Gln Val
1               5                   10                  15

Ile Lys Ser Ser Val Ile Thr Arg Ile Asp Val Gln Phe Lys Asn Leu

```
                    20                  25                  30
Arg Gly Val Thr Pro Tyr Thr Ala Lys Tyr Arg Arg Leu Asn Arg Glu
                35                  40                  45
Asn Thr Ala Gln Leu Lys Arg Trp Leu Lys Pro Gln Ala Arg Lys Arg
                50                  55                  60
Gln Gln Ala Leu Gln Ala Gln Ala Gln Ala Lys Leu Lys Pro Leu Arg
65                  70                  75                  80
Gln Ala Thr Gln Gln Leu Ala Ser Gln Val Pro Ala Gly Thr Ala Gln
                85                  90                  95
Leu Val Lys Leu Gln Ser Gln Leu Lys Arg Ala Lys Ala Gln Val Ala
                100                 105                 110
Ala Ile Thr Met Pro Thr Tyr Leu Tyr Thr Asp Arg Thr Asp Asn Pro
                115                 120                 125
Gly Tyr Thr Glu Tyr His Glu Asn Thr Gln Arg Val Val Ala Leu Ser
                130                 135                 140
Thr Val Phe Pro Leu Phe Phe Ile Ala Ile Ala Ala Leu Ile Cys Leu
145                 150                 155                 160
Thr Thr Met Thr Arg Met Val Glu Glu Leu Arg Leu Gln Met Gly Thr
                165                 170                 175
Leu Lys Ala Leu Gly Tyr Thr Asn Thr Ala Val Gly Ser Glu Phe Met
                180                 185                 190
Ile Tyr Gly Gly Leu Ala Ala Leu Ile Gly Thr Ala Leu Gly Val Leu
                195                 200                 205
Phe Gly Val Asn Phe Phe Pro Arg Phe Ile Ala Gln Ala Tyr Gly Ser
                210                 215                 220
Met Tyr Asn Leu Pro Ala Ile Asn Val Gln Tyr Ile Trp Met Asp Ile
225                 230                 235                 240
Gly Ile Ala Leu Ala Ile Ala Leu Leu Cys Thr Leu Gly Thr Ala Leu
                245                 250                 255
Val Val Leu Arg Val Asp Leu Asn Ser Leu Pro Ala Gln Leu Leu Gln
                260                 265                 270
Pro Arg Ser Pro Lys Ala Gly Lys Thr Leu Leu Glu Arg Trp Gln
                275                 280                 285
Trp Leu Trp His Arg Leu Ser Phe Asn His Lys Ile Thr Leu Arg Asn
                290                 295                 300
Leu Phe Arg Tyr Lys Gln Arg Leu Leu Met Thr Val Leu Gly Ile Ala
305                 310                 315                 320
Gly Cys Met Ala Met Met Ile Thr Gly Phe Gly Leu Lys Asp Ser Ile
                325                 330                 335
Gly Asp Ile Ser Val Lys Gln Phe Asn Glu Leu Trp His Tyr Asp Ala
                340                 345                 350
Val Val Thr Arg Ser Gly Asn Glu Thr Asp Gln Gln Arg Gln Ala Leu
                355                 360                 365
Ser Arg Gly Gln Leu Tyr Gln Ala Ser Leu Lys Leu Gln Ala Lys Gln
                370                 375                 380
Val Thr Val Lys Gln Ser Gly Val Ala Glu Gln Thr Ala Thr Leu Gly
385                 390                 395                 400
Ile Pro Ala Pro His Gln Ser Leu Ser Lys Phe Val Val Leu Arg His
                405                 410                 415
Arg Gln Ser His Gln Ala Ile His Ile Gly Asp Arg Gly Ala Val Ile
                420                 425                 430
Asp Glu Lys Leu Ala Lys Leu Tyr Gly Val Gln Ala Gly Asp Asp Leu
                435                 440                 445
```

```
Thr Ile Lys Leu Ala Gly Gln Thr Thr Lys Arg Ile His Ile Ser Ala
    450                 455                 460
Val Ala Glu Asn Tyr Val Asn His Phe Ile Tyr Met Ser Pro Thr Tyr
465                 470                 475                 480
Tyr Arg Arg Val Phe Lys Gln Ala Pro Val Tyr Asn Thr Asn Tyr Val
                485                 490                 495
Arg Phe Lys Gln Ala Thr Lys Lys Gln Glu Asn Ala Tyr Ala Asp Arg
            500                 505                 510
Leu Leu Lys Gln Ala Gly Val Gln Asn Val Thr Leu Met Ser Thr Glu
        515                 520                 525
Lys Ala Thr Asn Phe Lys Met Leu Asp Ser Met Asn Leu Val Val Leu
    530                 535                 540
Ile Phe Val Ile Ser Ala Gly Ala Leu Ala Leu Val Val Leu Tyr Asn
545                 550                 555                 560
Leu Thr Asn Ile Asn Val Ser Glu Arg Ile Arg Glu Leu Ser Thr Ile
                565                 570                 575
Lys Val Leu Gly Phe Tyr Asp Gly Glu Val Thr Met Tyr Ile Phe Arg
            580                 585                 590
Glu Asn Leu Ile Leu Thr Val Leu Gly Ile Ile Ala Gly Cys Phe Leu
        595                 600                 605
Gly Asn Trp Leu His Ala Tyr Ile Leu Gln Thr Ala Glu Thr Asn Ala
    610                 615                 620
Leu Met Phe Ser Pro Thr Ile His Pro Leu Ser Tyr Val Tyr Ala Ala
625                 630                 635                 640
Leu Leu Thr Leu Ala Phe Ser Leu Leu Val Met Gly Met Met His Arg
                645                 650                 655
Lys Leu Lys Arg Val Asn Met Leu Asp Ala Leu Lys Ser Val Asp
            660                 665                 670

<210> SEQ ID NO 151
<211> LENGTH: 626
<212> TYPE: DNA
<213> ORGANISM: Lactobacillus plantarum

<400> SEQUENCE: 151
aatattcgct ggattgggac aatactttac aagaatatgg ctacttaatg attttttgcag    60
gattattgta cgcctacgtt aatatgctga cccaagatag tgagattaaa ttacggttgg   120
cccagtttgc gagtcacgac gctttgactg agactgagaa ctttgccgct tacacggaac   180
atatcaaata tttattcgat gatagtgcca agaacaatct caactcatcg atgatgatgt   240
tcgatattga tcactttaag cacgttaatg acacgtacgg gcaccttgca ggggaccgcg   300
ttttgcaaga agttgccgcc acggtcacaa cggtcttggc cgccaatgac gagaaggtca   360
agctgtatcg caccggtggt gaagaattca atgtcctgtt tcccggttat gatctggcta   420
gtaccaaagt gattgtccgt caggtctttg aagcagtcaa tcatctcgtt gttaagtatg   480
aagacgagga aatcaatgtg tcgatttcgg ttggtgtctc gacactgcat caagccgatg   540
gtagtccgat tgatttgtac aaccgtgttg atcagaacct ctatttttca aagcggcacg   600
ggcggatgcg tgttacggtt gaatag                                         626

<210> SEQ ID NO 152
<211> LENGTH: 207
<212> TYPE: PRT
<213> ORGANISM: Lactobacillus plantarum
```

<400> SEQUENCE: 152

Tyr Ser Leu Asp Trp Asp Asn Thr Leu Gln Glu Tyr Gly Tyr Leu Met
1               5                   10                  15

Ile Phe Ala Gly Leu Leu Tyr Ala Tyr Val Asn Met Leu Thr Gln Asp
                20                  25                  30

Ser Glu Ile Lys Leu Arg Leu Ala Gln Phe Ala Ser His Asp Ala Leu
            35                  40                  45

Thr Glu Thr Glu Asn Phe Ala Ala Tyr Thr Glu His Ile Lys Tyr Leu
        50                  55                  60

Phe Asp Asp Ser Ala Lys Asn Asn Leu Asn Leu Ser Met Met Met Phe
65                  70                  75                  80

Asp Ile Asp His Phe Lys His Val Asn Asp Thr Tyr Gly His Leu Ala
                85                  90                  95

Gly Asp Arg Val Leu Gln Glu Val Ala Ala Thr Val Thr Thr Val Leu
                100                 105                 110

Ala Ala Asn Asp Glu Lys Val Lys Leu Tyr Arg Thr Gly Gly Glu Glu
            115                 120                 125

Phe Asn Val Leu Phe Pro Gly Tyr Asp Leu Ala Ser Thr Lys Val Ile
        130                 135                 140

Val Arg Gln Val Phe Glu Ala Val Asn His Leu Val Val Lys Tyr Glu
145                 150                 155                 160

Asp Glu Glu Ile Asn Val Ser Ile Ser Val Gly Val Ser Thr Leu His
                165                 170                 175

Gln Ala Asp Gly Ser Pro Ile Asp Leu Tyr Asn Arg Val Asp Gln Asn
            180                 185                 190

Leu Tyr Phe Ser Lys Arg His Gly Arg Met Arg Val Thr Val Glu
        195                 200                 205

<210> SEQ ID NO 153
<211> LENGTH: 358
<212> TYPE: DNA
<213> ORGANISM: Lactobacillus plantarum

<400> SEQUENCE: 153
atggcaacaa aagataatga aaagattaca ttgatggcgc tagtcatgat gatctttacg    60
accgttttcg gatttgccaa tagtacggtg gcctattatt taatgggtta cagctcgatt   120 ctatttacc agtcgcagc cgtactgttc ttcatcccgt tcgcgctaat gatggcggag   180 ttcgggcag cggttaagtc tgatagtagc gggatgtaca gtggctgga agtgagtgtg   240 aatgcgaaat ttgcgttcgt gggcacgttc atgtggtttg cgtcgtacat tatttggtta   300
gtctcaacgt cagctaaagt ctggattccg tttacgacca tcttctttgg gagcgatc   358

<210> SEQ ID NO 154
<211> LENGTH: 119
<212> TYPE: PRT
<213> ORGANISM: Lactobacillus plantarum

<400> SEQUENCE: 154

Met Ala Thr Lys Asp Asn Glu Lys Ile Thr Leu Met Ala Leu Val Met
1               5                   10                  15

Met Ile Phe Thr Thr Val Phe Gly Phe Ala Asn Ser Thr Val Ala Tyr
                20                  25                  30

Tyr Leu Met Gly Tyr Ser Ser Ile Leu Phe Tyr Leu Val Ala Ala Val
            35                  40                  45

Leu Phe Phe Ile Pro Phe Ala Leu Met Met Ala Glu Phe Gly Ala Ala

```
                 50                  55                  60
Val Lys Ser Asp Ser Ser Gly Met Tyr Lys Trp Leu Glu Val Ser Val
 65                  70                  75                  80

Asn Ala Lys Phe Ala Phe Val Gly Thr Phe Met Trp Phe Ala Ser Tyr
                 85                  90                  95

Ile Ile Trp Leu Val Ser Thr Ser Ala Lys Val Trp Ile Pro Phe Thr
                100                 105                 110

Thr Ile Phe Phe Gly Ser Asp
            115

<210> SEQ ID NO 155
<211> LENGTH: 5250
<212> TYPE: DNA
<213> ORGANISM: Lactobacillus plantarum

<400> SEQUENCE: 155
ggatcgagtg ttggaacata cacattggca ctctcaacgg ctggaattac taagctagct      60
gaagctaata gtagcgcgga tataacggct gctaacgtgg tgacaggaac actaacaatc     120
aagcaagctc cggtaccgac tgcgataatt accattggtt cagctagtat tgactatggg     180
gatgctaaac caagtacgta tacaattacg gtgccgagtc agtatgcagt tcccagcacc     240
tggacgttag ctagttcggc tactgatgga acgactaata cttatatgat tgcaagttct     300
agtggcgatg ttatagttcc cacagcaacc caatctggaa cgtatcagct tgtgttgtca     360
gatcaaggct tgacagcttt acaacaggct aatcctaatg ctgctattac tgctgatacg     420
attattgctg gtagtttagt tattgcggca catgacatta ttacgatggg tgcgacgaca     480
attgtcgtta ataaaacgac tagtacggtt ccggtgacgg tcaatagtcg tactattgtg     540
gttccaacag gttggacaat tcgttacgat gatattcaga ctgatgcgat tgtgtatgac     600
gtccccgttt ccgatacgac atattcggaa gcggttaata ctgctgtggt tgataaatac     660
accattacat tgactgatga tacgatagaa acattagcta accttaacag cagtacgact     720
tttaatagta cgacggttgg taagggcgta gtgcttgtca aggctagtgc cgcagttgcc     780
atctcacctg caaactatgg cgcgcaggct agtgccgaaa ctccggtaac agggctgaca     840
atttcacatg cccgaacaaa gggaattgat ttagcatatg gtcaggcgct gtatttgatc     900
ttgccgctta ttaatatgaa tccatcagga atgactgtgg ctaatcttac tgattatgtt     960
attattccat ctggttttaa ggttgctact aatagtgaag gagctattaa catagcgact    1020
gatccaagta gtgtgttaac gtctgctatt gaagcaatga tgacgaaaaa tgatgtgacc    1080
tatcagggt taaggtgac ccaactgaca gactacaggg gtcgccaaac atttaaaatt     1140
cattttgata aaccactgt ttatgacggt ggtgcatttg caacgctaaa atatgcatta    1200
ttaccggtca ttgctgttca aaacactggg gtgactagtg gtttaattgg taatcaagtt    1260
tcaagcccgg attcggcggt ggtttatgtt actgatgatt ctaatgaaaa taatggtagt    1320
tattcgttga atttgcaaaa ttatactaat attgacagtg tcgctgatgc attaggaatt    1380
gcggatgctg tcacgattgg tagtggtttc acaagttacc tatatcatta cacgctatcg    1440
gccaaaacga ttaccgatac ttatagttta gtaggaaacg atggcacgtc attaggcgaa    1500
gtaactttta cgggcgacag tggtaagacg tatgtaccga tgactaaatt acccatgaca    1560
attacacaaa atggcgtgac gtattatttg aacactagtg cagtttcgtt aactcagaca    1620
tattctggta atagtaattc aaattacaca gttacttacc agcgctacgt cacaacgacg    1680
actgatactg cggccaagat aacgattgca ccagcttcaa aagtctatga taacaacgcc    1740
```

```
acgactgatc caagtcgcta tacggtatac ttgccaactg aatatacggc cccaagcgat   1800
tggactgctg atagcgcggc gacggctgtg gatgggacga cggcgtacca agtcagtacc   1860 gactaccttta acaccactgc aatcgatcaa aacgtgggca cttacgctgt cacgctgaat   1920
agcgccggga tggcagcctt atccgctgct aatccagatt tcttgattgc aggcgatgtg   1980
aatgttggtg ggactctgac gattactcaa cgtccagtga cgattacttt gccggatacg   2040
attctgtggg ccaatggtca ggaacaaaat attacgccgg tcattactgg tgttgttgcg   2100
gtgcaaagtt tggattacac gttaacgtca gggttaactg atccggacac gacaaccatt   2160
acggccacgc tgacgaatgc cgctgctaat agtaattata aattgacgaa ttcacctagt   2220
ggtcagttga cggtgggcgc cgtaacggtt gtctatcagt atgggtaccg cgacaaagcg   2280
gggacgctac acgtggtaac aacggctaat ggaacggcga cgcacgggac tgatgttacc   2340
gctaaggact atttgagcta caccacgagt gatacgactg ctacgcatgc caaaactggt   2400
tatacgttac aaccagaaag taccggttac caagccgatg gcactctagc ggacgttggt   2460
gggcaggtcg tgtacaccta tttagcgaac accgaaaaga ttgcggtcgt ttacgtcgac   2520
caagataaga acaacgtgat tttaaaacag attcccctca gtgggagctt tggcacaccc   2580
acgaattata cgacagcgca ggacattgcg gcgtatgaaa aattaggcta cgtgttagct   2640
tcggataagg tcccagcgcc gcttgagttt gatcaggata ctgaacagac ctactacgta   2700
tacctgaaac atggcaccat cacggcgacg gttgatcagc caggtaacgt ggccgttagt   2760
gatttgatga agaccagtca gcgaacgatt cattacgttt atgctgataa cacacccacg   2820
gacttagcgg atgtgcttca aacggtcacg tatacgcgca cggcaacggg ggatgcggtg   2880
gatagaacgg tcctttcgta cggtaattgg acgaccaatg tgaatagcta tccggccatt   2940
gagtcgccga ccattactgg ttacacgcg gatcaaacaa ccatcgcggc ggctgtaccc   3000
gctagcatgg gcgagactac ggaaacaacg gtccgataca gcgttaattc tgaaacgatc   3060
cgggttcaat ttgtcgatgg aactacggat aaccaagtct taagttatat tgatttgaat   3120
gggaaatacg gtgatgctgc cgactatacg gtcactgctg atatcgcgaa gtatgcaaaa   3180
ttaggctatg aaccagttaa ctcggacttg cctgatcagc tgatttataa gcagaatacc   3240
caagtttata cggttacact agcgcatcgt cacgtgacgg tcagcgttga tcatccgggc   3300
caacctggtc aggccatcga tgctgattat ccagccggtc ctaaatatcc ggcaggcact   3360
ggtcgtgatt cgttggaaca aacagtgact cggacgatta cgtatcaata tgcgtcaggt   3420
gaatcagcgg ctgaaacggt taaccagtcg gtcacgttca atcgcacggc aactttcgac   3480
atggcaacgg gtaagcagct gacttacggt gactggacag tggcacctgg tcagtcagca   3540
ctattggccg cggtcacgtc accaacgatt acaggttatc aagccagtgt tacagaagtc   3600
gaagcagcgt cggtcactag tcacgataag ccgcacttga ttgcaatcac gtacacggcc   3660
aaatcacaga ccgcaaccgt tgcgtttgtg gatgtaacga gtggtaaaac actacctacg   3720
acggtagtaa ctggtgctta tggcactacg aatagttatt cgcccgtttc ccaaattgct   3780
gcgtatgaaa aactgggcta tcgattagtt tcgaataatg ttccgacgac tggtatcacc   3840
tttgatcaaa atgacgtcat taagtcatac acggtcaagc tagcgcatca aatgacgacg   3900
gtcacgccaa ctaagcctgg gcaaccaggt caaccagttg atcccgctca tccagaaggg   3960
cccaagtacc cagctggtac tgggcttaaa gatttaacaa ccagcgttca gcgagtcatt   4020
acctatgttt acaatgatgg tcaaactgcg gcgccaaccg tcacgcaaac ggtcagtttt   4080
```

-continued

```
gagcgcaagg cgacctttga tcaagtgaca aaggtggtga cgtatacgga ttggcgtaca    4140
cctgaatcag cgttgacggg ggcatacgca gtcgttgaat cgccaataat tgctggctac    4200
accccgaatg caacccgtgt tgctagtgta actgtcagtg ccaaagatac tgagtcgcga    4260
caaacggtta cttaccaagc aaatctggaa acggcgacgg tgacttatgt cgatgccacg    4320
acgggccacc gactgggtac aagcgtgacg ttaaccggac gattcggtac gcaagcggat    4380
tatcaaccaa cgacaatgat tgcgcagtat acccaggcag gctatgtctt gatggggagt    4440
gattatccgg caacgggtgt tactttaat caggcgggcg tcgttcagaa gtatacggtg    4500
tacttggctc ataacaaaat cgtgattacg gcaccagatc agctcaccaa acgatcacg    4560 caaacggttc actatcagga tcaggctggg cacacgcttc aagctgatac gatccgggcg    4620
ctgacgttca cgcgttctgg gatgaaagat gcggtgactg tgtggcaac gtatcgtgat    4680 tgggcaccga ccgggttgaa ctttacagcc gtgtctgcgc aacgattgc gaaataccat    4740 gcgttgacgg cgaccactca ggccgtggca atcacggctg ctagtgctga tgatgtccaa    4800
acgctaacat atgcgctgga cgtcccaaca ccgacgaaac cggtcaaact gactaagcca    4860
gccaaaccga ctaagccgac aacatcggac gatttaatca agccaacgac gaaaccaatc    4920
acggctgcta accaacgca actcactaag ccagcaacgg ttgtgaagga ttttcaagcc    4980
acaactggca accagacgcc agctaaatcg caaggacgt tggtatcgag tcgcattaag    5040
gctgtcaaaa cagctccggc atcagcaatc atcaagccgg gaagtaaagt aacggagccg    5100
gctcacaagg ctcaagcaga tacaacgagt cgattgccac agactggtga acgcggtgg    5160 tctgaaatgg ctgctgaaac actagggcta acactagcaa cattattgct gggctttggt    5220
ggcttgaagc gtaagcggca tgaaaagtaa                                       5250
```

<210> SEQ ID NO 156
<211> LENGTH: 1749
<212> TYPE: PRT
<213> ORGANISM: Lactobacillus plantarum

<400> SEQUENCE: 156

```
Gly Ser Ser Val Gly Thr Tyr Thr Leu Ala Leu Ser Thr Ala Gly Ile
1               5                   10                  15

Thr Lys Leu Ala Glu Ala Asn Ser Ser Ala Asp Ile Thr Ala Ala Asn
            20                  25                  30

Val Val Thr Gly Thr Leu Thr Ile Lys Gln Ala Pro Val Pro Thr Ala
        35                  40                  45

Ile Ile Thr Ile Gly Ser Ala Ser Ile Asp Tyr Gly Asp Ala Lys Pro
    50                  55                  60

Ser Thr Tyr Thr Ile Thr Val Pro Ser Gln Tyr Ala Val Pro Ser Thr
65                  70                  75                  80

Trp Thr Leu Ala Ser Ser Ala Thr Asp Gly Thr Thr Asn Thr Tyr Met
                85                  90                  95

Ile Ala Ser Ser Ser Gly Asp Val Ile Val Pro Thr Ala Thr Gln Ser
            100                 105                 110

Gly Thr Tyr Gln Leu Val Leu Ser Asp Gln Gly Leu Thr Ala Leu Gln
        115                 120                 125

Gln Ala Asn Pro Asn Ala Ala Ile Thr Ala Asp Thr Ile Ile Ala Gly
    130                 135                 140

Ser Leu Val Ile Ala Ala His Asp Ile Ile Thr Met Gly Ala Thr Thr
145                 150                 155                 160

Ile Val Val Asn Lys Thr Thr Ser Thr Val Pro Val Thr Val Asn Ser
```

```
                 165                 170                 175
Arg Thr Ile Val Val Pro Thr Gly Trp Thr Ile Arg Tyr Asp Asp Ile
                180                 185                 190
Gln Thr Asp Ala Ile Val Tyr Asp Val Pro Val Ser Asp Thr Thr Tyr
                195                 200                 205
Ser Glu Ala Val Asn Thr Ala Val Asp Lys Tyr Thr Ile Thr Leu
210                 215                 220
Thr Asp Asp Thr Ile Glu Thr Leu Ala Asn Leu Asn Ser Ser Thr Thr
225                 230                 235                 240
Phe Asn Ser Thr Thr Val Gly Lys Gly Val Leu Val Lys Ala Ser
                245                 250                 255
Ala Ala Val Ala Ile Ser Pro Ala Asn Tyr Gly Ala Gln Ala Ser Ala
                260                 265                 270
Glu Thr Pro Val Thr Gly Leu Thr Ile Ser His Ala Arg Thr Lys Gly
                275                 280                 285
Ile Asp Leu Ala Tyr Gly Gln Ala Leu Tyr Leu Ile Leu Pro Leu Ile
                290                 295                 300
Asn Met Asn Pro Ser Gly Met Thr Val Ala Asn Leu Thr Asp Tyr Val
305                 310                 315                 320
Ile Ile Pro Ser Gly Phe Lys Val Ala Thr Asn Ser Glu Gly Ala Ile
                325                 330                 335
Asn Ile Ala Thr Asp Pro Ser Ser Val Leu Thr Ser Ala Ile Glu Ala
                340                 345                 350
Met Met Thr Lys Asn Asp Val Thr Tyr Gln Gly Leu Lys Val Thr Gln
                355                 360                 365
Leu Thr Asp Tyr Arg Gly Arg Gln Thr Phe Lys Ile His Phe Asp Lys
                370                 375                 380
Thr Thr Val Tyr Asp Gly Gly Ala Phe Ala Thr Leu Lys Tyr Ala Leu
385                 390                 395                 400
Leu Pro Val Ile Ala Val Gln Asn Thr Gly Val Thr Ser Gly Leu Ile
                405                 410                 415
Gly Asn Gln Val Ser Ser Pro Asp Ser Ala Val Val Tyr Val Thr Asp
                420                 425                 430
Asp Ser Asn Glu Asn Asn Gly Ser Tyr Ser Leu Asn Leu Gln Asn Tyr
                435                 440                 445
Thr Asn Ile Asp Ser Val Ala Asp Ala Leu Gly Ile Ala Asp Ala Val
                450                 455                 460
Thr Ile Gly Ser Gly Phe Thr Ser Tyr Leu Tyr His Tyr Thr Leu Ser
465                 470                 475                 480
Ala Lys Thr Ile Thr Asp Thr Tyr Ser Leu Val Gly Asn Asp Gly Thr
                485                 490                 495
Ser Leu Gly Glu Val Thr Phe Thr Gly Asp Ser Gly Lys Thr Tyr Val
                500                 505                 510
Pro Met Thr Lys Leu Pro Met Thr Ile Thr Gln Asn Gly Val Thr Tyr
                515                 520                 525
Tyr Leu Asn Thr Ser Ala Val Ser Leu Thr Gln Thr Tyr Ser Gly Asp
                530                 535                 540
Ser Asn Ser Asn Tyr Thr Val Thr Tyr Gln Arg Tyr Val Thr Thr Thr
545                 550                 555                 560
Thr Asp Thr Ala Ala Lys Ile Thr Ile Ala Pro Ala Ser Lys Val Tyr
                565                 570                 575
Asp Asn Asn Ala Thr Thr Asp Pro Ser Arg Tyr Thr Val Tyr Leu Pro
                580                 585                 590
```

```
Thr Glu Tyr Thr Ala Pro Ser Asp Trp Thr Ala Asp Ser Ala Ala Thr
            595                 600                 605

Ala Val Asp Gly Thr Thr Ala Tyr Gln Val Ser Thr Asp Tyr Leu Asn
    610                 615                 620

Thr Thr Ala Ile Asp Gln Asn Val Gly Thr Tyr Ala Val Thr Leu Asn
625                 630                 635                 640

Ser Ala Gly Met Ala Ala Leu Ser Ala Ala Asn Pro Asp Phe Leu Ile
                645                 650                 655

Ala Gly Asp Val Asn Val Gly Gly Thr Leu Thr Ile Thr Gln Arg Pro
            660                 665                 670

Val Thr Ile Thr Leu Pro Asp Thr Ile Leu Trp Ala Asn Gly Gln Glu
        675                 680                 685

Gln Asn Ile Thr Pro Val Ile Thr Gly Val Val Ala Val Gln Ser Leu
    690                 695                 700

Asp Tyr Thr Leu Thr Ser Gly Leu Thr Asp Pro Asp Thr Thr Thr Ile
705                 710                 715                 720

Thr Ala Thr Leu Thr Asn Ala Ala Asn Ser Asn Tyr Lys Leu Thr
                725                 730                 735

Asn Ser Pro Ser Gly Gln Leu Thr Val Gly Ala Val Thr Val Val Tyr
            740                 745                 750

Gln Tyr Gly Tyr Arg Asp Lys Ala Gly Thr Leu His Val Val Thr Thr
        755                 760                 765

Ala Asn Gly Thr Ala Thr His Gly Thr Asp Val Thr Ala Lys Asp Tyr
    770                 775                 780

Leu Ser Tyr Thr Thr Ser Asp Thr Thr Ala His Ala Lys Thr Gly
785                 790                 795                 800

Tyr Thr Leu Gln Pro Glu Ser Thr Gly Tyr Gln Ala Asp Gly Thr Leu
                805                 810                 815

Ala Asp Val Gly Gly Gln Val Val Tyr Thr Tyr Leu Ala Asn Thr Glu
            820                 825                 830

Lys Ile Ala Val Val Tyr Val Asp Gln Asp Lys Asn Asn Val Ile Leu
        835                 840                 845

Lys Gln Ile Pro Leu Ser Gly Ser Phe Gly Thr Pro Thr Asn Tyr Thr
    850                 855                 860

Thr Ala Gln Asp Ile Ala Ala Tyr Glu Lys Leu Gly Tyr Val Leu Ala
865                 870                 875                 880

Ser Asp Lys Val Pro Ala Pro Leu Glu Phe Asp Gln Asp Thr Glu Gln
                885                 890                 895

Thr Tyr Tyr Val Tyr Leu Lys His Gly Thr Ile Thr Ala Thr Val Asp
            900                 905                 910

Gln Pro Gly Asn Val Ala Val Ser Asp Leu Met Lys Thr Ser Gln Arg
        915                 920                 925

Thr Ile His Tyr Val Tyr Ala Asp Asn Thr Pro Thr Asp Leu Ala Asp
    930                 935                 940

Val Leu Gln Thr Val Thr Tyr Thr Arg Thr Ala Thr Gly Asp Ala Val
945                 950                 955                 960

Asp Arg Thr Val Leu Ser Tyr Gly Asn Trp Thr Thr Asn Val Asn Ser
                965                 970                 975

Tyr Pro Ala Ile Glu Ser Pro Thr Ile Thr Gly Tyr Thr Ala Asp Gln
            980                 985                 990

Thr Thr Ile Ala Ala Ala Val Pro  Ala Ser Met Gly Glu  Thr Thr Glu
        995                 1000                1005
```

```
Thr Thr Val Arg Tyr Ser Val Asn Ser Glu Thr Ile Arg Val Gln
    1010                1015                1020

Phe Val Asp Gly Thr Thr Asp Asn Gln Val Leu Ser Tyr Ile Asp
    1025                1030                1035

Leu Asn Gly Lys Tyr Gly Asp Ala Ala Asp Tyr Thr Val Thr Ala
    1040                1045                1050

Asp Ile Ala Lys Tyr Ala Lys Leu Gly Tyr Glu Pro Val Asn Ser
    1055                1060                1065

Asp Leu Pro Asp Gln Leu Ile Tyr Lys Gln Asn Thr Gln Val Tyr
    1070                1075                1080

Thr Val Thr Leu Ala His Arg His Val Thr Val Ser Val Asp His
    1085                1090                1095

Pro Gly Gln Pro Gly Gln Ala Ile Asp Ala Asp Tyr Pro Ala Gly
    1100                1105                1110

Pro Lys Tyr Pro Ala Gly Thr Gly Arg Asp Ser Leu Glu Gln Thr
    1115                1120                1125

Val Thr Arg Thr Ile Thr Tyr Gln Tyr Ala Ser Gly Glu Ser Ala
    1130                1135                1140

Ala Glu Thr Val Asn Gln Ser Val Thr Phe Asn Arg Thr Ala Thr
    1145                1150                1155

Phe Asp Met Ala Thr Gly Lys Gln Leu Thr Tyr Gly Asp Trp Thr
    1160                1165                1170

Val Ala Pro Gly Gln Ser Ala Leu Leu Ala Ala Val Thr Ser Pro
    1175                1180                1185

Thr Ile Thr Gly Tyr Gln Ala Ser Val Thr Glu Val Glu Ala Ala
    1190                1195                1200

Ser Val Thr Ser His Asp Lys Pro His Leu Ile Ala Ile Thr Tyr
    1205                1210                1215

Thr Ala Lys Ser Gln Thr Ala Thr Val Ala Phe Val Asp Val Thr
    1220                1225                1230

Ser Gly Lys Thr Leu Pro Thr Thr Val Val Thr Gly Ala Tyr Gly
    1235                1240                1245

Thr Thr Asn Ser Tyr Ser Pro Val Ser Gln Ile Ala Ala Tyr Glu
    1250                1255                1260

Lys Leu Gly Tyr Arg Leu Val Ser Asn Asn Val Pro Thr Thr Gly
    1265                1270                1275

Ile Thr Phe Asp Gln Asn Asp Val Ile Lys Ser Tyr Thr Val Lys
    1280                1285                1290

Leu Ala His Gln Met Thr Thr Val Thr Pro Thr Lys Pro Gly Gln
    1295                1300                1305

Pro Gly Gln Pro Val Asp Pro Ala His Pro Glu Gly Pro Lys Tyr
    1310                1315                1320

Pro Ala Gly Thr Gly Leu Lys Asp Leu Thr Thr Ser Val Gln Arg
    1325                1330                1335

Val Ile Thr Tyr Val Tyr Asn Asp Gly Gln Thr Ala Ala Pro Thr
    1340                1345                1350

Val Thr Gln Thr Val Ser Phe Glu Arg Lys Ala Thr Phe Asp Gln
    1355                1360                1365

Val Thr Lys Val Val Thr Tyr Thr Asp Trp Arg Thr Pro Glu Ser
    1370                1375                1380

Ala Leu Thr Gly Ala Tyr Ala Val Val Glu Ser Pro Ile Ile Ala
    1385                1390                1395

Gly Tyr Thr Pro Asn Ala Thr Arg Val Ala Ser Val Thr Val Ser
```

Ala Lys Asp Thr Glu Ser Arg Gln Thr Val Thr Tyr Gln Ala Asn
1415                1420                1425

Leu Glu Thr Ala Thr Val Thr Tyr Val Asp Ala Thr Thr Gly His
1430                1435                1440

Arg Leu Gly Thr Ser Val Thr Leu Thr Gly Arg Phe Gly Thr Gln
1445                1450                1455

Ala Asp Tyr Gln Pro Thr Thr Met Ile Ala Gln Tyr Thr Gln Ala
1460                1465                1470

Gly Tyr Val Leu Met Gly Ser Asp Tyr Pro Ala Thr Gly Val Thr
1475                1480                1485

Phe Asn Gln Ala Gly Val Val Gln Lys Tyr Thr Val Tyr Leu Ala
1490                1495                1500

His Asn Lys Ile Val Ile Thr Ala Pro Asp Gln Leu Thr Lys Thr
1505                1510                1515

Ile Thr Gln Thr Val His Tyr Gln Asp Gln Ala Gly His Thr Leu
1520                1525                1530

Gln Ala Asp Thr Ile Arg Ala Leu Thr Phe Thr Arg Ser Gly Met
1535                1540                1545

Lys Asp Ala Val Thr Gly Val Ala Thr Tyr Arg Asp Trp Ala Pro
1550                1555                1560

Thr Gly Leu Asn Phe Thr Ala Val Ser Ala Pro Thr Ile Ala Lys
1565                1570                1575

Tyr His Ala Leu Thr Ala Thr Gln Ala Val Ala Ile Thr Ala
1580                1585                1590

Ala Ser Ala Asp Asp Val Gln Thr Leu Thr Tyr Ala Leu Asp Val
1595                1600                1605

Pro Thr Pro Thr Lys Pro Val Lys Leu Thr Lys Pro Ala Lys Pro
1610                1615                1620

Thr Lys Pro Thr Thr Ser Asp Asp Leu Ile Lys Pro Thr Thr Lys
1625                1630                1635

Pro Ile Thr Ala Ala Lys Pro Thr Gln Leu Thr Lys Pro Ala Thr
1640                1645                1650

Val Val Lys Asp Phe Gln Ala Thr Thr Gly Asn Gln Thr Pro Ala
1655                1660                1665

Lys Ser Thr Arg Thr Leu Val Ser Ser Arg Ile Lys Ala Val Lys
1670                1675                1680

Thr Ala Pro Ala Ser Ala Ile Ile Lys Pro Gly Ser Lys Val Thr
1685                1690                1695

Glu Pro Ala His Lys Ala Gln Ala Asp Thr Thr Ser Arg Leu Pro
1700                1705                1710

Gln Thr Gly Glu Thr Arg Trp Ser Glu Met Ala Ala Glu Thr Leu
1715                1720                1725

Gly Leu Thr Leu Ala Thr Leu Leu Leu Gly Phe Gly Gly Leu Lys
1730                1735                1740

Arg Lys Arg His Glu Lys
1745

<210> SEQ ID NO 157
<211> LENGTH: 879
<212> TYPE: DNA
<213> ORGANISM: Lactobacillus plantarum

<400> SEQUENCE: 157

```
atggatttaa agcaaagcga tggttggcga tacttagctg ggtggagctt cattctatta        60
atggtggcga gtgccacatt gcaacatgat gcgaaaatca ttttacccga aatcggtgct       120
ctgacagccg ggacgtgggt ttatcgtaag acggcgtgga ctcggcaacc cttaaagtta       180
ttcttagtac catctggaac tgcaattatt ggcttcttag tcaatcaact accttggtcg       240
cacgccctca aagtgcttgt cggtctatta ctgatgctat tattattgaa ggggttaaaa       300
tcgaatttgg cgccagcctt tgctactggc ttactgccaa ttatcattaa tgcaacgcac       360
tggacctta tcgtagccat cttttctgg actatttgcc tgatgattgg ggcttggatt         420
caacgaccgc gatcaatctc acgggtaacc gaagcttctg ctagtcgctg caaatgctc        480
ggctttatca gcctagtttt tgtctgggtg gtattgttt ggctagcggg acagccccag        540
atggccgcaa tcccacccgt gatcgtcgtt ttctttgaag cggctcaaca gtctgaatat       600
acggtaacga ccgcacttaa gcagtggctt gcattgtcgg ctgctgctag tattggggtc       660
ggcattcacc tattgattgc ttcgtggcta ttaacgacgg tcattgcctt accacttgtg       720
tatttgtggt tacgggcgct taacttacaa ttgccagcag cgtatgcctt tccactatta       780
gccttagtgt taccagccaa tatgtttaac aaactaccga catccgccgg cttagcggcc       840
gctttcttcc taggatcgtt actcatctac catcagatc                              879
```

<210> SEQ ID NO 158
<211> LENGTH: 586
<212> TYPE: PRT
<213> ORGANISM: Lactobacillus plantarum
<400> SEQUENCE: 158

```
Met Asp Leu Lys Gln Ser Asp Gly Trp Arg Tyr Leu Ala Gly Trp Ser
 1               5                  10                  15

Phe Ile Leu Leu Met Val Ala Ser Ala Thr Leu Gln His Asp Ala Lys
                20                  25                  30

Ile Ile Leu Pro Glu Ile Gly Ala Leu Thr Ala Gly Thr Trp Val Tyr
            35                  40                  45

Arg Lys Thr Ala Trp Thr Arg Gln Pro Leu Lys Leu Phe Leu Val Pro
        50                  55                  60

Ser Gly Thr Ala Ile Ile Gly Phe Leu Val Asn Gln Leu Pro Trp Ser
65                  70                  75                  80

His Ala Leu Lys Val Leu Val Gly Leu Leu Met Leu Leu Leu
                85                  90                  95

Lys Gly Leu Lys Ser Asn Leu Ala Pro Ala Phe Ala Thr Gly Leu Leu
               100                 105                 110

Pro Ile Ile Ile Asn Ala Thr His Trp Thr Phe Ile Val Ala Ile Phe
           115                 120                 125

Phe Trp Thr Ile Cys Leu Met Ile Gly Ala Trp Ile Gln Arg Pro Arg
       130                 135                 140

Ser Ile Ser Arg Val Thr Glu Ala Ser Ala Ser Arg Trp Gln Met Leu
145                 150                 155                 160

Gly Phe Ile Ser Leu Val Phe Val Trp Val Gly Ile Val Trp Leu Ala
               165                 170                 175

Gly Gln Pro Gln Met Ala Ala Ile Pro Pro Val Ile Val Met Asp Leu
           180                 185                 190

Lys Gln Ser Asp Gly Trp Arg Tyr Leu Ala Gly Trp Ser Phe Ile Leu
       195                 200                 205

Leu Met Val Ala Ser Ala Thr Leu Gln His Asp Ala Lys Ile Ile Leu
   210                 215                 220
```

| | | | | | | | | | | | |
|---|---|---|---|---|---|---|---|---|---|---|---|
| Pro | Glu | Ile | Gly | Ala | Leu | Thr | Ala | Gly | Thr | Trp | Val | Tyr | Arg | Lys | Thr |
| 225 | | | | 230 | | | | 235 | | | | 240 | | | |

Pro Glu Ile Gly Ala Leu Thr Ala Gly Thr Trp Val Tyr Arg Lys Thr
225                 230                 235                 240

Ala Trp Thr Arg Gln Pro Leu Lys Leu Phe Leu Val Pro Ser Gly Thr
                245                 250                 255

Ala Ile Ile Gly Phe Leu Val Asn Gln Leu Pro Trp Ser His Ala Leu
            260                 265                 270

Lys Val Leu Val Gly Leu Leu Met Leu Leu Leu Lys Gly Leu
        275                 280                 285

Lys Ser Asn Leu Ala Pro Ala Phe Ala Thr Gly Leu Leu Pro Ile Ile
    290                 295                 300

Ile Asn Ala Thr His Trp Thr Phe Ile Val Ala Ile Phe Phe Trp Thr
305                 310                 315                 320

Ile Cys Leu Met Ile Gly Ala Trp Ile Gln Arg Pro Arg Ser Ile Ser
                325                 330                 335

Arg Val Thr Glu Ala Ser Ala Ser Arg Trp Gln Met Leu Gly Phe Ile
            340                 345                 350

Ser Leu Val Phe Val Trp Val Gly Ile Val Trp Leu Ala Gly Gln Pro
        355                 360                 365

Gln Met Ala Ala Ile Pro Pro Val Ile Val Val Phe Phe Glu Ala Ala
370                 375                 380

Gln Gln Ser Glu Tyr Thr Val Thr Thr Ala Leu Lys Gln Trp Leu Ala
385                 390                 395                 400

Leu Ser Ala Ala Ala Ser Ile Gly Val Gly Ile His Leu Leu Ile Ala
                405                 410                 415

Ser Trp Leu Leu Thr Thr Val Ile Ala Leu Pro Leu Val Tyr Leu Trp
            420                 425                 430

Leu Arg Ala Leu Asn Leu Gln Leu Pro Ala Ala Tyr Ala Phe Pro Leu
        435                 440                 445

Leu Ala Leu Val Leu Pro Ala Asn Met Phe Asn Lys Leu Pro Thr Ser
450                 455                 460

Ala Gly Leu Ala Ala Ala Phe Phe Leu Gly Ser Leu Leu Ile Tyr His
465                 470                 475                 480

Gln Ile Val Phe Phe Glu Ala Ala Gln Gln Ser Glu Tyr Thr Val Thr
                485                 490                 495

Thr Ala Leu Lys Gln Trp Leu Ala Leu Ser Ala Ala Ala Ser Ile Gly
            500                 505                 510

Val Gly Ile His Leu Leu Ile Ala Ser Trp Leu Leu Thr Thr Val Ile
        515                 520                 525

Ala Leu Pro Leu Val Tyr Leu Trp Leu Arg Ala Leu Asn Leu Gln Leu
        530                 535                 540

Pro Ala Ala Tyr Ala Phe Pro Leu Leu Ala Leu Val Leu Pro Ala Asn
545                 550                 555                 560

Met Phe Asn Lys Leu Pro Thr Ser Ala Gly Leu Ala Ala Ala Phe Phe
                565                 570                 575

Leu Gly Ser Leu Leu Ile Tyr His Gln Ile
            580                 585

<210> SEQ ID NO 159
<211> LENGTH: 195
<212> TYPE: DNA
<213> ORGANISM: Lactobacillus plantarum

<400> SEQUENCE: 159
ttgacgaata cagacaatcg ttattatcaa ccaaccgaca tcaaagatgc gcttcaaaca    60

-continued

| | |
|---|---|
| atccaaaaat tatttaatac ttataccgat gccccattaa cacccgaatt aatggcctac | 120 |
| catcaaaaat tagttaatca gttagctact aatttattac cactagcaca acaacaacat | 180 |
| gacaaattac ggatc | 195 |

<210> SEQ ID NO 160
<211> LENGTH: 65
<212> TYPE: PRT
<213> ORGANISM: Lactobacillus plantarum

<400> SEQUENCE: 160

Leu Thr Asn Thr Asp Asn Arg Tyr Tyr Gln Pro Thr Asp Ile Lys Asp
1               5                   10                  15

Ala Leu Gln Thr Ile Gln Lys Leu Phe Asn Thr Tyr Thr Asp Ala Pro
            20                  25                  30

Leu Thr Pro Glu Leu Met Ala Tyr His Gln Lys Leu Val Asn Gln Leu
        35                  40                  45

Ala Thr Asn Leu Leu Pro Leu Ala Gln Gln Gln His Asp Lys Leu Arg
    50                  55                  60

Ile
65

<210> SEQ ID NO 161
<211> LENGTH: 61
<212> TYPE: DNA
<213> ORGANISM: Lactobacillus plantarum

<400> SEQUENCE: 161

| | |
|---|---|
| aagactatcc tgaaattgcg cctaagttac ccgaaatgcc attgaatgag cacttaaat | 60 |
| t | 61 |

<210> SEQ ID NO 162
<211> LENGTH: 19
<212> TYPE: PRT
<213> ORGANISM: Lactobacillus plantarum

<400> SEQUENCE: 162

Asp Tyr Pro Glu Ile Ala Pro Lys Leu Pro Glu Met Pro Leu Asn Glu
1               5                   10                  15

Ala Leu Lys

<210> SEQ ID NO 163
<211> LENGTH: 2119
<212> TYPE: DNA
<213> ORGANISM: Lactobacillus plantarum

<400> SEQUENCE: 163

| | |
|---|---|
| aagtgttcaa tcttcattcg acgctacccc gttttaatag tcgaacgcga ctcactgccg | 60 |
| gaattttaga cagttcagct attaggtcgg cttgttgtgg ctgctgtagg tcgtcgacgt | 120 |
| caatgatggt gtaagcaatc tggtgcttag cggcgttagc catggtagtg atgttgaggt | 180 |
| tggccgctgc tagtttggcc gtgatttgac tcaccatgtt aggcacattt tcgtgaatga | 240 |
| ctgtaaagcg gtaagccgcg ttaacgggga cgtttaagtc tggcagattg atggccgcat | 300 |
| gaacgttacc ggtttccaaa taagtcatga tagtgcgcgc agcttgtgtg caccgttga | 360 |
| tttcagcctc gatagtcgag ccgccgatat ggggtgtcac ggtaaccgcg gattggttgg | 420 |
| caagctgggg ttcgccaaaa tcggtgtagt agtgggcaac ttgtcccgtg gctaacgcat | 480 |

-continued

```
tcatgacggc agtattgtca acgatgccca gccgtgaata attaaataat tgaacgcctg      540
ttggcatggc ggctaacgca tctttattaa tcagatgaag tgtgtcggca ttttaggaa       600 cgtggacggt gacaaaatca gcttgtttga ctgcatctgg cagcgtggcc gctcgctgga     660
cttgtttagc aatgttccaa gcggcatctg cagatagata ggggtcgtaa ccaattacat     720
tcatgcctag actcaatgct gcattggcaa cgagagcgcc aacatggccg agtccgatga     780
cggccaaggt cttacccgtt aattcaatac cattaaattg cgtcttgtcg tgttctgtgc     840
gttgagaaat atcagcttcg gtatgctggg ccgaataggt cgttgcagct attagattac     900
gggatgccat aatgagcagg ccgatgatga gttccttaac ggcattagcg ttacttcccg     960
gggtgttgaa aactgcagtc ccgttggcgg ttgcctgatc gataggaatg ttgttaacgc    1020
cggcaccagc gcgcacaatg actttcaacg atgacggtaa tgtctcggta tgtaggttga    1080
ccgagcgaat taagtaagca tccggatgct cagattgatt gagcgtgtaa tcagcagtaa    1140
acgtgttgag gccggctggg gcgatggcgt tataggtttt aacttgatac ataaatatcc    1200
tccttgatta acgatggtgt gcttcaaaag cggctagata gtcaactaat gcctgaacac    1260
cggctaacgg catggcgtta tagaggctgg cacgcatacc gccaactaag cggtgaccct    1320
ttaggtttaa taacccgtgc tcacgggcgc cttgaatgac tgcggcatcg aggtcggcct    1380
gacctgtgac gaatggaacg ttcatggtcg aacggtcgct ggtcttgact ggattagtaa    1440
atagttgtga ctggtctaag aaatcataga gtaaggcggc tttagcgtga ttgcgagcag    1500
tcattgtgct gagcccgcct tgggccttta gccacttgag tacgagaccc gcggcgtaaa    1560
tagcaaaaac aggcggcgtg ttgaacatcg aatctttagc cgcgaatagc tggtaatcca    1620
gcatgcttgg caggttggcg acttgaccaa ttaaatcatc acggacaatg acgattgtca    1680
aaccagcggg acccagattc ttctgagcac cagcaaagat gagcccaaaa tcgctgactt    1740
ggtaaggttc acctaaaaag tttgatgaca tgtcggctac cagtggtact tgacccgtaa    1800
ctggcaggcg cgtcatcatg gttccttcaa tagtattatt agttgtaaga tgaatataat    1860
cgagggattg atcgatgggc tggacgaccg ttggcagttg gttaaaatgg ttggcagcgc    1920
tactccccag tatcgtgact ttagtaccga cccgtttagc ttcatcggcg gcgcgttgtg    1980
cccagtgacc gctgtcaagc aacccgatac gatgatgagg cgccagattt agtggcgcag    2040
ctgtgaactg tagcgtgccc ccgccttgaa agaagagcac gtgatagttg tcaggaatgg    2100
ccattaaatc gcgaagatc                                                 2119
```

<210> SEQ ID NO 164
<211> LENGTH: 2806
<212> TYPE: DNA
<213> ORGANISM: Lactobacillus plantarum

<400> SEQUENCE: 164

```
ggatcgaagg gaccattacg ccggctagtg gcacaattga tcgcccgatt ggccgggtgg      60
ctgacagtcc tcggcgagtg gtcaccacgg cgggccaacg cgccattacg acgtatcaag     120
tggaggcgga ccaattgcag cataacgtga gtcggttacg gttggaactt gtgactggac     180
ggacgcatca aattcgggtc catctaacga cgcttgggca cccctattta ggtgatgcgc     240
tgtatggcgg taacttgggg tggattcaac ggcaagcctt acacgccgct agtttacagt     300 tcttttgaccc cttttcggaa cagacttac acttttgaggc ggcattgcca gctgatctgc     360
aagccttgaa tcacgactaa gttcagttta ggaccagtga ccatccggat gaatggttaa     420
taaaaatcgg cactgctaga atgcgttgaa cattctggca gtgccgattt tggttggca      480
```

-continued

```
accgtctaaa atcaagctaa cgtttagcgg gtaagttgca ggcccgcgtt atcctgaagg    540
ttgcggtgac tattgaatga ggcgctagtg cttacgactg actaagtggc gcgttatcag    600
ccgttagcgt cgcaaaagtt gctgtaattg ctgtaatggt gcggttaacg tgagaaaata    660
aatatgctcg actccgttac tgcgcatatc aatgacccca gcttcacgca ttaagcgtag    720
atgatgtgaa acggcgggc gtgaaatatt gaccaaggcg gtaatatcag taacgttgag    780
accattatca ctgttcccca gagcaatgat aatctgacgc cgaattttt cggcgaagat    840
attaattagt gtggcacttt caataagtgc cgtttcggat tgttgaaaat tagccatggt    900
gactgcgtcc tttcaaattc aatttacact taaggactaa ctcccccccat cggcagtacg    960
ctgaattagt tgttaagtgt tggtatgaca gctcgattgt tcaagtcctg gtgaaatagt   1020
tgcagccaag aaaactttaa gtctacaagt tgtcagttag actaattgtt attggaacgt   1080
tcgtacttat gtataattaa agcaagtcgt taatcgattg tcaaatcttt ttgttaaaag   1140
taagtactat tagcgggttt aacaattgct gttcgtttga taaccatatt tttatgttga   1200
aatgcgttaa aataaaaata gcttttgaat gaatgatggg agtggaaaat gtgaaagtct   1260
taggaatatt aggtgcgcat cgcgctgatg gcgtgactgc ccagctactg caatccgtct   1320
taaagggggc cgcggccagc gctgacacgg aactagtcaa cctcaacgat tatgagttgc   1380
gaccagatca cgatagtcaa ccgaatgctg acttagacgc gctggaagca aaattaatgg   1440
cggcggatgt ctgggtatta gctgcaccaa cctatttggg gagcttatcg ggggtaatga   1500
aaaacttctg tgactgtttt cggggcgga tcgcacggtt taattccgtg ggtgaagcag   1560
tacctgatcg ctttaagaac aagcattatg tgacgatcac ggattgttac gcgggtggta   1620
ttgaaaatta tttgaccggc gtgactgacg caacgtttaa aacacttgat aaattttga   1680
cgatgggtgg tctcatcaaa ttacgggaga ttgtcgtaac taaaacgtgg ggtatgcaaa   1740
ccatcacagc tgctaagcaa gcagaatgtg aacgggtcgg cgcgcgggct gcacataaaa   1800
aggaaaggga tgacagtacg gtgaaacggt atattcaatt attcttcatg attgcggtga   1860
tggcactact aacaatggga atcgaagcgg ggattcaaca attgattccg ctgaacaatt   1920
tttgggccta ctacggcgtc tttgtcgtcg tcttttatgt tcttttagca atgattttac   1980
atttcttcac tgttgttaaa caccggcgtc gttaagggat acggcatgtg cattcagcaa   2040
caacgacatt aaaattcaat tgattagcaa gctgggcttg gcgtcttaat cgccggaggt   2100
cagcttgttt tgctataata agaacaatta cgaagtacca gcgattattt cagtgtccac   2160
gcgtataatt aatatggtat cgtcgaatta gaaaatgagg acacttggta ctggttgcca   2220
ggcgtatgaa ccataattaa aacatgttaa attagatgaa tttttatttg gcagcatgct   2280
gtgattggtt tcggttttgg cgcatccaag ctgccggttt ttgaatctaa ctttgtcaaa   2340
aactaatcat gggtcatgcc caaaaacgtg ttattgattt caaaattaat tttgttaaat   2400
aaaggctgtc aatcaaggta cgaggaggaa tagcatgcaa gttttggac aatttattgc   2460
aacagtcggt tggctaggat tggcactagt cgccagcgaa ctaggtgcga cgttaatcca   2520
ttggctcggt cagtgggtcg gatttcgatt aattggtgct cgaattgtcc ggattaccgg   2580
ttttcgactt caattaagtc gggttcgtgg tcattggaaa ttagaacgac cgctgacgcg   2640
tcatccacat atcgtggcag caccctcggc ggatgccaaa cggttcaatc acgccattta   2700
ttgttttggc ggtggcctgt tcaacttact gacggtcatg ctcagtttaa taactctgaa   2760
tcaatttaag tttagtttcg atttatggtt gtttgcgttc attatt              2806
```

<210> SEQ ID NO 165
<211> LENGTH: 1839
<212> TYPE: DNA
<213> ORGANISM: Lactobacillus plantarum

<400> SEQUENCE: 165

```
gatccattgt cgactttgtt gccgcgccgt aatcaaacag tgcatctaaa gtatcgttct      60
gcacagacga cggcggagct acgcaagacg ctacgtcaag cacggtattt acaggccggt     120
actcagaata ccgccacgcc ggtctttcaa aatcgacagc agcgaggtga tgcgacaacg     180
tacggtcgta tcagtaccag ccaagacggc cggatatgga cgaaactacc cattagttat     240
ccgcatgtgc aattgtcacg gccgagtgtc tggtacgcga atggccgctt gacgttgata     300
gatgggaaag accgttactg gacgactaat tttaaagatt ggcaacatca acggttgaac     360
tttaacgggg ctgattttaa gcaaggtcgg gttcaggccg tctttccagg tacgactcgt     420
tcagcggttg ttgtggttcg cggcattgat cgccaaagca gtcgcgccaa actctattat     480
ggacagctca cgaagactgg acgggtcaaa gcttggcacg cgttacaact aggaaagctc     540
ccagcgcgcc aagtcgctgg aatgagcttg attgatcaac acttataccl gtttcttcag     600
cgcggtacgc agttggccat ttatcgtgcc aatcggttga cgcgtccggt caggttggtt     660
ggtcgcgtta agctaaatca tgcgcagtca caacgagtga ccgcggtgaa tttgataccg     720
accaccaagc atcgctaccg gttaatattt gacttgacga cagctgaaaa agttcagaaa     780
cagccacgtt atcggttact tgatcggcga tttaaagcag tggggcagca gcatctattg     840
gtcactgatt atctctggag ccaatttcaa attagtctac gtgggagtga gtgaggcaca     900
tgaaggtaca gccaaaggaa cgctttagtc tagcgtggcg gtggttgccg ctcgaattgc     960
tgatcattat gctaagcgtc ggccttggat gggcgggcaa tcgatggcta cctaagccgg    1020
tgtatcaagc atctgttgat attcagattg cgcaaacgcc gcgttcaggg ctgtcaacag    1080
cccgtctaaa acgtcagcga cgccaggata tcaaagctat cacgcagttc aacgtgatgc    1140
cacaccagag tgcagtgctg actcaagcca gcacttatgc ctatgcgcat tatggcattt    1200
ggcaaccgat tcaggaactg agtgagtcgg tccaagcggc accagttgcg cggcgaccgg    1260
tcttacgggt gacagcaacg agtagttcac ggcaagtggc ccagcagaat gctcaggcgt    1320
tcaatgtggc gattaaagct aatctgacgg gcttaaaaaa ttatcgagtg aagacagtta    1380
aacgtaccgt aacgcgtgag acgaacgtga ttcgcggggc gctttggaag ttaatattag    1440
ttgttggggg cggcttggcg ttgctgagtc cgtacctcgt gaaatatggt cagggttggg    1500
ggcggcacga tgatgagacg taggggagca agtatgcagc agcaccgtaa tgtgctctat    1560
ctgattatct tcggaatcta cttagcctca gtcacactac agacgacgac ctttaacgag    1620
atgataccgc atcgagtggg cgttttgatt gaattagcga ctttggccgc attactgggc    1680
ctcgtggttt gcttagatac cttgaccccc ggccaaatta ttggagaagt cagtttactt    1740
gtactggtga ctgtcgtgac actcacatcg ggtgcgcatt atttgatgcc gacaatcatg    1800
ttggtgattg cagcccggga agtttcgttt cggcagatc                           1839
```

<210> SEQ ID NO 166
<211> LENGTH: 3239
<212> TYPE: DNA
<213> ORGANISM: Lactobacillus plantarum

<400> SEQUENCE: 166

```
gatcatcgag ggtcgctttt ttaaagtaca taattctagc tcctctcttg aacagcgatt      60
```

```
gactgccgaa gcagtaatcg acttttaaaa gtatacagaa tttttagaaa aatgaaacta      120
ttttctaccg attcttagga gattttcagt gacgattttc aagtaaaatc ttgcgcgctt      180
ctcgggccat gtcatgttgc gtattataag cagcgaccgc actcggtgca tattggtaag      240
tattagtctg caaagtttgt tcatagaatt cgaagtaggg taagtgggta ttttgcgcaa      300
tcgtgatagc acgctgccaa tcgaaatcta cggcgcggta atcaacatgc tggaggccag      360
tctcatcaat tgtcagaagc aagtagtttg ctcgtggttg gcgtaggtgg ggattaatgg      420
cagtcggaag accaactgtc ccggcgttta gaatcaactg tcccgtggtt gcgtagcgca      480
tgatgggctg gtgtgtgtgc gcgtaatgac gatatcgaca tcgccttcag cggcttggtc      540
aaagttggcc tgactggcag ttggtgcgag cgcgtgtcca ctagcgacgg tcggtaaaac      600
gtgttggaga cggatggtta acgggccgac gtgtttgatg actgtcattg gtaagttcag      660
taaccgttca aagtgtgtcg aactcagctg gcgccgatca aaagcggtga gaaccgttgc      720
cataatttgt ttgggtttag taaacgtgtt gggattggct gccattactt tttggtagtt      780
ttcctcgtga tttccgagaa cgtaggcggt ggggtgaacg cggtctagta aggtgagaca      840
gcgctccgat tctggcccgc gaacggtcat gtcgcctact gtccagtatt cgtcaacgtg      900
ttgtttctgg gcgtctgcta agactgcttc gagtgcagta gcgttaccgt gaacgtcaga      960
taggactgca attttaccaa tgttgagatg cttcctttct actatgtaat ctaaactctg     1020
gtgagatgtt ttattctggt aaacgtgggt tttaaaaatt tatgaatgta accactatga     1080
aaagccatcg taacttttat ctgttataat gggtatgaaa cgaagtaata tatagcacgt     1140
atattcaagc caattcgttt cgtgccgtgg ttatccttgc gataatcacg gttttatttt     1200
taccatagtg ccttatgatt agtttggttg gtgtcattta attgtatcag tacatggaat     1260
gcgggtgggt taccacacat gtaattgccc agagttcaag gtgacttaca tatggtgtga     1320
tattgtttaa actgaatgga ttgcttctaa atatagtggt taaactaatt gtttgtgaaa     1380
gaggttttgg ataaatgatg acaccttaca aaaagttaa cgtaacggat gcgcctcgac      1440
taaagctggc aattaatttg actagtgtct tgttgtcttt tcaatgttat ttagtaatat     1500
gattcgagcc agcaccattg atattgggca tgtagcttgg ctaaaatggt cattttagca     1560
attgggactg ttgcgattca tgggtgcggg ttgtactggg gaattttttac ctagcatagc    1620 aactagtgat aacgttgcga tactgtctga tagaagatac attgcggggt atgactattt     1680
atcgctaaaa attgggaaat tagtatccac gataattgag ttggagtatc aaaaggccat     1740
caacctgcgt atatgcttcg cggttgacgg ccttttagttt agtgctgaag tcaaagtagc    1800
tatgtgaatg gatctcatct caaaacaagc tatacaccaa ataaatattc aacaccgtaa     1860
taattccggc cagtccatat cccacccacg ttaccgccgg gcgattaacg tgggccttca     1920
tcaggctggc gtcatttgtc agcgcaacta gtggcaacaa ggtaaagggg agggcgatgc     1980
tgagtgccac ttgcgcgtaa atgatcaagt tttcaaaggc agcgtcacta aagccgacta     2040
acataccgat aatcagaatc ggaattagcg tgacagcgcg agtaagcagc cggcgttgcc     2100
atagcggtaa gcggatgtgt aaataaccTT ccatgacgat ctgaccagct aaggtgctag     2160
tgatggatga attaggccg gtaattagta gggctaatgc aaataaccag ctcatgaccg      2220
ggctagcaag ggcgccaacc acggtggtac ttttttaaccc atcgaagacg gcctgcagac    2280
tcgctaacgc gttggtgtga ccgaagaaaa gcgtcccacc aaggacgagc aaaagtgcgt     2340
tgatgagaaa agccgcaatc aagtgcactg ttgagtccca attggcgaag cgcagtgctt     2400
```

| | |
|---|---|
| ctgtgacttg ggctggatta tgataatcat aacgccggct ttgtgcaagc gatgagtgta | 2460 |
| agtataagtt atgtggcatg atggttgcgc ccaagattcc gagactgagg actagtgcgg | 2520 |
| tatgattttt gacgatcaat ggtgttggaa ctaagccgag caacacgttg ccaaattgaa | 2580 |
| cgtgggcccg tcccacctcg ataccaaaaa taatgccgac ggtcaaaata gcgacgagga | 2640 |
| cgattacttc gacacgccga atgccaaatc tcaaaaacaa caagacaact aagacgtccg | 2700 |
| caatcgtcag taaaattcct gcaagtagtg gtaagccgaa taacattttt aaggcgattg | 2760 |
| cggttccaat tacgcccgtc atatcagtcg ccatcatcgc gacttcgttt aaaatccacg | 2820 |
| cggcgtaacg cacgggccgg ggcagcttgc tagcgatggc ttgtgctaag tcttgccggg | 2880 |
| ctacaacgcc tagcctgatt gccaggcctt gcatgaacat ggcgacaatg atggctaatg | 2940 |
| cgagcacggc taaaagccgg tactgaaact gaccgccacc ggctagggat gtcaaccagt | 3000 |
| tgccgggatc catatagccg actgccacta gtgcaccggg accactatag gctaaaaatt | 3060 |
| tgcgccaaaa ggccgtctga tgaacgtcgg gaaccgcgac gctctgattg atttcttcaa | 3120 |
| gactttgatg acgatgtgat tgcatggttc gacgcctcct gcttttggat agcgaggtca | 3180 |
| gccagaaatt ggctgaagcc ggtatcctta ttcattggtg gtactaagtc aaaccgatc | 3239 |

<210> SEQ ID NO 167
<211> LENGTH: 1866
<212> TYPE: DNA
<213> ORGANISM: Lactobacillus plantarum

<400> SEQUENCE: 167

| | |
|---|---|
| tggcctgcca ggcaggacta tcaaagcgta agaggtctat atagtgtaca agtgtcaaat | 60 |
| tagacggact ccaaccaaga ctgcgttgtt tgagtagcga ttggagcacg atggcactga | 120 |
| atggcaggac aatagcaata ctgatgacta gggtgacgaa agtgcctgct aatgttgtca | 180 |
| ctccaagctg ccgatattgt gacgctgacc gttgtccggt gaacttaaca gctggccggc | 240 |
| gtaacaacca ttgctggata ccccaggcaa tcagggcaat ggtcagtagg agggtgccgg | 300 |
| tgagtacccc gttttggaaa tctaagggcc actgactgag gtcccttga atcgtagtcg | 360 |
| tcagaacttc gaagtggatg ctccgaccaa aggtggctgg cgttccaaat tcagccaagg | 420 |
| ttttggtaaa gactaaaatc catacagcta agtatgggac taacatgatt ggtaatgtga | 480 |
| ttcgcactag tcgttgccag gtgttgaccc catgaacttc ggccgcttga agccagcgct | 540 |
| ggttgaattg catgagggct cgcgtaagc ctaagtatgc cacgggatac aaatgcagac | 600 |
| tcatgataat gaccatcccg aacggtgaaa atagccactg aaattggtgg tgccaactcg | 660 |
| gattaagctg agccagtaat ccgtgtggtt gaaagaaata taaccagccc atcgcgttaa | 720 |
| tatatggtgg tgtcatgaat ggcactaaca agagccaatg caaccaggcg agcttttgtta | 780 |
| aacgggtgtg cgtcatgatc catgccaaag gggtggctag cagggttgtc ccgacgaccg | 840 |
| tgcccccact gaggaacaga ctgtgttgaa tgctcacacg gttggttggc tgcgtcagtt | 900 |
| gtgaccatag ctggcttggc gattgcccga ctagtgtttg accaatcagg gcgactaacg | 960 |
| ggccgataat cagagttgcc aacaagcaac tggtgatgat tgataaggac aagcggattt | 1020 |
| gatgattact cattggctaa agacctgatt gaatgcgaca acgttttggg tcagggccgc | 1080 |
| gttggcactg gtccaattga ccgtgtaggc tttgatggct tcgccattgc gtggatcggt | 1140 |
| caaagtgctc gtggtacctg gaattaagtt acttttttga atctgtcttt gaactttagc | 1200 |
| tgataagaga tagtcaataa attgtttggc ggcggcttga tgacgactag ccttcaaaat | 1260 |
| catcgccggt cgtggattga ccaaagtccc actcttagga taaacgaaac caatttttc | 1320 |

```
gccttttta atagctgtta gactcatgta atcgacccca ccaaagacgg cgattttgg      1380 ccagtgatga ctgcatcgag tacttccttg ttagcacccc cgatatcggc accgttttct    1440
tgaagggctt taagtagttg cgtaccgtgt ttcatttgat aagcgttaat gaagtccaag    1500
ctagaaccag aggtttgggg gtccggaatg gtcacttgat tgcgatacgg agcggttgtc    1560
aagtcagacc agtctgtcgg tgccgatttg atgtgccgcg tattgtaggt gatgccgact    1620
gccgaagcac tgtaattgat caactggtgg ctagtatctt taaattgttt attcaggtgt    1680
ttagcttgag aaggctgata ggttaatagc tggccattct tttgtaaatc gacgccagcg    1740
gccattgaag ctaaaatcag cacatcagct tggggattgc cttgctcggc cttgacctta    1800
cttaaaattt tcccggtcgt gccgtcaaaa cttttgactt taatgccagt tttggcttca    1860
aaaccg                                                               1866

<210> SEQ ID NO 168
<211> LENGTH: 889
<212> TYPE: DNA
<213> ORGANISM: Lactobacillus plantarum

<400> SEQUENCE: 168
gatcgcacgt aatgggcaag tcaccgtggc ttttgatgcg cagcacgatg ccatcatgga      60
attcgattta ccagtcaatt accaacggga gtttcccgag acgtggcag tcttagacga     120 tggtcagtat cagaccatga tgttgatgga cgaactctcc gtctgaacgc agcgattatt    180
caatgagctg aatacgagga aactcgtcac ttcaggccgg cgaataatcg cttttgatt     240 ggtggtcttt aactgggcag atgcgcctta aatttgtata attaaataga tggtgtgagg    300
tgtggttttg cgatgttagg ttccggttgc taatcaaggg ggccgcattg ttcacgtaat    360
tctcacgccg ggatcagaga aaggtgtgtg tctaatggcg aaaacagcag tgtgcattgt    420
cgatcaacaa cgttaccaag ttgtggacgg tatgcgatta aagaattgg aaactagttt     480 gcggcaaatg attttaaaag atttttccgca ggcccataat agcagtttca tttgtagtga    540
gcatctcgta cattatcgct tagcaaagat ggatgcgatg atcgagaacg attatcaaca    600
aaatgataag gtcaatgcgc aattatctaa gattctcgct aaccacacgt atcgggtcgt    660
cgatgttaat agcgagctgg aaagttcatt gacatttggt caacgggtcg cggatggggt    720
cgcacggttc ggggggagct gggcgtttat catttcgttt gtcgtggtga tgctcgtgtg    780
gatgttgctc aacgtcttac caattttag ccatcatttt gacccttatc cctttatttt     840
attaaattta ttttaagca tggtcgcagc aatccaggca ccattgatc                 889

<210> SEQ ID NO 169
<211> LENGTH: 2054
<212> TYPE: DNA
<213> ORGANISM: Lactobacillus plantarum

<400> SEQUENCE: 169
gatcgcattt ctgatgttga aagtcggatg tacgaaaagc cccaaaatat tgtagcttac      60
ttggaagata acccaaccaa acctttccta gattgtgaat atatgcatga catggggaat    120
tctctgggcg gtatgcaatc atataatgat ttgatcgaca agtatccgat gtatcaaggt    180
ggctttattt gggactttat tgatcaagcc ctcttcgttc atgacccaat taccgaccaa    240
gacgtgctcc ggtatggcgg tgatttcgac gaacgccact ccgattatga attctccggt    300
gacggcttaa tgtttgccga ccggacacca aaaccagcaa tgcaagaggt gaaatattat    360
```

| | |
|---|---|
| tatggcttac acaaataatc aactacacgt tatttacggc gacgggagtt taggactaca | 420 |
| ggggctaat ttccactacc tctttagcta cgaacgtggc ggacttgaat cactcgtcgt | 480 |
| caacgataaa gagtggctct atcgtacacc cacgcccatc tttttggcggg cgacaaccga | 540 |
| taatgatcac ggtagcggct tttcagtcaa atccgcacag tggtacgcgg ccgataagtt | 600 |
| ctcaacttgt caagatatcg aattgacggt tgacgaccaa ccagtcacac cgttaccaat | 660 |
| cgcgccactc aataacaaat acacggatca cgaaatcgcc acgaaagtct cactggctta | 720 |
| ccacttcgtt accacgaccg ttcctagtac catcgtcaca gtgacttata cggtgacagc | 780 |
| agacggtcag atcaatatcg ccacccatta tagcggtcag tctgatttgc cagagctacc | 840 |
| cgcatttggt ctgcggttta tcataccaac taccgcgacc ggcttcgact ataccggttt | 900 |
| gtccggtgag acttatcctg accggctggc cggcgcaacg cacgggcgat tccacgttga | 960 |
| cagtctgcca gtcacaccat acttggtccc acaagaatgc ggcatgcaca tgcaaactga | 1020 |
| acaagtgaca gtaacgcgat caacaacaca aaataacgct gaccacgaca acaccgtt | 1080 |
| cagtttgaca tttagccaag ccgatgcacc attcgccttc agctgccttc cctataccgc | 1140 |
| cgctgaacta gaaaacgcaa cgcacatgga agaattacca ttagcacggc gaacggtctt | 1200 |
| atcaatctac ggtgccgttc gtggggtcgg tggcattgat agttggggaa cagacgtaga | 1260 |
| atccccatat catatcccg ctgatcaaga cattgacttc agctttaata ttcatttcta | 1320 |
| aaagttattt tgatttcaaa agaacgctcc ggcgagttat ttgccagagc gttcttttag | 1380 |
| attaacgatg attaagtttt aatatgttta atggctgagc ttagtcctta gccttgaagt | 1440 |
| aatgtacctg cgccgtaaag tcactagttt gaacgggagt cgtgtagagt cctagttgca | 1500 |
| tcaattcatc gccaccgtac attttgtttg tgtcggtctc aacgtaggtc tgctgagggt | 1560 |
| ctaatcccgc taacttcgta atatgcggtt ctggttgaac tgcacctaaa ataacgaagg | 1620 |
| tgaacagcaa ggcttctttc tgatccggac taacaaacat ccacgccacc gtattagatt | 1680 |
| caaacgggct ctctaatcga taaaaggtcc cgtattgaac taactcacgg tgctgcttat | 1740 |
| agaaggcaac ctgtctttta acggcctgct tgtccgcatc acttagttgg ccgcgtcca | 1800 |
| gttcatagcc caaggtacca ctcattgcca cagcaccacg catcttcatc gacgtcgacc | 1860 |
| gtcctaacaa ttcatctggg ctcgtcccaa catgggcggt aattgcagaa attggataaa | 1920 |
| cgagtgaagt cccatattga attttgagcc gttcaatcgg gtcattatta tctgatggcc | 1980 |
| aactctgtgg catataatac attaaaccag catcaaagcg gccaccaccg ccagagcagc | 2040 |
| cttcaaataa gatc | 2054 |

<210> SEQ ID NO 170
<211> LENGTH: 2341
<212> TYPE: DNA
<213> ORGANISM: Lactobacillus plantarum

<400> SEQUENCE: 170

| | |
|---|---|
| gatctcgttc cggttttta tggtgtaaga ctgatatgag gtgtaatttt gattgctgaa | 60 |
| tactacatta ttattaatga actggcagga tctggtcacg gtaaggtcgt ttgggaaacc | 120 |
| gtcaagccga ttctagaaca acgacagatt cgatttgaat atcgaatttc tgaatatgcc | 180 |
| ggccacacaa ttcggctcgc aaatgagtac gttaaaacca ttcaacgacg accaaacgtg | 240 |
| accccggtca ttctggtcat tggtggtgat ggcacactga acgaggcctt gaatggtatt | 300 |
| atgcaggtcc cacaagctga accgatcccg ctcgcctaca ttcctggagg ttcgggcaac | 360 |
| gactttgctc gcggtctggg tatggcgact gatccagcaa ttgcacttgc acaagtactc | 420 |

```
aacaatatgc ggccccgttc gttaaatgtt ggttatttcc atgaaacctt gaaaaacgaa      480
caccggtatt tcgtcaacaa cgttggttta ggatttgacg ctcaaatcgt tgatgacaca      540
aaccgtagca aaagaaggg ccgtctgggt cgttgggctt atctcagtaa catgctggcc      600
gcatattccc aacaggaagg cttcccgcta accgtacacg ttaaccggaa gcgagactat      660
tataagcggg ctttcctttg tacagtctcg aacattccat actttggtgg cggagttaaa      720
attctgcctc aggctaatct gcacgataat cagctcgaat tgatcgttgt cgaagagcct      780
cactggtgga ttatcctctg gttgttcgtc ttactgctac tgggtggccg tcatcttaag      840
tcgcgtttcg ttcaccatta tcgcaacgct aacttgcact tgttggttaa ctctgttgaa      900
attggtcaga tggatggtca aattattggg aatcgtaatt acgacctcta cttgtccacc      960
catccctacc cattctggat cgacactagt atccatgacc accactaact ctactgctaa     1020
aacaatacaa attagcgata aaagtcgtt gcgaagatgc tcgcaacgac tttttatag     1080 gaccaagatt ggcaattcat actcttgag cgccatccac ttaccggcca gcaatgctaa     1140
tgaccactta attgactccc cacccactcg gctaataaaa aagactgctg accatctcaa     1200
tatggtcaca cagtcagtct tgattaatct tagtcctcag aagcgttgat tgcttccaga     1260
agcatgtcaa gttgttcaca tttacgagat aagtgactca cccgttcttt caaatgcgga     1320
taaatggtca caaccgtga gcgatcctgt tgccgaacgg ctagcgtcct taaatgatcg     1380
agttcggtat tagcctcttg atattcttcc agaatctcaa aacgattact cactgatagc     1440
acttccttat cacaatagat ggtccaattt ttcgaattga aaaacgacaa acataatata     1500
ccacaattat tggtaagttt aaatcataaa attcaaaaaa atttaaataa aaatacccct     1560
aacacttaac aatatcgtgt taggggtatt tgcaattaaa atcggcttac ttaaccgtac     1620
ctgcaaaact tggcatgaag taagaactga ttgtctgaac ttgaacgttt tggccttcag     1680
ttggagccgc aacgtattga ttatttccaa tatagatggc atcgtgataa gtgctaccac     1740
gactacccca gaataaaata tctccaggtt gagcatccgc aacggaatgc gtcgtcacat     1800
aagattcctg tgcaaccgta ctatgtggca aggtaatccc agctgcatgt tggtaaacat     1860
aggaaactaa accagaacaa tccattcccg aaagactcgc accaccccaa acataaggga     1920
tgttggcact agccaacttc agcgcaaggc cggttacaga accagtagct aaatcactcg     1980
ttgaactagt agtggtactg ctactattag tcgttgcggt actacttgcg gtattgcttg     2040
cactgctagt ggctgctgaa gaactactct gactggtcgt gcttgaacta gtcgctgccg     2100
agctactctg gctcgctgta ctcgtagttg atgctgcact agcagctgta cttgatgctt     2160
gactagccgt gctagtagca gtcgtactgc tagtactagt tgcactcgca gttgaagcgg     2220
tactttgact agtcgttgtt gaactagcag ctgatgagga cgcgctactc gttactgagg     2280
cactcgctgc aacactcttc gactgactgg tagcagtcga agaactagca ttacttgctg     2340
a                                                                      2341
```

<210> SEQ ID NO 171  
<211> LENGTH: 2477  
<212> TYPE: DNA  
<213> ORGANISM: Lactobacillus plantarum

<400> SEQUENCE: 171

```
tttagtgctt cggtttgtga ttcatcataa gtaatgttgc tagctcgacc gacatgctcg       60
atagcatgat ccacggcacg ttcagacaat ttttcatcat tatcggcggc taacaaccgt      120
```

| | |
|---|---:|
| tgtaaatgtt ccgcaacgcg ccactcggct tcatagaggc cgcgcaagta gatacgattc | 180 |
| tcgtcaccca cgattttatt ttccttcgcc aagacgacca actgatcagc cagcttcgaa | 240 |
| ggatcaattt gaacattgcg agcattctca agtagttgca acgtttgatt cagcaacggt | 300 |
| tgagccgtgg tatacgtatc accgttttcc acgcacagct cattaatctc agtcaatagg | 360 |
| gccgccttta accggtcatc cgcttgggga tcaattttaa gttgggccgc aatttgatcc | 420 |
| gcttttttga acccgacgcc tttgatatcc tcaaccaaac agtacggatt cgcttgaatc | 480 |
| ttagccaaag tgtcaccttg atagcgtgca tagatggccg cagctaaccg actcccaaaa | 540 |
| ccgtacgcat taagtccgat gatagtttgc tccaaaccgt tattgaccgt gagcgtgtcg | 600 |
| atcaaagtcg tctgaacgct ggcccgaagt ccgattggtt ttaaaacctt cggatcagct | 660 |
| aaaatttgat caatggcgtc ttcgcccaaa gtatcgacga ttcgctcagc agtccgctta | 720 |
| cccaacccag gaaaatcact accagataga taggcaatca agcctgcgcg tgtcgtgggc | 780 |
| gtttcatttt gataattatc cgcttgaaac tgaaccccgt atttgggatg cgtgaccgtt | 840 |
| ttaccggtaa aacgatacgt tgtctcctcc tgaatatccg caaaatttcc agtaacaacg | 900 |
| atctcatctt ccgaccaatc aatgttctgt tcagttactt tgactaataa gactttataa | 960 |
| aaactatcgg cactgctaaa aaaaacggca gcgactttac cgacgataaa gtgtgtgacc | 1020 |
| ggttcccgac caatatcgtc ggaaaataaa tgtgcttgtt cgtccgtcac ggaaatcctc | 1080 |
| ctaaattagt gattttgatt atctgcttgt gcggctaaca ttttttcaat atccgttagc | 1140 |
| tgttgctgat gacttttaaa atattgactg tccaatttct gcgcgcgttc aaaccaggtg | 1200 |
| gcatacggtt ttcccagtac cattgcggtc agtccaaggt taaaagcagc tcgcccagat | 1260 |
| tgcgaatcaa tcttatatgc gcgttgatag taatccgatg cttgctgatt attgcctaat | 1320 |
| gcaagtaata tgtctgctac taacaaatta gcgtcaagtt gttgtggacg tgcctcttga | 1380 |
| gccgtaatgg cccagactag ggcatgttgg taatcgtgtt gggccattaa gcttgtgca | 1440 |
| ctcattaaat aagcatcctg ttttagttga tcatccgtaa tttgttgata atatggtaac | 1500 |
| gctttgtcat aagtttgagc ttgataatag acatttccca acgcataacg caggtagtcg | 1560 |
| gctgcgggtt gttggtggtc aaactttccc aacgccttca ttgctaacgc ctctgcctgt | 1620 |
| tcaaaatctt gaccagccgt taataatacc actagttcat aataagcatg gtagtcctcg | 1680 |
| ggctgtgcat caatcttacc aatgagttga tggactagtg cttgctgttt agctttgcta | 1740 |
| ggacgtgatg ttttgccat ccgaaccact tccttctata ttaaatcgta tcagttgcat | 1800 |
| cgggccgccg tgataggtat gaggtgtcat tccaatctaa tagcttaaaa tgttgaccac | 1860 |
| ggtcacgcgt ctctaaaatt gttgttgacg tattcgacaa gccaccccgt tgccgtaacg | 1920 |
| tcgccagtgt cgctcccagt aatgagttga ccaaggcatt caaggccgca ccatgactaa | 1980 |
| cgatcaaaac attgtcatcg cgacgtggat ttgcttgaac aatttgctta atagcgggag | 2040 |
| tcatccgctt cagcagttgt tgaaagctct cccctgaat cgctgtcggg tcatactgat | 2100 |
| ccggatgatt tcgaaacgcg tcgaattcgg ccggatacgt agcttcaaca tccgtgaagg | 2160 |
| ccattccttc catcttaccg agattgaact cccgtaaacg actcagtacc gttatgggta | 2220 |
| actctgattg tgtcaaatca ttacgtagtg tcatcgctgt atcacgcgcc cgttttaacg | 2280 |
| gactgacata gatatgacta aaccgaatat cctggagcgc cgctgccaat tcatgaattt | 2340 |
| cttgataact agtcggtaat aatggtgaat ctccctgaga gccttgatag cgcccctcaa | 2400 |
| gattccactc tgttttccca tggcgaacaa ataatagttt tgtcaattgc ttacttcctt | 2460 |
| actctagtgt cttgatt | 2477 |

<210> SEQ ID NO 172
<211> LENGTH: 1965
<212> TYPE: DNA
<213> ORGANISM: Lactobacillus plantarum

<400> SEQUENCE: 172

```
aatgggtgtt ttcaatcatg acacttaatt atgagctatc aaaaaagctg gacaaggcca      60
gctttcttgt ttttaatctt catttttaaa caatgcatcc aacaactgcc ccgccactgg     120
ttgggcagta ccaaacattg ggaacaagtg cggatacaag tacggcgccg catgaatacc     180
caagtatacc gccatttcag gatgctctgg cactaattcg gcatagagat tgggaatcat     240
cacgtcgacc ccagcgaccg ccaagtgtaa gtctgctacc aacttttcca ccgcctgcac     300
ataggattga tgcatatcag ccgtcgcgtc tagcacgtcc gccccgttac caaaagtcgc     360
atcctctcgt aataagatct gagttccccg gctgaccaca gaatctaagg tcaagtgata     420
tgagtccagg cgataccgtt cgatcgttcc taactgtagc gctgattgag gccacttaaa     480
agcggtcccg cgcaacgctc gaccattttt gcgatcaagt aacgtcttga ccgttgagcg     540
accatcacca acaatattgg ctggaattcg ttcgacgatt gcttgcacac gactatcgat     600
aaccaaaaag cgataacttg atgcgactac cacttcctcg gccattaccg cggacgtttg     660
ctcgaatagt tgccggacga cttgttcaaa cagtccgcgt tcgggcataa tccgaaagac     720
aattactttg tgcgactcat ccgccgcttt taatacgatc ccaccagctt gaacgtaccg     780
atcataatca gcaatcaact gattagctgt atgatatgtc tgtgaagccg caccggaac      840
cccgtgctca gccagaattt gtttggccgc tgctttatgt gtcagtacgg tcgttagcgc     900
ctgtggattt aaatccgttc cgctcccatt cacaactaat tgcgaccgtc ctaacttagt     960
caatcgtaaa atgttagcgt gtgggtcaac aacgtccacc tgcactcccc gcgtcaaggc    1020
ctgctgggct agttgctggc tcgatagatc tagcgcggta aagcccgcaa gttcaaacgg    1080
acgttcattg ctcgattcct gatagcgtgc agcccgttcg agtgcccatg ctaacggatc    1140
ggcttgcatg gcaatctgcg cactcagcgt cttctttgga tcagtgaccc acgacttcaa    1200
ctgtttgagt aacacggcat cttcatttgg taggccatag gttttaacaa atcagcaag     1260
tgcatctaaa acttgaacag ccggcacggc ctgagcacta gccgtcgttg gattttcacc    1320
caaaacttga cgggtcaatt ggtcagcttg agcgttgact tgggatacca tcttagctgg    1380
aagtgccggc atcattacga ataactcgc caacaaacga acaaatgcca ccgcgttcgc    1440
gtccaccccg actggactag ttggatcgag atccaagccc cggtattcaa gataatagac    1500
ccctgccgg gccatcatag ctagctgccc attactccga agccgaactg gcccgtcaaa    1560
atcattgaca dacaacaact gctgttgacg aacagccgcc gtcaacttgg ccacgtagcg    1620
atcaattgac gtatagtctc ccgtcacttg actgtagcga ccatcgggat gttgaacact    1680
actgcgctgt ggacgactcg tagtatccgt aacggctagg cgtggtgaag cgccaaataa    1740
atactgaatc agccagttca tgcgcaccaa tccctgagcg actttcagat aaattgcatt    1800
gcgaaagtca acataactgt gatactgctg atggaaagtc tcagtatata aacgggtgaa    1860
taaagcttca ttcaagctca tattcacgtg actaccagtc gtcattaatc gctgtaactc    1920
atacttacga gctaagtcgc gacgacgctg atagctgact tgatc                    1965
```

<210> SEQ ID NO 173
<211> LENGTH: 3582
<212> TYPE: DNA

<213> ORGANISM: Lactobacillus plantarum

<400> SEQUENCE: 173

```
ggatcacgaa gattttttcga gttacttgca acggtttggg catcacgaat aactgaataa      60
cgcacaaccg tcaccacaat cattattaag ttagatacac cgagattcag tcgccttgct     120
caaaaaagt aatagtcatt tcaagaatca attcttgaaa cgactattac tttttttgaa     180
accttttccg gcacaattaa attcacactt attgacgttt ccgttaagcc agcaattccg     240
taatcatttt ttgataaatc tcgatgaagc gcccatacat atccaaatca acatattcat     300
taacttggtg cgctgtaata ttgccgggtc cgaagacaat cacttgcata tcaggactct     360
ttacaatata agacgatgcg tccgtcccac caggagcacc aaagtacggg agccgttgct     420
gtaaaacttg ttccccaacc ttcttcgcca actggaccaa ctggctatct tccggcgtat     480
gcactgggta gaacgaactt gcgatgtcca tcgttagatt ggcaccatct gcattgcatt     540
cagcaatgat ggcttccaaa tccttaatca agcggtcatt ccgtaattct ggaatcgtcc     600
gaattttac tgacatttcg gcactggctg gacggtgtt gacctgttcg ccaccactaa     660
ttaacgtcac gacaggcacg gttgggccca atacgggatt aacaatagtc ttgaaactgt     720
caaaataggc agtttgtttc tgatagtaag tcatcaacat atcgatggcg ttttgaccaa     780
tcgctggcat cgaactgtgg gccgccaccc cttgcgcttt aatcgtataa gtcagtgaac     840
ccttatgcgc taattcgatg aagtgttgtt cggtcgtcgg attcgcatcc gccatccgtt     900
gcgccgtatc gccgtcaaca cctaacatgg cttgaatcga cttggtcagt aaaagttgtt     960
tgtccgcacc gcttggttcc gcacagatca acgtttgaat atcatcggcg taaccgagtt    1020
ccgtcaattg ttcagcgcct aaatggtcga cttcttctcc cacagttgcg agtaacctca    1080
ccgtgccatg gagtggggcg tcctgatcgt gcaatgcaat catcgcgaag acttcagcca    1140
ttagtccagc cttcatgtcc gtcacaccgc gaccatacaa ccgattatct ttgatagttg    1200
ctgccaacgg gtccgtgtgc catttatctg catcacccaa cgccaccgta tcttcatgac    1260
catccaacgc gacgactggg ccgtgaccat caccaatttc ggccaccaag ttcacccgcc    1320
cgggagcgta ctcgattgat tgtgcttcaa taccatgttg cttttaaaagt gtgaccaaat    1380
aatccgccac caattgctca tggttatttta ccgtattcat tttttacaata tcgcttaatg    1440
cctgtacagc agcttctaac tgtgccgttt ctgccatgcc attcatcccc tagtcatcct    1500
taattaaact gttccaatca atttaattat accacttcgg ctaccgttgg ccgttgtcag    1560
acacgtttaa tcgacagatt tcagtgcatc cagcatattg actcgcttta acttacgatg    1620
catcattccc atgactaata aactaaaggc cagggtcaat aatgccgcgt aaacgtaact    1680
caacggatga tcgttggtg aaaacattaa cgcgttcgtt tcagccgttt gcaagatata    1740
tgcgtgcaac cagttgccca agaaacaacc ggcaataatg cctaaaaccg tcaatatcag    1800
attttcacgg aaaatataca tcgtcacttc accatcgtaa aagcccaaca ctttgattgt    1860
cgacaattcc cggatccgtt cagaaacatt aatattcgtt aagttataga gcactactag    1920
cgctagtgcc cccgccgaga tgacaaagat caatacgact aagttcatgc tatccagcat    1980
tttaaaatta gtggctttct ctgtactcat cagtgtcacg ttctgaaccc ccgcctgttt    2040
caatagccgg tccgcataag catttttcttg ctttttcgtt gcctgcttaa accggacata    2100
gttcgtgtta tatactggtg cctgcttgaa gacacgtcga taataagtcg gactcatata    2160
gataaagtga ttgacgtaat tttcagccac cgcactgatg tgaatccgct ggtggtttg    2220
cccggccaac ttgatcgtta aatcatcgcc cgcctgaacg ccatataact tagctaattt    2280
```

| | |
|---|---|
| ttcatcgatg accgcaccgc gatcaccaat atgaatggcc tgatgacttt gtcggtgccg | 2340 |
| taataccacg aacttgctta gcgattggtg gggtgccggt ataccgagcg tagccgtctg | 2400 |
| ttctgctacc ccggactgtt tgaccgtcac ctgcttggcc tgtaatttca aactagcctg | 2460 |
| gtaaagttga ccacgactga gtgcttgccg ttgttggtcc gtttcgttcc cactacgcgt | 2520 |
| caccacagca tcgtagtgcc acaattcgtt aaattgcttg acgctaatat caccaatgga | 2580 |
| atcctttaag ccaaaccccg taatcatcat tgccatgcag cccgcaatac cgagcacggt | 2640 |
| catcagcaac cgttgcttat accgaaatag attacgaagt gtgatttat gattaaaact | 2700 |
| cagccgatgc catagccatt gccagcgttc taatagcaaa gtcttaccgg ccttaggtga | 2760 |
| tcgtggctgt aagagttgcg cgggtaaact gtttaaatcc acgcggagca cgaccagtgc | 2820 |
| cgtccccaac gtgcacaaca acgcaatggc taaggcgata ccaatgtcca tccaaatgta | 2880 |
| ttgaacgttg attgcgggca aattatacat actaccatag gcctgcgcga taaccgcgg | 2940 |
| gaaaaaattg acgccgaaca ggacacctag cgcggtccca atcagcgcgg ctaaaccacc | 3000 |
| ataaatcata aactcgctac cgaccgcggt attcgtatac ccgagggcct ttaacgtccc | 3060 |
| catctgtagc cgcaattctt caaccatccg cgtcatcgtc gttagacaaa ttaacgcggc | 3120 |
| aatcgcaata agaacagcg gaaagacagt cgacagtgcc acgactcgtt gcgtattttc | 3180 |
| gtgatattct gtgtaacccg gattatccgt acggtcagtg tacaaataag tcggcattgt | 3240 |
| gatggccgcg acctgggcct tcgcgcgttt taattggctt tgtaactgac tagttgtgcc | 3300 |
| gttcccgctg gcacttgact agcaagttgc tgggtcgcct gtcgcaatgg tttcagctta | 3360 |
| gcctgggcct gggcttgtaa tgcctgctgc cgcttacgcg cttgtggttt taaccagcgt | 3420 |
| ttgagttgcg cggtgttctc gcgattcaag cgccgatact tcgccgtgta gggggtgacg | 3480 |
| ccccgcaaat ttttgaattg cacgtcaatg cgcgttatca cactggactt aatcacctgc | 3540 |
| ggacggacat agaccaagta gtccaaagtc cctttaccaa cg | 3582 |

<210> SEQ ID NO 174
<211> LENGTH: 1965
<212> TYPE: DNA
<213> ORGANISM: Lactobacillus plantarum

<400> SEQUENCE: 174

| | |
|---|---|
| gatccgccgc tgtcattggt cgtaatatca accgttccgt ttcaaactga gtcaaattgc | 60 |
| catctccaaa ttattattga ttcgttaatt ataataatct actggcaaat gtaaattatt | 120 |
| tcgttccact ctcaatgatt tggcaaagtc acctgtgcca gcatcgcagt tcctaccgct | 180 |
| tcaaatcggg cgcagttcta atccaattc tcgcaaattt taaccacaat aaaagggccg | 240 |
| gtaaccaacc gtcccttct ctgatcgact tgcaaacccc aagcttgcca ttgtgtatgt | 300 |
| gcctcgtcat ggacccagcc catcccgaga ggtataaatg cttgtcaaac gttatgattc | 360 |
| agctaactga gctacttatc actatcaata attgcttatt aacaatgtcc tgacaaagta | 420 |
| aatcgatccg gctcccaacc taaatccgct gacaaagcgt atgtattgct tcataacttt | 480 |
| gtctttagta tagcgagcca gcattgcgtt tagataacac gaagattaca aaaatgttac | 540 |
| aactggtcta aaccaactaa aagttagcct ggtattgctt aatcgtctct ggctacggac | 600 |
| acccagttta tctttaacga acaaagtcgc ccactatggt cttaacagtc ggcctttatt | 660 |
| gaactgaaag ccgttgattg acatgtgctt gaataacttg tcgccgagaa ccggtcaaga | 720 |
| aataaatcgt tatgccaaca aaaataatga cggtagcacc gattgtttgc cattcgaacg | 780 |

```
catccggctt aaccattgtc tggctacctg atgccatcat gctcaaaata tcaatagcag      840
catggatcac catcggcagc aagatactac ctgagtacag gtacgtcgag gctaaaaacc      900
agcctagtgt cgctgcaaaa atgatttgct caaccgtggc tgacaagggt tggcccgcaa      960
aaacgtttgt aatatgccac attccaaata ggccaccgct tagccacact gccaagtcga     1020
gttggtgacg ccgatgccga aaagcttgta ataacaaggt taaaacggca aaacgataca     1080
accattcctc tgcgattccc ggttctaacc cactcaaaaa cattttccaa gtcgctgacc     1140
gtagctggaa gtcccaatgt gtgaacgttg tcgcccatga accacccgca ctaaaggcat     1200
tccatagact aaaagccgtt cccaccacga tcagcccaac cactaaacta gtttgggcct     1260
gacgattaaa ccgccacgat gggcccgtca atccccatcc ccgcagtaag accccaacag     1320
caatcacaaa gcccagggcg cctaaaatac cagtatcact gaccatctcg aatactgatg     1380
gtgcttgcag attcggtaaa atcaaaaaag tctgctgcgc actgacgaca ccactaaaaa     1440
tagccgtaat taggaccgca atccggccaa tcacagattc gatcggttta gtgaccacca     1500
ctgccaccgg tacgaatgcg accattaaat aagccatccc cacagcaatc aatccctgct     1560
cgtctaacca tgacagctga cttaaccaag ccacgaggtt cgccagtaaa atcggcaaga     1620
gtgtgaactg cagtactgtt tggacataat aattaacatg tcgcaaacgc cgccactgtg     1680
cttggtcctc ctcggcagct ggccaccagg ctaacagtcc ccatatcagc aactgcatac     1740
caccaactgg gaaaaacaca ccaccatcaa acgtaaatag ttgaataaag gccgcgccaa     1800
ataacacgat gagctgcccc atgtaccagc gtcgtaataa ttgttcggtt tccggcgtca     1860 taaaaaatc ccccaatctg atatgcatta atcataccag attggggacg ctcacacgtg     1920
attttgttta gatttatcgg attccacgac taactaataa agatc                    1965
```

<210> SEQ ID NO 175
<211> LENGTH: 1777
<212> TYPE: DNA
<213> ORGANISM: Lactobacillus plantarum

<400> SEQUENCE: 175

```
cctcctagta cggcgacctt gtgaaccagt actgttcatg tgtccagtac tgcccctaac       60
tgcgttatta aaacgcacac ctcagccact actgcccatt caatgggctg cgtcgaagcg      120
tgacgtctag acacaccccg tatctaggac gtcgattgct tattgtcaaa caattaatta      180
ccttggggtg gcccgatcgt tgcgacccga tgattaccag ccatactggt cgtaatacct      240
gagataacag ttcccatcgg atcgacttga ttacttgctg ccagcaaccg ttctcgaaca      300
cgaacaaccg catgtctaat cgtcaatacc accgtcgttt taactggttg gagccgttgt      360
gtcagtagtg aaatcacttc aaccaacatc tgcccagcaa ctacccagtc acccggttta      420
acgttgaact taaatgtagg cgattccaaa gcactggtta attgtccaat tcgtagccag      480
cccaccagac cattggccgc tcgaaagcca attaaccgtt gattggctgc cacggctgtg      540
ataaccccag caagggcgc aacaatttga tctgttgccg gtataaattg ctgcttaaat      600
cctagtaacc catataagtg aaccgtattt gcaagggtcg tcacattgat cacttggcgt      660
ttaaccggcg caactacggg aattaatgag ctaatgacca ctggcacact tctcacttcc      720
ttactttata aattggcaac cattcgtatt taaataacct taacaaacgt aacgtaaaaa      780
acttgttttc tttaatatgt aagtcaatta gtttaagtca ttgactgtta tctttacaac      840
ataaaccata ccataattaa actagaatgc cagcataatt aacggtttcg attaaggttt      900
acatctgtta gcgttaattc gtaaactcaa ttaacgaacg atgctactaa atagctgaaa      960
```

```
ttggccacca taaccccaat gtcgcactca agcaatcttg tagatttgac atcatgtttc    1020
cccaatacgt caatcaggca atgacggtta ggcctacaat ttcagtcaga ccgattgcga    1080
gcaaaaaaga gcttccggct tttattccgg gagctcaaca agtcaacgtt atttatttt     1140 aatctcagcc actattcaac cgtaacacgc atccgcccgt gccgctttga aaatagagg     1200 ttctgatcaa cacggttgta caaatcaatc ggactaccat cggcttgatg cagtgtcgag    1260
acaccaaccg aaatcgacac attgatttcc tcgtcttcat acttaacaac gagatgattg    1320
actgcttcaa agacctgacg gacaatcact ttggtactag ccagatcata accgggaaac    1380
aggacattga attcttcacc accggtgcga tacagcttga ccttctcgtc attggcggcc    1440
aagaccgttg tgaccgtggc ggcaacttct tgcaaaacgc ggtcccctgc aaggtgcccg    1500
tacgtgtcat taacgtgctt aaagtgatca atatcgaaca tcatcatcga taagttgaga    1560
ttgttcttgg cactatcatc gaataaatat ttgatatgtt ccgtgtaagc ggcaaagttc    1620
tcagtctcag tcaaagcgtc gtgactcgca aactgggcca accgtaattt aatctcacta    1680
tcttgggtca gcatattaac gtaggcgtac aataatcctg caaaaatcat taagtagcca    1740
tattcttgta aagtattgtc ccaatccagc gaatatt                             1777

<210> SEQ ID NO 176
<211> LENGTH: 810
<212> TYPE: DNA
<213> ORGANISM: Lactobacillus plantarum

<400> SEQUENCE: 176
gatcgctccc aaagaagatg gtcgtaaacg gaatccagac tttagctgac gttgagacta     60
accaaataat gtacgacgca aaccacatga acgtgcccac gaacgcaaat ttcgcattca    120
cactcacttc cagccacttg tacatcccgc tactatcaga cttaaccgct gccccgaact    180
ccgccatcat tagcgcgaac gggatgaaga acagtacggc tgcgactagg taaaatagaa    240
tcgagctgta acccattaaa taataggcca ccgtactatt ggcaaatccg aaaacggtcg    300
taaagatcat catgactagc gccatcaatg taatctttc attatctttt gttgccatta     360
ttgcactccc tcacttactc ctttaatact tttgtaaagc tattccaatt taagattacc    420
gaacgaaggc aataaagcgc tttagttttc ctaacaatat tatgattttt tcatgtgata    480
gtcagcgcaa ttattcatct aaacaattgc cgcaacagtt attgacaaaa actatttcat    540
aacggaaacg ttcatttaat aacatagtaa cttttcttta acatagctga cacataattg    600
gcgtattcta cacttatcag cttagggaaa atataaaacg gggttataca tatcatgaaa    660
aaatttaact ttaaaaccat gttgctatta gttttggcta gttgtgtctt cggggtcgtc    720
gttaacgtga ctactagtct tggaccacaa accgcaatca ccgcccaggc ctccaagaag    780
ctcagccaag cccagcaaat tgctaagatc                                     810

<210> SEQ ID NO 177
<211> LENGTH: 3846
<212> TYPE: DNA
<213> ORGANISM: Lactobacillus plantarum

<400> SEQUENCE: 177
gatcaaaggt gataccagtc gtcggaacat tattcgaaac taatcgatag cccagttttt     60
catacgcagc aatttgggaa acgggcgaat aactattcgt agtgccataa gcaccagtta    120
ctaccgtcgt aggtagtgtt ttaccactcg ttacatccac aaacgcaacg gttgcggtct    180
```

```
gtgatttggc cgtgtacgtg attgcaatca agtgcggctt atcgtgacta gtgaccgacg    240
ctgcttcgac ttctgtaaca ctggcttgat aacctgtaat cgttggtgac gtgaccgcgg    300
ccaatagtgc tgactgacca ggtgccactg tccagtcacc gtaagtcagc tgcttacccg    360
ttgccatgtc gaaagttgcc gtgcgattga acgtgaccga ctggttaacc gtttcagccg    420
ctgattcacc tgacgcatat tgatacgtaa tcgtccgagt cactgtttgt tccaacgaat    480
cacgaccagt gcctgccgga tatttaggac cggctggata tcagcatcg atggcctgac     540 caggttggcc cggatgatca acgctgaccg tcacgtgacg atgcgctagt gtaaccgtat    600
aaacttgggt attctgctta taaatcagct gatcaggcaa gtccgagtta actggttcat    660
agcctaattt tgcatacttc gcgatatcag cagtgaccgt atagtcggca gcatcaccgt    720
atttcccatt caaatcaata taacttaaga cttggttatc cgtagttcca tcgacaaatt    780
gaacccggat cgtttcagaa ttaacgctgt atcggaccgt tgtttccgta gtctcgccca    840
tgctagcggg tacagccgcc gcgatggttg tttgatccgc cgtgtaacca gtaatggtcg    900
gcgactcaat ggccggatag ctattcacat tggtcgtcca attaccgtac gaaaggaccg    960
ttctatccac cgcatccccc gttgccgtgc gcgtatacgt gaccgtttga agcacatccg   1020
ctaagtccgt gggtgtgtta tcagcataaa cgtaatgaat cgttcgctga ctggtcttca   1080
tcaaatcact aacggccacg ttacctggct gatcaaccgt cgccgtgatg gtgccatgtt   1140
tcaggtatac gtagtaggtc tgttcagtat cctgatcaaa ctcaagcggc gctgggacct   1200
tatccgaagc taacacgtag cctaattttt catacgccgc aatgtcctgc gctgtcgata   1260
attcgtgggt gtgccaaagc tcccactgag gggaatctgt tttaaaatca cgttgttctt   1320
atcttggtcg acgtaaacga ccgcaatctt ttcggtgttc gctaaatagg tgtacacgac   1380
ctgcccacca acgtccgcta gagtgccatc ggcttggtaa ccggtacttt ctggttgtaa   1440
cgtataacca gttttggcat gcgtagcagt cgtatcactc gtggtgtagc tcaaatagtc   1500
cttagcggta acatcagtcc cgtgcgtcgc cgttccatta gccgttgtta ccacgtgtag   1560
cgtccccgct ttgtcgcggt acccatactg atagacaacc gttacggcgc ccaccgtcaa   1620
ctgaccacta ggtgaattcg tcaatttata attactatta gcagcggcat tcgtcagcgt   1680
ggccgtaatg gttgtcgtgt ccggatcagt taaccctgac gttaacgtgt aatccaaact   1740
ttgcaccgca acaaccagta atgaccggcg taatatttt gttcctgac cattggccca    1800 cagaatcgta tccggcaaag taatcgtcac tggacgttga gtaatcgtca gagtcccacc   1860
aacattcaca tcgcctgcaa tcaagaaatc tggattagca gcggataagg ctgccatccc   1920
ggcgctattc agcgtgacag cgtaagtgcc cacgttttga tcgattgcag tggtgttaag   1980
gtagtcggta ctgacttggt acgccgtcgt cccatccaca gccgtcgccg cgctatcagc   2040
agtccaatcg cttggggccg tatattcagt tggcaagtat accgtatagc gacttggatc   2100
agtcgtggcg ttgttatcat agacttttga agctggtgca atcgttatct tggccgcagt   2160
atcagtcgtc gttgtgacgt agcgctggta agtaactgtg taatttgaat tactatcacc   2220
agaatatgtc tgagttaacg aaactgcact agtgttcaaa taatacgtca cgccattttg   2280
tgtaattgtc atgggtaatt tagtcatcgg tacatacgtc ttaccactgt cgcccgtaaa   2340
agttacttcg cctaatgacg tgccatcgtt tcctactaaa ctataagtat cggtaatcgt   2400
tttggccgat agcgtgtaat gatataggta acttgtgaaa ccactaccaa tcgtgacagc   2460
atccgcaatt cctaatgcat cagcgacact gtcaatatta gtataatttt gcaaattcaa   2520
cgaataacta ccattatttt cattagaatc atcagtaaca taaaccaccg ccgaatccgg   2580
```

```
gcttgaaact tgattaccaa ttaaaccact agtcacccca gtgttttgaa cagcaatgac    2640
cggtaataat gcatatttta gcgttgcaaa tgcaccaccg tcataaacag tggttttatc    2700
aaaatgaatt ttaaatgttt ggcgacccct gtagtctgtc agttgggtca cctttaaccc    2760
ctgataggtc acatcatttt tcgtcatcat tgcttcaata gcagacgtta acacactact    2820
tggatcagtc gctatgttaa tagctccttc actattagta gcaaccttaa aaccagatgg    2880
aataataaca taatcagtaa gattagccac agtcattcct gatggattca tattaataag    2940
cggcaagatc aaatacagcg cctgaccata tgctaaatca attcccttg ttcgggcatg     3000 tgaaattgtc agccctgtta ccggagtttc ggcactagcc tgcgcgccat agtttgcagg    3060
tgagatggca actgcggcac tagccttgac aagcactacg cccttaccaa ccgtcgtact    3120
attaaaagtc gtactgctgt taaggttagc taatgtttct atcgtatcat cagtcaatgt    3180
aatggtgtat ttatcaacca cagcagtatt aaccgcttcc gaatatgtcg tatcggaaac    3240
ggggacgtca tacacaatcg catcagtctg aatatcatcg taacgaattg tccaacctgt    3300
tggaaccaca atagtacgac tattgaccgt caccggaacc gtactagtcg ttttattaac    3360
gacaattgtc gtcgcaccca tcgtaataat gtcatgtgcc gcaataacta aactaccagc    3420
aataatcgta tcagcagtaa tagcagcatt aggattagcc tgttgtaaag ctgtcaagcc    3480
ttgatctgac aacacaagct gatacgttcc agattgggtt gctgtgggaa ctataacatc    3540
gccactagaa cttgcaatca tataagtatt agtcgttcca tcagtagccg aactagctaa    3600
cgtccaggtg ctgggaactg catactgact cggcaccgta attgtatacg tacttggttt    3660
agcatcccca tagtcaatac tagctgaacc aatggtaatt atcgcagtcg gtaccggagc    3720
ttgcttgatt gttagtgttc ctgtcaccac gttagcagcc gttatatccg cgctactatt    3780
agcttcagct agcttagtaa ttccagccgt tgagagtgcc aatgtgtatg ttccaacact    3840
cgatcc                                                              3846

<210> SEQ ID NO 178
<211> LENGTH: 1466
<212> TYPE: DNA
<213> ORGANISM: Lactobacillus plantarum

<400> SEQUENCE: 178
gatctgatgg tagatgagta acgatcctag gaagaaagcg gccgctaagc cggcggatgt      60
cggtagtttg ttaaacatat tggctggtaa cactaaggct aatagtggaa aggcatacgc     120
tgctggcaat tgtaagttaa gcgcccgtaa ccacaaatac acaagtggta aggcaatgac     180
cgtcgttaat agccacgaag caatcaatag gtgaatgccg accccaatac tagcagcagc     240
cgacaatgca agccactgct taagtgcggt cgttaccgta tattcagact gttgagccgc     300
ttcaaagaaa acgacgatca cgggtgggat tgcggccatc tggggctgtc ccgctagcca     360
aacaataccc acccagacaa aaactaggct gataaagccg agcatttgcc agcgactagc     420
agaagcttcg gttacccgtg agattgatcg cggtcgttga atccaagccc caatcatcag     480
gcaaatagtc cagaaaaaga tggctacgat aaaggtccag tgcgttgcat taatgataat     540
tggcagtaag ccagtagcaa aggctggcgc caaattcgat tttaaccccct tcaataataa     600 tagcatcagt aatagaccga caagcacttt gagggcgtgc gaccaaggta gttgattgac     660
taagaagcca ataattgcag ttccagatgg tactaagaat aactttaagg gttgccgagt     720
ccacgccgtc ttacgataaa cccacgtccc ggctgtcaga gcaccgattt cgggtaaaat     780
```

| | |
|---|---|
| gattttcgca tcatgttgca atgtggcact cgccaccatt aatagaatga agctccaccc | 840 |
| agctaagtat cgccaaccat cgctttgctt taaatccatt tcgacaaaat attcctttct | 900 |
| tatattcgat tagatatatt tatgttatca agtgtcaacg actagcattg taccataaat | 960 |
| acaatcgtct cctcaaataa tcctgaaaac acatcaacag ttttcaggat tattttcaat | 1020 |
| cactttcctg acctataaat caaaattcga ctgagtaaag tcttacccag tcgaattcag | 1080 |
| tcgtcgcgcc aacgcagtcg caacgttatc aacaccgcag tcagaaaatt atgcattttg | 1140 |
| cataagcctt ttgataacta aacggttatg ctatttatcg tactagtaat tggttaacca | 1200 |
| gcctacgtac actagccgtt acggcctaac atcaaaaata tgaagatggc ttctgctact | 1260 |
| cgtaaccacc accgatatcg gtgccagcgt aataccgacc aatggtgttt tagccactga | 1320 |
| ttggcatagt gcgcaatcag tggcgccccg ataatcataa aaccctcggt ccaaaaatcg | 1380 |
| acgcgggcgg gccaagtcgt gttatcaaag ccagcaccaa tggtcgcaac tacgagcaag | 1440 |
| atgtagaggc cccacaaact gatttg | 1466 |

<210> SEQ ID NO 179
<211> LENGTH: 16876
<212> TYPE: DNA
<213> ORGANISM: Lactobacillus plantarum

<400> SEQUENCE: 179

| | |
|---|---|
| aatggcagat gaacggccac ttaacttggt acaatttgtc gttggctatt ttgatattgg | 60 |
| aactttaggt gaaatatcag agtgccttct ccactttgcc aaaacgttca gttgttacta | 120 |
| cggcgattca gaataacgag ctatcacaat atcattttca gcctaacagt tgattgacaa | 180 |
| gattactgtc tataagaaac aacgacaaag ccatcaaaaa ctgagtacgc acatgtccgc | 240 |
| cattcgaata ctgtcccgag cacgtttcac caatatggca ttaaagcgtg gaagaccagt | 300 |
| atttaagacg tggtcttcgg attaaatctg tgtccaccgc gttccagcaa ttggcagaaa | 360 |
| tgcctggaag tcggcttagg acgaactaac taagcaagtt tacgctaact cgaactgttt | 420 |
| ccagcgaacc taagctggct gattttgaac tcaaaaaatg gcatgtttta atcatagtta | 480 |
| atgctagtta ttttcgatgg ttaccagtgt ccaaatatgc tgatttaagc gtcaagtgga | 540 |
| ctgggattgt tgttgatgag cccgctgaaa atggcgttag gtcgactaat aacacgtctg | 600 |
| ctggtgtgat tgcggtgca gtcgtgattg agattgggtc acagtccaat aacgatgtaa | 660 |
| cggtatcagg cgacagttct attgtaatat actaacgcgt aatttgaatg aataagaccc | 720 |
| ataatgatga aacagataaa agaccgacta caagcaatc gcaccgcttg ttagtcggtc | 780 |
| ttagtgttca ttgattaaag cttttttacca gattttgacc cgcttatctg gtgccaaata | 840 |
| catggcatcg tcgggttgaa tgtcgaaggt tgtgtagaaa tcatctaagt tcttaggttg | 900 |
| tacgtttgct cggagcttag ctggagcgtg gacgtcgatt gaaagtaaga gttgcatgta | 960 |
| ttcagtcgtg gccttcatac gccaaaccat ggcccagtta gtgaagaacg cactcaaatc | 1020 |
| aacgtcatct tcgcccttag cagcttcttc cgcgcaactt aagcctcccg catcggcgat | 1080 |
| gttttcggat acggtcaacg tcccgttaac tttcgcacca gcaaagtcta agccatcgaa | 1140 |
| ttcactgatc atggacttgg caagttcctt gaagtgggca gaatcttcct cggtccacca | 1200 |
| attatgcaag ttaccgaatt catcaaatag ggcaccattg ttgtcaaaag cgtgcgagat | 1260 |
| ttcatgagca ataactgcac caataccacc atagttagcg ctagaagatt gttctaagct | 1320 |
| gtagaaaggt gcttgtagga tagcagctgg aaagacaata atgttcataa atgggtggta | 1380 |
| gtaagcattg acggtgtccg cactcatttc ccagcgggtc cgatcagtgg ctttgcccca | 1440 |

```
ctttgagaac atgtcttggc gtgccaaacg gttaaagtgg aggacattgc tcaatacgtt    1500
gccaccttgt tcgggcgtgt gcgtcttgaa tttcgtgtaa atcgtttcta gtttatcagg    1560
gtaaccgact tgaatgccga gtttatcaag cttggtcacg gctttagcac gcgtatctgc    1620
actgagccaa gtgttcactt gcaatcggcg tttgtagacg gcaatcatct tttcgaccat    1680
ctgatgaacg tccgctttgg ccgcttcacc aaaatacttg tggccgtaat agagtccaac    1740
gacttgatca aaagttccgg tagctagata gtaggcactc ttagcctggt tccgcggttc    1800
tttttgacca gacaatgccc gtgaataagt cgtggctaat acccgcattt catcactgag    1860
gtaaccactg taccgttgaa cgagtttagc tttcatccag ttcttcatca gaccgaagtt    1920
atcaggattg actacttcgt taaagtgatc gaagaaggcg ggttctggca agatgacgag    1980
gtcgggatta ccatcgatga cggagtaggt gatggcggct aagtctaaat aacgactagt    2040
gttaacaaaa tcgttgaatt tgcgaggatt atacatctta ctgtaatcag ccgactcttc    2100
agcggatttg atccacggaa cgatcaaacg atcgaattgc agcgtgtcat caacgatttt    2160
ttgtgcttcg tcctttcgt aaccagtttt ttgcaacagt tcggtcatca ttttagcgta    2220
aattgctagt aacttagggc cggcctggtt gccttcgtcg tagtatgtct tgtctggcaa    2280
gatagtccca ggtgcttggg caaataaggc gttgaccttg gtatttttca tatcagcgtc    2340
gacatccaag ctgaatggta atgggaggcc gtcgtagatc caatcgggca tccgttgttg    2400
taagtcagca aagtcgctta aactatcaat ttgcttgaga cacggcagaa ttggttccgc    2460
accattggca ttgcgttggt cgaaatcttt agctaagcgg taaaacttaa tgaattcggt    2520
tagctgagga tcgtcggggg taactgttcc cgccgccatt gcatcaaagt catgcattaa    2580
cgttttttca atggcatcaa ctaagtccat aaagcccccg gttgaagaat ggtcatccgg    2640
aatgacggcg gtttgagcca ctcgccgttg acggcatcgt agagatcttg ttttactgct    2700
gcttgattaa tggttgccat taaatccact ccctaataaa ttttctaata ctaagttaat    2760
tataccttag attattctca gtggtatcat ctggtaccga ctcagtaaaa aatgatacta    2820
atcatcttaa tagtcctgaa tcagtagctg atgggttgtg aatgttaatg taaaggtcaa    2880
gattacttct gaattatcgg catgcaggag ctgttagtgc ctgtaaatca ccttatgagg    2940
cagcgtgatg gttgacgtaa aagccccgg atgactaaca gtgatttcgc tagtcatccg    3000
ggggaaggga taatttaatt agtagtcatt attcagttaa taatagctgg tcggcatcgt    3060
taatttcgat gaccttgcca ggcttttgcg taattaggcc ttgacgctcg aataaggcga    3120
gcttacggct gatgctttca ggggtggtgc cgaggaacgt cgccaggtct ttttctttta    3180
atggtagttt aaacgtgtcg gttttgagcg ctgccgctgt ttcagtgata tagttcgcta    3240
aacgggcttc gacggattca gtggccgtgc tggttgtttg acgttccagt tgactgagac    3300
gtttgccaaa gacgtttaag acgttgatgc tgatactggg atattttgc atcaagtctt    3360 gaaagtctga acggcgaata ctgcaaacat ccgtcggtac taaggcttca ccgaatgagg    3420
ttcgccgttg attttcaaat aaggcagctt cgccatcgat atcaccagtt tgtaataggt    3480
atagtaactg ctcgcgacca ttggcagcta gctgatagac tttaacctgc ccattggcaa    3540
caatcatcag tgaatccagt ggatcgtcag caccaaataa agtgctgccg gctggatagt    3600
ggtggtgacg aacgatcgat tcgatagtgt ctaattgttc actaccgagt tcgctaaaaa    3660
ttgggactaa ctgcacacat tcatgttctg ccataaggcc cacctcctga ataaattcac    3720
cctaactata acagattttg cttggtagat agggtttgac gttttaaatt tcctactgtt    3780
```

```
ttaataacta tattgtagcg taaaactttt ttgaatttct tgacggccgt caagttctgg   3840
tcaatcaaat ccggttatga tagaaccatc aaatgaacga cacggaggta attgattatg   3900
aaaattatta tgcaattagg aacgttgact tgcccatcat gcatgaccaa gatcgaaaag   3960
gccgttgcta accatgacgg cgttgagaat gttaaggtgc tattcaatgc cagcaaggtc   4020
aaggctaact ttgatcctga agtgacgaat gccgatgatt tggcacaagt tgttaccgga   4080
cttggttacg aagttgaaaa cgtcaaggtt aagtaggagg aataaacgat gagtgaacta   4140
acgatcgacg aacaatacgc agcggaatta aaacagagtg acattgatca ccatgtccca   4200
acagcgggcg caatgacgaa tcacatttta tctaacttaa tggttgctta cgttaagttg   4260
acccaagtga agtggtacgt taaaggacca caatcattgg cattgcggac agcatatcaa   4320
cgtttgttag atcagaatgt ccgtcagttt gctgaattag gcgaattact cctagatgaa   4380
aaccagaagc catcttccac aacggctgaa ttaaccaagt attccatgtt ggaagaaaat   4440
ggggctttca gtatcaatc tgttgatgaa ctcgtagccg caacaatcaa ggattttgat   4500
acggaaaacc tattcgttga ccgggctatc aagcttgctg aaaagaaaa ccggccggca   4560
ctggcagctt ggttagttgc ttatcgtggc agtaacaatc gcaatattcg ggaattacaa   4620
gcttatcttg gtaacgatgc tcgaactggt ttggatgaag aagatgagga tgacgacgat   4680
taggtcgttg tcgctgaaga attaaacgct ctggatagcg attgtgtggg caaactatcc   4740
agggcgtttt tgctattaca acgggcctgc gctatactaa cgacaattaa attatatggg   4800
agggccccga gatggcgatt agcgacattg tgatgtggac atttgtcttt attattgcga   4860
ctgggttcgt aacggtgatt tcaacggcgg tactgttgaa gcgagcaaaa cgagcgccca   4920
aggatgccga gcagtcccac agtgatgacg acgatgactg gaaaaagat gattggaacc   4980
atgatgactg gaaaagggc gattggaaag attgactcga taagttgcct gacagatacg   5040
gtgcttaact gagtcaactg gcactaaaaa gacggtataa ccaactgaga ttggcgacac   5100
cgtcttttt ggcgttattt ggttttagc agtagatcca aggagtgttc aagattctga   5160
acatcagccg tggtcatcgc atctacacaa ttattaatat tacgggcgat gacgagtttc   5220
atggccttgt cgatacttga tttcactgct gaaagctgaa ccaagacatc ttcgcaagga   5280
cgattttcgt ccatcatacg caaaacgccg tccagttgac cagccgagcg ttttagccgg   5340
gtcttgatct gcttgctagt gacatattct tcagtagttg ccatgattca tgatgcccct   5400
ttcgtaatta agcaagtgct tttttgagtt cggcttcaaa atcaggctta ggacgtgctc   5460
cgaccatgtg actgacgact tggccatctt tcttaatcag gaaggttgga attccttgaa   5520
cttggaattg actggccgta gcttggtcat ggtcaatatt caatgaaacg aagttgacct   5580
ggtccttgta agctgggtct tcagaaaggg acttaagaat tgggtccatc atgcgacatg   5640
gtgggcacca gtctgcgcga aaatcaataa cggcgatacc agtatctgtt tctttggcaa   5700
aatcttggtc atgtatttct ttaatcattt tagttgactc ctttagtaag tatttgtcac   5760
taaacaatat accccatag gtatacacga gcaagtattc tgcttctggc cgtgggggat   5820
ttaaaagga ctgatgtatt gggtaattag ataataacga tttgttgtgg aagctagcgt   5880
cacctgagaa tcttctagtt gtgatcgcga gcattaacgt tgaagatctc atgttgacgc   5940
gacgtgttat actagcgctt cataattata caacccaggg tatctggtag aattatgttg   6000
aattattaga aaccgcttat ttaagcaaaa taaagcgttt acataaacag ctttatctgg   6060
tatcttcaaa ttatcataga tgctcggtac catacgagga ggatttacag atgacaggtt   6120
catgggaagc acgctacgcc gctgaatttt ttggcacgct gatcctagta ctactaggta   6180
```

```
atggtgctgt cgctaacgca ttcctgaaga acacgactgg taacgatgat ccaggactcg    6240
ccaatggagg atggctcctg gttgcatcgg gatatggact tggggtcatg ctcccagcca    6300
tgatgtttgg ctcgatttct ggtaaccatt taaaccccgc gattacgatt gggcaagccg    6360
tgattggaat cttttccatgg gcgcacgttg cgccttactt aatctggcaa tttctaggag    6420
caattgcagg ccaatgcttg attttggcac tgtactggcc ccattatcgg caaacgactg    6480
ataatgaggc agtcttaggg acgtttgcaa ctagtgatca tgcgaacagt cagttaaacg    6540
gttttgttac ggaaatggta ggaaccgcag tcctgatttt tggtgccatg ggattatatc    6600
gcgggatgtt ttttcatcaa aatatcgata tcgccaatat tggcgttgga cttttgattg    6660
ctgccatggt tatttcgtta ggcggtccaa ccggtccggc cctaaatccg gcccgtgact    6720
tgggaccacg gctagtacac gcgttattcc cagtaccgaa caagggtagt tctcactggg    6780
aatatagttg ggttcccgtg gttgccccaa ttgttggtgc cgttattgga atttggattt    6840
ataagatctt ttttggttta taatcgcaat taattaaccg agcgtattta tgaaattatt    6900
attggtctat cattttttgat tgcaatatga taaaacggtc cgccgactag ctggggaaga    6960
ctagtcggcg gaccgttatt tttttgctagg cctgtaacca agttggggag acttgattaa    7020
gctgtggctg cttgaatggt tttagttggt tggtgcttgt cgaacttggt ttggaaattg    7080
attaaccgca tagcgttgaa gataacgact aagatactag cttcatggac aaacatccca    7140
ctggccatgt agatataacc gaagattagc ccaatcagta ggaaggccac ggtggcaatg    7200
gcgatgaaga tgttttcacg agtgttcaag acagttttct tggcgagacc gtgggcgtgt    7260
actaatgcgg ggaagcttga ttgcatcaag acgacatcgg atgtgtcgat ggcaacgtca    7320
gtcccactac ccattgcgat tccgatatcg gcgttagcga ttgaaggact gtcgttgatg    7380
ccatctccaa taaaggcgac cgtattaccg gctgctttta gtttcttaac gtattcgact    7440
tttcttctg gcaagaggtt ggcgtgaact tcatctaggt tcaattcgtt ggcaacggct    7500
tgagcggtga gttcattgtc tccagttaac ataacgagtt tcttgattcc ttgggcttttt   7560
aatgcggcga gggaatcctt cacgcctgga cgaatcgtat cggcaatccc gaagatgagt    7620
tgaacttgtc cgtcgactgc catgataacg gttgattgac caccagcttg taaaccattg    7680
agatctttga gttgggtagg atttagtttg atattatgag ccgtcaacat ttttttgatta   7740
ccaatgacaa cttcttgctt accgacttgt gcacagattc cttggccctt aacggtttca    7800
gtgtcatcta ggacgggagc gacccccgct gactgctggt cggcataact gacgattgct    7860
tggcctaacg gatggtcgga aacgccctca atagcggcag cgagagctag ttgattatcc    7920
gcattgtttg tgtaagtgtg catggttgta acggcagtgt taccttccgt taaagtaccg    7980
gtcttatcga agaccagggt atcgactttg gcaaaagtat cgacgacttc accacccttg    8040
atcaggatac cacgcttggc accattcccg attccggcaa cgtttgacac tggggcaccg    8100
ataactaagg cacctgggca accgagaacc agtaccgtga ttgctaagcg gaagtcacgg    8160
gagaaggcga agactaagac tgctaaaacg aggacggcag gcgtataata ttgagcaaag    8220
cggtcgatga acttttcagc tttggacttg gtatcttgag cttcttcaac caattcaata    8280
attttggcaa aagtcgtgtc gtcgccaacc tgagtcgctt tgatcttcag atagccatttt   8340
tcaaccattg ttccggagta aaccgagtcc ttgagttgct tgttgatttg gcgtgcttca    8400
cccgtaattg aggcttcgtt aaggtagccg ttaccttcaa caacaatccc gtcaacggga    8460
acctgactcc cagttttaac taggacaacg tcaccttcgt ccacatcatc aacgtcgact    8520
```

```
tcttcggtgc catcatcagt aactaaagtt gcggtagttg gtgacatgtc agtcaagcct    8580
ttgattgcgg tccgcgtctt ctgcaaggtc ttgctttcga gataggagcc aaacaagaag    8640
aggaaagtaa cgattgcgga ttcgttgaat tcaccaataa tgaatgcccc aatcactgcg    8700
atactaacta acagttcaat actgaaaact ttgttccgaa gtgcgctcca agcacgaacc    8760
gcaatcggaa tgacggcaat aattgaagca actgctaaaa tgacttggta accgagcgta    8820
aattgtaaga gatatttact gagcatccca aggacaatca gaatcccgt aactaatgta     8880
atgtgattcg tatgtttagt gagaaataat tggaatttca taatttgcaa ctccttattt    8940
gatttgatga ccctagtata gtgagttcag cttgatggca acttgatagg cgtcaagttt    9000
tgaaaaataa cagtattaat tctggattgc tggcagtgat tatgattaaa acatgccatt    9060
ttttaaattc aaaagcagcc agcttagacc cactggaaac agttcgggtt agcgtaaacc    9120
tgcttagttc gttcgtccta cgccgacctc caggcatttc tgccaattgc cggaacgtgg    9180
tgggcacaga tttgagccga aaaaacacgt ctcaaatact ggccttttac taaccaagca    9240
aaggacgctt gctaagtgaa atttcaccac tgggcattgt cagaaacgcc ttccggtcgg    9300
gacagtattc gaatggcaga cggagatgta cccaacttt attggactca tcattttct     9360
ttataaacag taattttgtc gagcaactgt caggtagaag gtaacatttt gatagctcac    9420
tatttcgaaa tcactatagt aataatcgaa cgtctcgaca aagtggttaa tgtaaccta     9480
aagtctcgtt taaaattcca ttatcaaaat agtcaacgac caattgtacc aagttaagtg    9540
gccgttcatc tgccattcga gcggcttccc gactggaggg gctggatggc aatgctcagt    9600
agccaaatta ttcttagtcg gaagtgcctt tcttccggct tagaataaga ctcgtatttg    9660
agatgacgcg gtttgtgcgt tagctcaaat cgacgtcggc tgcgttccag caattgtcat    9720
ccagccccgg aggtcggaat agaacgctca ccggctgacg aacagtaagc caactaaatg    9780
gcatgtttta atcatgtttc atgacaagtt aacggaagaa taggtaggat gatcaagttt    9840
gagtaaacaa gaggtatagg agggaaaaac gtggattatc aaataacgca ggccaatcag    9900
cccttgatgc cggcatactt tcaggggcgt tgggcggtca agcaaattgc ggatcgagac    9960
gtgatgtata gcactaattt gggtgctgaa atcgattttc aagtcactga tgctagtttt   10020
gtgcggttga cattcttgcc gttggcgtat gagctaccga gttgggtggc gatccagatt   10080
gatggcttgc cttttcaacg gcaggcggtg acgaatgacc ccctatggtt gacactggat   10140
ggtcggcctc acgtggtacg ggtagttttg agtggtaata ctgatgagga ccgtgtgtgg   10200
gatggcaatc aaggttttac agtgaaagcc ctgacgacag atggtgagtt acagccagtt   10260
cggttaggcc gacacagtgt gacgtggatt ggggattcac tgacggccgg ctgctgggtc   10320
atgggtaaga cccctgccga agattatcgc gcggaagcca actatgcggc ggttgcgagt   10380
gacttgttga atgcacggaa tgtccgcatt gcttatagtg ccgttggtct cagtaaacca   10440
ggaactggtg gcgtaccggt actgccggag gttttaacag ccgtggatag taaaacgacg   10500
tggcaaccag tacccacgga tttagttgtg attaatgttg gtactaatga tcgtcatacg   10560
gatgatacga cgttcacggt agttttgcgc cgcttcctta atcaggtgca gacgctttac   10620
ccgaatagcc ggcttgctgt aatgatcccg tttaatcaga attttgcgtc gattattcgc   10680
gcggtcgtgg ctgaatttat gcaattgcaa ctcattgaaa cggctacttg caactcagt    10740
accacggacg gggtgcattt agatttagct ggctcccgga tggcgggcga attaacagca   10800
caagcgttgc ggacacagta tccagatgtt tttaaatcgt gatcaaccca tcttataaaa   10860
atcccgtttt actgtagcaa tgttctgctg cagtgaaacg ggatttttg gtggcactac    10920
```

```
tagattttaa aaataaacgt taacgctggc ggtgtagtga ttgcgactgt aaataccggg   10980
ccgcagcgag aacttcttcg ggaatatcca catgggcgat gaagccctga ccacggggac   11040
cataaccggt gggggtatcc actaggcgtt gaaattcacc gagtaagagt tcagtaaaat   11100
aagcgggttg ccagccagct actattgtgt ttggcgtaaa ttgcattggt tgtagccggt   11160
ttaattgcaa ggtcgccggc gcatagcgaa taaagttggc attggaccaa ttggctgaga   11220
acgttagggt agtccgccgc gcgagtaacg ggtcttgtac gagtaggacg tggcgccaat   11280 cggtggggc taacgcgcgg gcatgcgtgg cattgctacc ggtattggta gaagtcttgt   11340
cgaggcggat actaccttga tagccagtct ttcgaacaag cgtcgccatc aactcagcct   11400
cactagcttg agattttggc aggtttaagt tttgccgcaa atacttagtg gcgtggccga   11460
cgccgcccgc aataatgagt agtggtaatt gatagtcttg ggctaactgg cccgctgcag   11520
tggctgttgc tgggaggctg ttgccacaaa ggaccaggcc atcgaggtgc tcaggcaagg   11580
cggtggtgtg tgtcaaccaa gccagacatt gattgaaagc ggtcagttcg tccaattact   11640
tggcctcctt agtcccaaag tgagccgctg cggccccaaa gttgaaccgt tggaagtgaa   11700
cattttgaaa gcctgcttgc tgaaacatcg ttgctaattg ttgatagctt gcaaagtgac   11760
gagtggtttc ctgtaaatag gaatattcct gatattgatg ggcgaataag cgcccgaata   11820
gtgggactac ttttgtgaaa taccactgcc agactggttt aatcaatggc tgatcgggtt   11880
gggacgtctc taagcagacc aagcgagccc ccggttttag gacgcgataa atttcagtta   11940
aagcttgggc tttatcaggc aagttgcgga gtccgaagcc aatcgtgacg aggtcaaagg   12000
tgttgtcttt aaacggaaga tgcatcgcat taccgcggcg caaccagacc cgatcggcaa   12060
cctgttgctg ggtcactttt tgttgtgcca gttttaacat tggggctgaa aagtctaatc   12120
cgatgacttc accgggtgcc tgtaattctt tagccagcgc gatcgtccaa tcacccgtac   12180
cacaacagag gtcaagaaca tgggcgttag acgctaaatg gatttgggcc atcgtttgct   12240
tgcgccaatg acgatgcgtt ccgagactga tgatgttatt catccgatca tagttcggcg   12300
cgatggtgtc gaacaaacct tggacattat gtaaataacg atttgccata aatgataccct   12360 cctgatagtt gctttactta ctactatagc agatgttagt tgccagttac cgtgaaaagg   12420
aatgataatc aatataaagc tacgatattg atttcgttgc tgttaatatt gttcgtgaat   12480
aaaccgttaa actaaagtta aaataacata aaggcagtct cgattggtat ttattaagta   12540
ccaatcaaga ctgccttttt tgacagcgcg ttcctaatcg aagccttaac gtcaaaacga   12600
gtacgctagt aatagcttaa aaatcatcat ctgcaatttg agctaacagg tcacgtgatg   12660
gaatgaagaa cgcttgtccg gatagtaagg tggagaaagt tagtaaaaag tcactttggt   12720
cgaccatgtt ttgcagcatg cctttggtaa ccgtccagtg acgggcataa ccaatgaagt   12780
acgtccctgt gttaccagct gctggattgg agtacgggac attcatccga acgatttttt   12840
gttcgacacc atcaatttcc aatttttgaag caacgttgtg agcattctta aacttgtctt   12900
cgtcttctaa ctcgaagtcg ctgaattttt cacggcccac ggcttttttcc tgatcctcgg   12960 tgtgcatatg ttcccacacg ggcatatcat gttgccatt ctgtgcaaag gcgtaagaac   13020
cgttgatgaa ctggggatct tcgtcaccaa ctaaggcata atcagcggca tcttctacgg   13080
ccggcgcttc cgtaccgtcg ataaagccaa tgatggcccg gccttcgaag taacgaaagc   13140
ccttcgtctc atcgaggacg gtcgtgattg gcgctaaaac ccgctggaac tgcgtttggc   13200
attcgtagac gaccgcttcg ttgcttgcgc gaatgtggaa gaagaggtcg ccgggtgttg   13260
```

```
ctggcatagt gtatttgggt ccacttaagg tggtgtaagt ttctaattct ttaggtttgg   13320
gtgcgccagg aaacaggtaa tcccaagcgg cactactgat gccgatgcta acttttaatt   13380
gggtgccagt ttcaggtttg gcgtcccgga tgcgtaacga gcgaatgatg gcttgtgacc   13440
gatctgcaaa ttcttgaaag acttcacggt cgtgttgctg atcctgacga tttaattgaa   13500
gaacggtaaa ttgaacgtgt tcaccgacat ccttccagac atcttgggcg cgatttggat   13560
tgattggcat ggtatatttc ctccataaat tgtttgatat tgttagcgta catggtggta   13620
cgggtagcgt caaataaagg caaacggcgg gggtgaataa tgacgacatt cgccaccatc   13680
agggacaggc ggccaaacta ccgtggtgtg tatcatgata actaaacgga ttagtcagtt   13740
ggaattgttg gtgcttgtaa gacattagga attaattgaa taaatagccg gtaagtctca   13800
attctgctga gtgttggctg cgtggtcgca agttgccaag ctaactgatg aagacagttg   13860
ccgagataag ttgccataaa atgccgttgc ttaggatgga tggctaagct agttagcagc   13920
tgttgggcaa aaccaacttc taatgggatg acccgatcgc gacactgtgc ccatgacacg   13980
agtaagggga gatccagatg cgcgcgaagc gtcgtgacga ttgcaccagc aatggtcgcg   14040
taagatgtgg tagttaagtc atttaacgct tgtcctaact gttgtaaggc aattaagtat   14100
tcaatcacaa tgatatcttc aatatcctgg tgatggcgat aaaaagtggc acgtccaacg   14160
tgagcatcca gacaaagttg tttgacagtt aactcgttga agatcttttg agccttgaaa   14220
ttcgcttgca gggcagtaat caatttacga tgagtttgat gagttcgctg atcaatatgc   14280
aattgattgt tcataattaa ttttgtcata tgtcaatgat acaccaactt gtgatatgtc   14340
tcaaaacgtc ccttttttag catgtgaaag cgtctataat agctgtcaca gttagatata   14400
gctgaccaat taaggagatt gtcgactaat gaaattaatt accgttgaag agcattttga   14460
atcggcagct gtgactgccg caatgcgtca agctgttggt aacgctgcgt taccaacagt   14520
tagtccagcg ctacgccagt acatgcggga caatttaccg agtctgcaat tatgcaagac   14580
acccagcatg aacgcctggc atttatggct caatcgggca ttgatatgca ggtgttatct   14640
tatggtaatt catcaccaca gaacttatcg ccggaacaag cagttccatt ctcacaatta   14700
gctaatgatg aattagcgaa agcggtggcg gctcatcctg atcgttatgc tgggttagcc   14760
gttctaccag ttggtgatcc gcaagctgcg gtcgctgaat taaaccgagc ggtgacgacg   14820
ctgggattac ggggtgtgtt gctgaaagga aattatcaga ataaatttttt tgatgagcca   14880 ttcttcttac caatctttga agcagctgcg acgcttgatg tccccgtgta ttttcacccc   14940
tcatttattc cgcaagcagt aacgagtcat tattttgaaa gtaaccaatg gtctgacgtt   15000
gtcacgggga tcttatcatc tgccggttat ggttggcata tggatgttgg gattcaagtg   15060
atacggatga ttgctagtgg tatttttgat aaattgcctg gcttgaaact catttcagga   15120
cactggggcg aactagtccc gctatttttg gaacgtttgg atgatgagtt aacaacatat   15180
acagacttgc agtatccatt tagtacttat tatcggcata atgtgtacgt gacgccaagt   15240
ggtattttga gtgcacctca gttgcaattt atgttagcgg agatgggggc ggatcacctg   15300
atgtattcga tcgattaccc gtataagcag ccggagacga gtggaagttt cctggatatc   15360
gccgacttga ccgatgaaca acgggctcaa atcgcgtttg gcacggcaac cacgttattt   15420
aaattatagg aggaacgaaa taatgtcatt aaacgcacaa caaatgcagg caacccggga   15480
tgaattacaa gctaactttg cgttgactgg tcttacgaaa gcccaggtag ctgatgattt   15540
agcgattagt gcaactaagc tcgatcactt atttgactta acacaacaat ctttgaacga   15600
tccgtggatc ttacgtaatt atttgattga aaaggtggaa gcaggcggga agacgccggt   15660
```

```
gccatttacg gcattaagtg gcgactggca tcgtcattgg tttttgaata gcgttgtcat    15720
tgatcgccgc gaaatgtcgg ccggtgattg ctaaaatgat tggaggaaat cgtcaatgag    15780
taacggaact gatatggcac taattagtga actagtggcc cgtgagcgct tatttcgtgc    15840
ccggcataac cctgaaatcc gagattgcta ttacgccgac gcgactgtgg caactagtta    15900
gcaacaagga ccactaagta catttattgg cgcagaatcg aaggaagttg atccgcgctt    15960
tgttattgtg gggagcgtca gtacgcctgt cgttcatctg aatggcgata aggcatacgt    16020
ggaactacca accacgacgc atatgcgcat gatggtcaat ggtactttag cggaattaga    16080
atcatatcgg cgactgattt accgcgtcga acgccgtgat actaagtgga agattagtcg    16140
attgacctca attaacgaaa gtgataattt cgaccagtc attgtgggac aggatttaca    16200
cgtgatacct caagatttta acggtttacg gtcctcgtat caattcctag cctatgtccg    16260
acaagctgcc ggtggtcaaa ttagtcagga tttattaggg acggatcgac cagaagaagt    16320
tgagcgattg tacaaggaaa cgaatgcgtg gttgcgagct ggagtatagt tgaaggtaaa    16380 ataaaaaag cgatatcatg taaaatcaaa tactttagc gtcttgtaac cagaaacgaa    16440
aataatttag tacattcgtt aaaataacag accgttactt tgataaatat aaataaatga    16500
tgatccaaaa aataaggtgt gttgcaatcg aaagttgatt gcaacacacc ttattttgga    16560
cgtctattaa aatggaccct accggatttg aaccgacgac ctcctgcatg cgaagcaggc    16620
gctctcccaa ctgagctaag ggcccaatac acttttagta taccgcaaaa tgctagtcgt    16680
gcaagtctag tttggtcatc aatggcgact agcacgatga ttttgattgc cacgaatttt    16740
atgcactcgt cgtttgtact gtgctttttg gttgctgaca aacttgaagt gttgcatttt    16800
gccgccgaag acttgaccat tcagccttaa ttttagccaa tcttgcataa cggccatcat    16860
tgaattaatt tgggtg                                                   16876

<210> SEQ ID NO 180
<211> LENGTH: 1972
<212> TYPE: DNA
<213> ORGANISM: Lactobacillus plantarum

<400> SEQUENCE: 180
ctttcctaga ttgtgaatat atgcatgaca tggggaattc tctgggcggt atgcaatcat      60
ataatgattt gatcgacaag tatccgatgt atcaaggtgg ctttatttgg gactttattg     120
atcaagccct cttcgttcat gacccaatta ccgaccaaga cgtgctccgg tatggcggtg     180
atttcgacga acgccactcc gattatgaat tctccggtga cggcttaatg tttgccgacc     240
ggacaccaaa accagcaatg caagaggtga atattatta tggcttacac aaataatcaa     300
ctacacgtta tttacggcga cgggagttta ggactacagg gggctaattt ccactacctc     360
tttagctacg aacgtggcgg acttgaatca ctcgtcgtca acgataaaga gtggctctat     420
cgtacaccca cgcccatctt ttggcgggcg acaaccgata atgatcacgg tagcggcttt     480
tcagtcaaat ccgcacagtg gtacgcggcc gataagttct caacttgtca agatatcgaa     540
ttgacggttg acgaccaacc agtcacaccg ttaccaatcg cgccactcaa taacaaatac     600
acggatcacg aaatcgccac gaaagtctca ctggcttacc acttcgttac cacgaccgtt     660
cctagtacca tcgtcacagt gacttatacg gtgacagcag acggtcagat caatatcgcc     720
acccattata gcggtcagtc tgatttgcca gagctaccccg catttggtct gcggtttatc     780
ataccaacta ccgcgaccgg cttcgactat accggtttgt ccggtgagac ttatcctgac     840
```

```
cggctggccg gcgcaacgca cgggcgattc cacgttgaca gtctgccagt cacaccatac    900
ttggtcccac aagaatgcgg catgcacatg caaactgaac aagtgacagt aacgcgatca    960
acaacacaaa ataacgctga ccacgacaac acaccgttca gtttgacatt tagccaagcc   1020
gatgcaccat tcgccttcag ctgccttccc tataccgccg ctgaactaga aaacgcaacg   1080
cacatggaag aattaccatt agcacggcga acggtcttat caatctacgg tgccgttcgt   1140
ggggtcggtg gcattgatag ttggggaaca gacgtagaat ccccatatca tatccccgct   1200
gatcaagaca ttgacttcag ctttaatatt catttctaaa agttattttg atttcaaaag   1260
aacgctccgg cgagttattt gccagagcgt tcttttagat taacgatgat taagttttaa   1320
tatgtttaat ggctgagctt agtccttagc cttgaagtaa tgtacctgcg ccgtaaagtc   1380
actagtttga cgggagtcg tgtagagtcc tagttgcatc aattcatcgc caccgtacat    1440
tttgtttgtg tcggtctcaa cgtaggtctg ctgagggtct aatcccgcta acttcgtaat   1500
atgcggttct ggttgaactg cacctaaaat aacgaaggtg aacagcaagg cttctttctg   1560
atccggacta acaaacatcc acgccaccgt attagattca aacgggctct ctaatcgata   1620
aaaggtcccg tattgaacta actcacggtg ctgcttatag aaggcaacct gtcttttaac   1680
ggcctgcttg tccgcatcac ttagtttgggc cgcgtccagt tcatagccca aggtaccact   1740
cattgccaca gcaccacgca tcttcatcga cgtcgaccgt cctaacaatt catctgggct   1800
cgtcccaaca tgggcggtaa ttgcagaaat tggataaacg agtgaagtcc catattgaat   1860
tttgagccgt tcaatcgggt cattattatc tgatggccaa ctctgtggca tataatacat   1920
taaaccagca tcaaagcggc caccaccgcc agagcagcct tcaaataaga tc           1972
```

<210> SEQ ID NO 181
<211> LENGTH: 1402
<212> TYPE: DNA
<213> ORGANISM: Lactobacillus plantarum

<400> SEQUENCE: 181

```
tgatggtgga cgttaaacca actaacgaaa aactcgtgat tcgcgcgaaa cacatgatcg     60
aactggccac cggcgtttct gccgatgaag ccagcgaact attcgctgca gctcatcaaa    120
acgttaagac agcgattgtc atggacttgg ctggcgtctc tgtcagcgac gccgagcagc    180
gtttacagcg cgcacacggt gtcgttcgtg acgcactcgc actgcaatga ggaggtctaa    240
aatgacatat ttaattggcg ttgactgtgg tggcacgcac atcgttggtc aaacttggac    300
gacagccccc gagcatctag tccaaagcgt tacgggtggc cctggtaacg ttgtcctaga    360
ctactctgct gccgttacta acttaaccac tgtcttagac cagctcactg ccgcaattcc    420
agctagtcag cttgggttga ttttaatcgg aattgctggc attgaaactg ctggccgggc    480
tgatcaggtc caacaaacca tcacccaacg ttaccacgct aatacccagg tcataagcga    540
tgcaaaactg gccctactga acggtcttgc aggagcagac ggcgccttag tgattgccgg    600
cacgggctcg tcgtttatg ccgccaagc cggaaaattt ctgcgcgttg gcggctgggg      660
ttacgtttta ggtgacgaag gcagtgccta tgacattagc aagcgggcac ttaaacaggt    720
tctgacccag actgataacg gtcaaactag tcaactaaca gctcccctat ggcacaact     780
taaagttacc gatattgctg ccgccgtcca gaaatttac gctcaagatc gacaaactaa     840
cgctcaatta gcacagttaa tcgccaaact ggccgagcaa caaaattctg aagccatcac    900
ggtattagtc acgtcagccc aagcactggc acaacaagtc gttaccttat atcagccggtt   960
tgcagagtcc tggccacaac gggtcgccct ctctggttcc gttttacaac acaatcgcct   1020
```

```
ggtccgcgac acgttaacga cgacagtgca ccagtcaata ccaacaattg ctttttaacga   1080 tattacaact aacaacgccc acgccgtcat ctattggcac cggtggactc aggaggaaat   1140
taattcatga caatgcgtca actaggttta tccatttatc ccgatcatag cgactttgaa   1200
gaaaacgccg cttatctcaa attaggccaa cactacggct tcactcgaat ttttatgagc   1260
atgctggaaa tatctggtac ggtcgccgaa accaaagcta agtaccagaa aatcattgac   1320
gttggaaatc agttgggtta ccaaacgatt ttggacgttt caccacggat ttttaaacaa   1380
ctaggaattt cctataaaga tc                                             1402
```

<210> SEQ ID NO 182
<211> LENGTH: 61
<212> TYPE: DNA
<213> ORGANISM: Lactobacillus plantarum

<400> SEQUENCE: 182

```
aatttaagtg cctcattcaa tggcatttcg ggtaacttag gcgcaatttc aggatagtct   60
t                                                                    61
```

<210> SEQ ID NO 183
<211> LENGTH: 706
<212> TYPE: DNA
<213> ORGANISM: Lactobacillus plantarum

<400> SEQUENCE: 183

```
agcgtcccca atctggtatg attaatgcat atcagattgg gggatttttt taggccgact   60
gttaagacca tagtgggcga cttttgttcgt taaagataaa ctgggtgtcc gtagccagag  120
acgattaagc aataccaggc taacttttag ttggtttaga ccagttgtaa catttttgta  180
atcttcgtgt tatctaaacg caatgctggc tcgctatact aaagacaaag ttatgaagca  240
atacatacgc tttgtcagcg gatttaggtt gggagccgga tcgatttact ttgtcaggac  300
attgttaata agcaattatt gatagtgata agtagctcag ttagctgaat cataacgttt  360
gacaagcatt tataccctctc gggatgggct gggtccatga cgaggcacat acacaatggc  420
aagcttgggg tttgcaagtc gatcagagaa agggacggtt ggttaccggc ccttttattg  480
tggttaaaat ttgcgagaat tggatttaga actgcgcccg atttgaagcg gtaggaactg  540
cgatgctggc acaggtgact ttgccaaatc attgagagtg gaacgaaata atttacattt  600
gccagtagat tattataatt aacgaatcaa taataatttg gagatggcaa tttgactcag  660
tttgaaacgg aacggttgat attacgacca atgacagcgg cggatc                 706
```

<210> SEQ ID NO 184
<211> LENGTH: 104
<212> TYPE: DNA
<213> ORGANISM: Lactobacillus plantarum

<400> SEQUENCE: 184

```
gatctttatt agttagtcgt ggaatccgat aaatctaaac aaaatcacgt gtgagcgtcc   60
ccaatctggt atgattaatg catatcagat tgggggattt tttt                   104
```

<210> SEQ ID NO 185
<211> LENGTH: 111
<212> TYPE: DNA
<213> ORGANISM: Lactobacillus plantarum

<400> SEQUENCE: 185

```
gtcgacggat ctttattagt tagtcgtgga atccgataaa tctaaacaaa atcacgtgtg    60
agcgtcccca atctggtatg attaatgcat atcagattgg gggattttttt t           111

<210> SEQ ID NO 186
<211> LENGTH: 655
<212> TYPE: DNA
<213> ORGANISM: Lactobacillus plantarum

<400> SEQUENCE: 186
aggccgactg ttaagaccat agtgggcgac tttgttcgtt aaagataaac tgggtgtccg    60
tagccagaga cgattaagca ataccaggct aacttttagt tggtttagac cagttgtaac   120
atttttgtaa tcttcgtgtt atctaaacgc aatgctggct cgctatacta aagacaaagt   180
tatgaagcaa tacatacgct ttgtcagcgg atttaggttg ggagccggat cgatttactt   240
tgtcaggaca ttgttaataa gcaattattg atagtgataa gtagctcagt tagctgaatc   300
ataacgtttg acaagcattt atacctctcg ggatgggctg ggtccatgac gaggcacata   360
cacaatggca agcttggggt ttgcaagtcg atcagagaaa gggacggttg gttaccggcc   420
cttttattgt ggttaaaatt tgcgagaatt ggatttagaa ctgcgcccga tttgaagcgg   480
taggaactgc gatgctggca caggtgactt tgccaaatca ttgagagtgg aacgaaataa   540
tttacatttg ccagtagatt attataatta acgaatcaat aataatttgg agatggcaat   600
ttgactcagt ttgaaacgga acggttgata ttacgaccaa tgacagcggc ggatc         655

<210> SEQ ID NO 187
<211> LENGTH: 650
<212> TYPE: DNA
<213> ORGANISM: Lactobacillus plantarum

<400> SEQUENCE: 187
aggccgactg ttaagaccat agtgggcgac tttgttcgtt aaagataaac tgggtgtccg    60
tagccagaga cgattaagca ataccaggct aacttttagt tggtttagac cagttgtaac   120
atttttgtaa tcttcgtgtt atctaaacgc aatgctggct cgctatacta aagacaaagt   180
tatgaagcaa tacatacgct ttgtcagcgg atttaggttg ggagccggat cgatttactt   240
tgtcaggaca ttgttaataa gcaattattg atagtgataa gtagctcagt tagctgaatc   300
ataacgtttg acaagcattt atacctctcg ggatgggctg ggtccatgac gaggcacata   360
cacaatggca agcttggggt ttgcaagtcg atcagagaaa gggacggttg gttaccggcc   420
cttttattgt ggttaaaatt tgcgagaatt ggatttagaa ctgcgcccga tttgaagcgg   480
taggaactgc gatgctggca caggtgactt tgccaaatca ttgagagtgg aacgaaataa   540
tttacatttg ccagtagatt attataatta acgaatcaat aataatttgg agatggcaat   600
ttgactcagt ttgaaacgga acggttgata ttacgaccaa tgacagcggc                650

<210> SEQ ID NO 188
<211> LENGTH: 1263
<212> TYPE: DNA
<213> ORGANISM: Lactobacillus plantarum

<400> SEQUENCE: 188
atggctaata aatcattaat caaagtcgca gtaaccgcac tagtagctgg tttaatcggt    60
ggtggtgttg cttacggcgg tattaattat ttccaaaaca ataacatcgc aacgtcatcg   120
accagtgtac caactggttc taataaatcg gggtcaacgt caacgacgaa cgttaaggtc   180
aatgtcagtt cacaggcgac caaggtgttt gaaaataaca aggcggccgt tgtatcggtc   240
```

```
attaatctcc aaaagaagag ctcttcaagc agttggagtg gtattttggg tggcgatgac      300
tcgtctggca gtgatagttc atccagttca gattctagct ctagtaagct ggaagagtac      360
agtgaaggtt ctgggttgat ctataagaag agcggtgacg cggcttatat tgtaacgaat      420
aatcacgtgg tgagtggttc aagtgccatt cgagtgatta tgagtgatgg gactaagttg      480
tcagctaaaa ttgtcggaac cgattctgtg actgacttgg ccgttctgaa aatcaattct      540
tctaaagtaa cgaagacggc tagctttggt aactcagata tatcaaggt tggtgaaacg       600
gccttagcca ttgggtcacc gatgggctct aattacgcaa cgaccttgac gcaaggaatc      660
atttcagcga agaagcggac cgtggcgacg acgaatacat ctggtcaaac gacggggtac      720
gcgacggtta tccaaacaga tacggcaatt aactctggaa actctggtgg tccgttgttc      780
aacattgctg acaagttat cgggatcaac tcgatgaagt tggcctcaga taattctggg       840
actagtgtcg aagggatggg ctttgcaatt ccaagtaatg aagttgtgaa gatcatcaat      900
gaattggttc aaaagggtga agtcgttcgg ccggctttag gggttgcaac ctatgaccta      960
tccaatattt cttctagtga tcagaagtct gttcttaagt taccaaccag tgtgacgaag     1020
ggtgtcgtca tcatgaagac gtactcaggt tcaccggcta agctgctgg gttaacgaag      1080
tacgatgtga ttacggagct aggtggcaag aaagtgacca gcttagccac gttacggagt     1140
gccctgtatg cccattcggt taatgatacc gtgacggtga atactacca taacggaaaa     1200
ctcaagacag ccaacatgaa gttgacggaa actaccaaaa cgttaactaa acaaagtaac     1260
taa                                                                   1263
```

```
<210> SEQ ID NO 189
<211> LENGTH: 420
<212> TYPE: PRT
<213> ORGANISM: Lactobacillus plantarum

<400> SEQUENCE: 189

Met Ala Asn Lys Ser Leu Ile Lys Val Ala Val Thr Ala Leu Val Ala
1               5                   10                  15

Gly Leu Ile Gly Gly Gly Val Ala Tyr Gly Gly Ile Asn Tyr Phe Gln
            20                  25                  30

Asn Asn Asn Ile Ala Thr Ser Thr Ser Val Pro Thr Gly Ser Asn
        35                  40                  45

Lys Ser Gly Ser Thr Ser Thr Thr Asn Val Lys Val Asn Val Ser Ser
    50                  55                  60

Gln Ala Thr Lys Val Phe Glu Asn Asn Lys Ala Ala Val Val Ser Val
65                  70                  75                  80

Ile Asn Leu Gln Lys Lys Ser Ser Ser Ser Trp Ser Gly Ile Leu
                85                  90                  95

Gly Gly Asp Asp Ser Ser Gly Ser Ser Ser Ser Ser Asp Ser
            100                 105                 110

Ser Ser Ser Lys Leu Glu Glu Tyr Ser Glu Gly Ser Gly Leu Ile Tyr
        115                 120                 125

Lys Lys Ser Gly Asp Ala Ala Tyr Ile Val Thr Asn Asn His Val Val
    130                 135                 140

Ser Gly Ser Ser Ala Ile Arg Val Ile Met Ser Asp Gly Thr Lys Leu
145                 150                 155                 160

Ser Ala Lys Ile Val Gly Thr Asp Ser Val Thr Asp Leu Ala Val Leu
                165                 170                 175

Lys Ile Asn Ser Ser Lys Val Thr Lys Thr Ala Ser Phe Gly Asn Ser
```

```
                180               185                190
Asp Asn Ile Lys Val Gly Glu Thr Ala Leu Ala Ile Gly Ser Pro Met
            195                 200                 205

Gly Ser Asn Tyr Ala Thr Thr Leu Thr Gln Gly Ile Ile Ser Ala Lys
            210                 215                 220

Lys Arg Thr Val Ala Thr Thr Asn Thr Ser Gly Gln Thr Thr Gly Tyr
225                 230                 235                 240

Ala Thr Val Ile Gln Thr Asp Thr Ala Ile Asn Ser Gly Asn Ser Gly
                245                 250                 255

Gly Pro Leu Phe Asn Ile Ala Gly Gln Val Ile Gly Ile Asn Ser Met
                260                 265                 270

Lys Leu Ala Ser Asp Asn Ser Gly Thr Ser Val Glu Gly Met Gly Phe
            275                 280                 285

Ala Ile Pro Ser Asn Glu Val Val Lys Ile Ile Asn Glu Leu Val Gln
            290                 295                 300

Lys Gly Glu Val Val Arg Pro Ala Leu Gly Val Ala Thr Tyr Asp Leu
305                 310                 315                 320

Ser Asn Ile Ser Ser Ser Asp Gln Lys Ser Val Leu Lys Leu Pro Thr
                325                 330                 335

Ser Val Thr Lys Gly Val Val Ile Met Lys Thr Tyr Ser Gly Ser Pro
            340                 345                 350

Ala Lys Ala Ala Gly Leu Thr Lys Tyr Asp Val Ile Thr Glu Leu Gly
            355                 360                 365

Gly Lys Lys Val Thr Ser Leu Ala Thr Leu Arg Ser Ala Leu Tyr Ala
370                 375                 380

His Ser Val Asn Asp Thr Val Thr Val Lys Tyr Tyr His Asn Gly Lys
385                 390                 395                 400

Leu Lys Thr Ala Asn Met Lys Leu Thr Glu Thr Thr Lys Thr Leu Thr
                405                 410                 415

Lys Gln Ser Asn
            420

<210> SEQ ID NO 190
<211> LENGTH: 285
<212> TYPE: DNA
<213> ORGANISM: Lactobacillus plantarum

<400> SEQUENCE: 190
gtgttaaaac cattaggaga tcgcgttatc ttgcaacaac aagaagaaga agaacaaaca      60
attggcggta ttgtcattgc caataacgct aaggaaaagc cccaaagcgg taaggttgtt     120
gccgtcaatg acggtcgtgt tttagataac gggacaaaag ttgaccccag cgtgaaggtc     180
ggcgatcaag tattattcga taagtatgcc ggtaccgaag tcaagtatca aggtgctaag     240
tatttggtat tgcacgaaaa agatatcgtt gcaatcgaag actaa                    285

<210> SEQ ID NO 191
<211> LENGTH: 94
<212> TYPE: PRT
<213> ORGANISM: Lactobacillus plantarum

<400> SEQUENCE: 191

Met Leu Lys Pro Leu Gly Asp Arg Val Ile Leu Gln Gln Gln Glu Glu
1               5                  10                  15

Glu Glu Gln Thr Ile Gly Gly Ile Val Ile Ala Asn Asn Ala Lys Glu
                20                  25                  30
```

Lys Pro Gln Ser Gly Lys Val Val Ala Val Asn Asp Gly Arg Val Leu
            35                  40                  45

Asp Asn Gly Thr Lys Val Asp Pro Ser Val Lys Val Gly Asp Gln Val
50                  55                  60

Leu Phe Asp Lys Tyr Ala Gly Thr Glu Val Lys Tyr Gln Gly Ala Lys
65                  70                  75                  80

Tyr Leu Val Leu His Glu Lys Asp Ile Val Ala Ile Glu Asp
                85                  90

<210> SEQ ID NO 192
<211> LENGTH: 1626
<212> TYPE: DNA
<213> ORGANISM: Lactobacillus plantarum

<400> SEQUENCE: 192

| | | | | | |
|---|---|---|---|---|---|
| atggctaaag | aattaaagtt | ctctgaagat | gcacgttcag | cgatgctaaa | aggtgtcgat | 60 |
| caattagctg | acacagttaa | gtcaacgtta | ggtcctaagg | gtcgcaacgt | tgttttggaa | 120 |
| caatcatatg | gttcaccaac | aattactaat | gatggtgtaa | cgattgctaa | ggcgatcgaa | 180 |
| ttagacgatc | atttcgaaaa | catgggtgct | aagttagttt | ctgaagttgc | ttcaaagact | 240 |
| aatgacatcg | ctggtgatgg | gacgactact | gcaacggtct | taacacaatc | aatcgttaat | 300 |
| gaaggtatga | agaacgttac | ggccggtgct | aaccctgttg | gcattcgtcg | tgggattgaa | 360 |
| gaagctacta | agacggcggt | tgactcatta | acgctatgg | cacacgaagt | taagacgcaa | 420 |
| gaagatattg | cgcaaatcgc | ttctgtatct | tcagcaagtg | aagaaactgg | taaattgatt | 480 |
| gccgaagcca | tggaaaaagt | tggtcatgac | ggtgttatca | cgattgaaga | atcacgtggt | 540 |
| gttgatacta | gcttagacgt | tgttgaaggg | atgcaattcg | accgcggcta | cttatcacaa | 600 |
| tacatggtta | ctgataatga | taagatggaa | gcggatcttg | acaatccata | tatcttaatt | 660 |
| actgataaga | agatttcaaa | cattcaagat | atcttaccac | tattacaatc | catcgttgaa | 720 |
| caaggcaagc | cattgttgat | cattgctgat | gacatttctg | gtgaagcttt | accaaccttg | 780 |
| gtcttgaaca | agatgcgtgg | gacgtttaac | gttgtcgccg | ttaaggcacc | cggttttggt | 840 |
| gatcggcgta | aggaacaatt | acaagatatc | gctatcttaa | ctggcgggac | ggttatcact | 900 |
| gacgaccttg | gccttgaatt | gaaggacacg | accatcgatc | aattaggtca | agccaacaaa | 960 |
| gttacggtta | ctaaggataa | caccaccatt | gttgaaggcg | ctggttccaa | ggatgctatc | 1020 |
| tcagaacggg | ttgaatttat | ccgtaaccaa | atcggtgaaa | caacttctga | ctttgacaaa | 1080 |
| gaaaagttac | aagaacgttt | agctaaatta | gctggtgggg | ttgccgttgt | tcgtgtcggt | 1140 |
| gccgctactg | aaactgaatt | gaaggaacgt | aaataccgga | ttgaagatgc | tttgaacgca | 1200 |
| actcgggccg | ccgttgaaga | aggctttgtt | gctggtggtg | gtactgcttt | gattaacgtt | 1260 |
| atcaaagatg | ttgctgcatt | gaaggaaact | ggtgacgttc | aaactgggat | caacattgtt | 1320 |
| aaacgtgctt | tggaagaacc | agttcgccaa | atcgctgaaa | atgctggttt | agaaggctct | 1380 |
| gttatcgttg | aaaagatgaa | ggaacaaaag | ccaggtgttg | gtttcaacgc | cgcaactgat | 1440 |
| gaatgggttg | acatgatcaa | agctggtatc | gtggacccaa | ctaaggtaac | gcgttctgct | 1500 |
| ttacaaaatg | ccgcttctgt | ttcagcccct | ctcttaacga | ctgaagccgt | tgtcgctgaa | 1560 |
| aaacctgaag | aaaatgcacc | agctgcacca | gccgcaccaa | acccaggtat | gggcggtatg | 1620 |
| atgtaa | | | | | | 1626 |

<210> SEQ ID NO 193
<211> LENGTH: 539

<212> TYPE: PRT
<213> ORGANISM: Lactobacillus plantarum

<400> SEQUENCE: 193

```
Met Ala Lys Glu Leu Lys Phe Ser Glu Asp Ala Arg Ser Ala Met Leu
1               5                   10                  15

Lys Gly Val Asp Gln Leu Ala Asp Thr Val Lys Ser Thr Leu Gly Pro
            20                  25                  30

Lys Gly Arg Asn Val Val Leu Glu Gln Ser Tyr Gly Ser Pro Thr Ile
        35                  40                  45

Thr Asn Asp Gly Val Thr Ile Ala Lys Ala Ile Glu Leu Asp Asp His
50                  55                  60

Phe Glu Asn Met Gly Ala Lys Leu Val Ser Glu Val Ala Ser Lys Thr
65                  70                  75                  80

Asn Asp Ile Ala Gly Asp Gly Thr Thr Thr Ala Thr Val Leu Thr Ser
                85                  90                  95

Ile Val Asn Glu Gly Met Lys Asn Val Thr Ala Gly Ala Asn Pro Val
            100                 105                 110

Gly Ile Arg Arg Gly Ile Glu Glu Ala Thr Lys Thr Ala Val Asp Ser
        115                 120                 125

Leu His Ala Met Ala His Glu Val Lys Thr Gln Glu Asp Ile Ala Gln
130                 135                 140

Ile Ala Ser Val Ser Ala Ser Glu Glu Thr Gly Lys Leu Ile Ala
145                 150                 155                 160

Glu Ala Met Glu Lys Val Gly His Asp Gly Val Ile Thr Ile Glu Glu
                165                 170                 175

Ser Arg Gly Val Asp Thr Ser Leu Asp Val Val Glu Gly Met Gln Asp
            180                 185                 190

Arg Gly Tyr Leu Ser Gln Tyr Met Val Thr Asp Asn Asp Lys Met Glu
        195                 200                 205

Ala Asp Leu Asp Asn Pro Tyr Ile Leu Ile Thr Asp Lys Lys Ile Ser
210                 215                 220

Asn Ile Gln Asp Ile Leu Pro Leu Leu Gln Ser Ile Val Glu Gln Gly
225                 230                 235                 240

Lys Pro Leu Leu Ile Ile Ala Asp Asp Ile Ser Gly Glu Ala Leu Pro
                245                 250                 255

Thr Leu Val Leu Asn Lys Met Arg Gly Thr Phe Asn Val Ala Val
            260                 265                 270

Lys Ala Pro Gly Phe Gly Asp Arg Arg Lys Glu Gln Leu Gln Asp Ile
        275                 280                 285

Ala Ile Leu Thr Gly Gly Thr Val Ile Thr Asp Asp Leu Gly Leu Glu
290                 295                 300

Leu Lys Asp Thr Thr Ile Asp Gln Leu Gly Gln Ala Asn Lys Val Thr
305                 310                 315                 320

Val Thr Lys Asp Asn Thr Thr Ile Val Glu Gly Ala Gly Ser Lys Asp
                325                 330                 335

Ala Ile Ser Glu Arg Val Glu Phe Ile Arg Asn Gln Ile Gly Glu Thr
            340                 345                 350

Thr Ser Asp Phe Asp Lys Glu Lys Leu Gln Glu Arg Leu Ala Lys Leu
        355                 360                 365

Ala Gly Gly Val Ala Val Val Arg Val Gly Ala Ala Thr Glu Thr Glu
370                 375                 380

Leu Lys Glu Arg Lys Tyr Arg Ile Glu Asp Ala Leu Asn Ala Thr Arg
385                 390                 395                 400
```

Ala Ala Val Glu Glu Gly Phe Val Ala Gly Gly Thr Ala Leu Ile
            405                 410                 415

Asn Val Ile Lys Asp Val Ala Ala Leu Lys Glu Thr Gly Asp Val Gln
        420                 425                 430

Thr Gly Ile Asn Ile Val Lys Arg Ala Leu Glu Pro Val Arg Gln
            435                 440                 445

Ile Ala Glu Asn Ala Gly Leu Glu Gly Ser Val Ile Val Glu Lys Met
    450                 455                 460

Lys Glu Gln Lys Pro Gly Val Gly Phe Asn Ala Ala Thr Asp Glu Trp
465                 470                 475                 480

Val Asp Met Ile Lys Ala Gly Ile Val Asp Pro Thr Lys Val Thr Arg
                485                 490                 495

Ser Ala Leu Gln Asn Ala Ala Ser Val Ser Ala Leu Leu Leu Thr Thr
            500                 505                 510

Glu Ala Val Val Ala Glu Lys Pro Glu Glu Asn Ala Pro Ala Ala Pro
        515                 520                 525

Ala Ala Pro Asn Pro Gly Met Gly Gly Met Met
    530                 535

<210> SEQ ID NO 194
<211> LENGTH: 591
<212> TYPE: DNA
<213> ORGANISM: Lactobacillus plantarum

<400> SEQUENCE: 194
atgtatccag ttcctacagt tattgaacag tcatcacgtg gcgaacgtgc ttatgacatc      60
tattcacgac tattaaagga ccgtatcatt atgttatccg gtcccattga agataacatg     120
gcaaacgcca ttattgccca actactcttc ttggatgccc aagattcagg taaggacatc     180
tatctctata tcaactcacc aggtggtgtc gttactgccg gcttagcaat ctacgatacg     240
atgaacttca tcaaatctga tgttcaaacc atcgttatgg ggatggctgc ttccatggcc     300
agcgtcttag cttcatctgg tactaagggc aagcgttttg ctttacctaa ctctgaaatc     360
ttgattcacc aaccatctgg tggtgctcaa ggtcaacaaa cggaaattga aattgttgcg     420
gaagaaatct tgaagactcg taaaaagatc aaccagattt tagctgacaa ctcgggacaa     480
tccgttgaaa agttgaacca tgatactgaa cgtgataact acttaagcgc acaagaggct     540
aaagactacg gtttgatcga tgatattatg gaaaacaaca aattaaaata a              591

<210> SEQ ID NO 195
<211> LENGTH: 196
<212> TYPE: PRT
<213> ORGANISM: Lactobacillus plantarum

<400> SEQUENCE: 195

Met Tyr Pro Val Pro Thr Val Ile Glu Gln Ser Ser Arg Gly Glu Arg
1               5                   10                  15

Ala Tyr Asp Ile Tyr Ser Arg Leu Leu Lys Asp Arg Ile Ile Met Leu
            20                  25                  30

Ser Gly Pro Ile Glu Asp Asn Met Ala Asn Ala Ile Ile Ala Gln Leu
        35                  40                  45

Leu Phe Leu Asp Ala Gln Asp Ser Gly Lys Asp Ile Tyr Leu Tyr Ile
    50                  55                  60

Asn Ser Pro Gly Gly Val Val Thr Ala Gly Leu Ala Ile Tyr Asp Thr
65                  70                  75                  80

Met Asn Phe Ile Lys Ser Asp Val Gln Thr Ile Val Met Gly Met Ala
                85                  90                  95

Ala Ser Met Ala Ser Val Leu Ala Ser Ser Gly Thr Lys Gly Lys Arg
            100                 105                 110

Phe Ala Leu Pro Asn Ser Glu Ile Leu Ile His Gln Pro Ser Gly Gly
        115                 120                 125

Ala Gln Gly Gln Gln Thr Glu Ile Glu Ile Val Ala Glu Glu Ile Leu
    130                 135                 140

Lys Thr Arg Lys Lys Ile Asn Gln Ile Leu Ala Asp Asn Ser Gly Gln
145                 150                 155                 160

Ser Val Glu Lys Leu Asn His Asp Thr Glu Arg Asp Asn Tyr Leu Ser
                165                 170                 175

Ala Gln Glu Ala Lys Asp Tyr Gly Leu Ile Asp Asp Ile Met Glu Asn
            180                 185                 190

Asn Lys Leu Lys
        195

<210> SEQ ID NO 196
<211> LENGTH: 1173
<212> TYPE: DNA
<213> ORGANISM: Lactobacillus plantarum

<400> SEQUENCE: 196
atgttagaca aaatcattta taaaaactta tttagtaaag cgttcgatat tactattgaa      60
gtcacttatt gggatgggca aattgaacgg tatggtaccg gcatgccagc tgttaaagtt     120
cgattaaata aagaaatccc aattaagcta ttaactaatc agccaacatt ggttttaggt     180
gaagcataca tgaatgggga tattgaagta gacgggagca ttcaggaatt aattgcctct     240
gcttaccgcc aaaaagacag tttttttgaca cataattcat ttttgaaaca cttgcccaaa     300
atatcacatt ccgaaaaaag cagcacaaaa gatattcaaa gtcattatga tatcggcaat     360 gattttttata aactatggtt agatgatacc atgacctact cttgtgcgta ctttgaacat     420
gacgatgata cttttaaaaca ggcacaactc aataaagtga acatattttt aaataagctg     480
gcaacccagc ctggtaaaag attattgat gttgggagtg ttggggaac attattattt        540 atggccgcgg atgagtttgg gttagatgca acgggtatta ctttaagtca agaacagtat     600
gattatacac aagcgcaaat caagcagcgt catttggagg aaaaagtgca tgtgcagtta     660
aaggactatc gagaagtcac tggccaattt gattatgtca cctcggtagg tatgtttgaa     720
catgttggta agaaaaatct aggggttgtac tttaataaaa ttcaagcgtt cttagttcca     780
ggaggccgag ctttaattca tggcattaca ggtcaacatg aaggtgccgg cgttgatcca     840
tttattaacc aatatatttt cccagggggc tatatcccaa atgttgctga aatctcaaa       900 catattatgg ctgctaagtt acaatttca gacattgaac ccttgcggcg ccattaccaa      960
aagacgttag aaatctggta tcacaattat cagcaggtcg aacaacaggt cgtcaagaat    1020
tatggggaac gatttgaccg catgtggcaa ttatatttac aggcatgtgc agctgctttt    1080
gaggccggaa atatcgatgt tattcaatat ctattagtga aagcgccgag tggaactggc    1140
cttccgatga ctcgccatta tatttatgat tga                                 1173

<210> SEQ ID NO 197
<211> LENGTH: 390
<212> TYPE: PRT
<213> ORGANISM: Lactobacillus plantarum

<400> SEQUENCE: 197

```
Met Leu Asp Lys Ile Ile Tyr Lys Asn Leu Phe Ser Lys Ala Phe Asp
1               5                   10                  15

Ile Thr Ile Glu Val Thr Tyr Trp Asp Gly Gln Ile Glu Arg Tyr Gly
            20                  25                  30

Thr Gly Met Pro Ala Val Lys Val Arg Leu Asn Lys Glu Ile Pro Ile
        35                  40                  45

Lys Leu Leu Thr Asn Gln Pro Thr Leu Val Leu Gly Glu Ala Tyr Met
50                  55                  60

Asn Gly Asp Ile Glu Val Asp Gly Ser Ile Gln Glu Leu Ile Ala Ser
65                      70                  75                  80

Ala Tyr Arg Gln Lys Asp Ser Phe Leu Thr His Asn Ser Phe Leu Lys
                85                  90                  95

His Leu Pro Lys Ile Ser His Ser Glu Lys Ser Ser Thr Lys Asp Ile
                100                 105                 110

Gln Ser His Tyr Asp Ile Gly Asn Asp Phe Tyr Lys Leu Trp Leu Asp
        115                 120                 125

Asp Thr Met Thr Tyr Ser Cys Ala Tyr Phe Glu His Asp Asp Asp Thr
        130                 135                 140

Leu Lys Gln Ala Gln Leu Asn Lys Val Arg His Ile Leu Asn Lys Leu
145                 150                 155                 160

Ala Thr Gln Pro Gly Lys Arg Leu Leu Asp Val Gly Ser Gly Trp Gly
                165                 170                 175

Thr Leu Leu Phe Met Ala Ala Asp Glu Phe Gly Leu Asp Ala Thr Gly
                180                 185                 190

Ile Thr Leu Ser Gln Glu Gln Tyr Asp Tyr Thr Gln Ala Gln Ile Lys
            195                 200                 205

Gln Arg His Leu Glu Glu Lys Val His Val Gln Leu Lys Asp Tyr Arg
210                 215                 220

Glu Val Thr Gly Gln Phe Asp Tyr Val Thr Ser Val Gly Met Phe Glu
225                 230                 235                 240

His Val Gly Lys Glu Asn Leu Gly Leu Tyr Phe Asn Lys Ile Gln Ala
                245                 250                 255

Phe Leu Val Pro Gly Gly Arg Ala Leu Ile His Gly Ile Thr Gly Gln
                260                 265                 270

His Glu Gly Ala Gly Val Asp Pro Phe Ile Asn Gln Tyr Ile Phe Pro
        275                 280                 285

Gly Gly Tyr Ile Pro Asn Val Ala Glu Asn Leu Lys His Ile Met Ala
        290                 295                 300

Ala Lys Leu Gln Phe Ser Asp Ile Glu Pro Leu Arg Arg His Tyr Gln
305                 310                 315                 320

Lys Thr Leu Glu Ile Trp Tyr His Asn Tyr Gln Gln Val Glu Gln Gln
                325                 330                 335

Val Val Lys Asn Tyr Gly Glu Arg Phe Asp Arg Met Trp Gln Leu Tyr
                340                 345                 350

Leu Gln Ala Cys Ala Ala Ala Phe Glu Ala Gly Asn Ile Asp Val Ile
            355                 360                 365

Gln Tyr Leu Leu Val Lys Ala Pro Ser Gly Thr Gly Leu Pro Met Thr
        370                 375                 380

Arg His Tyr Ile Tyr Asp
385                 390

<210> SEQ ID NO 198
<211> LENGTH: 2268
```

<212> TYPE: DNA
<213> ORGANISM: Lactobacillus plantarum

<400> SEQUENCE: 198

```
atgcccaaac aacctacctg gactgcccag gatgtcctgg acatggttca aaagtatatg      60
aatagtgatc acgtcgcgtt agttaaacgg gcgtgtgatt ttgcaactta tgtgcataag     120
gatcagtatc gccaatctgg tgagccgtat attatgcatc cgattcaagt tgctggtatc     180
ttagctgaat tgaagatgga ccctgaaacc gtcgcttcgg gtttcttaca cgacgttgtg     240
gaagatactg gtgttacttt aggagacgtt gaagaactgt ttggtcatga cgtggccgtt     300
attgttgacg gggtcaccaa gctgggtaag attcggtaca agtccaacaa agaacagctt     360
gctgaaaatc accgtaaatt actgttggcg atgtctaaag atattcgagt catgattgtc     420
aaattagctg atcgcttgca taatatgcgg acattgcagc atctgcggcc cgataaacag     480
cggcgaattg caaatgaaac gttggaaatt tacgccccca ttgccgatcg attagggatc     540
agcacgatta atgggaact agaagatatt tcactacgtt atttgaatcc tcaacagtat     600
tatcgcattg tccacttgat gaattcgcgg cgtgaggacc gtgaaaagta catcgagatt     660
gccattcaag acattcaaaa ggcgctccat gatctgaaac taccagaagc tgaaatttat     720
ggtcgtccga agcatatcta ttcaatttat aagaagatgc gggacaaaca caaacagttt     780
agccaacttt acgatctgct ggcaattcgg gtggtcgtgg attcaatcaa ggactgttat     840
gcagttttag gtgcgattca cacacaatgg aagcccatgc cggggcgttt taaagattat     900
attgcgatgc ccaaggccaa tatgtatcaa tctttgcata ccacggtggt cggtcctgaa     960
ggtaagcccc tcgaaataca gatccggacg tttgaaatgc accgggtcgc tgaatacggg    1020
gtcgcagcac actgggcgta taggaaggt aaacgcgacg aggtccaaga gactcagtcg    1080
ggcaacaagt tgaacttagt caaagaaatc attgagctac aggatgaaag taaggacgct    1140
gccgactta tggagggcgt caagggcgac ctctttagtg accgggtcta tgcttttacg    1200
cccaagggtg acgtgacaga attaccaaag gcgctggac cactggatat ggcatattcg    1260
atccatacgg aagtgggtaa ccatacgact ggtgcgaaag tcaatggcaa gatcgttcca    1320
ttggattacc aaatcaaaaa tggtgatatc gtggatattt aacgtccac tagttcaact    1380
ggtcctagcc gtgattggca gaaattagtc tatacgcggc gggcccgtaa taaaatcaaa    1440
cagttcttcc gcaatgctga ccgtgaggaa aacatcatta cgggtcgtga tttgcttgag    1500
aagcagctac gtgatttaga gtttaatcca aaagaaatca tgactaagga caaggtgacg    1560
gcggtcgctc aaaagatgca ctacggtagt gaggatgatt tgttcgcggc cttgggtt     1620
ggtgacgtcc aaccggtagg gattgctaac cggttaacga gtgatgttcg taaacagcgc    1680
gaggctaatc ggcagcgtga acgtgaggag gccattttgg cagactctac ggaagcgcca    1740
gcgaagaaga aatcgaaaga tcatcataat gaggatcagg agaagcagga tcggaagcgg    1800
caaaaggtct catcttctgg tggggtgatt attcaaggcg tcgacaactt actcgtacgt    1860
ctaagtcatt gctgttctcc aattccgggt gatgagattg ttggttatat tacgaagggg    1920
cgcggtgttt cggttcaccg tgttgattgt ccgaacgtta agagcgcaga agcaaatggt    1980
gaacggttga ttgatgttca gtgggagaat cccgagggtg accgaacgaa ctacaattct    2040
gatttggaaa ttcaaggtta taaccgtaat ggcatgctca acgatgtgtt gaaagttatc    2100
aataatcaca cgaaatttt gaccaatgtc aacggtaagg tcgatcacaa caagatggtc    2160
attattagtg tttcgttggg ggttcgcaac ttggaacatc tccaacgaat cattgacagt    2220
```

```
ctgaaaaatg ttcaggatct ttacgttgtc gaacggaaaa tgttttag              2268
```

<210> SEQ ID NO 199
<211> LENGTH: 755
<212> TYPE: PRT
<213> ORGANISM: Lactobacillus plantarum

<400> SEQUENCE: 199

| | | | | | | | | | | | | | | |
|---|---|---|---|---|---|---|---|---|---|---|---|---|---|---|
| Met | Pro | Lys | Gln | Pro | Thr | Trp | Thr | Ala | Gln | Asp | Val | Leu | Asp | Met | Val |
| 1 | | | | 5 | | | | | 10 | | | | | 15 | |
| Gln | Lys | Tyr | Met | Asn | Ser | Asp | His | Val | Ala | Leu | Val | Lys | Arg | Ala | Cys |
| | | | 20 | | | | | 25 | | | | | 30 | | |
| Asp | Phe | Ala | Thr | Tyr | Val | His | Lys | Asp | Gln | Tyr | Arg | Gln | Ser | Gly | Glu |
| | | 35 | | | | | 40 | | | | | 45 | | | |
| Pro | Tyr | Ile | Met | His | Pro | Ile | Gln | Val | Ala | Gly | Ile | Leu | Ala | Glu | Leu |
| | 50 | | | | | 55 | | | | | 60 | | | | |
| Lys | Met | Asp | Pro | Glu | Thr | Val | Ala | Ser | Gly | Phe | Leu | His | Asp | Val | Val |
| 65 | | | | | 70 | | | | | 75 | | | | | 80 |
| Glu | Asp | Thr | Gly | Val | Thr | Leu | Gly | Asp | Val | Glu | Leu | Phe | Gly | His | |
| | | | | 85 | | | | | 90 | | | | | 95 | |
| Asp | Val | Ala | Val | Ile | Val | Asp | Gly | Val | Thr | Lys | Leu | Gly | Lys | Ile | Arg |
| | | | 100 | | | | | 105 | | | | | 110 | | |
| Tyr | Lys | Ser | Asn | Lys | Glu | Gln | Leu | Ala | Glu | Asn | His | Arg | Lys | Leu | Leu |
| | | 115 | | | | | 120 | | | | | 125 | | | |
| Leu | Ala | Met | Ser | Lys | Asp | Ile | Arg | Val | Met | Ile | Val | Lys | Leu | Ala | Asp |
| 130 | | | | | 135 | | | | | 140 | | | | | |
| Arg | Leu | His | Asn | Met | Arg | Thr | Leu | Gln | His | Leu | Arg | Pro | Asp | Lys | Gln |
| 145 | | | | | 150 | | | | | 155 | | | | | 160 |
| Arg | Arg | Ile | Ala | Asn | Glu | Thr | Leu | Glu | Ile | Tyr | Ala | Pro | Ile | Ala | Asp |
| | | | | 165 | | | | | 170 | | | | | 175 | |
| Arg | Leu | Gly | Ile | Ser | Thr | Ile | Lys | Trp | Glu | Leu | Glu | Asp | Ile | Ser | Leu |
| | | | 180 | | | | | 185 | | | | | 190 | | |
| Arg | Tyr | Leu | Asn | Pro | Gln | Gln | Tyr | Tyr | Arg | Ile | Val | His | Leu | Met | Asn |
| | | 195 | | | | | 200 | | | | | 205 | | | |
| Ser | Arg | Arg | Glu | Asp | Arg | Glu | Lys | Tyr | Ile | Glu | Ile | Ala | Ile | Gln | Asp |
| | 210 | | | | | 215 | | | | | 220 | | | | |
| Ile | Gln | Lys | Ala | Leu | His | Asp | Leu | Glu | Leu | Pro | Glu | Ala | Glu | Ile | Tyr |
| 225 | | | | | 230 | | | | | 235 | | | | | 240 |
| Gly | Arg | Pro | Lys | His | Ile | Tyr | Ser | Ile | Tyr | Lys | Lys | Met | Arg | Asp | Lys |
| | | | | 245 | | | | | 250 | | | | | 255 | |
| His | Lys | Gln | Phe | Ser | Gln | Leu | Tyr | Asp | Leu | Leu | Ala | Ile | Arg | Val | Val |
| | | | 260 | | | | | 265 | | | | | 270 | | |
| Val | Asp | Ser | Ile | Lys | Asp | Cys | Tyr | Ala | Val | Leu | Gly | Ala | Ile | His | Thr |
| | | 275 | | | | | 280 | | | | | 285 | | | |
| Gln | Trp | Lys | Pro | Met | Pro | Gly | Arg | Phe | Lys | Asp | Tyr | Ile | Ala | Met | Pro |
| | 290 | | | | | 295 | | | | | 300 | | | | |
| Lys | Ala | Asn | Met | Tyr | Gln | Ser | Leu | His | Thr | Thr | Val | Val | Gly | Pro | Glu |
| 305 | | | | | 310 | | | | | 315 | | | | | 320 |
| Gly | Lys | Pro | Leu | Glu | Ile | Gln | Ile | Arg | Thr | Phe | Glu | Met | His | Arg | Val |
| | | | | 325 | | | | | 330 | | | | | 335 | |
| Ala | Glu | Tyr | Gly | Val | Ala | Ala | His | Trp | Ala | Tyr | Lys | Glu | Gly | Lys | Arg |
| | | | 340 | | | | | 345 | | | | | 350 | | |
| Asp | Glu | Val | Gln | Glu | Thr | Gln | Ser | Gly | Asn | Lys | Leu | Asn | Leu | Val | Lys |
| | | 355 | | | | | 360 | | | | | 365 | | | |

```
Glu Ile Ile Glu Leu Gln Asp Glu Ser Lys Asp Ala Ala Asp Phe Met
    370                 375                 380
Glu Gly Val Lys Gly Asp Leu Phe Ser Asp Arg Val Tyr Ala Phe Thr
385                 390                 395                 400
Pro Lys Gly Asp Val Thr Glu Leu Pro Lys Gly Ala Gly Pro Leu Asp
                405                 410                 415
Met Ala Tyr Ser Ile His Thr Glu Val Gly Asn His Thr Thr Gly Ala
            420                 425                 430
Lys Val Asn Gly Lys Ile Val Pro Leu Asp Tyr Gln Ile Lys Asn Gly
        435                 440                 445
Asp Ile Val Asp Ile Leu Thr Ser Thr Ser Thr Gly Pro Ser Arg
450                 455                 460
Asp Trp Gln Lys Leu Val Tyr Thr Arg Arg Ala Arg Asn Lys Ile Lys
465                 470                 475                 480
Gln Phe Phe Arg Asn Ala Asp Arg Glu Glu Asn Ile Ile Thr Gly Arg
                485                 490                 495
Asp Leu Leu Glu Lys Gln Leu Arg Asp Leu Glu Phe Asn Pro Lys Glu
            500                 505                 510
Ile Met Thr Lys Asp Lys Val Thr Ala Val Ala Gln Lys Met His Tyr
        515                 520                 525
Gly Ser Glu Asp Asp Leu Phe Ala Ala Leu Gly Phe Gly Asp Val Gln
    530                 535                 540
Pro Val Gly Ile Ala Asn Arg Leu Thr Ser Asp Val Arg Lys Gln Arg
545                 550                 555                 560
Glu Ala Asn Arg Gln Arg Glu Arg Glu Ala Ile Leu Ala Asp Ser
                565                 570                 575
Thr Glu Ala Pro Ala Lys Lys Ser Lys Asp His His Asn Glu Asp
            580                 585                 590
Gln Glu Lys Gln Asp Arg Lys Arg Gln Lys Val Ser Ser Gly Gly
        595                 600                 605
Val Ile Ile Gln Gly Val Asp Asn Leu Leu Val Arg Leu Ser His Cys
    610                 615                 620
Cys Ser Pro Ile Pro Gly Asp Glu Ile Val Gly Tyr Ile Thr Lys Gly
625                 630                 635                 640
Arg Gly Val Ser Val His Arg Val Asp Cys Pro Asn Val Lys Ser Ala
                645                 650                 655
Glu Ala Asn Gly Glu Arg Leu Ile Asp Val Gln Trp Glu Asn Pro Glu
            660                 665                 670
Gly Asp Arg Thr Asn Tyr Asn Ser Asp Leu Glu Ile Gln Gly Tyr Asn
        675                 680                 685
Arg Asn Gly Met Leu Asn Asp Val Leu Lys Val Ile Asn Asn His Thr
    690                 695                 700
Lys Phe Leu Thr Asn Val Asn Gly Lys Val Asp His Asn Lys Met Val
705                 710                 715                 720
Ile Ile Ser Val Ser Leu Gly Val Arg Asn Leu Glu His Leu Gln Arg
                725                 730                 735
Ile Ile Asp Ser Leu Lys Asn Val Gln Asp Leu Tyr Val Val Glu Arg
            740                 745                 750
Lys Met Phe
        755

<210> SEQ ID NO 200
<211> LENGTH: 1044
<212> TYPE: DNA
```

<213> ORGANISM: Lactobacillus plantarum

<400> SEQUENCE: 200

```
atgatcacgt taactgaacg acaaagccta attttaaagg ccattgtccg tgactatacc      60
gagggcggta atccagttgg atccaaatcg ctagttcaag aactaccgat caaggtcagt     120
tcagcgacga ttcgtaatga atggcccga ctagaagatt taggattaat cgtcaaaacg      180
catttgtctt cagggcgaat tccatcgatt aaggggtatc ggtactatgt tgaccatatc     240
ctaaagcctg aaaaggtgga tggcaaagac ttgaaggtga ttcaacattc attaggcggt     300
gaatttcaca gatcgatga gatcgttgct cagtcggcgg atatcttgtc gcaactgaca      360
agttacacga cctttacatt gcgacctgaa cttaaagata gtcggttgag tggtttcaga     420
ctcgttccgt tggggaatca tcaagtaatg gcgattctag tgacgaataa tggtgacgtt     480
gaaaaccaga cgtttactat tcctagtgac attaccggcg atgagctgga accggtcgtt     540
cgtttcattg acgatcaact ggttggcctg ccgttacaag acgtcctccg ccaattaacg     600
catgagattc cgttaaaact tgcacagtat ttgcaagatc cagatggttt cttagatatt     660
tttggcagtg tgttgtccaa ggcagcttcc gagcgctttt atgttggtgg taagttgaat     720
ttgttcaact atacggacca gcagagccct aaagagttac agtcattgta ctcgttactc     780
gaccaaacgg accggttagc taacgtgatt ggtccacccg gtcaacggat tcaagtccga     840
atcggtaatg agatcaccaa cgatttgttg aagaactaca gtttaattac cgcgacttac     900
gatgttgatc aacacggaca aggtgtgatt gctttgctcg ggccgaccgc catgccgtat     960
tcacggatga ttggactgat gggtgcgttc aacgagaat tagcccgcaa attattagat    1020
tattaccggt actttgacga gtga                                            1044
```

<210> SEQ ID NO 201
<211> LENGTH: 347
<212> TYPE: PRT
<213> ORGANISM: Lactobacillus plantarum

<400> SEQUENCE: 201

```
Met Ile Thr Leu Thr Glu Arg Gln Ser Leu Ile Leu Lys Ala Ile Val
1               5                   10                  15

Arg Asp Tyr Thr Glu Gly Gly Asn Pro Val Gly Ser Lys Ser Leu Val
            20                  25                  30

Gln Glu Leu Pro Ile Lys Val Ser Ala Thr Ile Arg Asn Glu Met
        35                  40                  45

Ala Arg Leu Glu Asp Leu Gly Leu Ile Val Lys Thr His Leu Ser Ser
    50                  55                  60

Gly Arg Ile Pro Ser Ile Lys Gly Tyr Arg Tyr Tyr Val Asp His Ile
65                  70                  75                  80

Leu Lys Pro Glu Lys Val Asp Gly Lys Asp Leu Lys Val Ile Gln His
                85                  90                  95

Ser Leu Gly Gly Glu Phe His Lys Ile Asp Glu Ile Val Ala Gln Ser
            100                 105                 110

Ala Asp Ile Leu Ser Gln Leu Thr Ser Tyr Thr Thr Phe Thr Leu Arg
        115                 120                 125

Pro Glu Leu Lys Asp Ser Arg Leu Ser Gly Phe Arg Leu Val Pro Leu
    130                 135                 140

Gly Asn His Gln Val Met Ala Ile Leu Val Thr Asn Asn Gly Asp Val
145                 150                 155                 160

Glu Asn Gln Thr Phe Thr Ile Pro Ser Asp Ile Thr Gly Asp Glu Leu
```

```
                    165                 170                 175
Glu Pro Val Val Arg Phe Ile Asp Asp Gln Leu Val Gly Leu Pro Leu
                180                 185                 190

Gln Asp Val Leu Arg Gln Leu Thr His Glu Ile Pro Leu Lys Leu Ala
            195                 200                 205

Gln Tyr Leu Gln Asp Pro Asp Gly Phe Leu Asp Ile Phe Gly Ser Val
        210                 215                 220

Leu Ser Lys Ala Ala Ser Glu Arg Phe Tyr Val Gly Lys Leu Asn
225                 230                 235                 240

Leu Phe Asn Tyr Thr Asp Gln Gln Ser Pro Lys Glu Leu Gln Ser Leu
                245                 250                 255

Tyr Ser Leu Leu Asp Gln Thr Asp Arg Leu Ala Asn Val Ile Gly Pro
            260                 265                 270

Pro Gly Gln Arg Ile Gln Val Arg Ile Gly Asn Glu Ile Thr Asn Asp
        275                 280                 285

Leu Leu Lys Asn Tyr Ser Leu Ile Thr Ala Thr Tyr Asp Val Asp Gln
290                 295                 300

His Gly Gln Gly Val Ile Ala Leu Leu Gly Pro Thr Ala Met Pro Tyr
305                 310                 315                 320

Ser Arg Met Ile Gly Leu Met Gly Ala Phe Gln Arg Glu Leu Ala Arg
                325                 330                 335

Lys Leu Leu Asp Tyr Tyr Arg Tyr Phe Asp Glu
            340                 345

<210> SEQ ID NO 202
<211> LENGTH: 1194
<212> TYPE: DNA
<213> ORGANISM: Lactobacillus plantarum

<400> SEQUENCE: 202
atgctagaaa aaacctttta ccacacccct ctaagccact cattcaatat gcccgtcaca      60
gtcaactact gggatggaag tagtgaaact tatggtgaag gcacaccaga agtcacggtg     120
acttttaaag aagccattcc aatgcgtgaa attaccaaga acgcttcaat tgcccttggt     180
gaagcttata tggatggcaa gattgaaatt gatggcagta ttcaaaaatt aattgaatcg     240
gcctatgaat cggcagaaag tttcttcaac aattctaagt tcaagaagtt catgcctaaa     300
caatctcact ctgaaaagaa gagtcaacaa gacatccaaa gccattacga tgtgggtaac     360
gacttctaca gatgtggct tgatccaacc atgacctatt cttgtgctta cttcaaacat     420
gacactgata cattagaaga gcccagatt cataaggttc atcacatcat tcaaaagctc     480
aacccacaac ctggcaagac cttactagac attggttgcg gttggggtac gttgatgttg     540
actgccgcta agaatacgg cttaaaagtc gtcggggtca cgttatcaca agaacaatat     600
aacctagttg ctcaacgcat caaggatgaa ggcctcagtg atgttgctga agtccggtta     660
caagattacc gtgaacttgg caacgaaact ttcgactaca ttaccagtgt tgggatgttc     720
gaacacgtcg gtaaggacaa cttagcaatg tactttgaac gcgttaacca ctatcttaaa     780
gctgacgggg ttgccttatt gcacggcatc acccggcaac aaggtggcgc cactaacggt     840
tggttagata agtacatttt cccaggtggc tacgttcctg ggatgacaga aaacttacaa     900
cacattgttg acgccggctt acaagtcgct gacgttgaaa ccctccgtcg ccattaccaa     960
cggacgactg aaatctggga taaaaacttt aacgctaagc gcgctgccat cgaagaaaag    1020
atgggcgtgc gcttcactcg catgtgggat ctctacctac aagcctgtgc cgcttccttc    1080
```

```
cagtctggta acattgacgt catgcagtac ctcgtaacta aaggtgcttc atcacgaacc   1140
ttaccaatga cccggaaata catgtatgcg gataaccgaa tcaataaagc ttaa         1194
```

<210> SEQ ID NO 203
<211> LENGTH: 397
<212> TYPE: PRT
<213> ORGANISM: Lactobacillus plantarum

<400> SEQUENCE: 203

```
Met Leu Glu Lys Thr Phe Tyr His Thr Leu Leu Ser His Ser Phe Asn
1               5                   10                  15

Met Pro Val Thr Val Asn Tyr Trp Asp Gly Ser Glu Thr Tyr Gly
            20                  25                  30

Glu Gly Thr Pro Glu Val Thr Val Thr Phe Lys Glu Ala Ile Pro Met
            35                  40                  45

Arg Glu Ile Thr Lys Asn Ala Ser Ile Ala Leu Gly Glu Ala Tyr Met
        50                  55                  60

Asp Gly Lys Ile Glu Ile Asp Gly Ser Ile Gln Lys Leu Ile Glu Ser
65                  70                  75                  80

Ala Tyr Glu Ser Ala Glu Ser Phe Phe Asn Asn Ser Lys Phe Lys Lys
                85                  90                  95

Phe Met Pro Lys Gln Ser His Ser Glu Lys Lys Ser Gln Gln Asp Ile
            100                 105                 110

Gln Ser His Tyr Asp Val Gly Asn Asp Phe Tyr Lys Met Trp Leu Asp
        115                 120                 125

Pro Thr Met Thr Tyr Ser Cys Ala Tyr Phe Lys His Asp Thr Asp Thr
130                 135                 140

Leu Glu Glu Ala Gln Ile His Lys Val His His Ile Ile Gln Lys Leu
145                 150                 155                 160

Asn Pro Gln Pro Gly Lys Thr Leu Leu Asp Ile Gly Cys Gly Trp Gly
                165                 170                 175

Thr Leu Met Leu Thr Ala Ala Lys Glu Tyr Gly Leu Lys Val Val Gly
            180                 185                 190

Val Thr Leu Ser Gln Glu Gln Tyr Asn Leu Val Ala Gln Arg Ile Lys
        195                 200                 205

Asp Glu Gly Leu Ser Asp Val Ala Glu Val Arg Leu Gln Asp Tyr Arg
    210                 215                 220

Glu Leu Gly Asn Glu Thr Phe Asp Tyr Ile Thr Ser Val Gly Met Phe
225                 230                 235                 240

Glu His Val Gly Lys Asp Asn Leu Ala Met Tyr Phe Glu Arg Val Asn
                245                 250                 255

His Tyr Leu Lys Ala Asp Gly Val Ala Leu Leu His Gly Ile Thr Arg
            260                 265                 270

Gln Gln Gly Gly Ala Thr Asn Gly Trp Leu Asp Lys Tyr Ile Phe Pro
        275                 280                 285

Gly Gly Tyr Val Pro Gly Met Thr Glu Asn Leu Gln His Ile Val Asp
    290                 295                 300

Ala Gly Leu Gln Val Ala Asp Val Glu Thr Leu Arg Arg His Tyr Gln
305                 310                 315                 320

Arg Thr Thr Glu Ile Trp Asp Lys Asn Phe Asn Ala Lys Arg Ala Ala
                325                 330                 335

Ile Glu Glu Lys Met Gly Val Arg Phe Thr Arg Met Trp Asp Leu Tyr
            340                 345                 350

Leu Gln Ala Cys Ala Ala Ser Phe Gln Ser Gly Asn Ile Asp Val Met
```

```
            355                 360                 365
Gln Tyr Leu Val Thr Lys Gly Ala Ser Ser Arg Thr Leu Pro Met Thr
    370                 375                 380

Arg Lys Tyr Met Tyr Ala Asp Asn Arg Ile Asn Lys Ala
385                 390                 395
```